(12) United States Patent
Takehara et al.

(10) Patent No.: US 7,145,047 B2
(45) Date of Patent: Dec. 5, 2006

(54) NAPHTHALENE DERIVATIVE AND LIQUID CRYSTAL COMPOSITION COMPRISING THE SAME

(75) Inventors: Sadao Takehara, Chiba (JP); Masashi Osawa, Saitama (JP); Haruyoshi Takatsu, Tokyo (JP); Makoto Negishi, Tokyo (JP)

(73) Assignee: Dainippon Ink and Chemicals, Inc., Tokyo (JP)

( * ) Notice: Subject to any disclaimer, the term of this patent is extended or adjusted under 35 U.S.C. 154(b) by 0 days.

(21) Appl. No.: 10/224,424

(22) Filed: Aug. 21, 2002

(65) Prior Publication Data

US 2003/0136944 A1 Jul. 24, 2003

Related U.S. Application Data

(62) Division of application No. 09/296,550, filed on Apr. 22, 1999, now Pat. No. 6,468,607.

(30) Foreign Application Priority Data

| Apr. 22, 1998 | (JP) | ................................. | 10-112147 |
| Jul. 2, 1998 | (JP) | ................................. | 10-187349 |
| Jul. 7, 1998 | (JP) | ................................. | 10-191471 |
| Jul. 15, 1998 | (JP) | ................................. | 10-200352 |
| Aug. 14, 1998 | (JP) | ................................. | 10-229680 |
| Dec. 8, 1998 | (JP) | ................................. | 10-348428 |

(51) Int. Cl.
*C07C 23/18* (2006.01)
*C07C 23/36* (2006.01)
*C09K 19/32* (2006.01)

(52) U.S. Cl. .................. 570/183; 252/299.62; 570/187

(58) Field of Classification Search ........... 252/299.62; 428/1.1; 570/183, 187
See application file for complete search history.

(56) References Cited

U.S. PATENT DOCUMENTS

| 5,098,930 A | 3/1992 | Edwards et al. |
| 5,252,253 A | 10/1993 | Gray et al. |
| 5,487,845 A | 1/1996 | Reiffenrath et al. |
| 5,536,442 A | 7/1996 | Reiffenrath et al. |
| 5,641,429 A | 6/1997 | Reiffenrath et al. |
| 5,707,547 A | 1/1998 | Fujimoto et al. |
| 5,779,934 A | 7/1998 | Higashii et al. |
| 6,159,561 A * | 12/2000 | Schmidt et al. ............... 428/1.1 |
| 7,014,890 B1 * | 3/2006 | Bremer et al. ............... 428/1.1 |

FOREIGN PATENT DOCUMENTS

| DE | 3328638 A1 | 2/1985 |
| DE | 41 16 158 A1 | 11/1992 |
| DE | 18522167 | 12/1995 |
| DE | 19522195 | 12/1995 |
| EP | 0667384 A1 | 8/1995 |
| GB | 2227019 A | 7/1990 |
| GB | 2 271 771 A | 4/1994 |
| JP | 9-52859 | 2/1997 |
| WO | WO 90/08119 | 7/1990 |
| WO | WO98/27037 | * 6/1998 |

OTHER PUBLICATIONS

Communication dated Nov. 13, 2002; European Search Report dated Nov. 5, 2002 and Annex.
CAPLUS 1996: 115271.
CAPLUS 1996: 209654.
CAPLUS 1997: 283949.
Lauk et al: "Synthese un Flussigkristalline Eigenschaften 2,6-disubstituierter Naphthaline", Helvetica Chimica Acta; vol. 68 (1985); pp. 1406-1426.
Chemical Abstracts, vol. 122, No. 8, Feb. 20, 1995 Columbus, Ohio, US; abstract No. 092970, Tamai K et al: "Ferroelectric Liquid Crystal Display" XP002105388 abstract & JP 06 157371 A (Sharp KK; JAPAN).
Chemical Abstracts, vol. 127, No. 20, Nov. 17, 1997 Columbus, Ohio, US; abstract No. 286023, Nohira H et al; "Optically-Active Fluoralkyl Compounds, Liquid-Crystal Compositions Containing Them, and the Devices, Display Method, and Displays Using the Compositions" XP-00 2105389 abstract & JP 09 221441 (Canon K.K., Japan).
Chemical Abstracts, vol. 106, No. 22 Jun. 1, 1987 Columbus, Ohio, US; abstract No. 187087 Sugimori S. et al; "Naphthalene Liquid Crystals" XP 002105390 abstract JP 61 91141 (Chisso corp. Japan).

(Continued)

*Primary Examiner*—Shean C Wu
(74) *Attorney, Agent, or Firm*—Armstrong, Kratz, Quintos, Hanson & Brooks, LLP

(57) ABSTRACT

Disclosed in a novel liquid-crystalline compound which is a naphthalene derivative useful as an electro-optical liquid crystal display material, a liquid crystal composition containing such naphthalene derivatives and a liquid crystal display device comprising the same. The naphthalene derivative provided by the present invention exhibits an excellent liquid-crystallinity and miscibility with currently widely used liquid crystal compositions or compositions. The addition of the naphthalene derivative makes it possible to drastically lower the threshold voltage of the liquid crystal composition while maintaining its high response. The naphthalene derivative of the present invention is characterized by a large birefringence index. Further, most of the naphthalene derivative of the present invention has no strongly polar group in its molecule and thus can also be used for active matrix driving. Moreover, as shown in the foregoing examples, the naphthalene derivative of the present invention can be easily produced and is colorless and chemically stable. Accordingly, the liquid crystal composition comprising the naphthalene derivative of the present invention is extremely useful as a practical liquid crystal composition, particularly a liquid crystal composition which can operate within a wide temperature range and requires a high speed response and a low voltage driving.

5 Claims, No Drawings

OTHER PUBLICATIONS

Chemical Abstracts, vol. 106, No. 22 Jun. 1, 1987 Columbus, Ohio, US; abstract No. 186681 Isoyama, T et al; "Liquid Crystal Compositions Containing Naphthalene" XP 002105391 abstract JP 61 246158 (Chisso Corp, Japan).

Chemical Abstracts, vol. 105, No. 12 Sep. 22, 1986 Columbus, Ohio, US; abstract No. 105906 Sugimori S. et al; "Naphthalene Compounds in Liquid Crystal Compositions" XP 002105392 abstract JP 61 000031 (Chisso Corp.).

D. Coates and G.W. Gray: "The Liquid Crystal Properties of Some Cyano-Substituted Aryl Esters"; Mol. Cryst. Liq. Cryst., 1976, vol. 37, pp. 249-262.

G.W. Gray and D. Lacey; "Molecular Crystals and Liwuid Crystals"; Mol. Cryst. Liq. Cryst., 1983, vol. 99, pp. 123-138.

Shin-Tson Wu et al; "High Birefringent Liquid Crystals"; Mol. Cryst. Liq. Cryst. 1995, vol. 261, pp. 79-86.

* cited by examiner

NAPHTHALENE DERIVATIVE AND LIQUID CRYSTAL COMPOSITION COMPRISING THE SAME

This application is a division of prior application Ser. No. 09/296,550 filed Apr. 22, 1999 now U.S. Pat. No. 6,468,607.

FIELD OF THE INVENTION

The present invention relates to a novel liquid-crystalline compound which is a naphthalene derivative useful as an electro-optical liquid crystal display material, a liquid crystal composition containing such naphthalene derivatives and a liquid crystal display device comprising the same.

BACKGROUNDS OF THE INVENTION

A liquid crystal display device has been used more and more in watch and electronic calculator as well as various measuring instrument, panel for automobile, word processor, electronic note, printer, computer, television, etc. Representative examples of liquid crystal display system include TN (twisted nematic) system, STN (super-twisted nematic) system, DS (dynamic scattering) system, GH (guest-host) system, and FLC (ferroelectric liquid crystal) system, which allows high speed response. Referring to driving system, multiplex driving has been more common than the conventional static driving. Further, simple matrix system has been recently put into practical use. Moreover, active matrix system has been put into practical use.

As the liquid crystal materials to be incorporated in these liquid crystal display devices there have been synthesized a very large number of kinds of liquid-crystalline compounds to date. These liquid-crystalline compounds are used depending on their display systems driving systems or purposes. However, the requirement for improvement of the properties of liquid crystal display device (enhancement of display quality or increase of the size of display) has been growing more and more. In order to satisfy these requirements, the development of now liquid crystal compounds are under way.

A liquid crystal compound is composed of a central skeleton moiety generally called core and a terminal moiety at both ends thereof. In general, the majority of the ring structure constituting the core moiety of a liquid crystal compound is occupied by 1,4-phenylene group (which may be substituted by one or two halogen atoms, cyano groups, methyl groups, etc.) and trans-1,4-cyclohexylene group. However, a liquid-crystalline compound merely made of 1,4-phenylene group and trans-1,4-cyclohexylene group is limited in its kind or properties. As a matter of fact these components cannot sufficiently meet the foregoing demands.

Besides the ring structures such as 1,4-phenylene group and trans-1,4-cyclohexylene group, heterocyclic groups such as pyridine-2,5-diyl group, pyrimidine-2,5-diyl group and 1,3-dioxane-trans-2,5-diyl group, condensed rings such as trans-decahydronaphthalene-2,6-diyl group, naphthalene-2,6-diyl group, tetrahydronaphthalene-2,6-diyl group, bicyclo[2,2,2]octane-1,4-diyl group and spiro[3,3]heptane-2,6-diyl group, etc. have been under study. However, few of these compounds have been put into practical use due to problems in production (technique, cost, etc.) and stability.

Though being a ring structure which has long bean reported, naphthalene-2,6-diyl group among these condensed rings is little known for properties other than liquid crystallinity (phase transition temperature), particularly nematic liquid crystallinity. (For smectic liquid crystal, it has recently been reported that an optically active alcohol ester of naphthalenecarboxylic acid exhibits interesting properties as a ferroelectric liquid crystal.)

An ordinary liquid crystal compound is terminated by a chain (side chain) group at one and thereof at least. A so-called p-type liquid crystal the dielectric anisotropy of which is positive is mostly terminated by a polar group at the other end thereof.

In order to lower the driving voltage in TN or STY display system a so-called strong P-type compound (the dielectric anisotropy of which is positive and great) is required. For this purpose, a compound terminated by cyano group at the molecular end thereof and having one or more fluorine atoms in the same direction per molecule is normally used. As a naphthalene derivative there has been reported only a compound having phenylnaphthalene skeleton (GB2271771A: Citation (a)). There is no reference to physical properties and application.

As the foregoing P-type compound to be used in active matrix driving there is used a compound containing as a polar group fluorine atom, fluoroalkoxyl group or fluoroalkyl group alone. As a naphthalene derivative there is described only a compound having phenylnaphthalene skeleton in GB2227019B (Citation (b)) and the above Citation (a). However, there is little reference to specific physical properties. Further, there is no reference to application to active matrix system.

In general, a liquid-crystalline compound which is a naphthalene derivative mostly exhibits a poor miscibility with other liquid crystal compounds. It is thought effective to introduce side substituents (preferably fluorine atom in particular) into the naphthalene skeleton for the purpose of improving the miscibility of the naphthalene derivative. The substitution by fluorine atom is thought effective also if an end polar group is directly introduced into the naphthalene ring in the application to the foregoing active matrix system. Some examples of such a fluoronaphthalene derivative are shown in the foregoing Citation (a). However, there is little reference to production process, not to mention physical properties. Thus, it is by no means thought that these exemplified compounds are actually produced compounds. Further, it cannot be presumed what properties these compounds have. No compounds having a structure having a fluoroalkoxyl group or fluoroalkyl group directly connected to naphthalene ring as a polar group have been known.

It has been known that a liquid crystal compound having an alkenyl group instead of an alkyl group, which is normally used as a side chain moiety, exhibits excellent improvements such as improved liquid crystallinity, reduced viscosity and improved sharpness in display. However, these alkenyl groups are mostly introduced directly connected to cyclohexane ring. Thus, no compounds having alkenyl groups introduced in naphthalene ring have been reported.

Similarly, no naphthalene derivatives having as side chain alkoxylalkyl group, fluoroalkyl group, fluoroalkenyl group, fluoroalkenyloxy group, etc. have been reported.

As groups connecting the ring structures in the core moiety of a liquid crystal compound, there have been known many divalent organic groups besides single bond and 1,2-ethylene group ($—CH_2CH_2—$).

Liquid crystal compounds having 1,4-butylene group or 1,2-propylene group are known to have a low melting point and an excellent miscibility with other liquid crystal compounds as compared with the corresponding liquid crystal compounds having single bond or ethylene group. However, no liquid-crystalline compounds having 1,4-butylene group or 1,2-propylene group have been known among naphthalene derivatives.

It has been reported that a liquid crystal compound having difluoroxymethylene group ($-CF_2O-$, $-OCF_2-$) or difluoroethenyl group ($-CF=CF-$) exhibits a low viscosity and thus is effective for the enhancement of response. However, no such naphthalene derivatives have been known.

SUMMARY OF THE INVENTION

An object of the present invention is to provide a novel liquid-crystalline compound having a naphthalene ring and a practical liquid crystal composition comprising the same.

The present invention has the following constitutions to accomplish the foregoing object:

1. A naphthalene derivative represented by the following general formula (I):

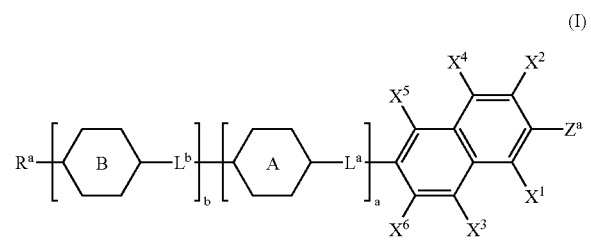

(I)

wherein $R^a$ represents a $C_{1-20}$ alkyl, alkoxy, alkoxyalkyl, alkenyl or alkenyloxy group which maybe substituted by a $C_{1-7}$ alkoxyl group or from 1 to 7 fluorine atoms; a and b each represent an integer of 0 or 1 and satisfy the relationship a≧b; rings A and B each independently represent a trans-1,4-cyclohexylene group, 1,4-phenylene group which may be substituted by one or more fluorine atoms, pyridine-2,5-diyl group, pyrimidine-2,5-diyl group, pyrazine-2,5-diyl group, pyridazine-3,6-diyl group, trans-1,3-dioxane-2,5-diyl group, trans-decahydronaphthalene-2,6-diyl group or tetrahydronaphthalene-2,6-diyl group; $L^a$ and $L^b$ each independently represent $-CH_2CH_2-$, $-CH_2CH_2CH_2CH_2-$, $-CH=CH-$, $-CH=CHCH_2CH_2-$, $-CH_2CH_2CH=CH-$, $-CH(CH_3)CH_2-$, $-CH_2CH(CH_3)-$, $-CF=CF-$, $-CF_2O-$, $-OCF_2-$, $-COO-$, $-OCO-$, $-C\equiv C-$ or single bond; $X^1$ to $X^6$ each independently represent a hydrogen atom or fluorine atom; and $Z^a$ represents a fluorine atom, chlorine atom, trifluoromethoxy group, $C_{1-7}$ alkoxyl group, $C_{1-20}$ alkyl, alkoxyl, alkenyl or alkenyloxy group which may be substituted by from 1 to 7 fluorine atoms or group represented by the following general formula (IIa) or (IIb):

(IIa)

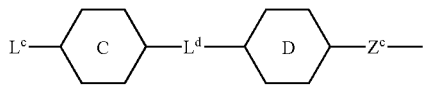

(IIb)

wherein $L^c$ and $L^d$ each independently represent $-CH_2CH_2-$, $-CH_2CH_2CH_2CH_2-$, $-CH=CH-$, $-CH=CHCH_2CH_2-$, $-CH_2CH_2CH=CH-$, $-CH(CH_3)CH_2-$, $-CH_2CH(CH_3)-$, $-CF=CF-$, $-CF_2O-$, $-OCF_2-$, $-COO-$, $-OCO-$, $-C\equiv C-$ or single bond; rings C and D each independently represent a trans-1,4-cyclohexylene group, 1,4-phenylene group which may be substituted by one or more fluorine atoms, pyridine-2,5-diyl group, pyrimidine-2,5diyl group, pyrazine-2,5-diyl group, pyridazine-3,6-diyl group, trans-1,3-dioxane-2,5-diyl group, trans-decahydronaphthalene-2,6-diyl group or tetrahydronaphthalene-2,6-diyl group; $Z^b$ and $Z^c$ each independently represent a fluorine atom, chlorine atom, bromine atom, iodine atom, hydrogen atom, cyano group, $-SCN$, $-OCN$, $-R'$, $-OR'$, $-OCOR'$ or $-COOR'$, wherein $R'$ represents a $C_{1-20}$ alkyl or alkoxy group or $C_{2-20}$ alkenyl or alkenyloxy group, and these groups may be substituted by a $C_{1-10}$ alkoxyl, acyl, acyloxy or alkoxycarbonyl group and one or more hydrogen atoms contained in these groups may be substituted by one or more fluorine atoms, and in the case of forming an asymmetric carbon by the substitution or branching, it may form an optically active form or racemic form, with the proviso that (1) if $Z^a$ represents a group represented by the general formula (IIa), b is 0, if $Z^a$ represents a group represented by the general formula (IIb), a is 0, and if $Z^a$ represents a fluorine atom, chlorine atom, trifluoromethoxy group, $C_{1-7}$ alkoxyl group or $C_{1-20}$ alkyl, alkoxyl, alkenyl or alkenyloxy group which may be substituted by from 1 to 7 fluorine atoms, a is 1; (2) if $Z^a$ represents the group represented by the general formula (IIa), ring C represents a 1,4-phenylene group which may be substituted by fluorine atom and $Z^b$ represents a fluorine atom, chlorine atom, trifluoromethoxy group or an alkyl or alkoxyl group which may be substituted by fluorine atom, $L^a$ represents $-CH_2CH_2CH_2CH_2-$, $-CH=CH-$, $-CH=CHCH_2CH_2-$, $-CH_2CH_2CH=CH-$, $-CH(CH_3)CH_2-$, $-CH_2CH(CH_3)-$, $-CF=CF-$, $-CF_2O-$ or $-OCF_2-$ and/or at least one of $X^1$ to $X^6$ represents a fluorine atom; (3) if $Z^a$ represents an alkyl or alkoxyl group, at least one of $X^1$ to $X^6$ represents a fluorine atom and/or $L^c$ represents $-CH_2CH_2CH_2CH_2-$, $-CF=CF-$, $-CF_2O-$ or $-OCF_2-$; (4) if $Z^a$ represents a fluorine or chlorine atom, $L^a$ represents a single bond; and if ring A represents a 1,4-phenylene group which may be substituted by fluorine atom, b represents 0, or b represents 1 and $L^b$ represents a single bond; and (5) if a and b each represent 0, $X^1$ represents a fluorine atom and $X^2$ to $X^5$ each represent a hydrogen atom; and if $L^c$ represents a single bond, $Z^b$ represents fluorine atom, chlorine atom, hydrogen atom, trifluoromethoxy group, alkenyl group, alkenyloxy group, cyanato group or cyano group.

2. The compound according to Clause 1 above, wherein in the general formula (I) a and b each represent 1.

3. The compound according to Clause 1 above, wherein in the general formula (I) a is 1, b is 0 and $Z^a$ is a group selected from the group consisting of fluorine atom, chlorine atom, trifluoromethoxy group, and $C_{1-20}$ alkyl, alkoxyl, alkenyl or alkenyloxy group which may be substituted by $C_{1-7}$ alkoxyl group or from 1 to 7 fluorine atoms.

4. The compound according to Clause 1 above, wherein in the general formula (I) a is 1, b is 0 and $Z^a$ is a group represented by the general formula (IIa).

5. The compound according to Clause 1 above, wherein in the general formula (I) a and b each are 0 and $Z^a$ represents a group represented by the general formula (IIa).

6. The compound according to Clause 1 above, wherein in the general formula (1) a and b each are 0 and $Z^a$ represents a group represented by the general formula (IIb).

7. The compound according to any one of Clauses 1 to 6 above, wherein $L^a$, $L^b$, $L^c$ and $L^d$ in the general formula (I) each independently represent a group selected from the group consisting of —CH$_2$CH$_2$— and single bond.

8. The compound according to any one of Clauses 1 to 4 and 7 above, wherein ring A in the general formula (I) represents a group selected from the group consisting of trans-1,4-cyclohexylene group, 1,4-phenylene group, 2-fluoro-1,4-phenylene group, 2,6-difluoro-1,4-phenylene group and trans-decahydronaphthalene-2,6-diyl group.

9. The compound according to any one of Clauses 1, 2, 7 and 8 above, wherein ring B in the general formula (I) represents a trans-1,4-cyclohexylene group.

10. The compound according to any one of Clauses 1 and 4 to 7 above, wherein rings C and D in the general formula (I) each independently represent a group selected from the group consisting of 1,4-phenylene group, 2-fluoro-1,4-phenylene group, 3-fluoro-1,4-phenylene group, 2,3-difluoro-1,4-phenylene group and 3,5-difluoro-1,4-phenylene group.

11. The compound according to any one of Clauses 1 to 3 and 7 to 9 above, wherein $Z^a$ in the general formula (I) represents a group selected from the group consisting of $C_{4-12}$ alkenyl group which may be substituted by from 1 to 3 fluorine atoms and $C_{3-12}$ alkenyloxy group which may be substituted by from 1 to 3 fluorine atoms.

12. The compound according to any one of Clauses 1 to 3 and 7 to 9 above, wherein $Z^a$ in the general formula (I) represents a group selected from the group consisting of $C_{1-12}$ alkyl or alkoxyl group which may be substituted by from 1 to 7 fluorine atoms.

13. The compound according to Clause 12 above, wherein $Z^a$ in the general formula (I) represents a trifluoromethoxy group.

14. The compound according to any one of Clauses 1 to 13 above, wherein $X^1$ in the general formula (I) represents a fluorine atom.

15. The compound according to Clause 14 above, wherein $X^2$ in the general formula (I) represents a fluorine atom.

16. The compound according to Clause 2 or 3 above, wherein $X^1$ and $X^2$ in the general formula (I) each represent a fluorine atom.

17. A liquid crystal composition comprising a compound represented by the general formula (I) described in Clause 1 above.

18. The liquid crystal composition described in Clause 17 above for use in active matrix driving.

19. A liquid crystal device comprising as a constituent element a liquid crystal composition described in Clause 17 above.

20. An active matrix driving liquid crystal display device comprising a liquid crystal composition described in Clause 18 above.

In more detail, the present invention provides a novel liquid-crystalline compound which is a naphthalene derivative represented by the following general formula (I):

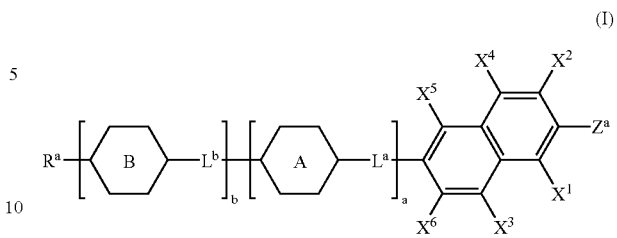

(I)

In the foregoing general formula (I), $R^a$ represents a $C_{1-20}$ alkyl, alkoxy, alkoxyalkyl, alkenyl or alkenyloxy group which may be substituted by a $C_{1-7}$ alkoxyl group or from 1 to 7 fluorine atoms. $R^a$ preferably is a $C_{1-7}$ straight-chain alkyl or alkenyl group. The alkyl group is preferably an unsubstituted alkyl group or an alkyl group terminated by a plurality of fluorine atoms, particularly an unsubstituted alkyl group. The alkenyl group, if the ring structure to which it is directly connected is a saturated ring, is preferably a 1-alkenyl group or 3-alkenyl group. In this case, the double bond is preferably at the end of side chain. Alternatively, the configuration of the double bond is preferably in trans-position. A particularly preferred example of the alkenyl group is a vinyl group or 3-butenyl group. Further, the hydrogen atom which is directly connected to the double bond is preferably substituted by a fluorine atom. Preferred examples of such a substituted alkenyl group include (E)-2-fluorovinyl group, 2,3-difluorovinyl group, 3-fluoro-2-propenyl group, 3,3-difluoro-2-propenyl group, 4-fluoro-3-butenyl group, and 4,4-difluoro-3-butenyl group. The alkenyl group, if the ring structure to which it is directly connected is an aromatic ring, is preferably a 3-alkenyl group. In this case, the double bond is preferably at the end of side chain. Alternatively, the configuration of the double bond is preferably in trans-position. A particularly preferred example of the alkenyl group is a 3-butenyl group or trans-3-pentenyl group.

a and b each represent 0 or 1 and satisfy the relationship a≧b.

Rings A and B each independently represent a trans-1,4-cyclohexylene group, 1,4-phenylene group which may be substituted by one or more fluorine atoms, pyridine-2,5-diyl group, pyrimidine-2,5-diyl group, pyrazine-2,5-diyl group, pyridazine-3,6-diyl group, trans-1,3-dioxane-2,5-diyl group, trans-decahydronaphthalene-2,6-diyl group or tetrahydronaphthalene-2,6-diyl group. Preferred among these groups are trans-1,4-cyclohexylene group, 1,4-phenylene, 2-fluoro-1,4-phenylene group, 3-fluoro-1,4-phenylene group, 2,3-difluoro-1,4-phenylene group, 2,6-difluoro-1,4-phenylene group, and trans-decahydro naphthalene-2,6-diyl group. In particular, ring B is preferably a cyclohexane ring. Ring A, if a strong p-type liquid crystal composition is particularly required, is preferably a 2-fluoro-1,4-phenylene group or 2,6-difluoro-1,4-phenylene group. If a strong n-type (negative dielectric anisotropy) is particularly required, ring A is preferably a 3-fluoro-1,4-phenylene group or 2,3-difluoro-1,4-phenylene group.

$L^a$ and $L^b$ each independently represent —CH$_2$CH$_2$—, —CH$_2$CH$_2$CH$_2$CH$_2$—, —CH=CH—, —CH=CHCH$_2$CH$_2$—, —CH$_2$CH$_2$CH=CH—, —CH(CH$_3$)CH$_2$—, —CH$_2$CH(CH$_3$)—, —CF=CF—, —CF$_2$O—, —OCF$_2$—, —COO—, —OCO—, —C≡C— or single bond. Preferred among these groups are —CH$_2$CH$_2$—, —CF=CF—, —CF$_2$O—, —OCF$_2$— and single bond, and —CH$_2$CH$_2$— and single bond are particularly preferred. If L$^a$ and L$^b$ are present at the same time, at least one of them is more preferably a single bond.

X$^1$ to X$^6$ each independently represent a hydrogen atom or fluorine atom. In particular, X$^1$ preferably represents a fluorine atom. If the liquid-crystalline compound is a p-type compound, one or more of X$^1$ to X$^3$ each are preferably a fluorine atom while X$^4$ to X$^6$ each are preferably a hydrogen atom. Further, if Z$^a$ is a polar group such as fluorine atom, X$^1$ and X$^2$ or X$^1$ to X$^3$ each preferably represent a fluorine atom at the same time. If the liquid-crystalline compound is a n-type compound, at least one of X$^4$ to X$^6$ is preferably a fluorine atom. Alternatively, all X$^1$ to X$^6$ each represent a hydrogen atom. Alternatively, X$^1$ is preferably a fluorine atom while the others are each preferably a hydrogen atom.

Z$^a$ represents a fluorine atom, chlorine atom, trifluoromethoxy group, C$_{1-7}$ alkoxyl group, C$_{1-20}$ alkyl, alkoxyl, alkenyl or alkenyloxy group which may be substituted by from 1 to 7 fluorine atoms or group represented by the following general formula (IIa) or (IIb):

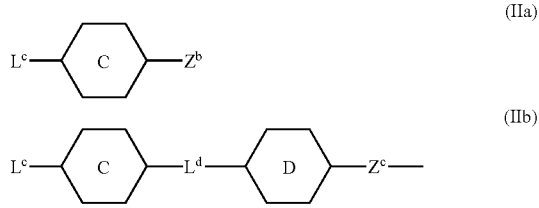

Preferred among these groups are fluorine atom, trifluoromethoxy group, difluoromethoxy group, C$_{1-7}$ straight-chain alkyl group, C$_{1-3}$ straight-chain alkoxyl group, C$_{4-7}$ straight-chain 3-alkenyl group, C$_{3-7}$ straight-chain alkenyloxy group, and group represented by the foregoing general formula (IIa) or (IIb). Particularly preferred among these groups are fluorine atom, trifluoromethoxy group, methyl group, ethyl group, propyl group, butyl group, pentyl group, methoxy group, ethoxy group, 3-butenyl group, trans-3-pentenyl group, allyloxy group, crotyloxy group, and group represented by the general formula (IIa).

In the general formula (IIa) or (IIb), L$^c$ and L$^d$ each independently represent —CH$_2$CH$_2$—, —CH$_2$CH$_2$CH$_2$CH$_2$—, —CH=CH—, —CH=CHCH$_2$CH$_2$—, —CH$_2$CH$_2$CH=CH—, —CH(CH$_3$)CH$_2$—, —CH$_2$CH(CH$_3$)—, —CF=CF—, —CF$_2$O—, —OCF$_2$—, —COO—, —OCO—, —C≡C— or single bond. Preferred among these groups are —CH$_2$CH$_2$—, —CF=CF—, —CF$_2$O—, —OCF$_2$— or single bond. Particularly preferred among these groups are —CH$_2$CH$_2$— or single bond. Further, if L$^c$ and L$^d$ are present at the same time, or if L$^c$ and the foregoing L$^a$ are present at the same time, at least one of them is preferably a single bond.

Rings C and D each independently represent a trans-1,4-cyclohexylene group, 1,4-phenylene group which may be substituted by one or more fluorine atoms, pyridine-2,5-diyl group, pyrimidine-2,5-diyl group, pyrazine-2,5-diyl group, pyridazine-3,6-diyl group, trans-1,3-dioxane-2,5-diyl group, trans-decahydronaphthalene-2,6-diyl group or tetrahydronaphthalene-2,6-diyl group. Preferred among these groups are trans-1,4-cyclohexylene group and 1,4-phenylene group which may be substituted by one or more fluorine atoms. Particularly preferred among these groups are 1,4-phenylene group, 2-fluoro-1,4-phenylene group, 3-fluoro-1,4-phenylene group, 2,3-difluoro-1,4-phenylene group, and 3,5-difluoro-1,4-phenylene group. In particular, if the liquid-crystalline compound is a p-type compound, rings C and D each are preferably a 3-fluoro-1,4-phenylene group or 3,5-difluoro-1,4-phenylene group.

Z$^b$ and Z$^c$ each independently represent a fluorine atom, chlorine atom, bromine atom, iodine atom, hydrogen atom, cyano group, —SCN, —OCN, —R', —OR', —OCOR' or —COOR', wherein R' represents a C$_{1-20}$ alkyl or alkoxy group or C$_{2-20}$ alkenyl or alkenyloxy group, and these groups may be susbstituted by a C$_{1-10}$ alkoxyl, acyl, acyloxy or alkoxycarbonyl group and one or more hydrogen atoms contained in these groups may be substituted by one or more fluorine atoms, and in the case of forming an asymmetric carbon by the substitution or branching, it may form an optically active form or racemic form.

Preferably, Z$^b$ and Z$^c$ each represent a fluorine atom, chlorine atom, hydrogen atom, trifluoromethoxy group, C$_{1-7}$ alkoxyl group or C$_{1-20}$ alkyl, alkoxyl, alkenyl or alkenyloxy group which may be substituted by from 1 to 20 fluorine atoms, cyanato group or cyano group. Preferred among these groups are fluorine atom, trifluoromethoxy group, difluoromethoxy group, C$_{1-7}$ straight-chain alkyl group, C$_{1-3}$ straight-chain alkoxyl group, C$_{4-7}$ straight-chain 3-alkenyl group, C$_{3-7}$ straight-chain alkenyloxy group or cyano group. Particularly preferred among these groups are fluorine atom, trifluoromethoxy group, methyl group, ethyl group, propyl group, butyl group, pentyl group, methoxy group, ethoxy group, 3-butenyl group, trans-3-pentenyl group, allyloxy group, crotyloxy group, and cyano group.

There are the following provisions:

(1) If Z$^a$ represents the group represented by the general formula (IIa), b is 0, if Z$^a$ represents the group represented by the general formula (IIb), a is 0, and if Z$^a$ represents a fluorine atom, chlorine atom, trifluoromethoxy group, C$_{1-7}$ alkoxyl group or C$_{1-20}$ alkyl, alkoxyl, alkenyl or alkenyloxy group which may be substituted by from 1 to 7 fluorine atoms, a is 1;

(2) If Z$^a$ represents the group represented by the general formula (IIa), ring C represents a 1,4-phenylene group which may be substituted by fluorine atom and Z$^b$ represents a fluorine atom, chlorine atom, trifluoromethoxy group or an alkyl or alkoxyl group which may be substituted by fluorine atom, L$^c$ represents —CH$_2$CH$_2$CH$_2$CH$_2$—, —CH=CH—, —CH=CHCH$_2$CH$_2$—, —CH$_2$CH$_2$CH=CH—, —CH(CH$_3$)CH$_2$—, —CH$_2$CH(CH$_3$)—, —CF=CF—, —CF$_2$O— or —OCF$_2$— and/or at least one of X$^1$ to X$^6$ represents a fluorine atom;

(3) If Z$^a$ represents an alkyl or alkoxyl group, at least one of X$^1$ to X$^6$ represents a fluorine atom and/or L$^c$ represents —CH$_2$CH$_2$CH$_2$CH$_2$—, —CF=CF—, —CF$_2$O— or —OCF$_2$—;

(4) if Z$^a$ represents a fluorine or chlorine atom, L$^a$ represents a single bond; and if ring A represents a 1,4-phenylene group which may be substituted by fluorine atom, b represents 0, or b represents 1 and L$^b$ represents a single bond; and (5) If a and b each represent 0, X$^1$ represents a fluorine atom and X$^2$ to X$^6$ each represent a hydrogen atom; and if L$^c$ represents a single bond, Z$^b$ represents fluorine atom, chlorine atom, hydrogen atom, trifluoromethoxy group, alkenyl group, alkenyloxy group, cyanato group or cyano group.

As mentioned, there are a variety of compounds represented by the general formula (I). Preferred are those represented by the following general formulae (Ia) to (Ie) as classified by the structure of core moiety:

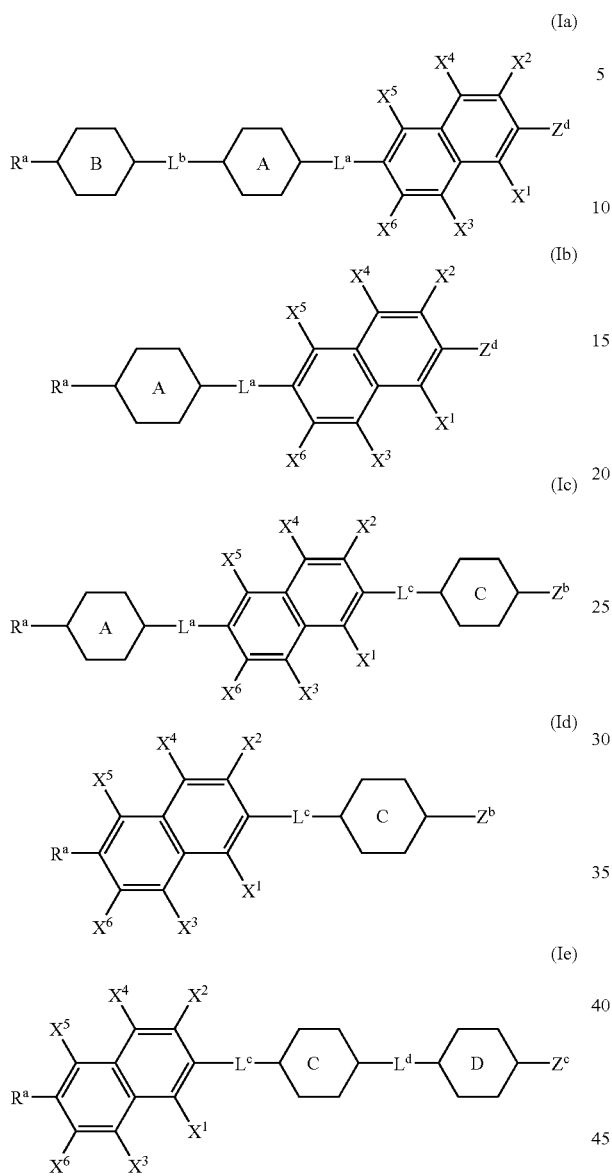

wherein $R^a$, ring A, ring B, $L^a$, $L^b$, $Z^b$, $Z^c$ and $X^1$ to $X^6$ are as defined in the general formula (I); ring C and ring D are as defined in the general formula (IIa) or (IIb); and $Z^d$ represents a fluorine atom, chlorine atom, trifluoromethoxy group, $C_{1-7}$ alkoxyl group or $C_{1-20}$ alkyl, alkoxyl, alkenyl or alkenyloxy group which may be substituted by from 1 to 7 fluorine atoms.

Particularly preferred among the compounds represented by the general formula (Ia) are those shown below.

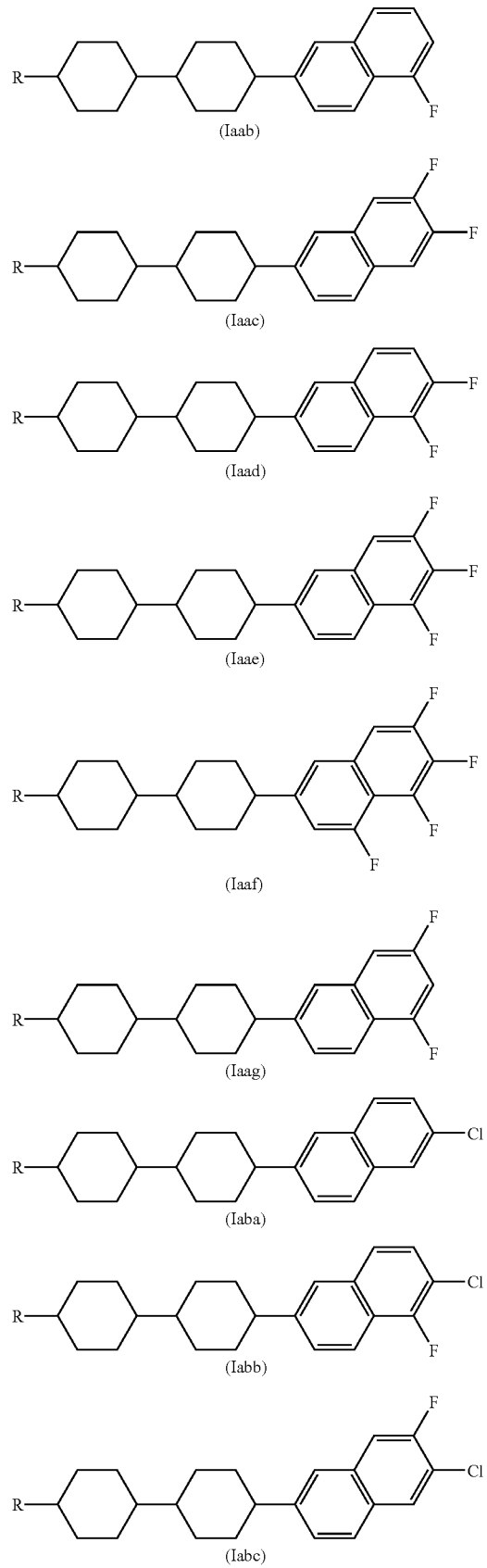

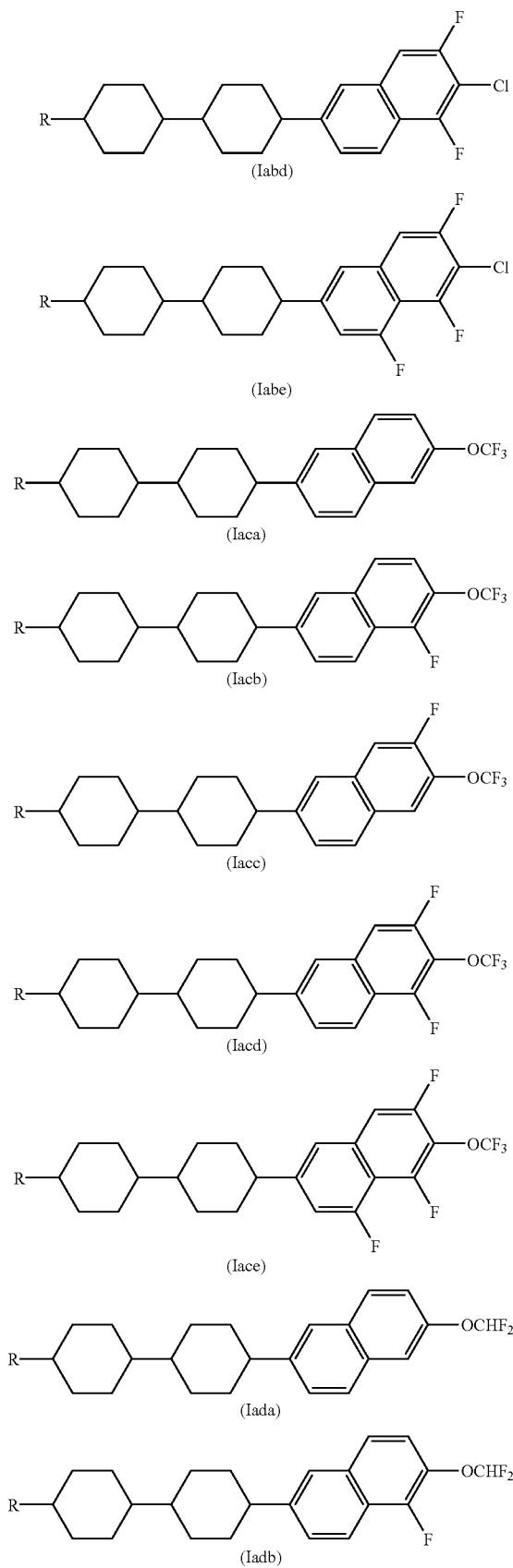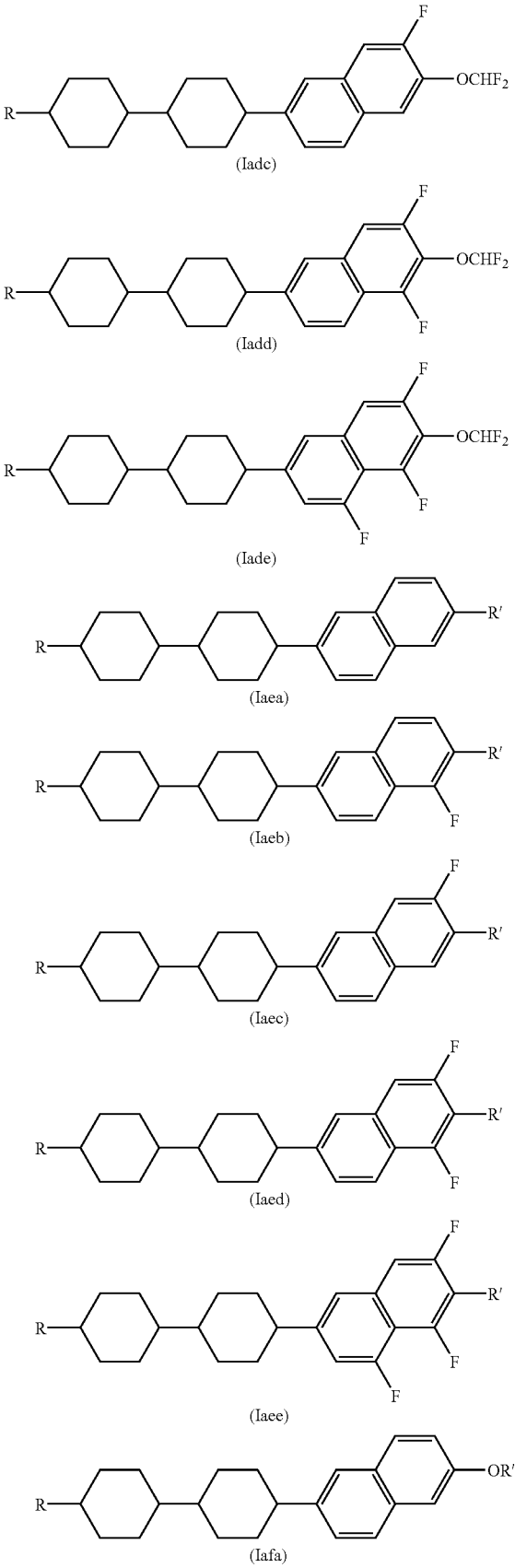

-continued (Iafb), (Iafc), (Iafd), (Iafe), (Iaga), (Iagb), (Iagc), (Iagd), (Iage)

-continued (Iagd), (Iage), (Iaha), (Iahb), (Iahc), (Iahd), (Iahe), (Iaia), (Iaib)

-continued
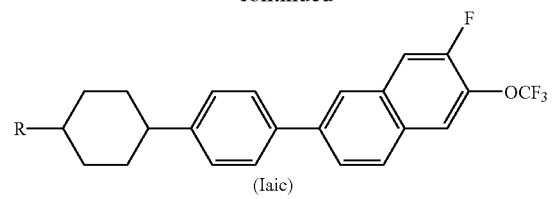
(Iaic)
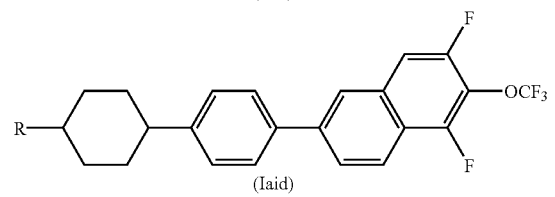
(Iaid)
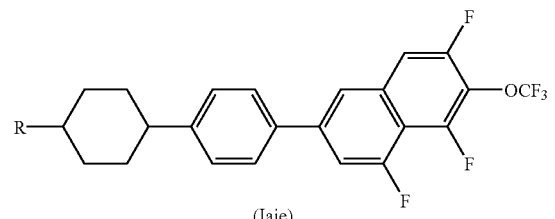
(Iaie)
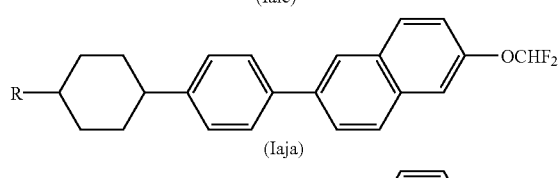
(Iaja)
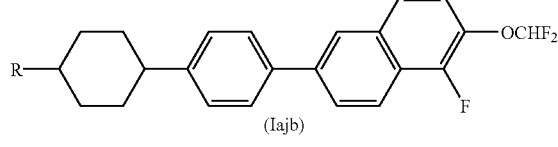
(Iajb)
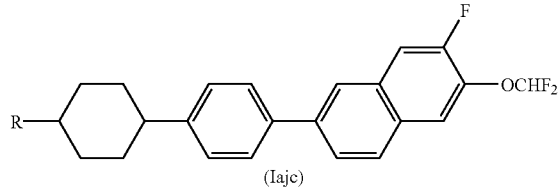
(Iajc)
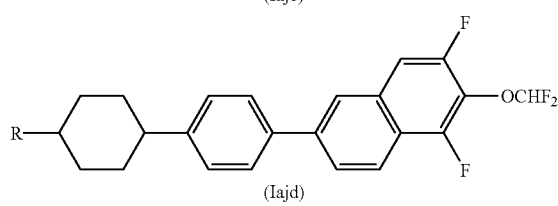
(Iajd)
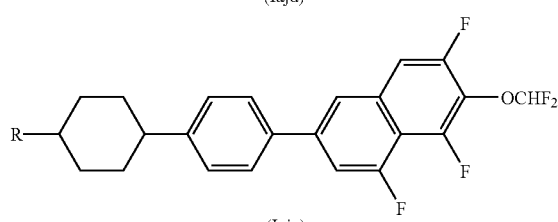
(Iaje)
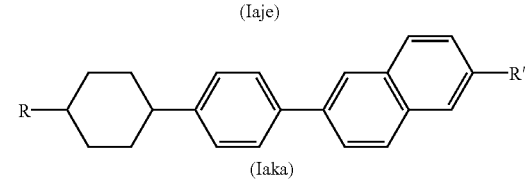
(Iaka)
-continued
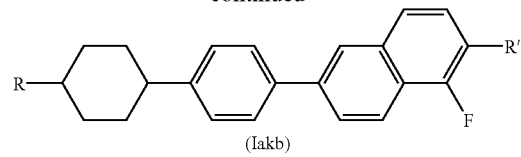
(Iakb)
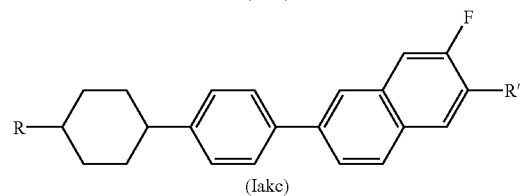
(Iakc)
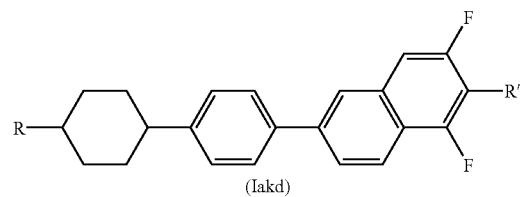
(Iakd)
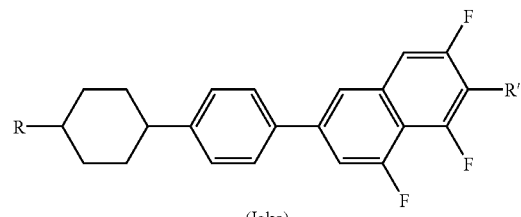
(Iake)
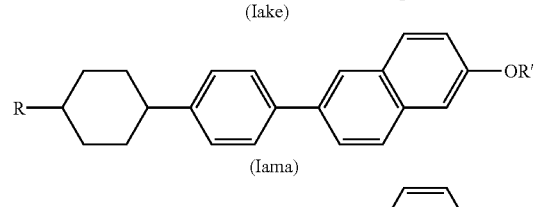
(Iama)
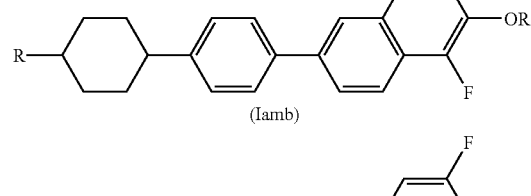
(Iamb)
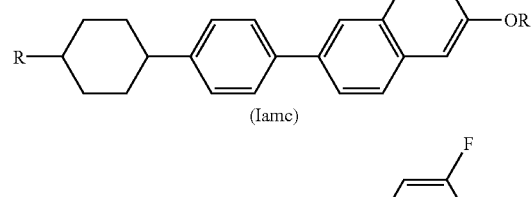
(Iamc)
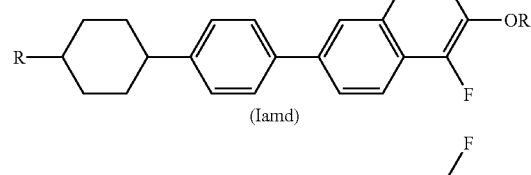
(Iamd)
(Iame)

-continued
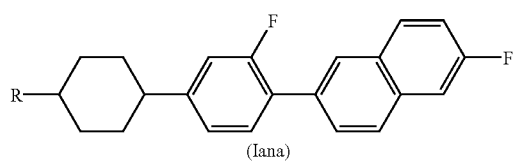
(Iana)
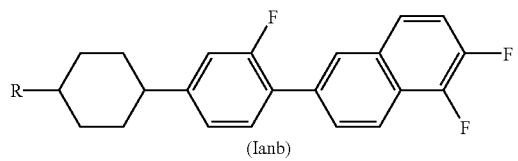
(Ianb)
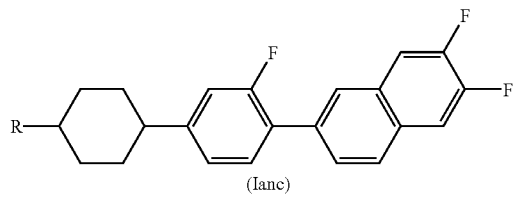
(Ianc)
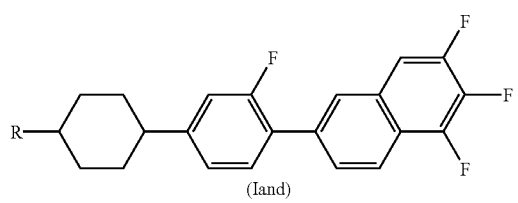
(Iand)
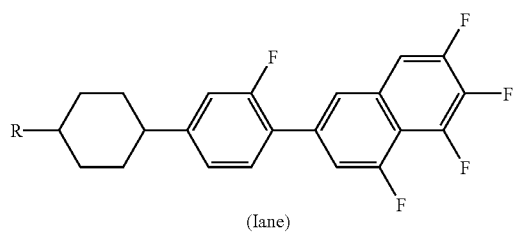
(Iane)
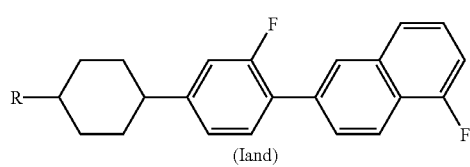
(Iand)
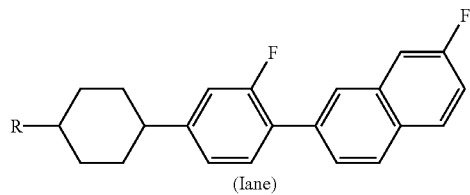
(Iane)
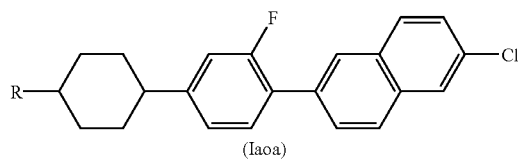
(Iaoa)
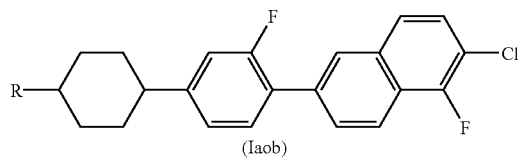
(Iaob)
-continued
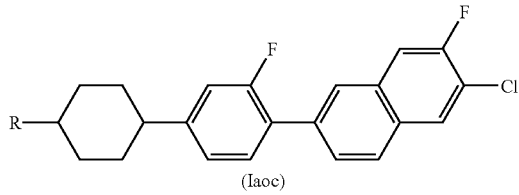
(Iaoc)
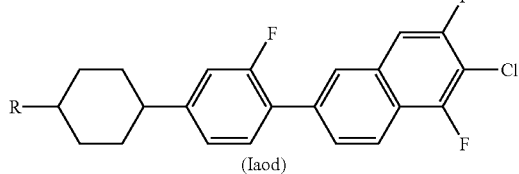
(Iaod)
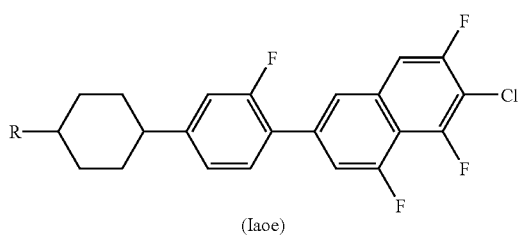
(Iaoe)
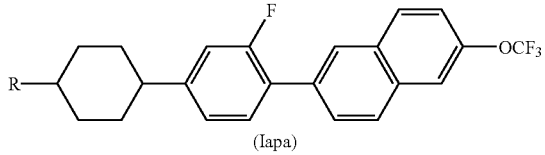
(Iapa)
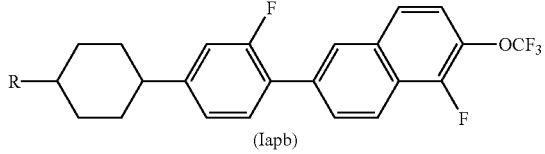
(Iapb)
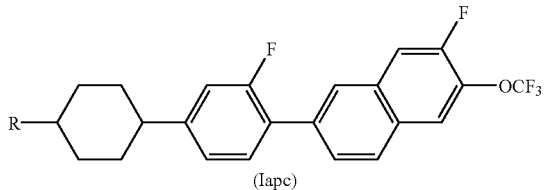
(Iapc)
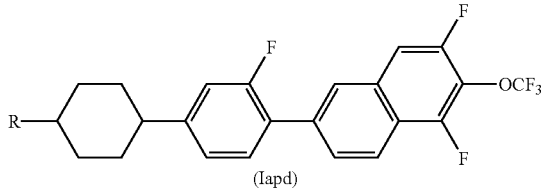
(Iapd)
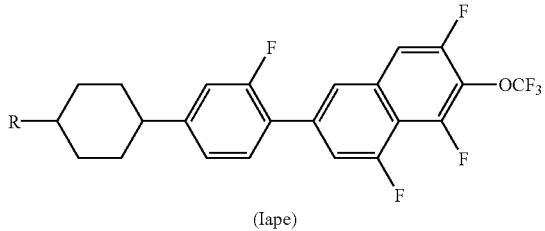
(Iape)

-continued

Structures (Iaqa), (Iaqb), (Iaqc), (Iaqd), (Iaqe), (Iara), (Iarb), (Iarc), (Iard), (Iare), (Iasa), (Iasb), (Iasc), (Iasd), (Iase), (Iata), (Iatb)

-continued
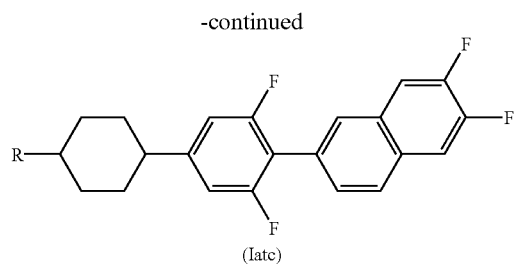
(Iatc)
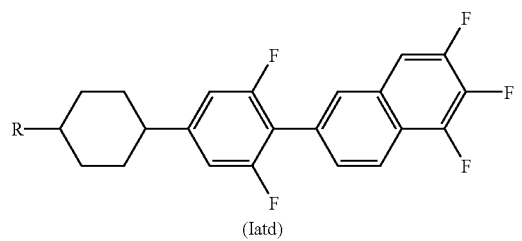
(Iatd)
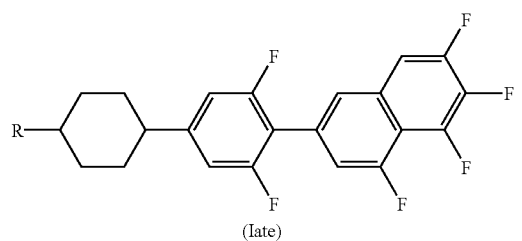
(Iate)
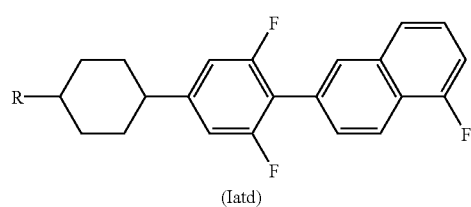
(Iatd)
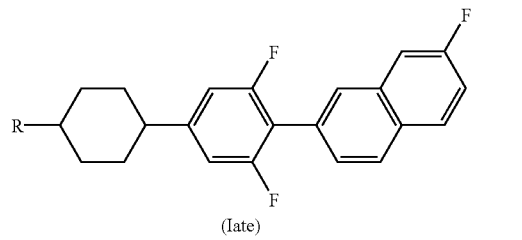
(Iate)
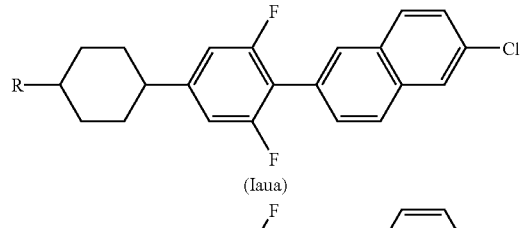
(Iaua)
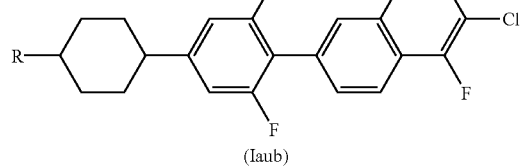
(Iaub)
-continued
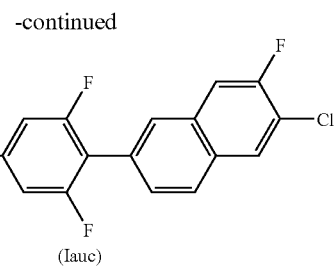
(Iauc)
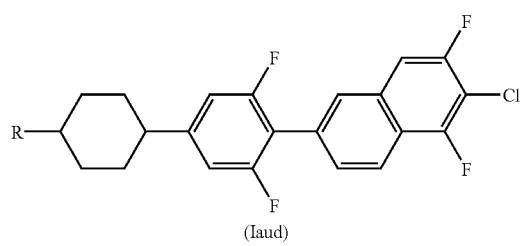
(Iaud)
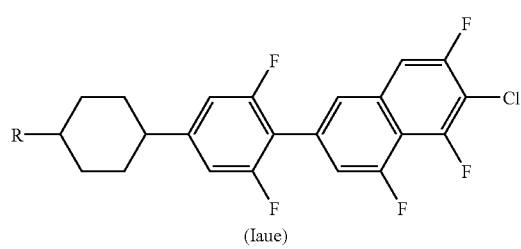
(Iaue)
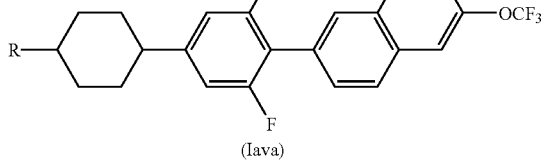
(Iava)
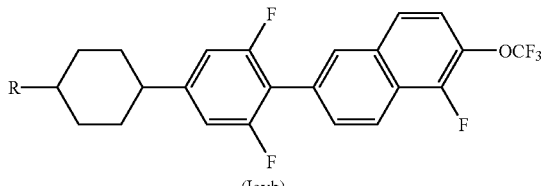
(Iavb)
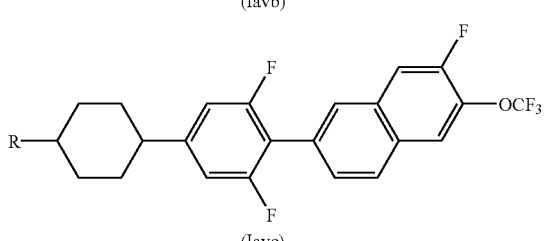
(Iavc)
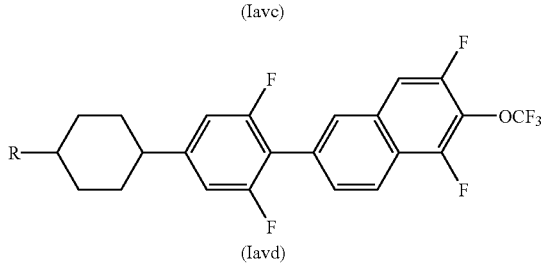
(Iavd)

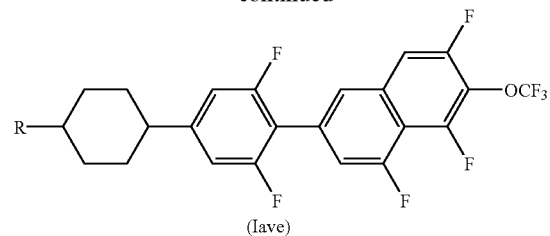
(Iave)
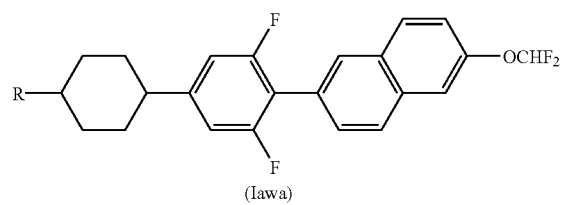
(Iawa)
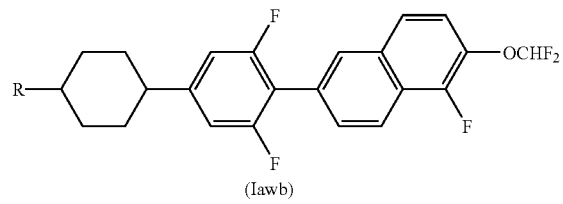
(Iawb)
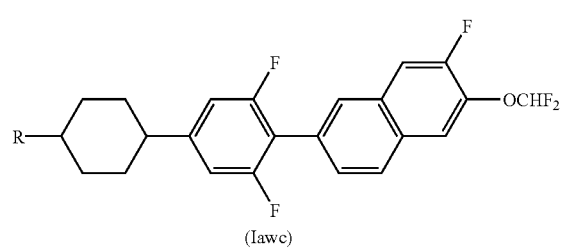
(Iawc)
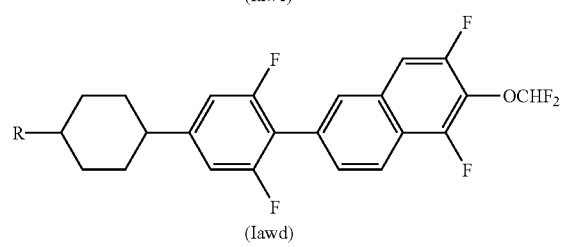
(Iawd)
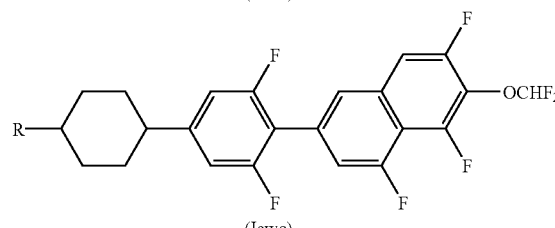
(Iawe)
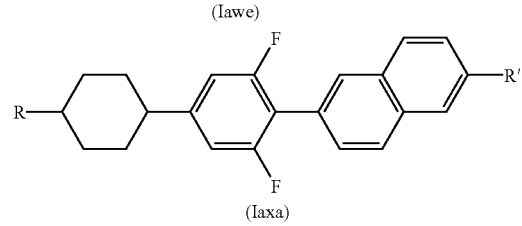
(Iaxa)
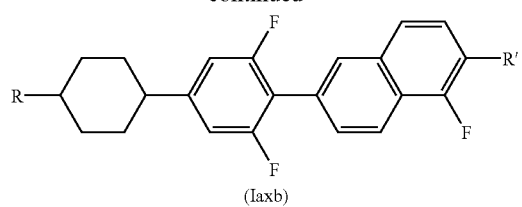
(Iaxb)
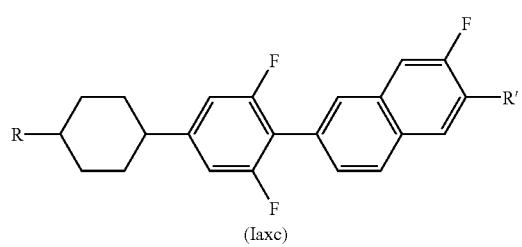
(Iaxc)
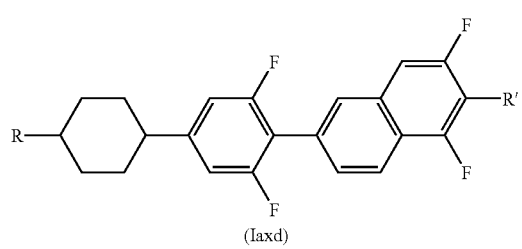
(Iaxd)
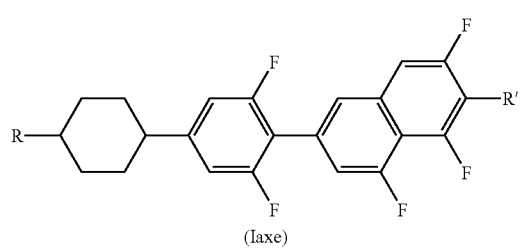
(Iaxe)
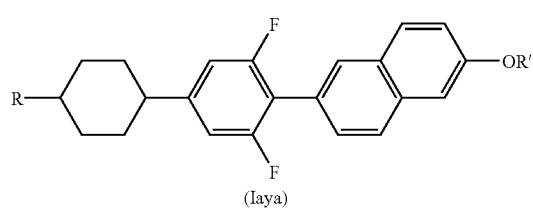
(Iaya)
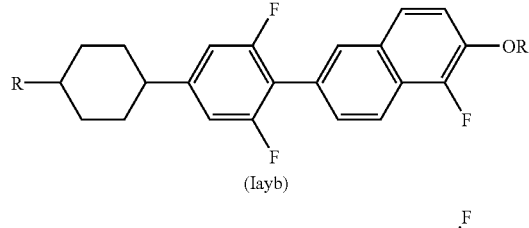
(Iayb)
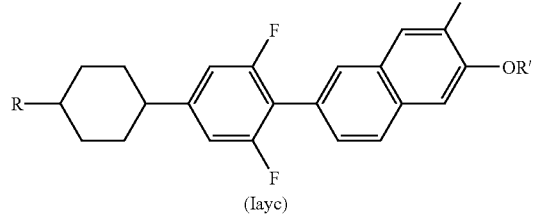
(Iayc)

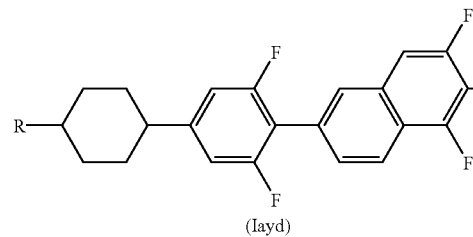
(Iayd)
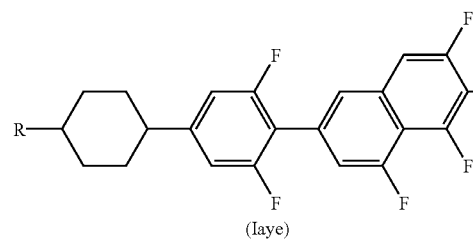
(Iaye)
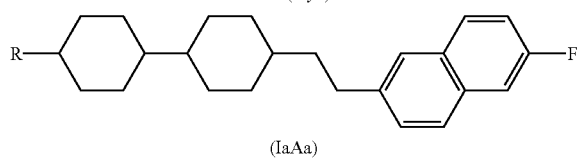
(IaAa)
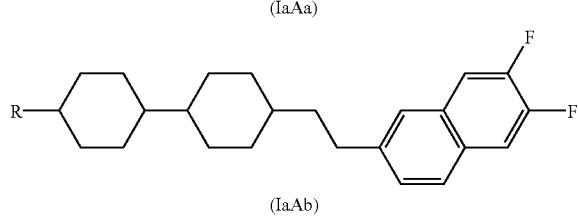
(IaAb)
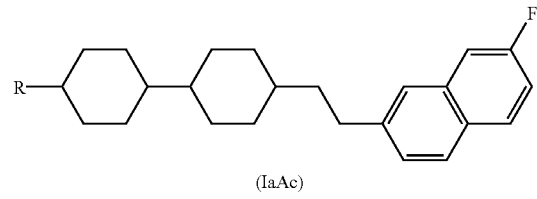
(IaAc)
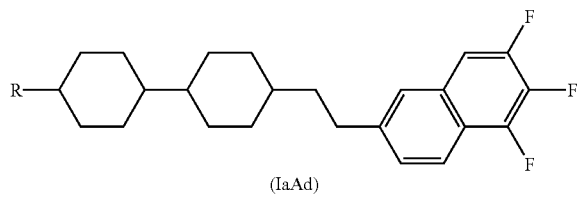
(IaAd)
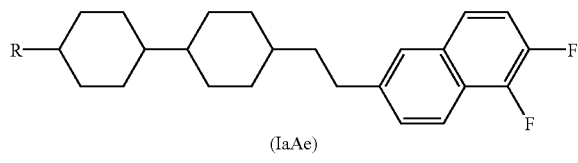
(IaAe)
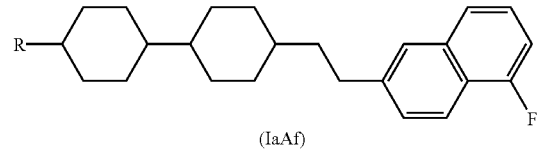
(IaAf)
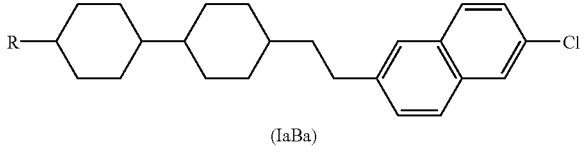
(IaBa)
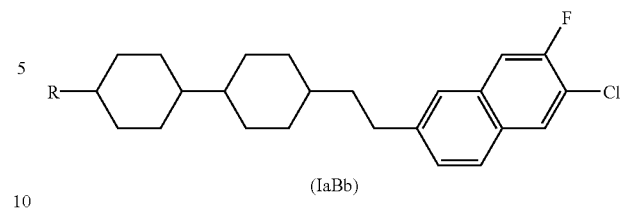
(IaBb)
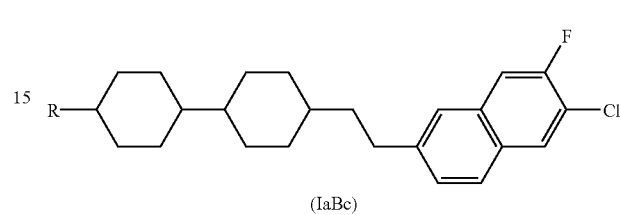
(IaBc)
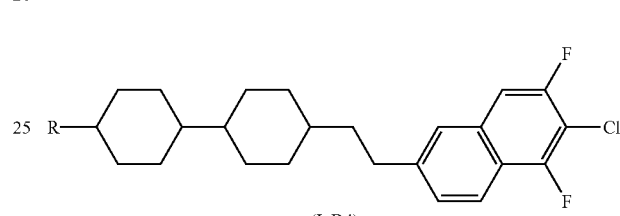
(IaBd)
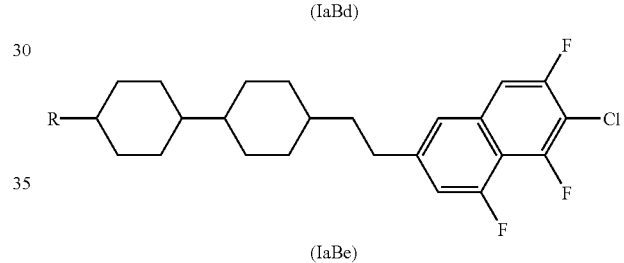
(IaBe)
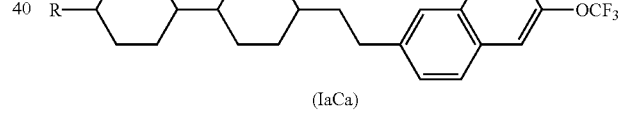
(IaCa)
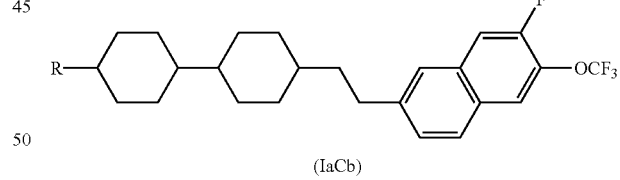
(IaCb)
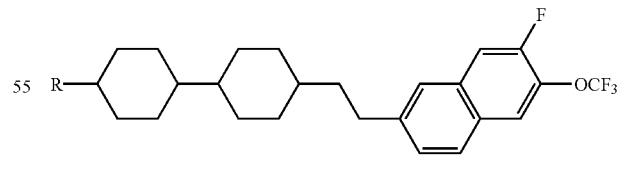
(IaCc)
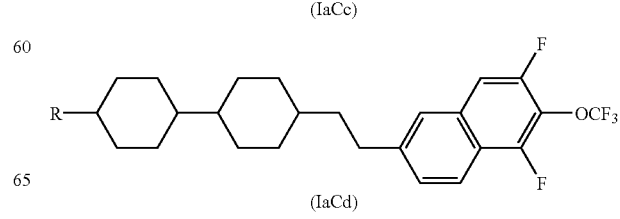
(IaCd)

-continued
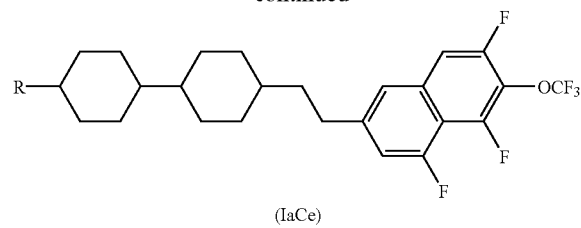
(IaCe)
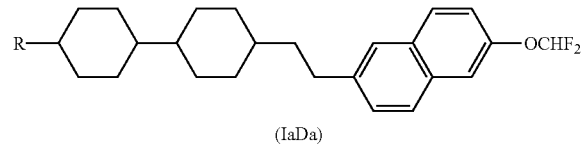
(IaDa)
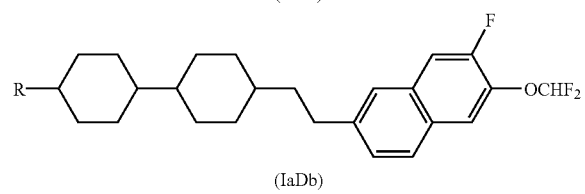
(IaDb)
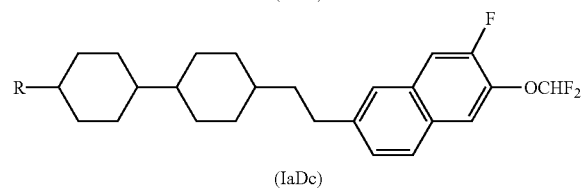
(IaDc)
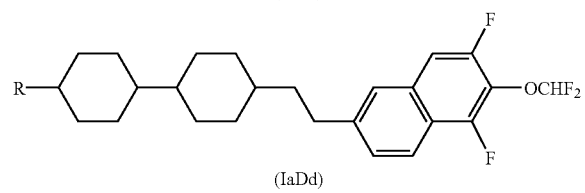
(IaDd)
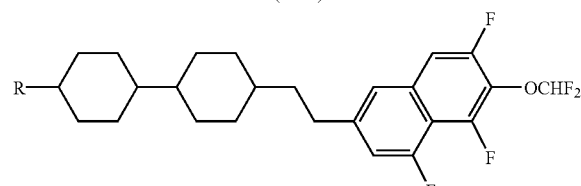
(IaDe)
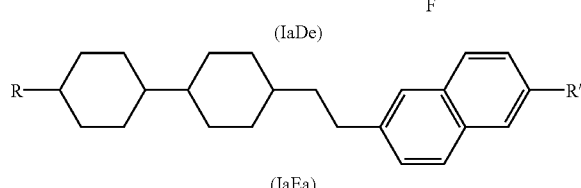
(IaEa)
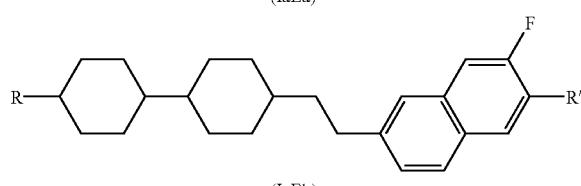
(IaEb)
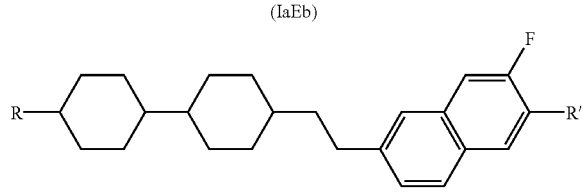
(IaEc)
-continued
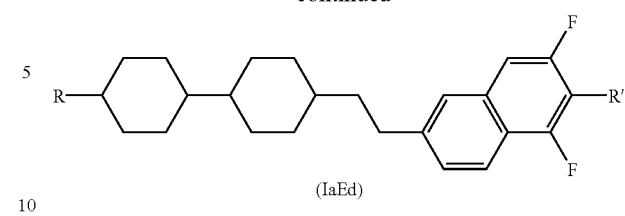
(IaEd)
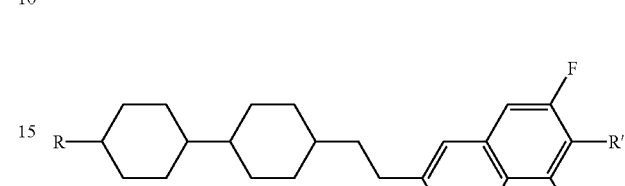
(IaEe)
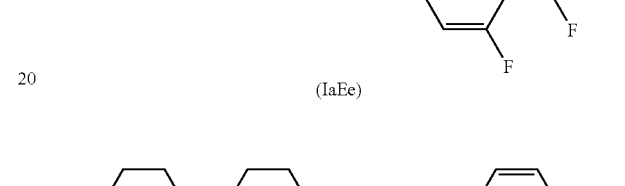
(IaFa)
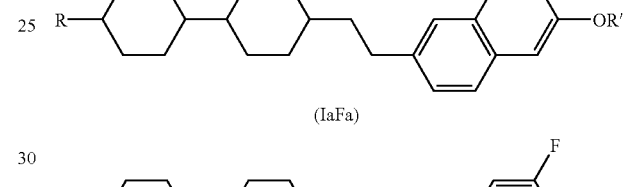
(IaFb)
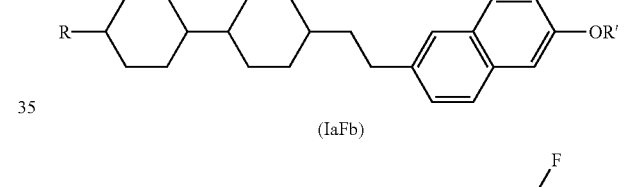
(IaFc)
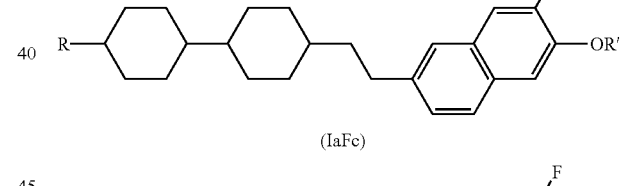
(IaFd)
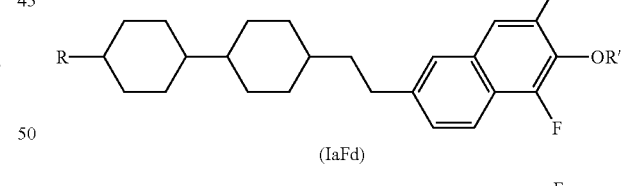
(IaFe)
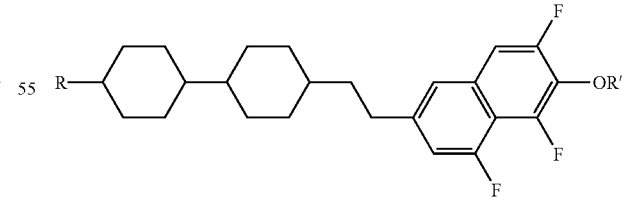
(IaGa)

-continued
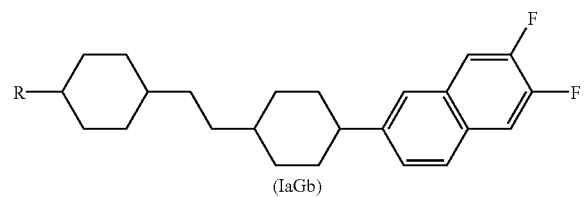
(IaGb)
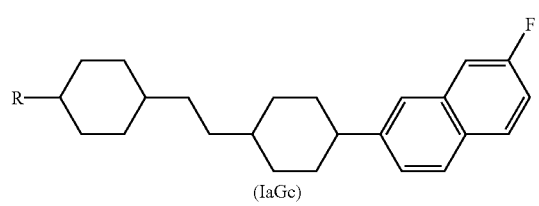
(IaGc)
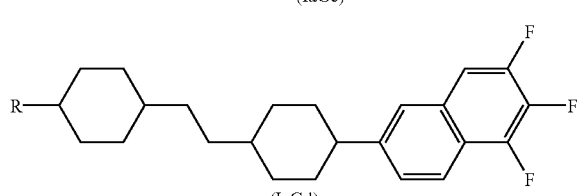
(IaGd)
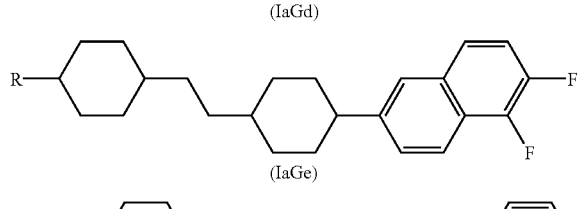
(IaGe)
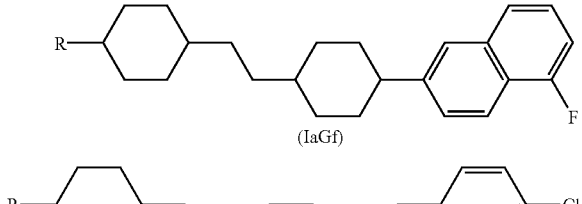
(IaGf)
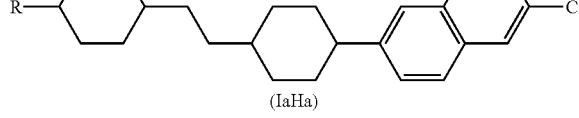
(IaHa)
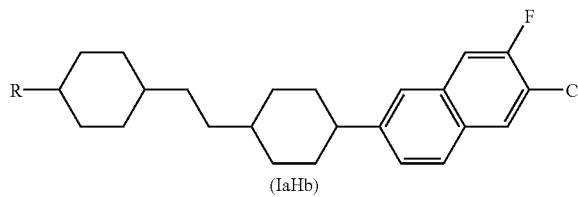
(IaHb)
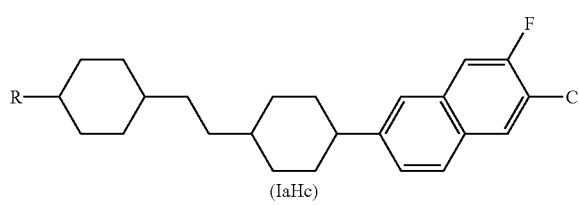
(IaHc)
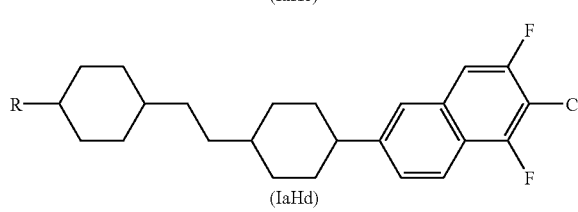
(IaHd)
-continued
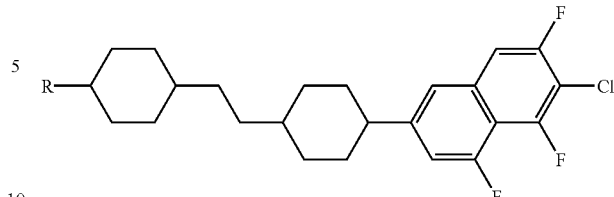
(IaHe)
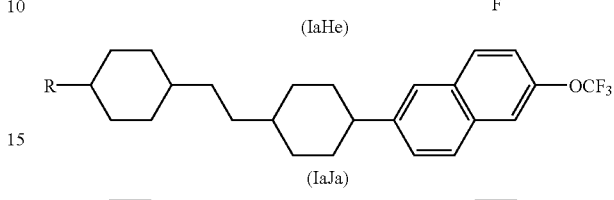
(IaJa)
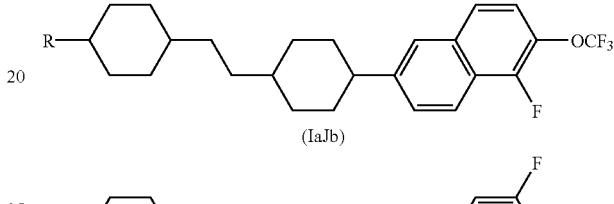
(IaJb)
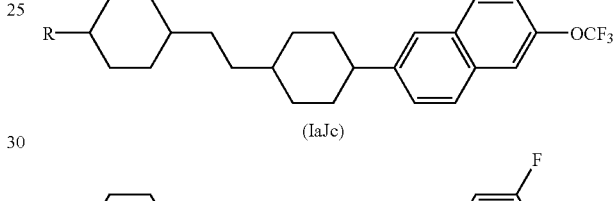
(IaJc)
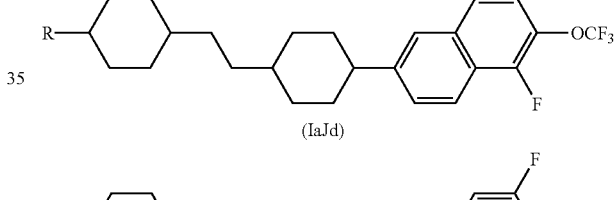
(IaJd)
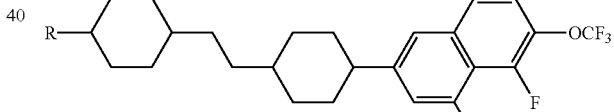
(IaJe)
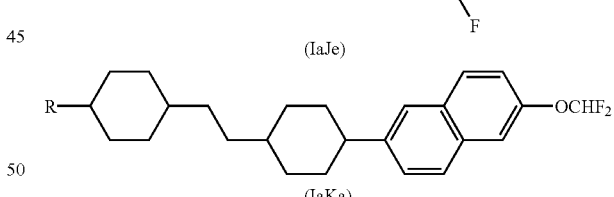
(IaKa)
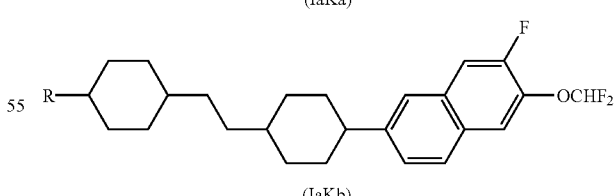
(IaKb)
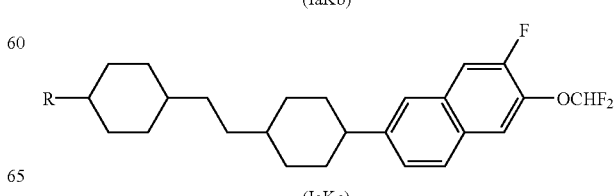
(IaKc)

-continued
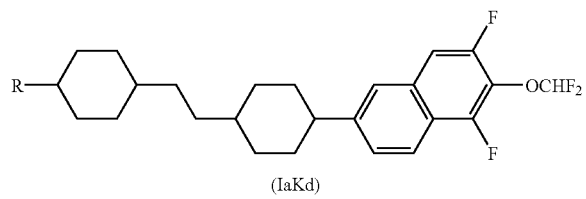
(IaKd)
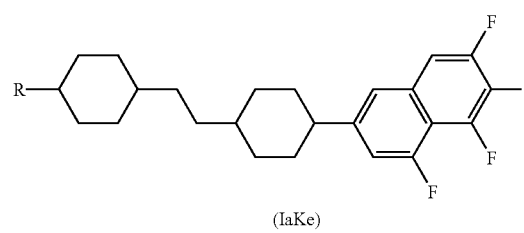
(IaKe)
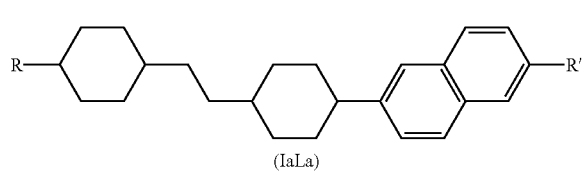
(IaLa)
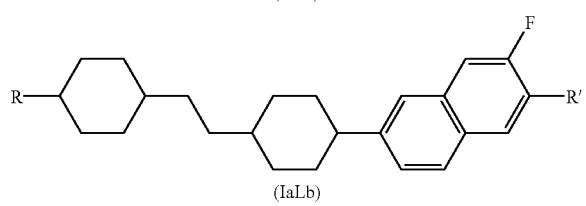
(IaLb)
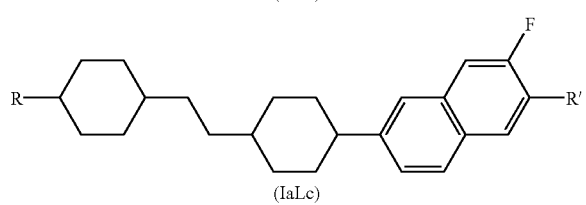
(IaLc)
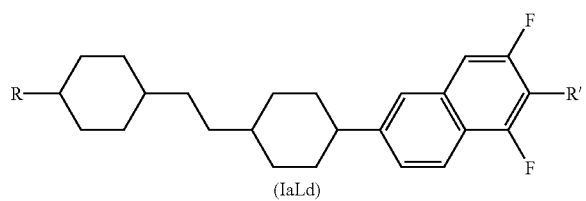
(IaLd)
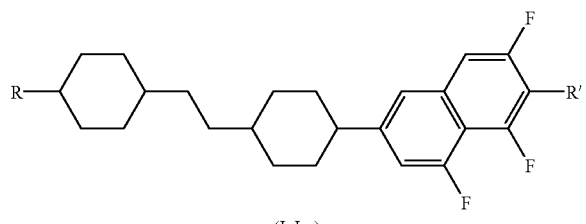
(IaLe)
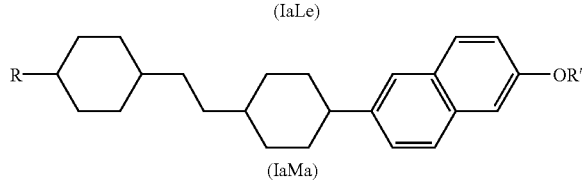
(IaMa)
-continued
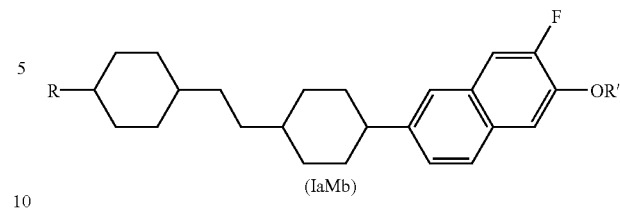
(IaMb)
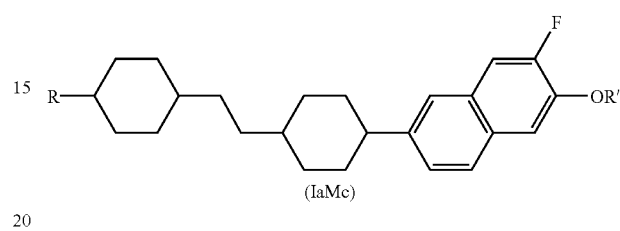
(IaMc)
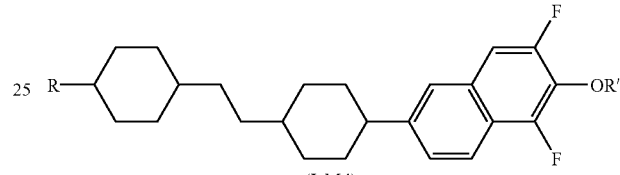
(IaMd)
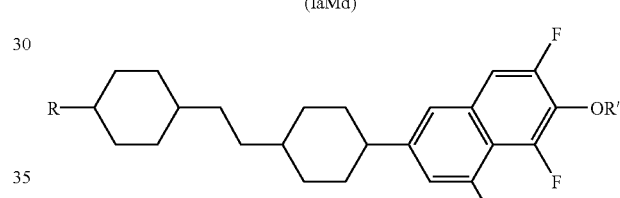
(IaMe)
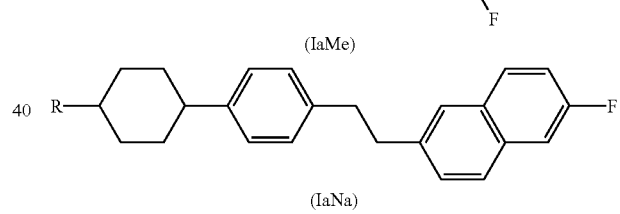
(IaNa)
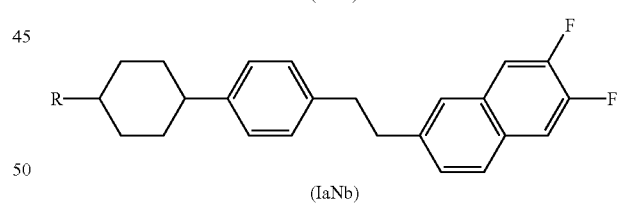
(IaNb)
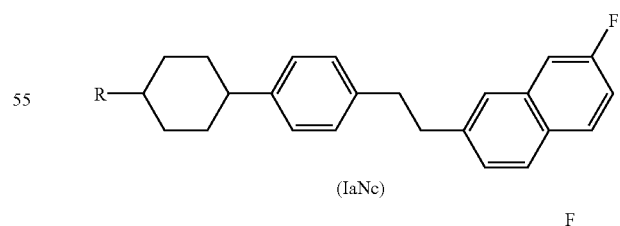
(IaNc)
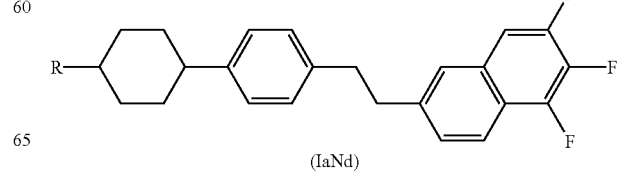
(IaNd)

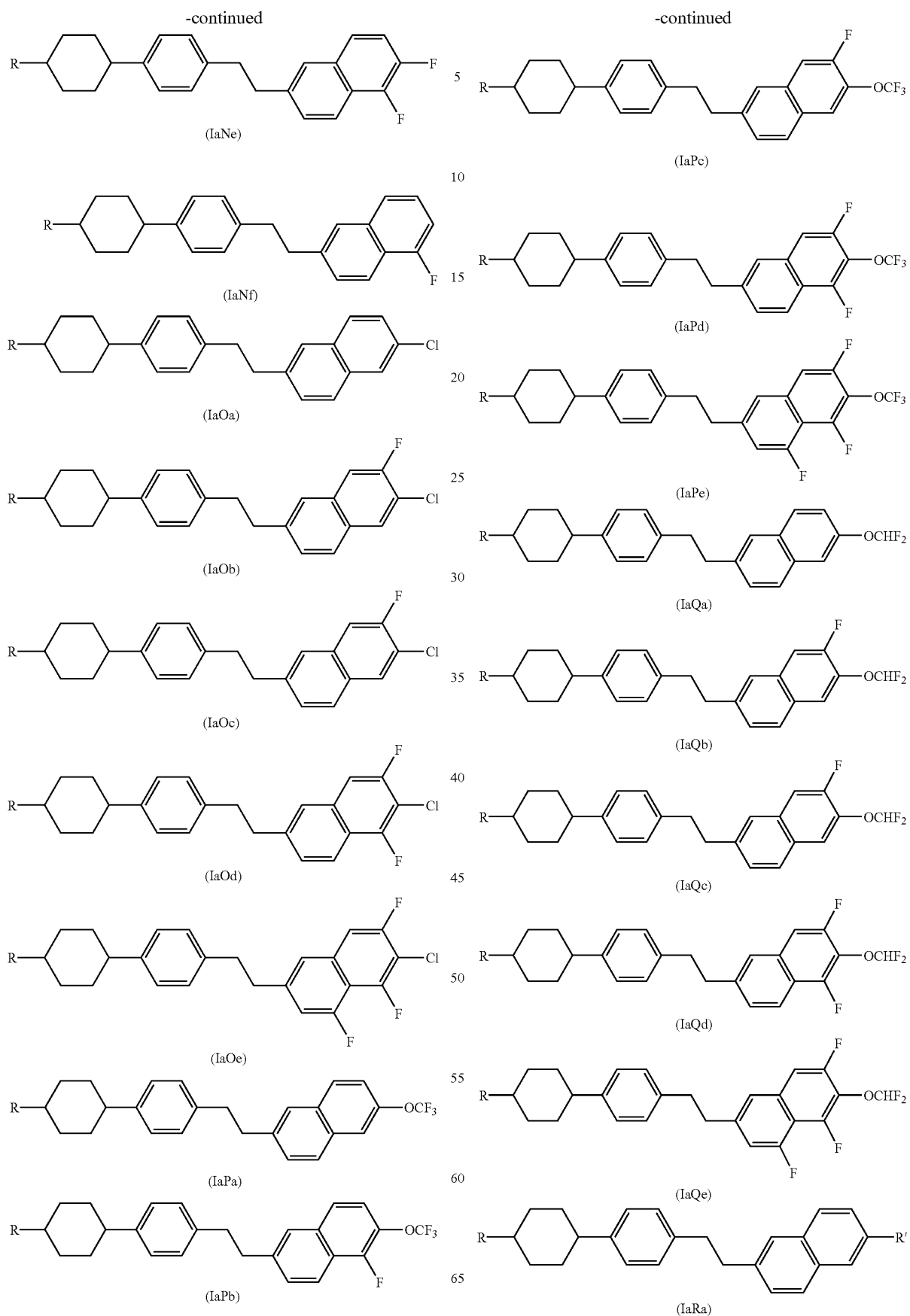

-continued (IaRb)

(IaRc)

(IaRd)

(IaRe)

(IaSa)

(IaSb)

(IaSc)

(IaSd)

-continued (IaSe)

(IaTa)

(IaTb)

(IaTc)

(IaTd)

(IaTe)

(IaTf)

(IaUa)

-continued
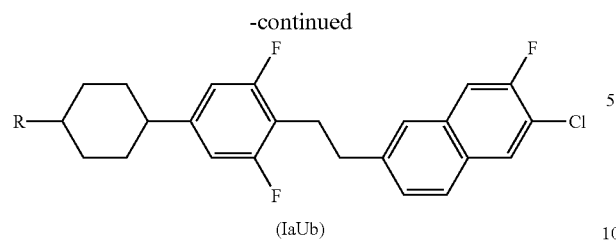
(IaUb)
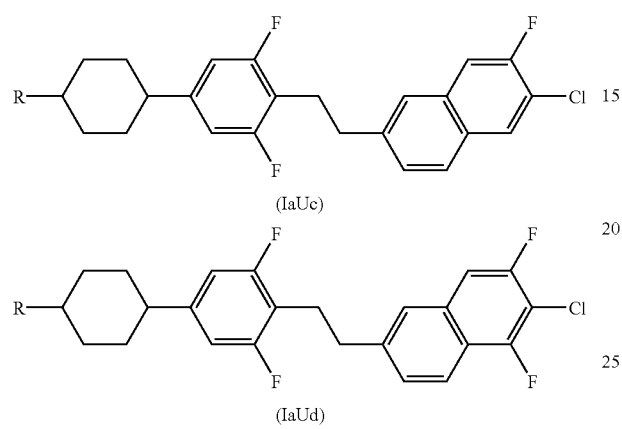
(IaUc)
(IaUd)
(IaUe)
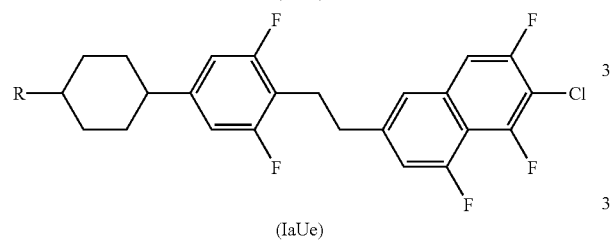
(IaVa)
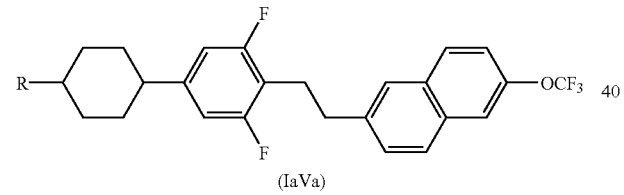
(IaVb)
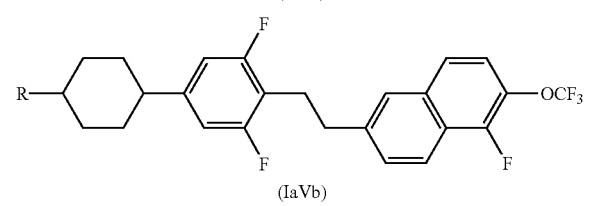
(IaVc)
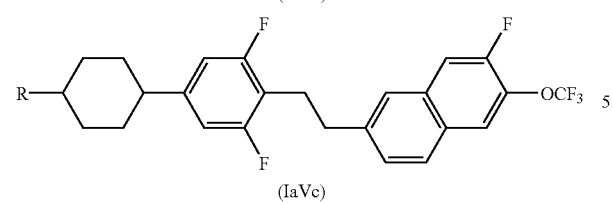
(IaVd)
-continued
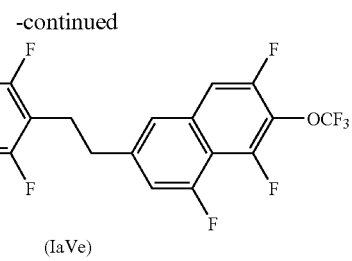
(IaVe)
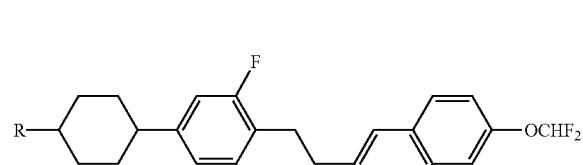
(IaWa)
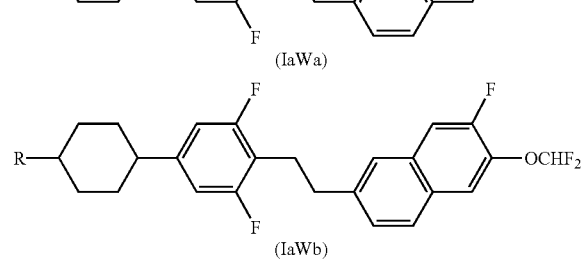
(IaWb)
(IaWc)
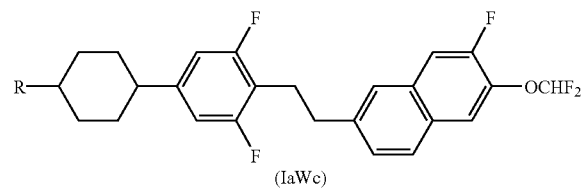
(IaWd)
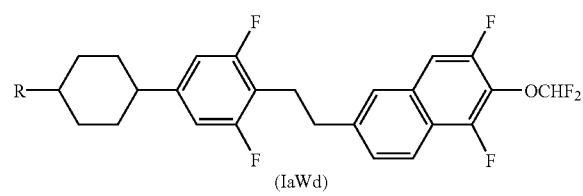
(IaWe)
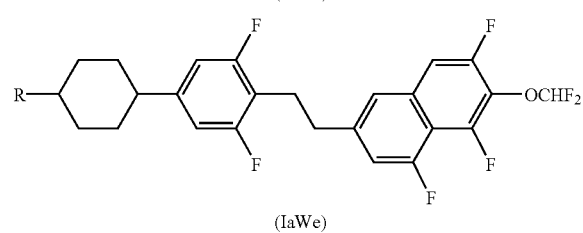
(IaXa)
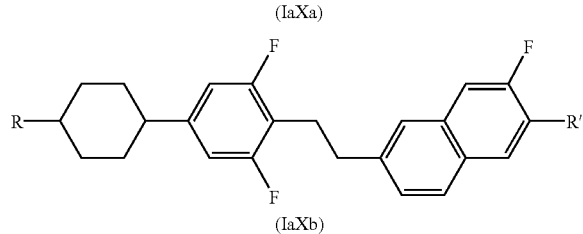
(IaXb)

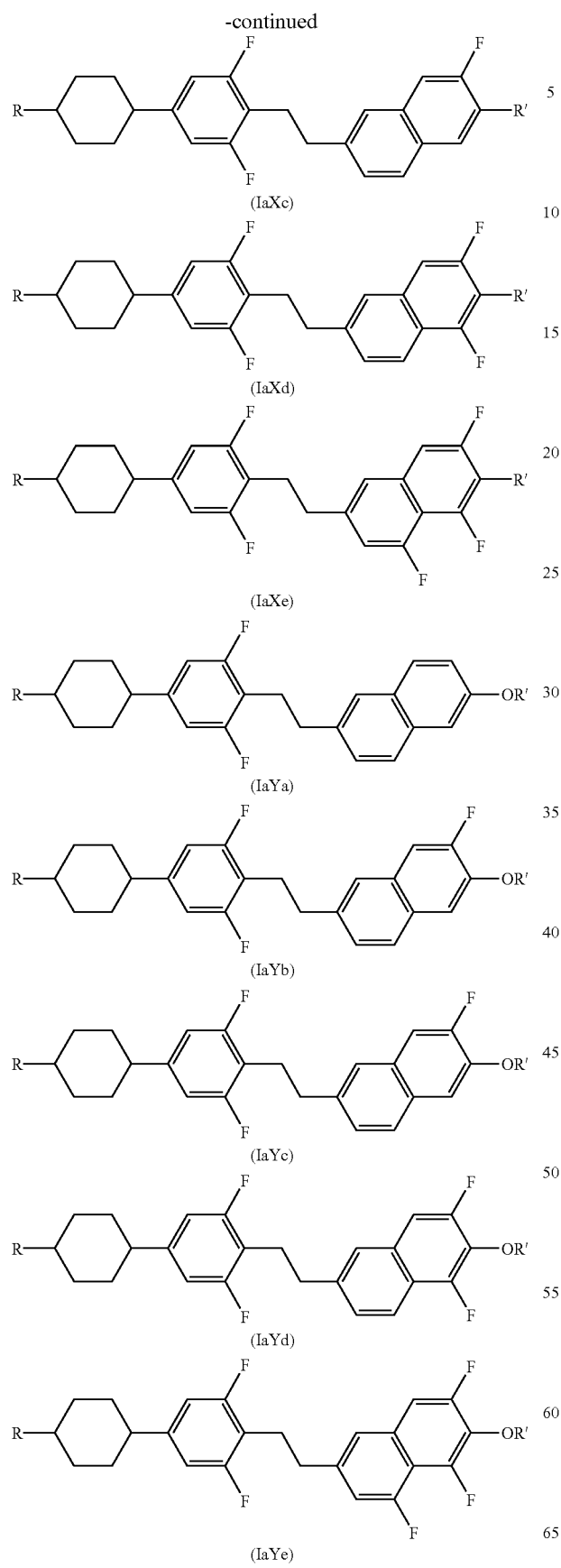
Particularly preferred among the compounds represented by the general formula (Ib) are those shown below.

-continued (Ibab), (Ibac), (Ibad), (Ibae), (Ibaf), (Ibba), (Ibbb), (Ibbc), (Ibbd)

(Ibbe), (Ibca), (Ibcb), (Ibcc), (Ibcd), (Ibce), (Ibda), (Ibdb)

-continued
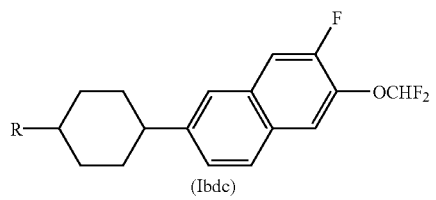
(Ibdc)
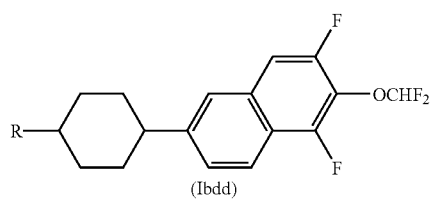
(Ibdd)
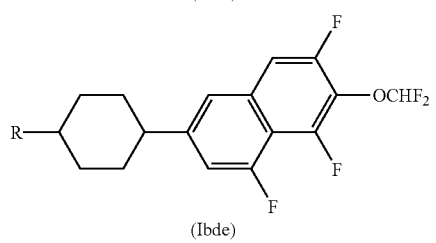
(Ibde)
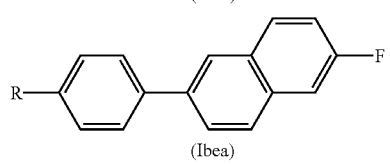
(Ibea)
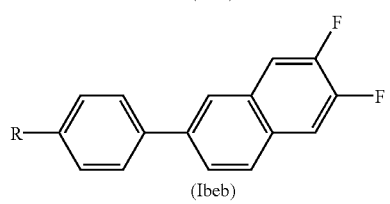
(Ibeb)
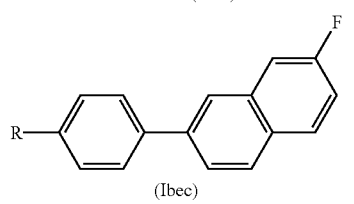
(Ibec)
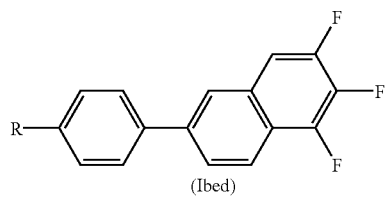
(Ibed)
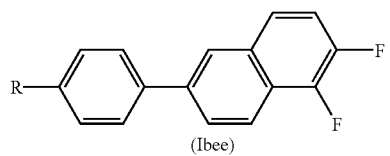
(Ibee)
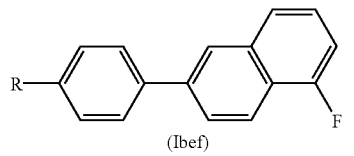
(Ibef)
-continued
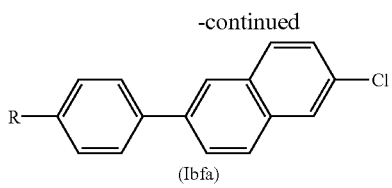
(Ibfa)
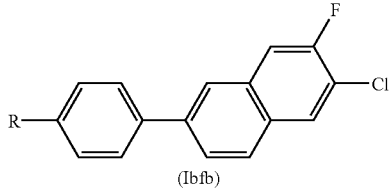
(Ibfb)
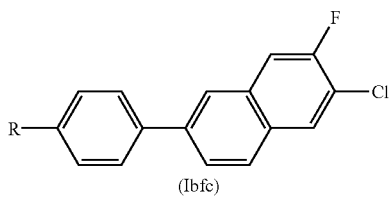
(Ibfc)
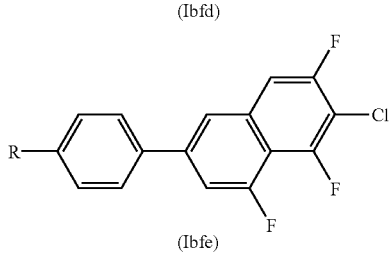
(Ibfd)
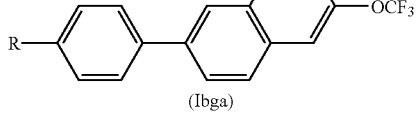
(Ibfe)
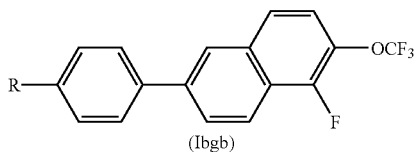
(Ibga)
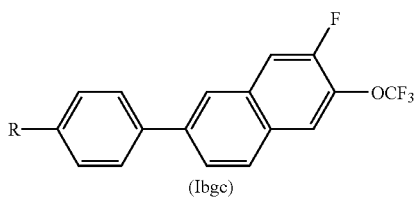
(Ibgb)
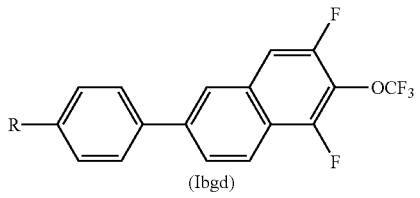
(Ibgc)
(Ibgd)

-continued
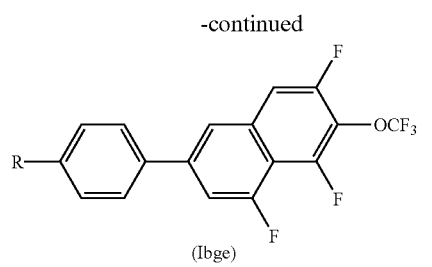
(Ibge)
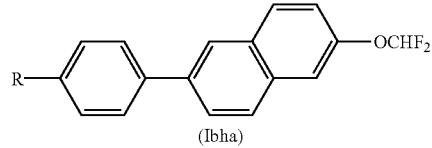
(Ibha)
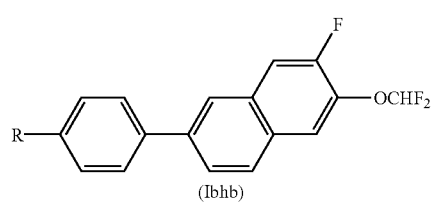
(Ibhb)
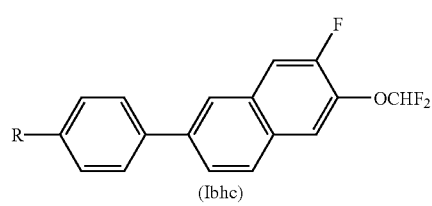
(Ibhc)
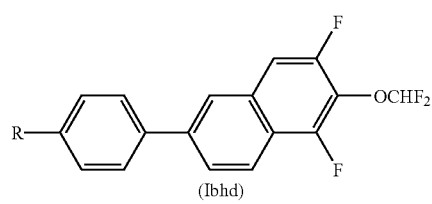
(Ibhd)
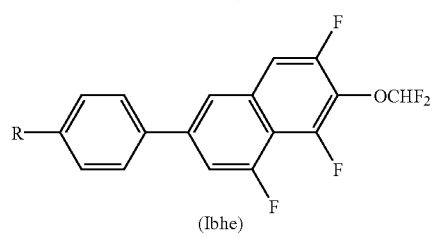
(Ibhe)
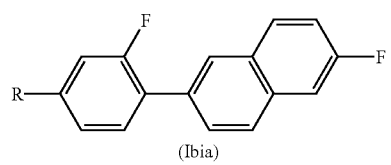
(Ibia)
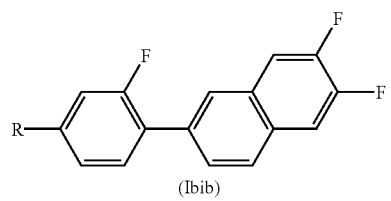
(Ibib)
-continued
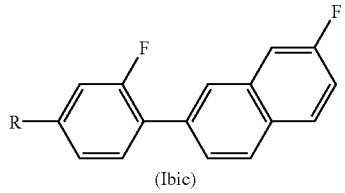
(Ibic)
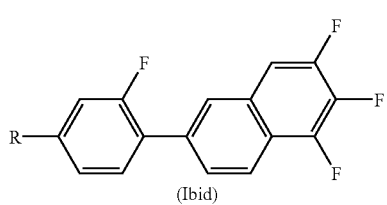
(Ibid)
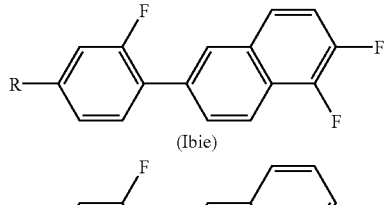
(Ibie)
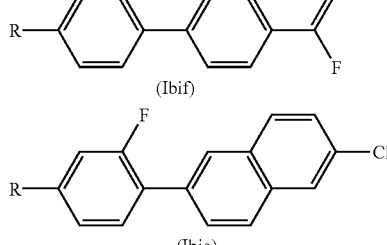
(Ibif)
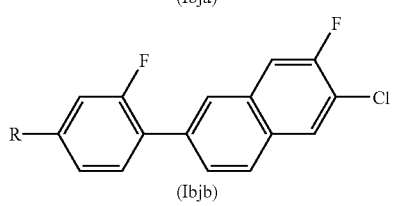
(Ibja)
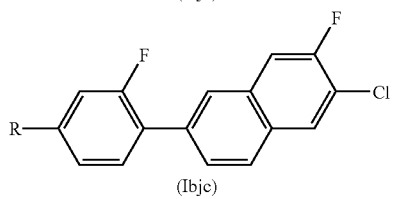
(Ibjb)
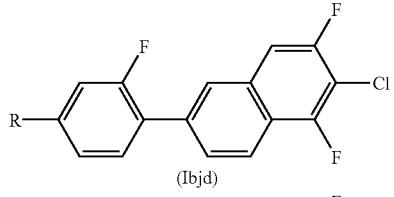
(Ibjc)
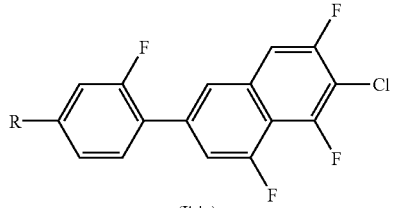
(Ibjd)
(Ibje)

-continued
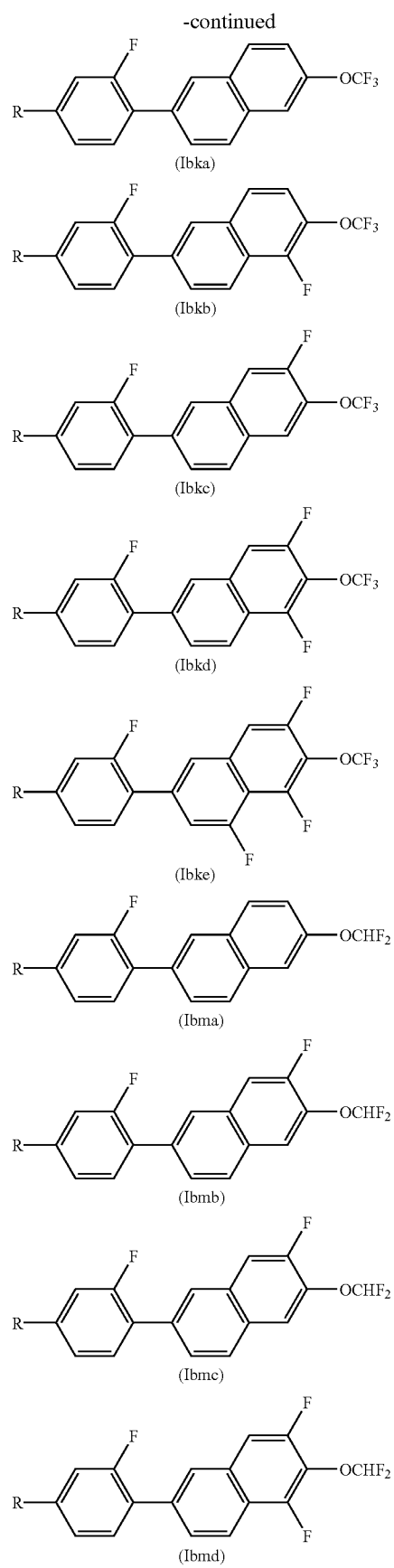
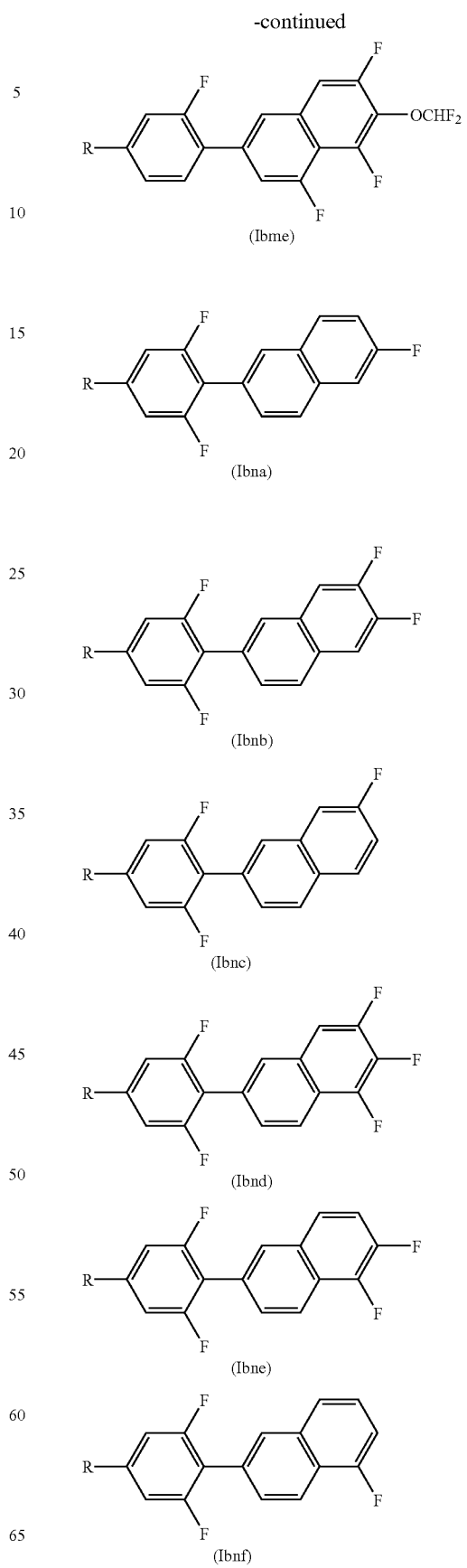

-continued
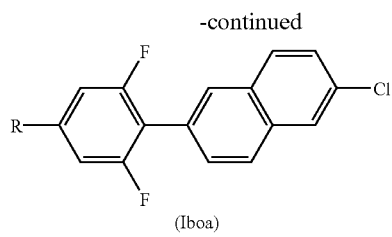
(Iboa)
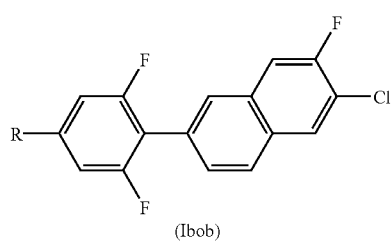
(Ibob)
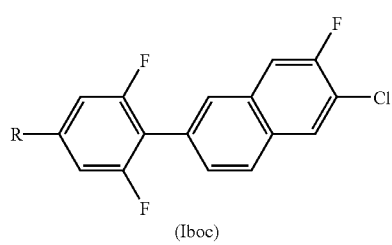
(Iboc)
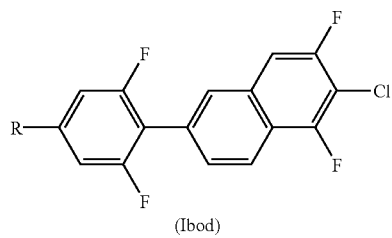
(Ibod)
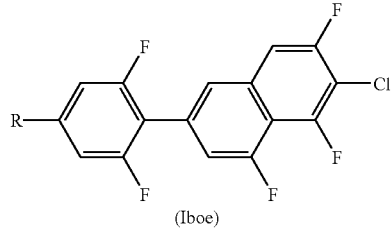
(Iboe)
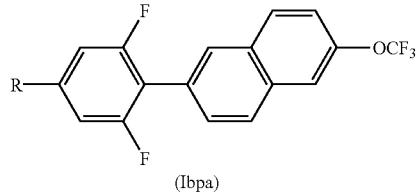
(Ibpa)
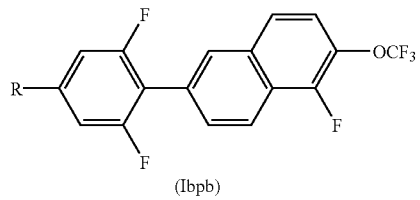
(Ibpb)
-continued
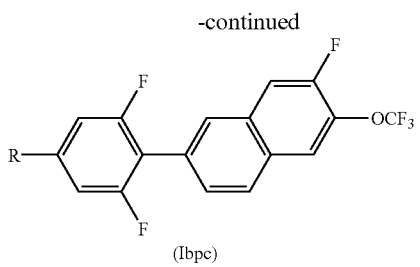
(Ibpc)
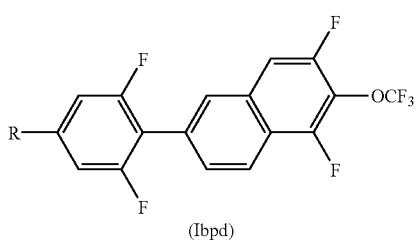
(Ibpd)
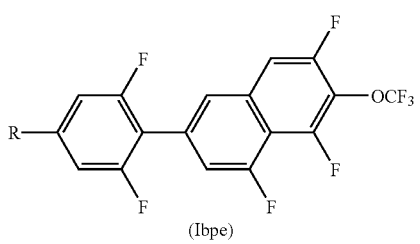
(Ibpe)
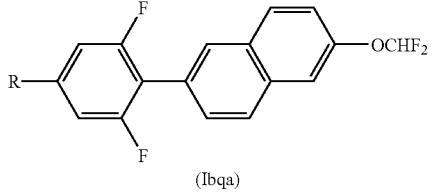
(Ibqa)
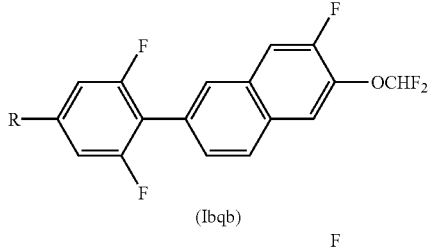
(Ibqb)
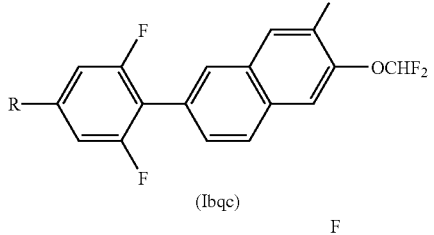
(Ibqc)
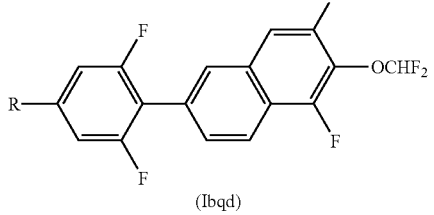
(Ibqd)

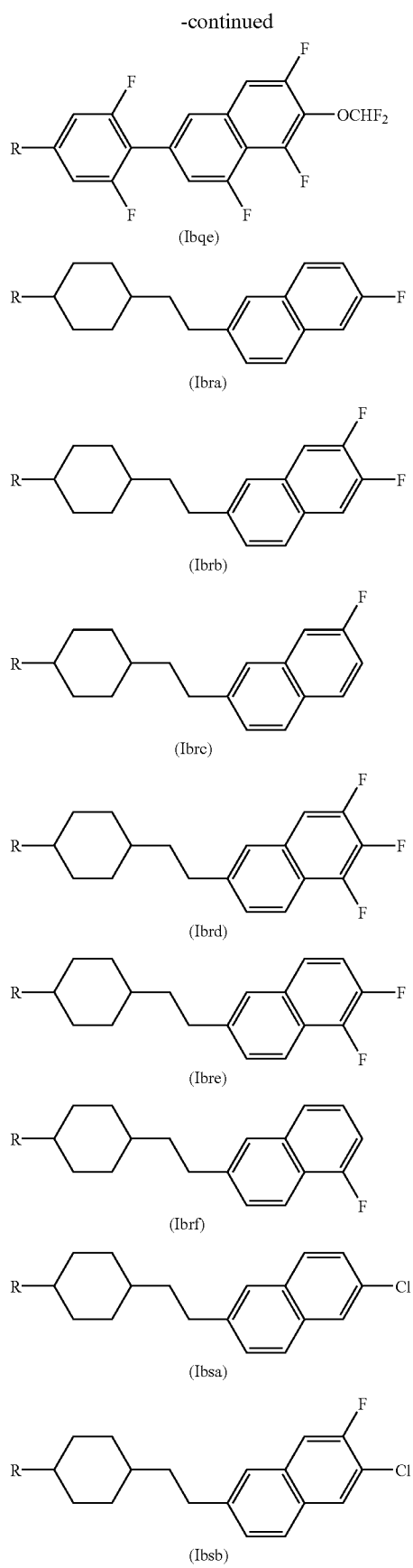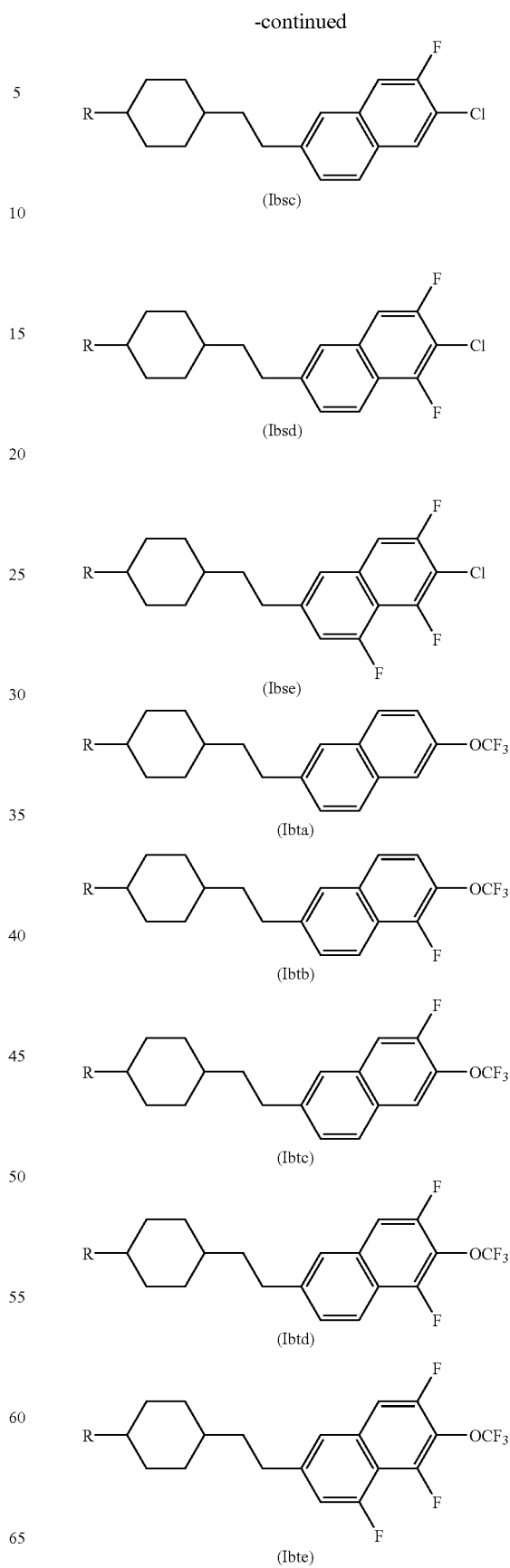

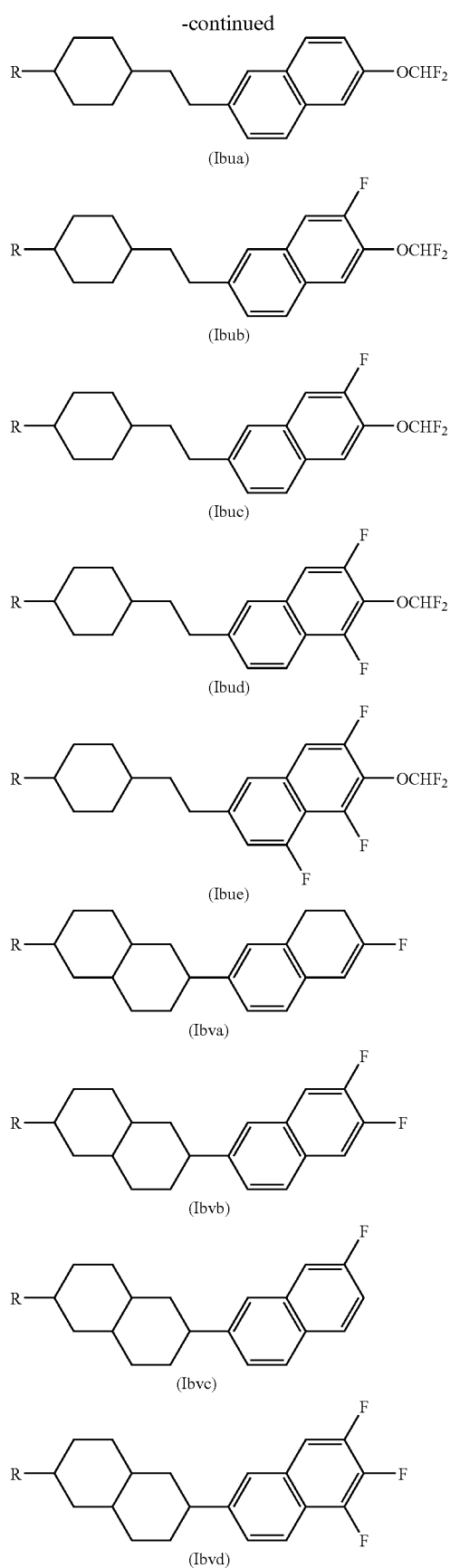
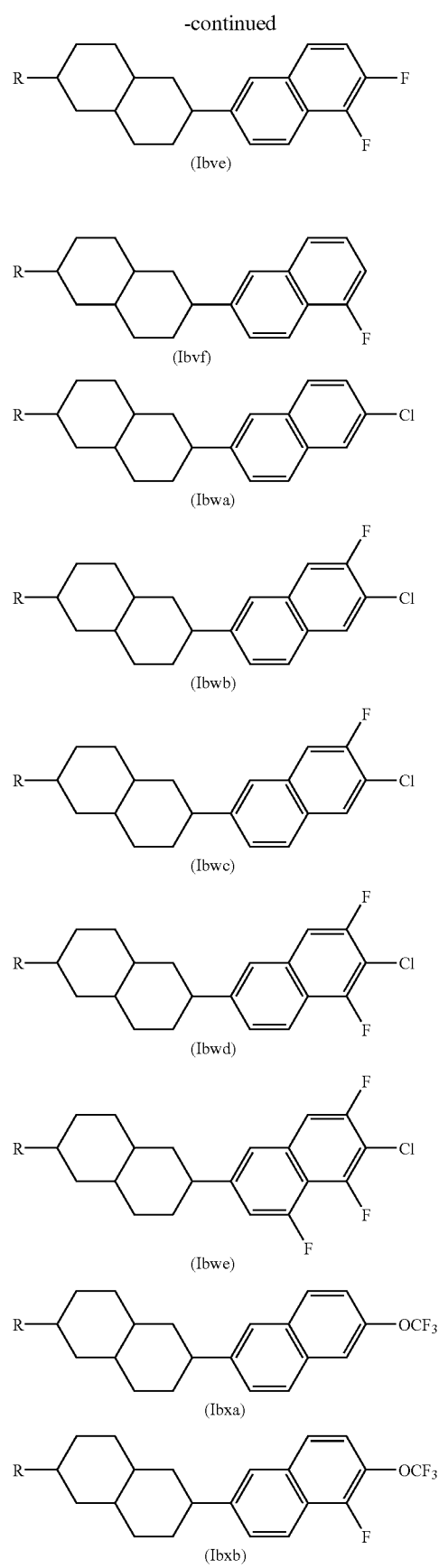

-continued
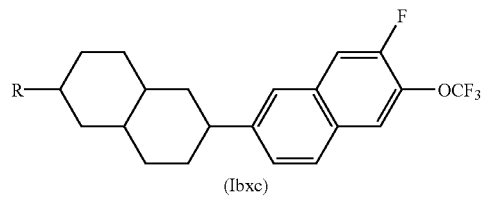
(Ibxc)
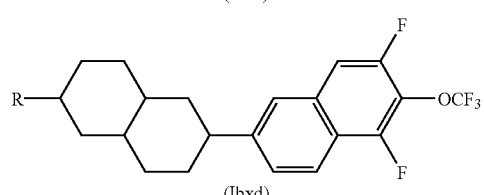
(Ibxd)
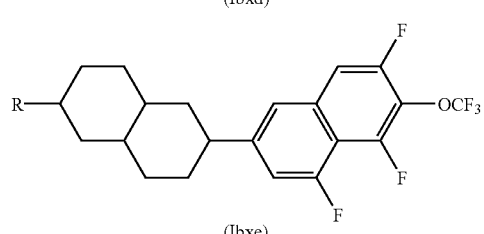
(Ibxe)
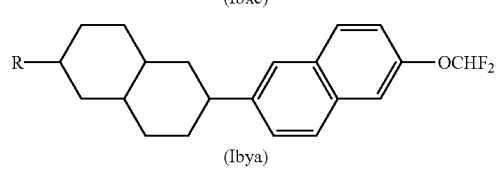
(Ibya)
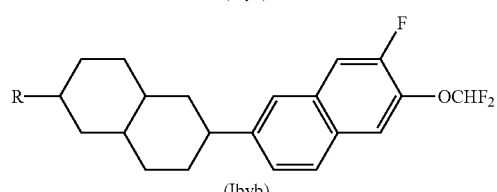
(Ibyb)
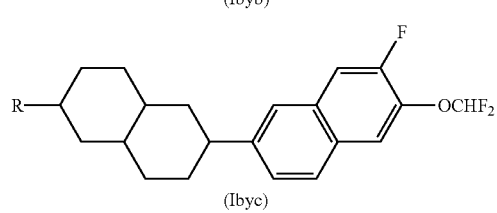
(Ibyc)
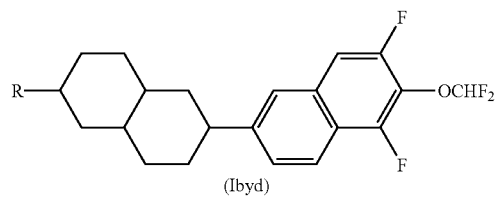
(Ibyd)
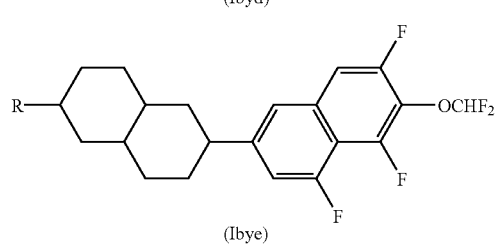
(Ibye)
Particularly preferred among the compounds represented by the general formula (Ic) are those shown below.
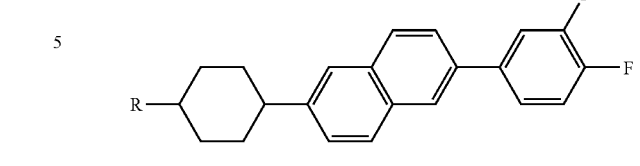
(Icaa)
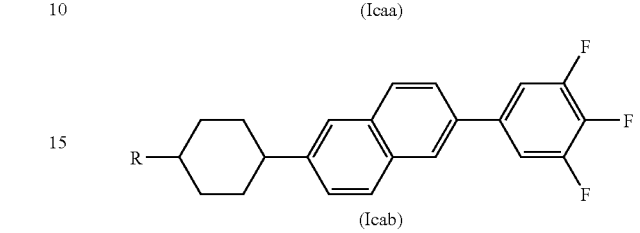
(Icab)
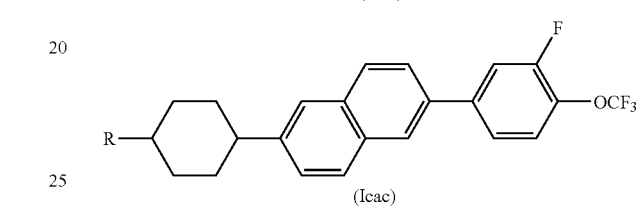
(Icac)
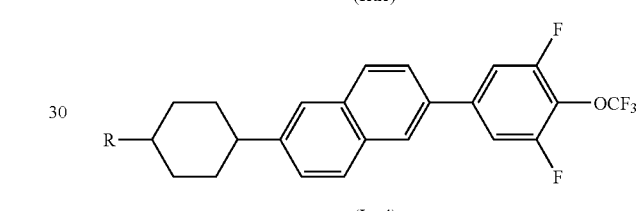
(Icad)
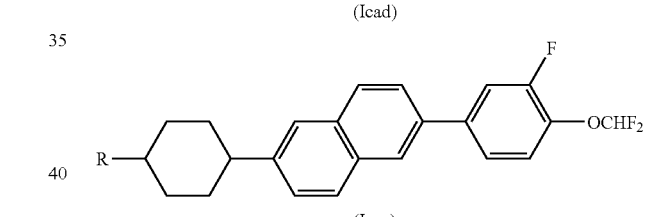
(Icae)
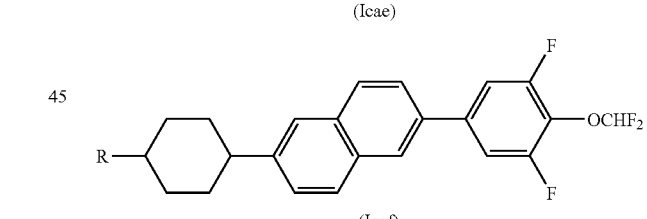
(Icaf)
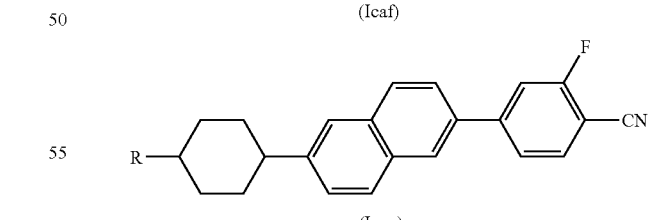
(Icag)
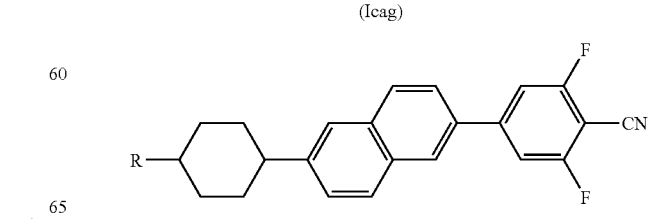
(Icah)

-continued
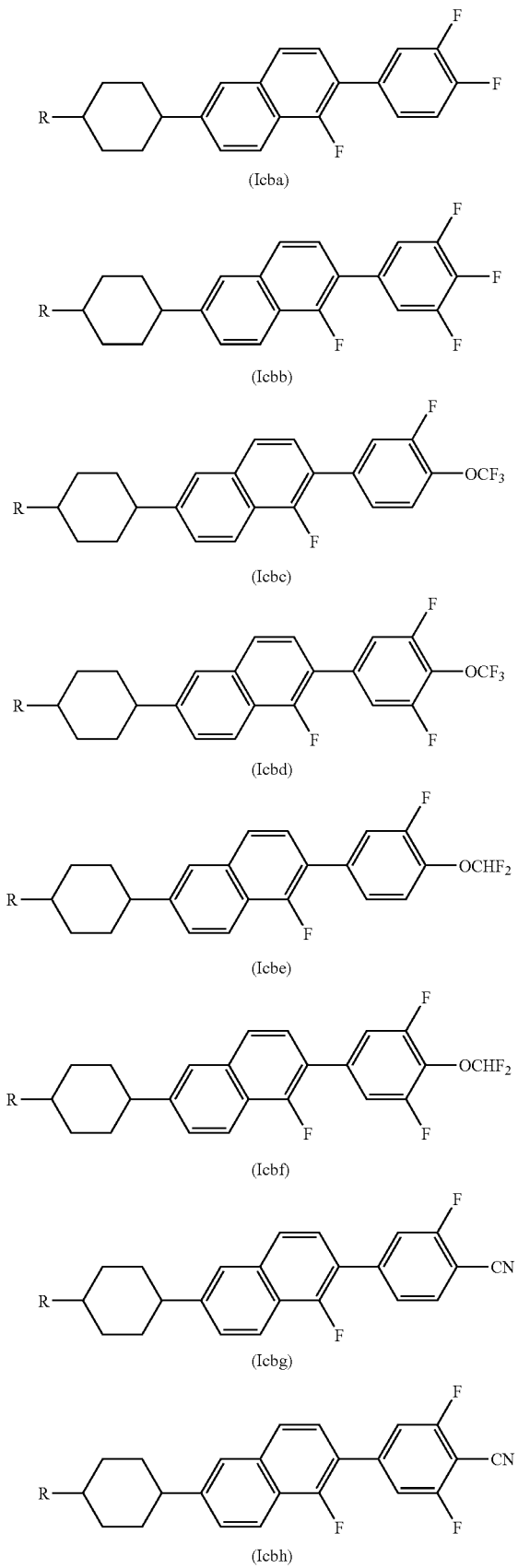
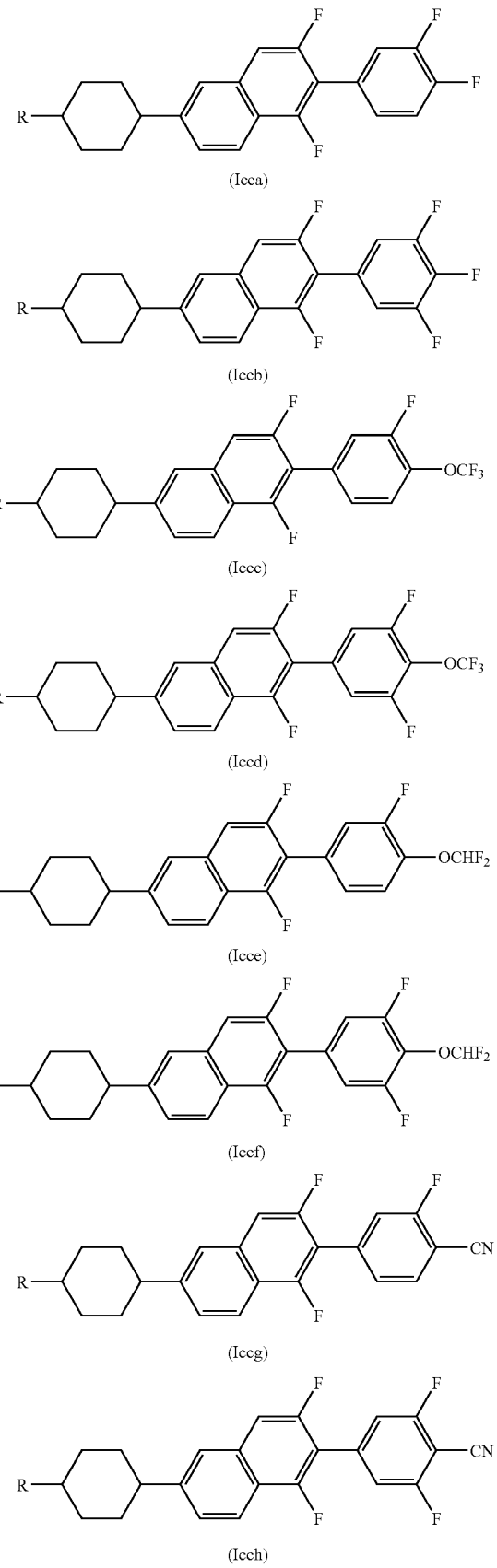

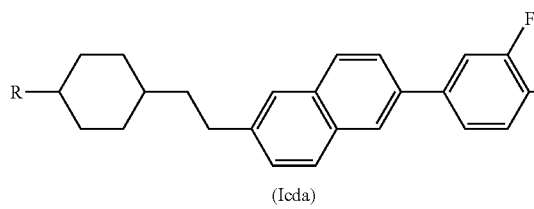
(Icda)
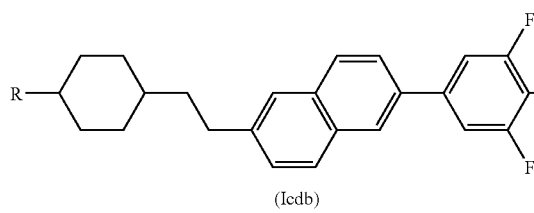
(Icdb)
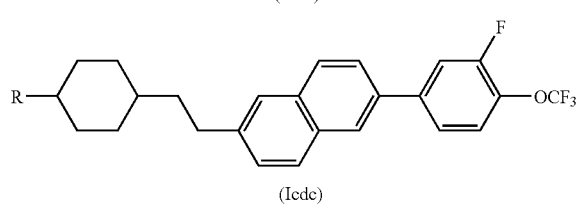
(Icdc)
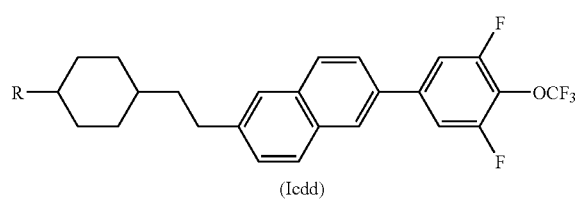
(Icdd)
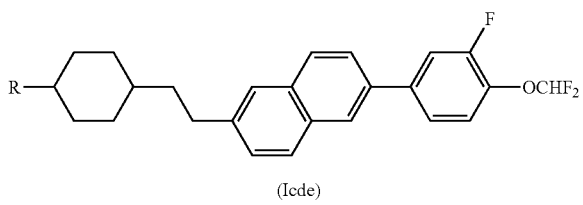
(Icde)
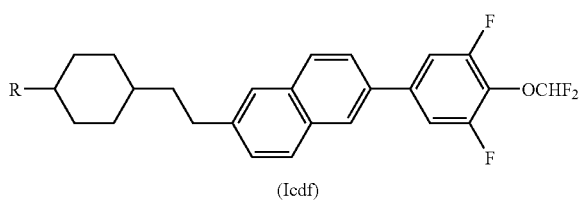
(Icdf)
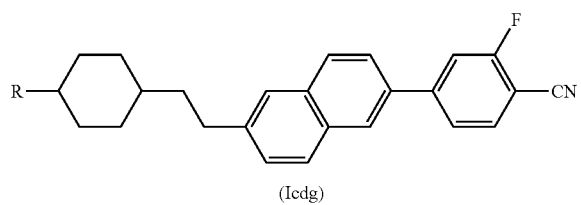
(Icdg)
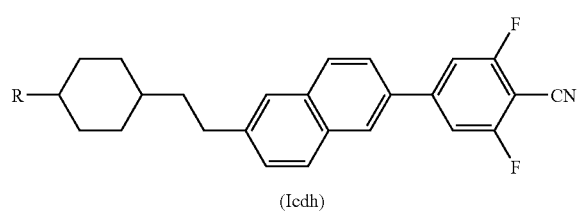
(Icdh)
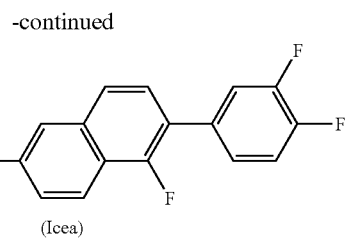
(Icea)
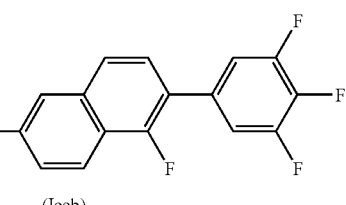
(Iceb)
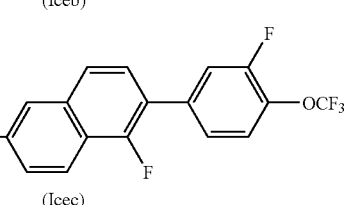
(Icec)
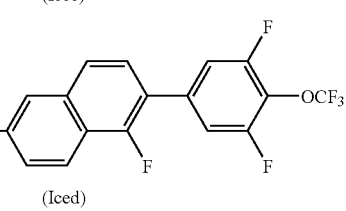
(Iced)
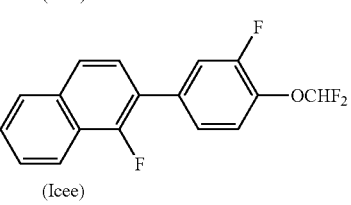
(Icee)
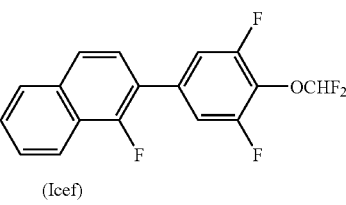
(Icef)
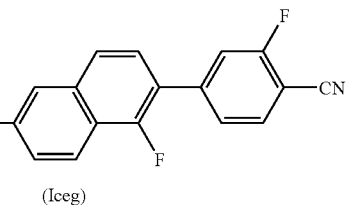
(Iceg)
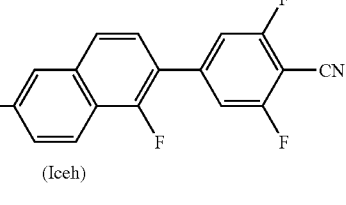
(Iceh)

-continued
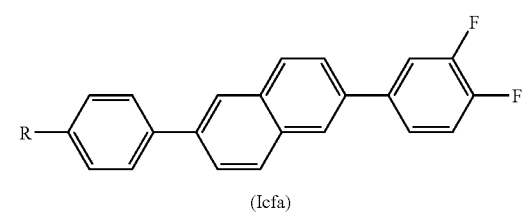
(Icfa)
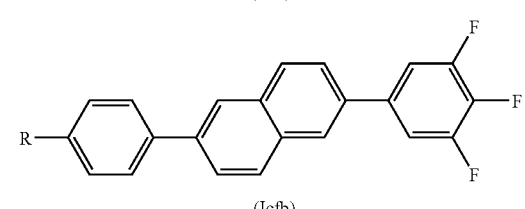
(Icfb)
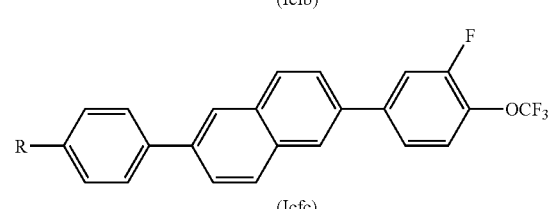
(Icfc)
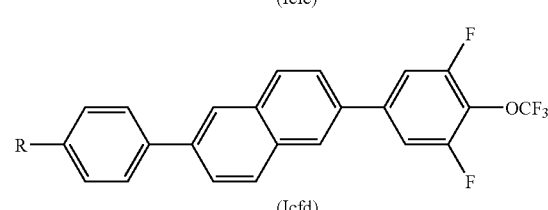
(Icfd)
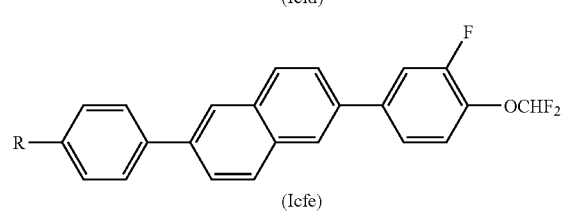
(Icfe)
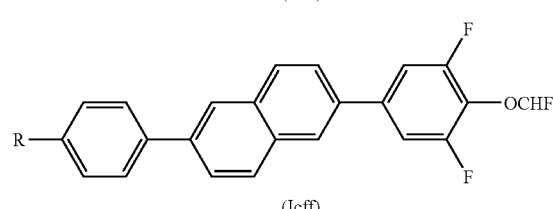
(Icff)
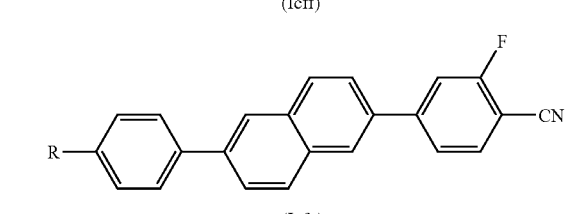
(Icfg)
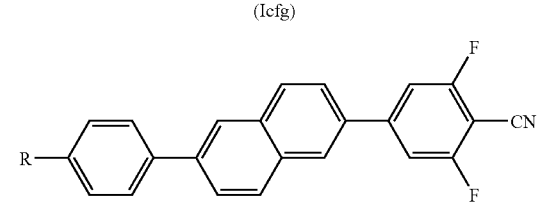
(Icfh)
-continued
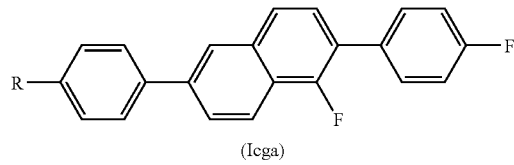
(Icga)
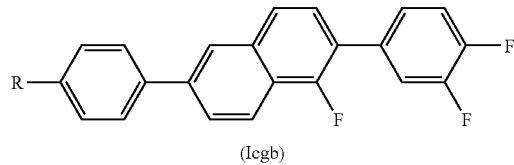
(Icgb)
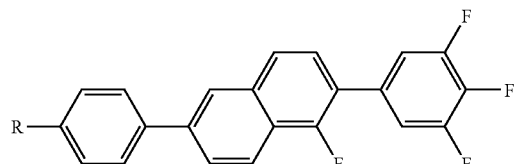
(Icgc)
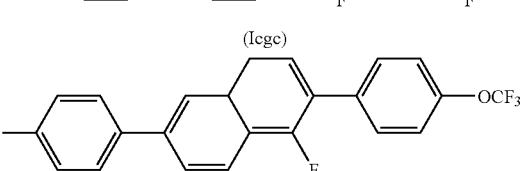
(Icgd)
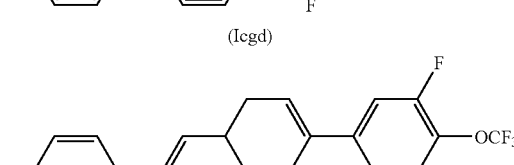
(Icge)
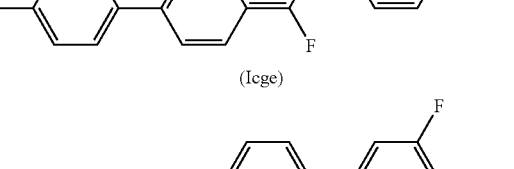
(Icgf)
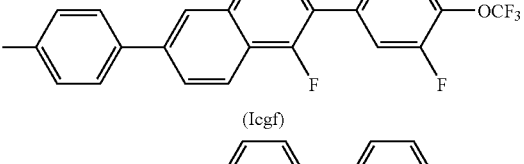
(Icgg)
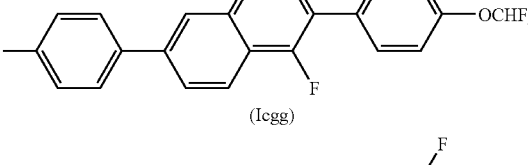
(Icgh)
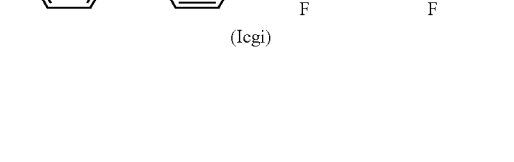
(Icgi)

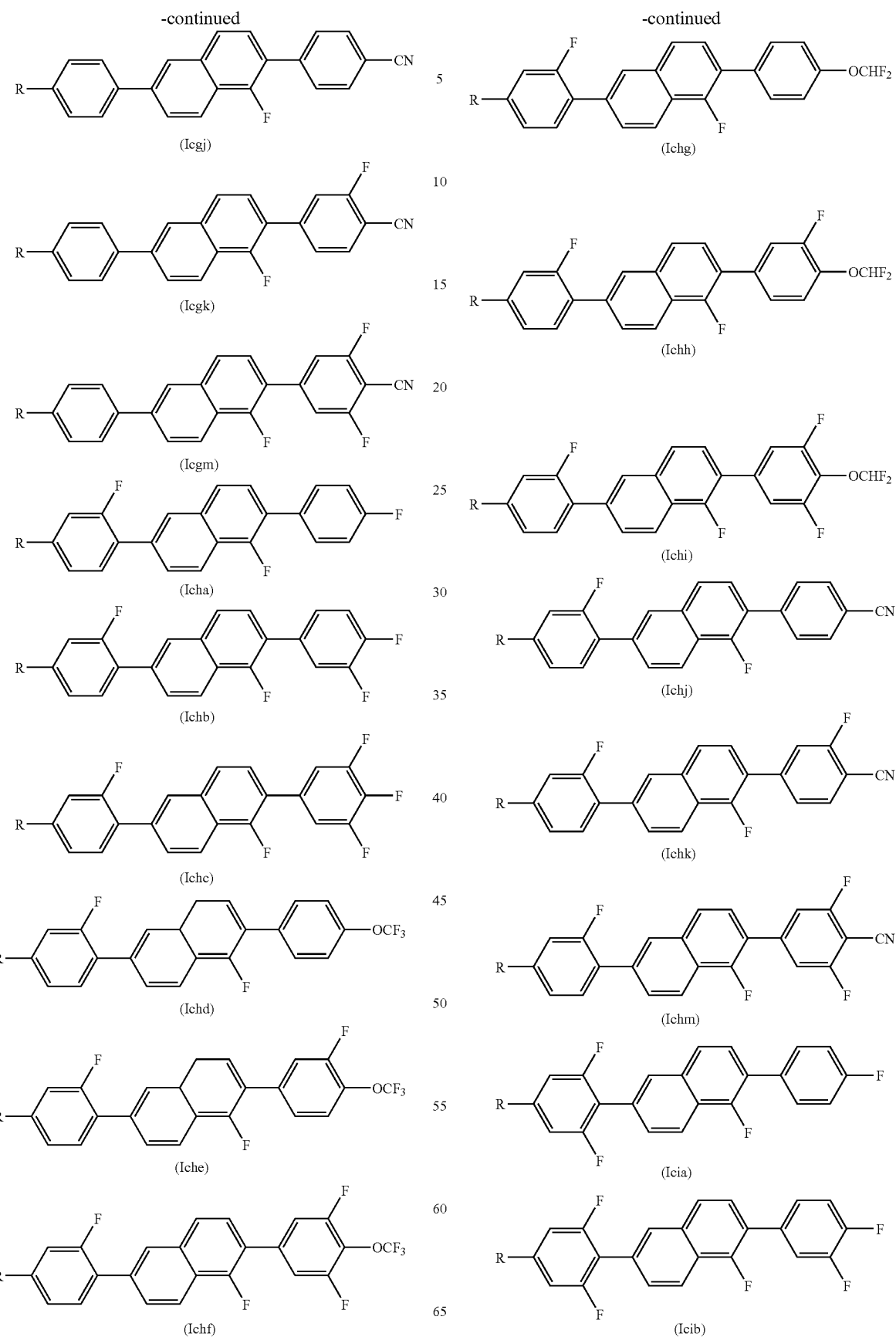

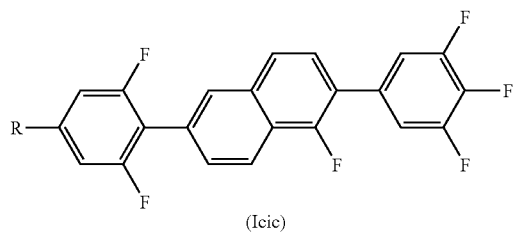
(Icic)
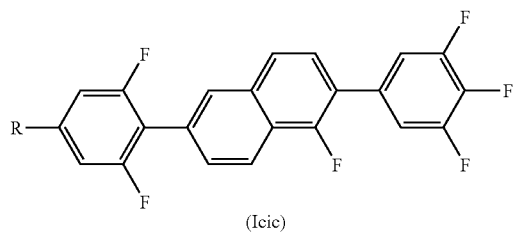
(Icid)
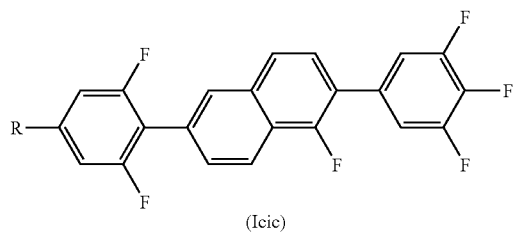
(Icie)
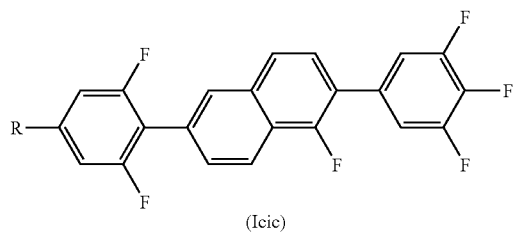
(Icif)
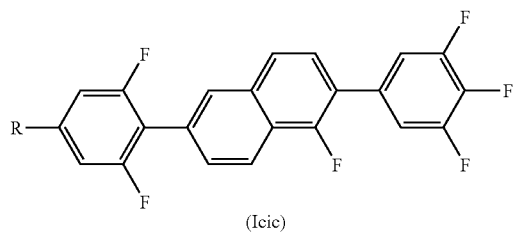
(Icig)
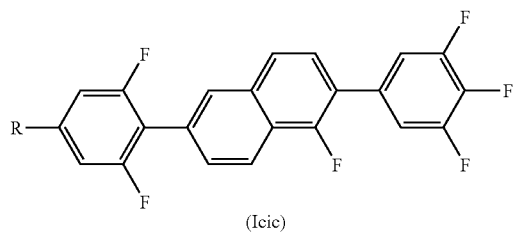
(Icih)
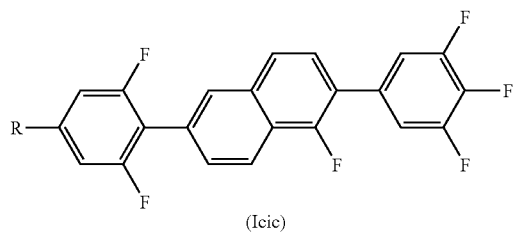
(Icii)
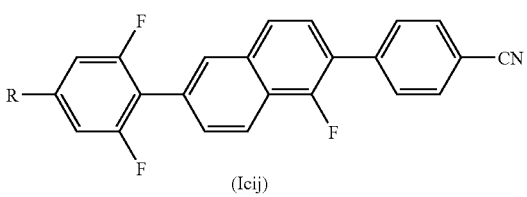
(Icij)
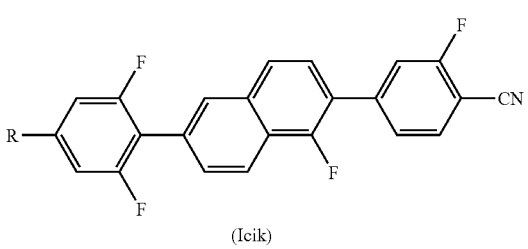
(Icik)
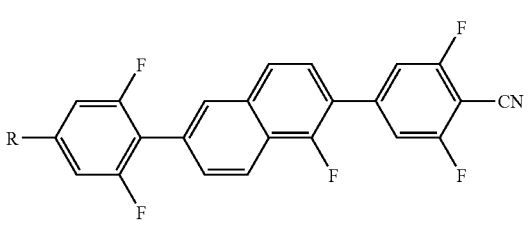
(Icim)
Particularly preferred among the compounds represented by the general formula (Id) are those shown below.
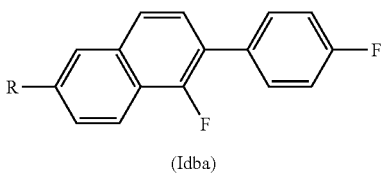
(Idba)
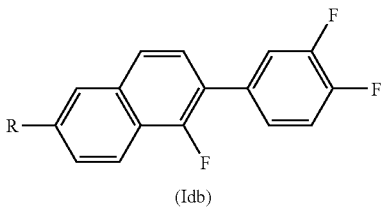
(Idb)
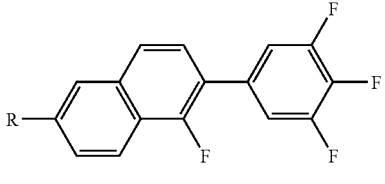
(Idbc)
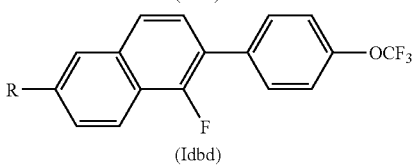
(Idbd)

-continued
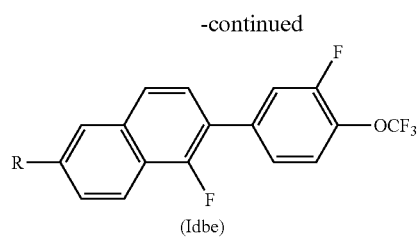
(Idbe)
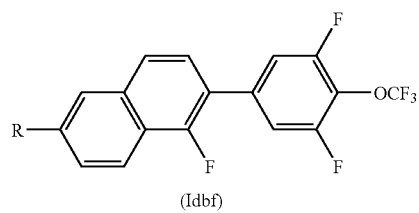
(Idbf)
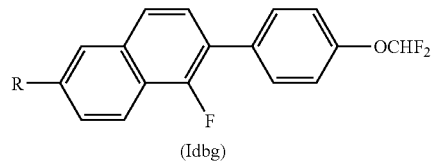
(Idbg)
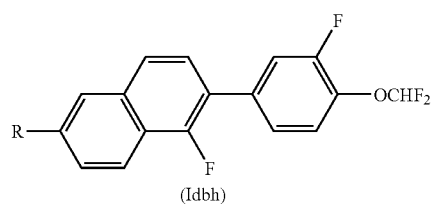
(Idbh)
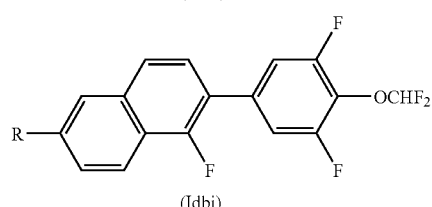
(Idbi)
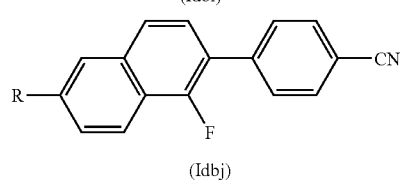
(Idbj)
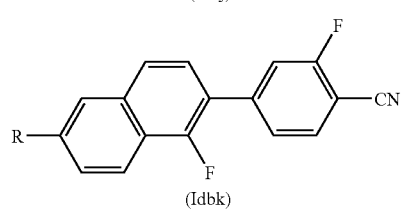
(Idbk)
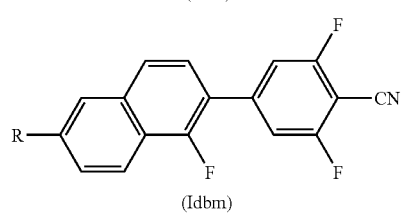
(Idbm)
-continued
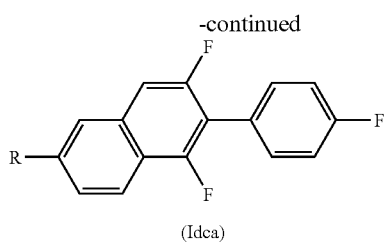
(Idca)
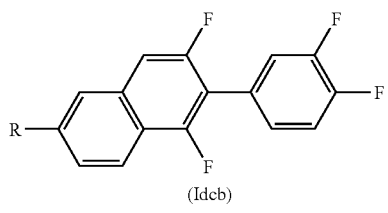
(Idcb)
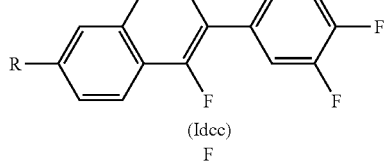
(Idcc)
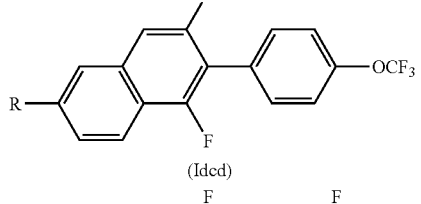
(Idcd)
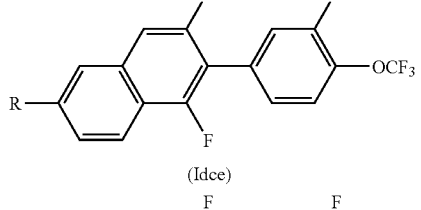
(Idce)
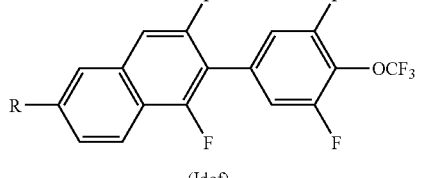
(Idcf)
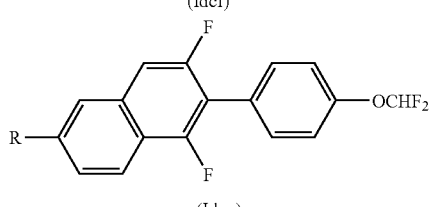
(Idcg)
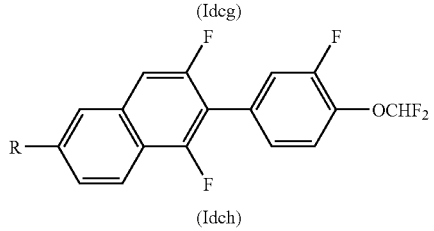
(Idch)

-continued
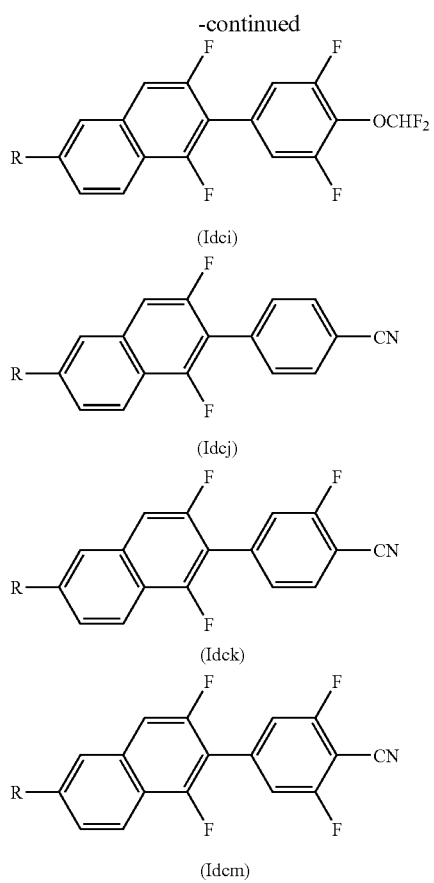
Particularly preferred among the compounds represented by the general formula (Ie) are those shown below.
-continued
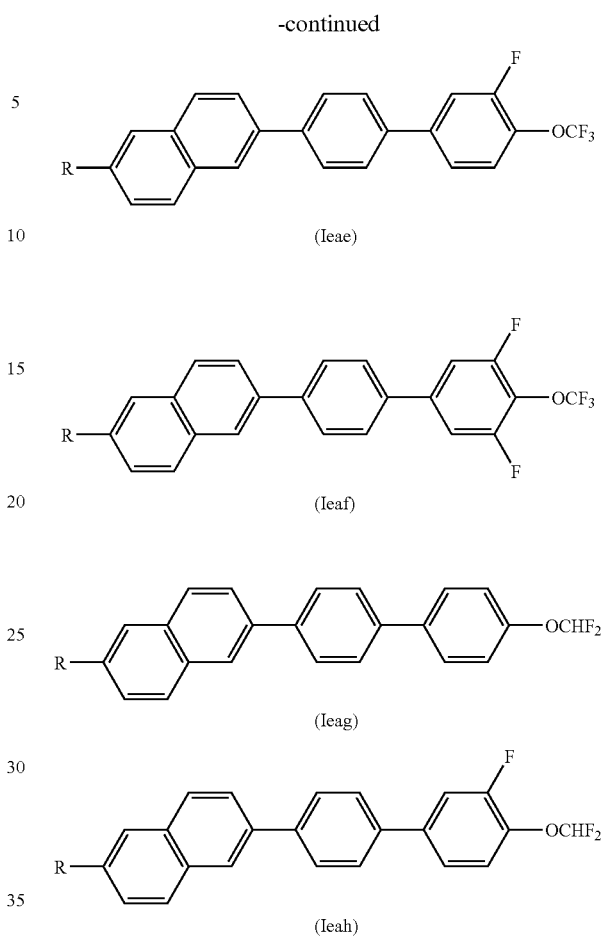
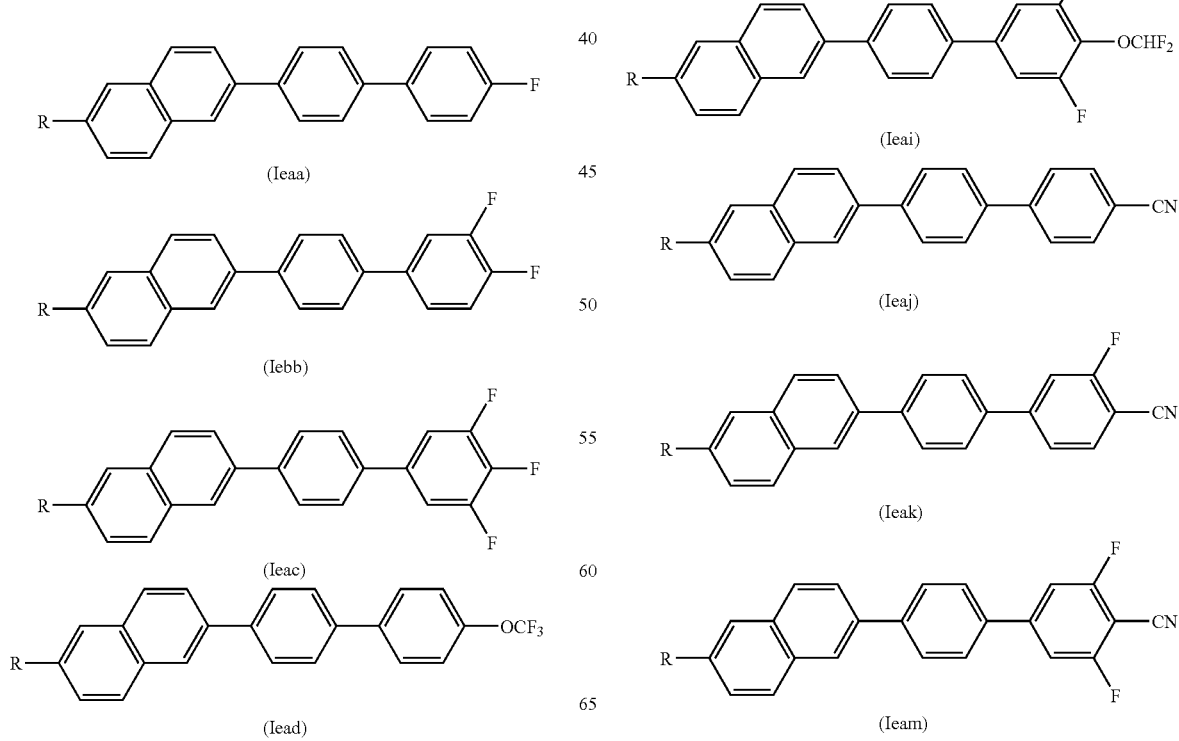

-continued
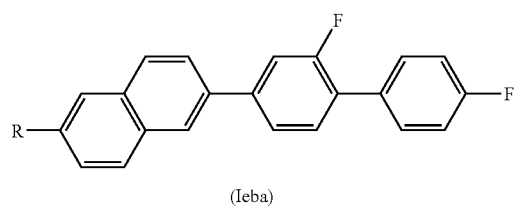
(Ieba)
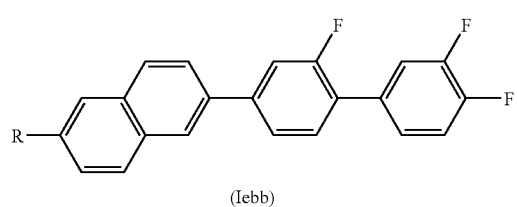
(Iebb)
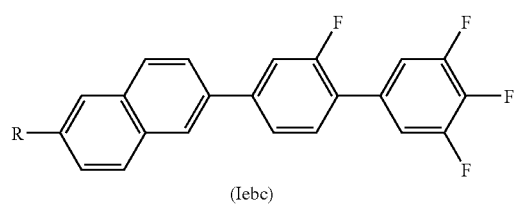
(Iebc)
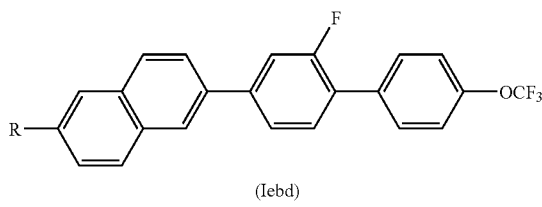
(Iebd)
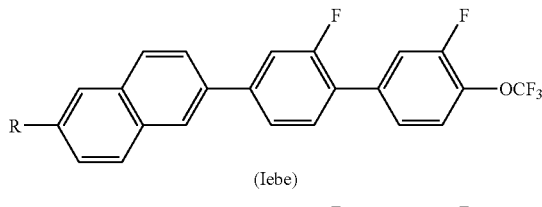
(Iebe)
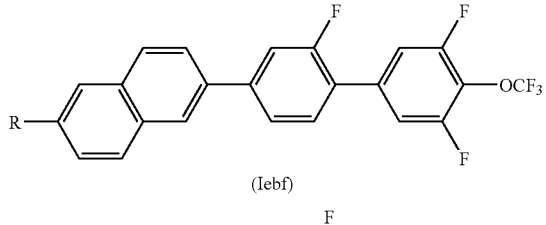
(Iebf)
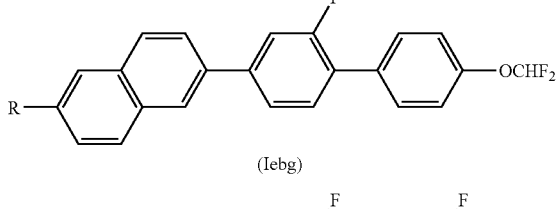
(Iebg)
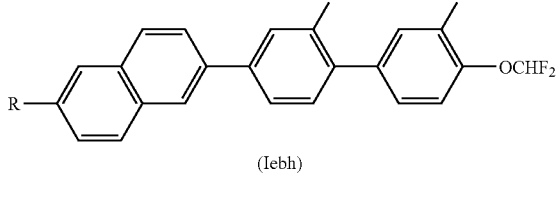
(Iebh)
-continued
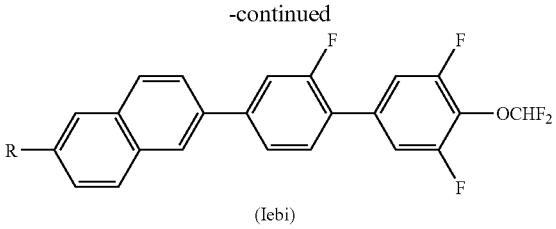
(Iebi)
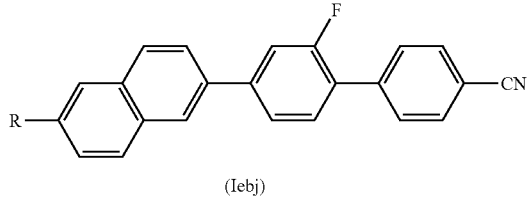
(Iebj)
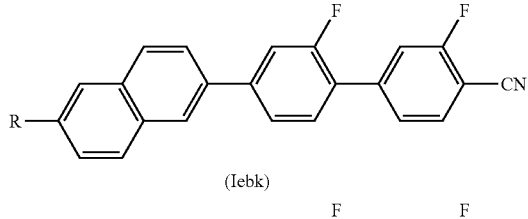
(Iebk)
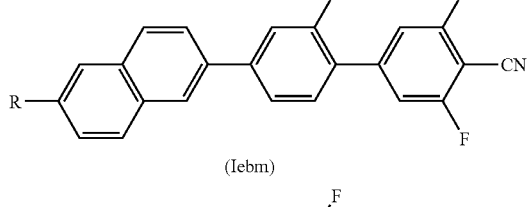
(Iebm)
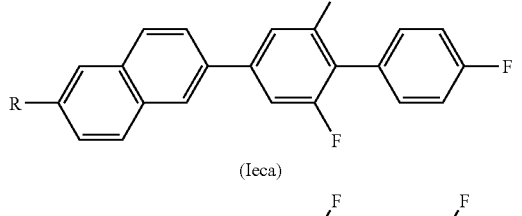
(Ieca)
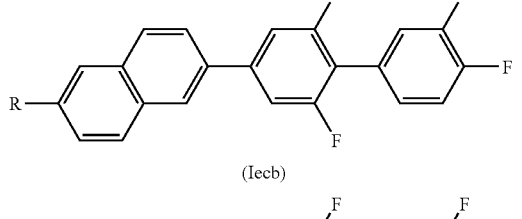
(Iecb)
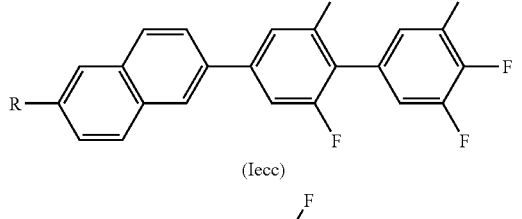
(Iecc)
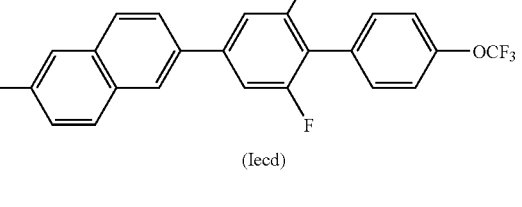
(Iecd)

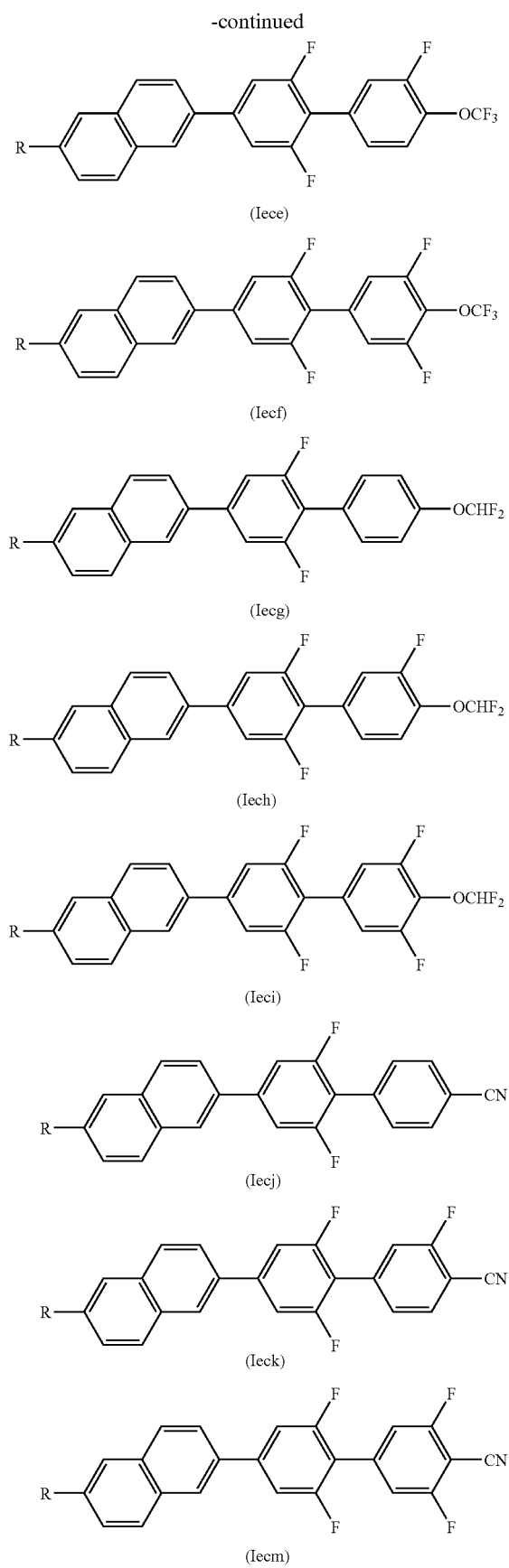

-continued
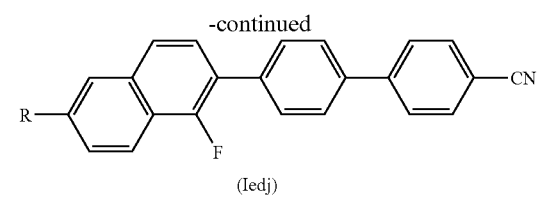
(Iedj)
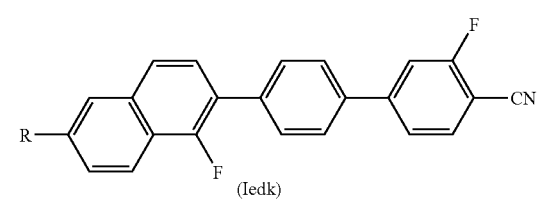
(Iedk)
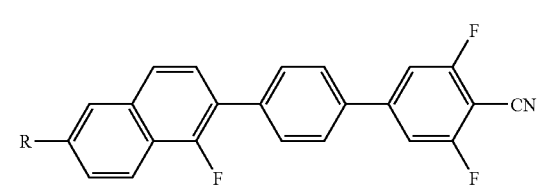
(Iedm)
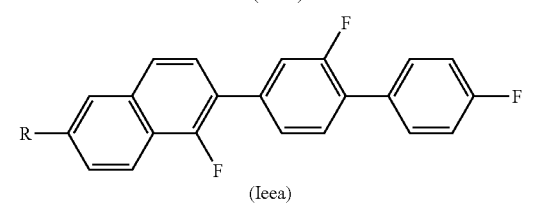
(Ieea)
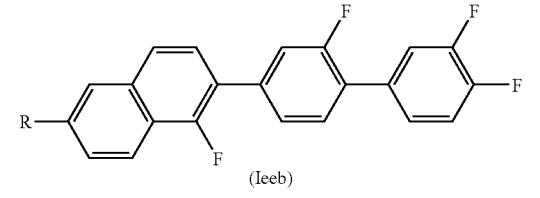
(Ieeb)
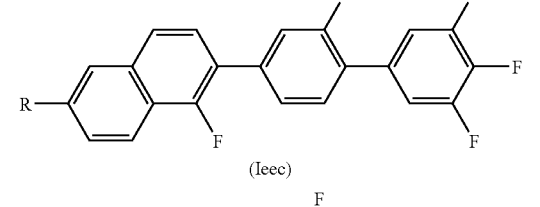
(Ieec)
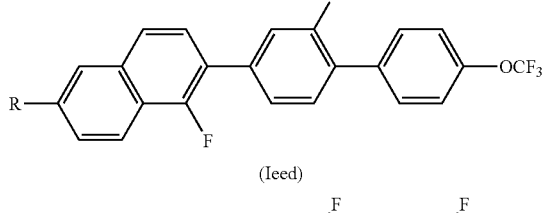
(Ieed)
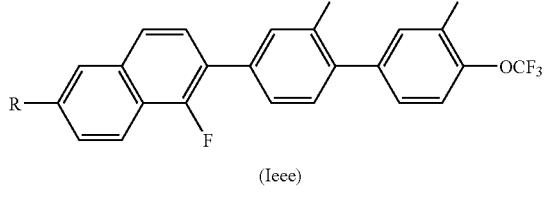
(Ieee)
-continued
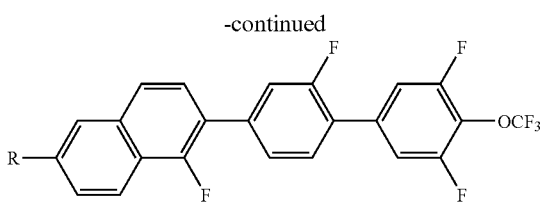
(Ieef)
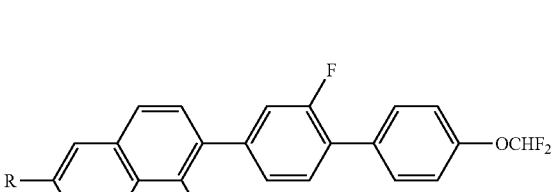
(Ieeg)
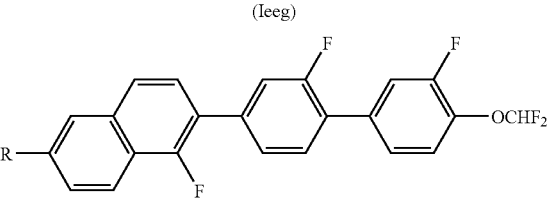
(Ieeh)
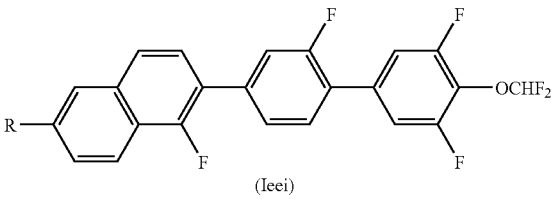
(Ieei)
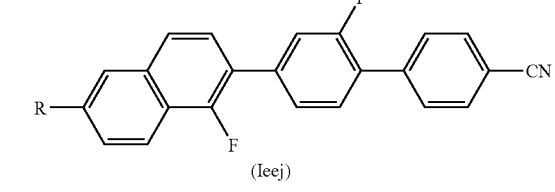
(Ieej)
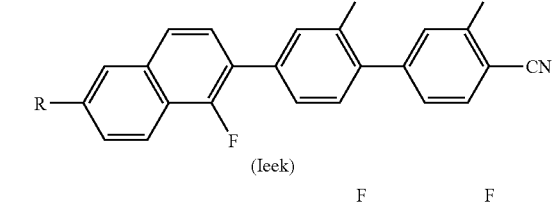
(Ieek)
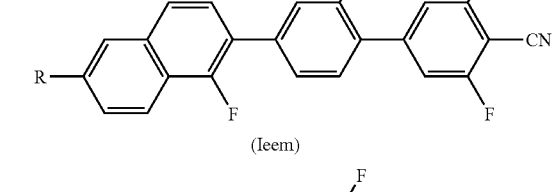
(Ieem)
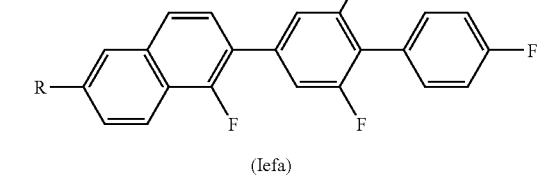
(Iefa)

-continued

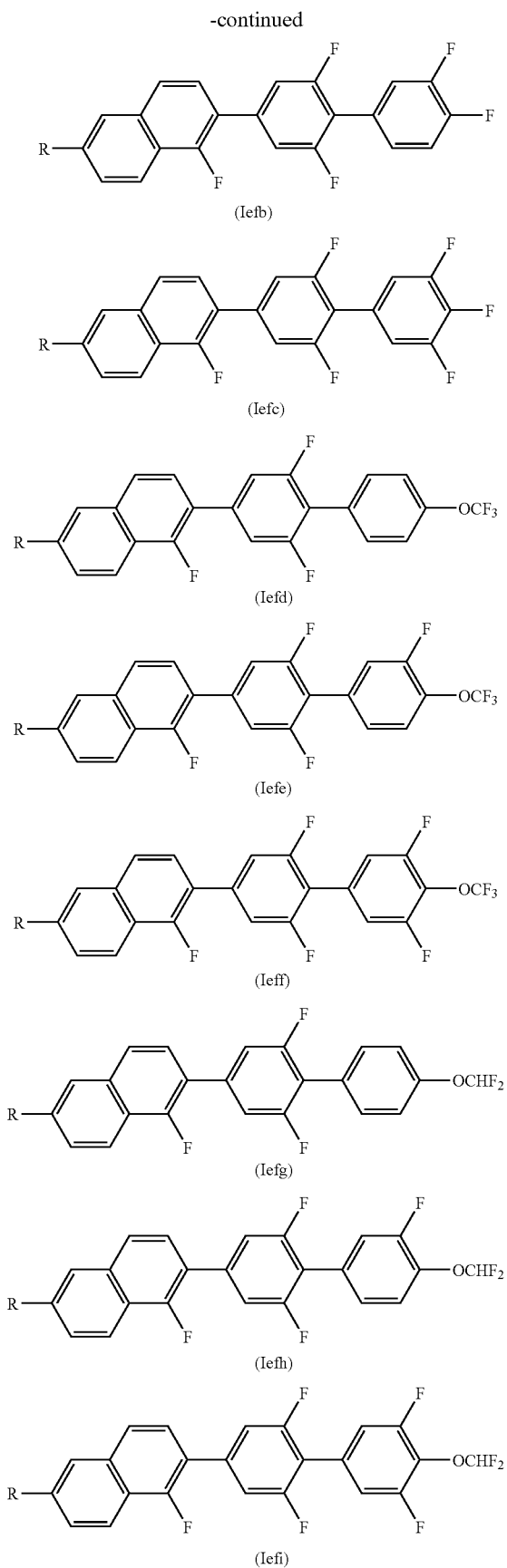

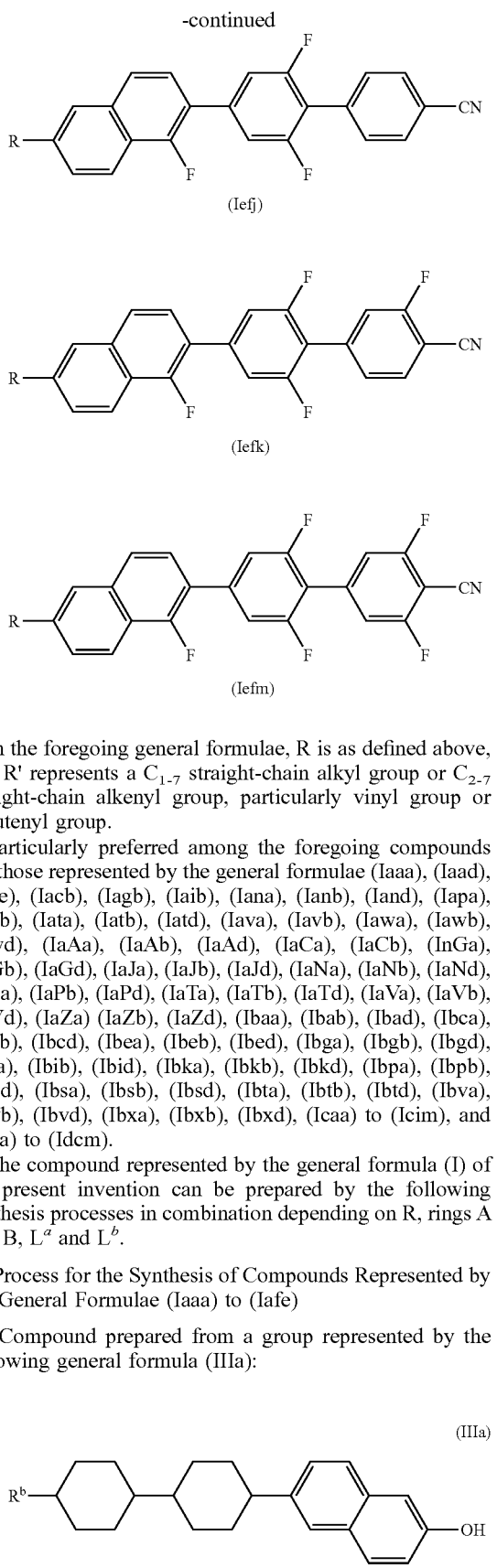

In the foregoing general formulae, R is as defined above, and R' represents a $C_{1-7}$ straight-chain alkyl group or $C_{2-7}$ straight-chain alkenyl group, particularly vinyl group or 3-butenyl group.

Particularly preferred among the foregoing compounds are those represented by the general formulae (Iaaa), (Iaad), (Iaae), (Iacb), (Iagb), (Iaib), (Iana), (Ianb), (Iand), (Iapa), (Iapb), (Iata), (Iatb), (Iatd), (Iava), (Iavb), (Iawa), (Iawb), (Iawd), (IaAa), (IaAb), (IaAd), (IaCa), (IaCb), (InGa), (IaGb), (IaGd), (IaJa), (IaJb), (IaJd), (IaNa), (IaNb), (IaNd), (IaPa), (IaPb), (IaPd), (IaTa), (IaTb), (IaTd), (IaVa), (IaVb), (IaVd), (IaZa) (IaZb) (IaZd), (Ibaa), (Ibab), (Ibad), (Ibca), (Ibcb), (Ibcd), (Ibea), (Ibeb), (Ibed), (Ibga), (Ibgb), (Ibgd), (Ibia), (Ibib), (Ibid), (Ibka), (Ibkb), (Ibkd), (Ibpa), (Ibpb), (Ibpd), (Ibsa), (Ibsb), (Ibsd), (Ibta), (Ibtb), (Ibtd), (Ibva), (Ibvb), (Ibvd), (Ibxa), (Ibxb), (Ibxd), (Icaa) to (Icim), and (Idaa) to (Idcm).

The compound represented by the general formula (I) of the present invention can be prepared by the following synthesis processes in combination depending on R, rings A and B, $L^a$ and $L^b$.

[I] Process for the Synthesis of Compounds Represented by the General Formulae (Iaaa) to (Iafe)

(1) Compound prepared from a group represented by the following general formula (IIIa):

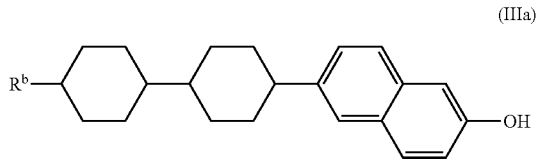

(IIIa)

wherein $R^b$ represents an alkyl group as a key intermediate (i) A naphthalene derivative represented by the following general formula (IVa):

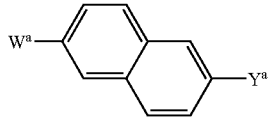

(IVa)

wherein $W^a$ represents a halogen atom such as chlorine, bromine and iodine, preferably bromine atom; and $Y^a$ represents a phenolic hydroxyl group protected by methoxy or benzyloxy group, hydrogen atom or trifluoromethoxy group, is reacted with magnesium to produce a Grignard reagent or lithioated with an alkyl lithium such as butyl lithium to produce an organic metal reagent. The Grignard reagent or organic metal reagent thus prepared is then reacted with a 4-alkylcyclohexanene represented by the following general formula (Va):

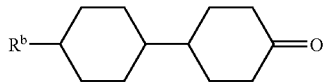

(Va)

wherein $R^b$ represents an alkyl group. Subsequently, the resulting cyclohexanol derivative is dehydrated in the presence of an acid catalyst to obtain a cyclohexenylnaphthalene derivative represented by the following general formula (IVa):

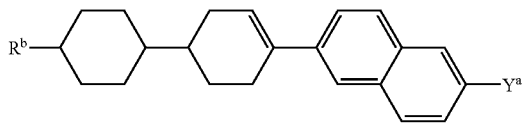

(VIa)

wherein $R^b$ represents an alkyl group; and $Y^a$ is as defined in the general formula (IVa). The cyclohexenylnaphthalene derivative thus obtained is subjected to catalytic reduction, optionally subjected to isomerization of cyclohexane ring, and then freed of $Y^a$, if it is a protective group for phenolic hydroxyl group such as methoxy group, with hydrobromic acid to obtain a naphthol derivative represented by the foregoing general formula (IIIa).

(ii) The naphthol derivative (IIIa) obtained in the process (i) can be reacted with a halogenated alkyl or halogenated alkenyl in the presence of a base to obtain a compound represented by the general formula (Iafa) wherein R is an alkyl group.

(iii) The naphthol derivative (IIIa) obtained in the process (i) can be reacted with trifluoromethanesulfonic anhydride or trifluoromethanesulfonic acid chloride in the presence of a base such as pyridine to obtain a sulfonate represented by the following general formula (VIIa):

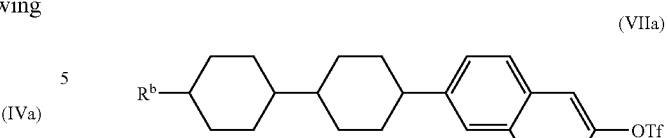

(VIIa)

wherein $R^b$ is as defined above; and Tf represents a trifluoromethanesulfonyl group.

(iv) The sulfonate (VIIa) can be reacted with an organic metal reagent represented by the following general formula (VIIIa):

$R^b$-$M^a$ (VIIIa)

wherein $R^b$ is as defined above; and $M^a$ represents MgBr, MgCl, MgI or Li, preferably MgBr, in the presence of a nickel catalyst to obtain a compound represented by the general formula (Iaea) wherein R is an alkyl group. Preferred examples of the nickel catalyst employable herein include
dichlorobis(triphenylphosphine)nickel (II), dichloro[1,2-bis(triphenylphosphino)ethane]nickel (II), and tetrakis(triphenylphosphine) nickel (0).

(v) The naphthol derivative represented by the general formula (IIIa) can be reacted with carbon disulfide in the presence of a strong base, and then reacted with an alkylating agent to obtain a dithiocarbonic acid ester represented by the following general formula (IXa):

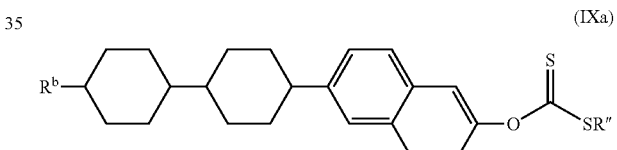

(IXa)

wherein $R^b$ is as defined above; and R" represents a lower alkyl group. Preferred examples of the strong base employable herein include hydrogenated alkaline metal such as sodium hydride, alkyl lithium such as butyl lithium, lithium amide such as lithium diisopropyl amide, and alcoholate such as potassium t-butoxide. Preferred examples of the alkylating agent employable herein include methyl iodide, ethyl iodide, methyl bromide, ethyl bromide, dimethyl sulfate, and methyl p-toluenesulfonate. The dithiocarbonic acid ester thus obtained can then be reacted with fluoride ion in the presence of a halonium ion generator to produce a compound represented by the foregoing general formula (Iaca) wherein R is an alkyl group. As the halonium ion generator there may be used N-iodosuccinic acid imide (NIS), N-bromosuccinic acid imide (NBS), N-chlorosuccinic acid imide (NCS), 1,3-dibromo-5,5-dimethylhydantoin (DBH) or the like. As the fluoride ion source there may be used tetrabutylammonium dihydrotrifluoride (TBAH$_2$F$_3$), hydrogen fluoride-pyridine complex (HF-Py), hydrogen fluoride-melamine complex (HF-mel) or the like. If the dithiocarbonic acid ester has an aromatic ring, the aromatic ring may be halogenated with halonium ion. In this case, the halide thus obtained can be lithioated with alkyl lithium such as butyl lithium, and then protonated to obtain the desired compound.

(vi) The compound represented by the general formula (IIIa) obtained in the foregoing process (i) can be reacted with ammonium in the presence of sodium hydrogensulfide to obtain a compound represented by the following general formula (Xa):

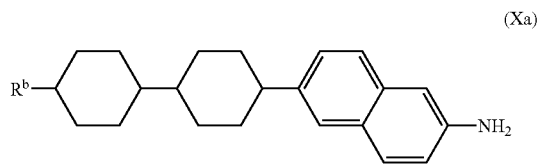

(Xa)

wherein $R^b$ is as defined above. The compound (Xa) can then be reacted with a fluorine source such as hydrofluoric acid in the form of nitrite represented by the following general formula (XIa):

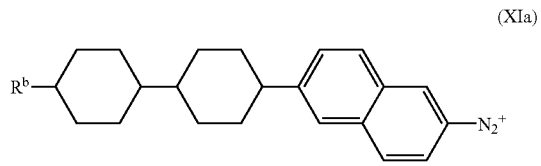

(XIa)

wherein $R^b$ is as defined above, to obtain a compound represented by the general formula (Iaaa).

(vii) The compound represented by the general formula (XIa) obtained in the foregoing process (vi) can then be reacted with a chlorine source such as copper chloride (I) to obtain a compound represented by the foregoing general formula (Iaba) wherein R is an alkyl group.

(viii) The naphthol derivative represented by the general formula (IIIa) can be reacted with fluoride ion in the presence of a halonium ion generator in the form of thioformic acid ester represented by the following general formula (XIIa):

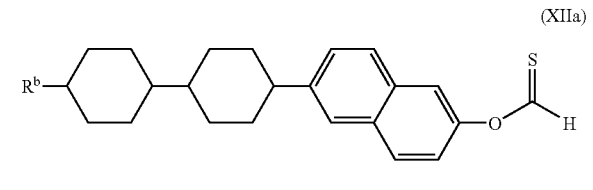

(XIIa)

wherein $R^b$ is as defined above to produce a compound represented by the foregoing general formula (Iada) wherein R is an alkyl group. As the halonium ion generator there may be used N-iodosuccinic acid imide (NIS), N-bromosuccinic acid imide (NBS), N-chlorosuccinic acid imide (NCS), 1,3-dibromo-5,5-dimethylhydantoin (DBH) or the like. As the fluoride ion source there may be used tetrabutylamonium dihydrotrifluoride (TBAH$_2$F$_3$) hydrogen fluoride-pyridine complex (HP-Py), hydrogen fluoride-melamine complex (HF-mel) or the like. If the thioformic acid ester has an aromatic ring, the aromatic ring may be halogenated with halonium ion. In this case, the halide thus obtained can be lithioated with alkyl lithium such as butyl lithium, and then protonated to obtain the desired compound.

(ix) The naphthol derivative represented by the general formula (IIIa) can be fluorinated with one equivalent of a fluorinating agent such as N,N'-difluoro-2,2'-dipyridinium bistetrafluoroborate and N-fluoro-5-trifluoromethoxy pyridinium-2-sulfonate to obtain a compound represented by the following general formula (XIII):

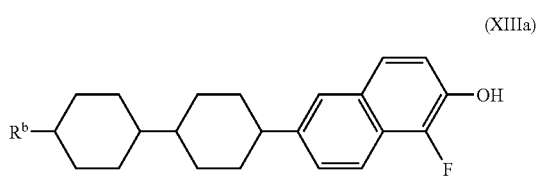

(XIIIa)

and by-products represented by the following general formulas (XIVa) and (XVa):

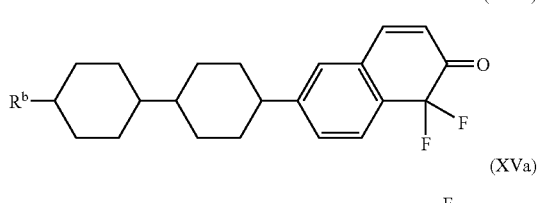

(XIVa)

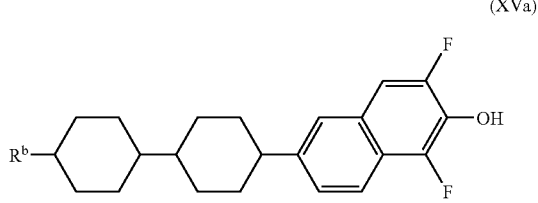

(XVa)

wherein $R^b$ is as defined above.

(x) The naphthol derivative represented by the general formula (IIIa) can be fluorinated with two equivalents of a fluorinating agent such as 1-chloromethyl-4-fluoro-1,4-diazoniabicyclo[2,2,2]octane bistetrafluoroborate and 1-fluoro-4-hydroxy-14-diazoniabicyclo[2,2,2]octane bistetrafluoroborate to selectively obtain a compound represented by the following general formula (XIVa):

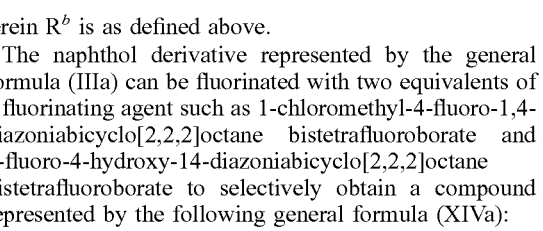

(XIVa)

wherein $R^b$ is as defined above. The compound (XIVa) can then be fluorinated with a fluorinating agent such as DAST and HF-pyridine to obtain a compound represented by the following general formula (XVIa):

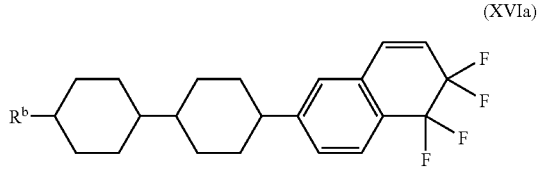

(XVIa)

wherein R^b is as defined above. The compound (XVIa) can then be subjected to catalytic reduction to obtain a compound represented by the general formula (Iaad) wherein R is an alkyl group.

(xi) The compound (Iaad) obtained in the foregoing process (x) can be lithioated with butyl lithium, and then reacted with a fluorinating agent such as 1-chloromethyl-4-fluoro-1,4-diazoniabicyclo[2 2,2]octane bistetrafluoroborate and 1-fluoro-4-hydroxy-1,4-diazoniabicyclo[2,2,2] octane bistetrafluoroborate to obtain a compound represented by the general formula (Iaae) wherein R is an alkyl group.

(xii) The compound (XIIIa) shown in the foregoing process (ix) can be converted to a sulfonate in accordance with the foregoing process (iii), and then subjected to catalytic reduction to obtain a compound represented by the general formula (Iaab) wherein R is an alkyl group.

(xiii) The compound (XVa) shown in the foregoing process (ix) can be converted to a sulfonate in accordance with the foregoing process (iii), and then subjected to catalytic reduction to obtain a compound represented by the general formula (Iaag) wherein R is an alkyl group.

(xiv) The procedure of the foregoing process (vi) can be followed except that the compound represented by the general formula (IVa) is replaced by a compound represented by the following general formula (XVIIa):

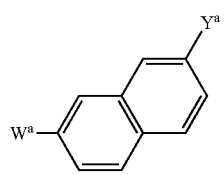

(XVIIa)

wherein $W^a$ and $Y^a$ are as defined above to obtain a compound represented by the following general formula (XIXa):

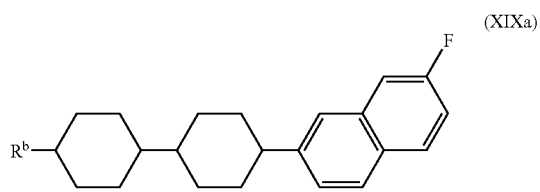

(XIXa)

wherein $R^b$ is as defined above, via a compound represented by the following general formula (XVIIIa):

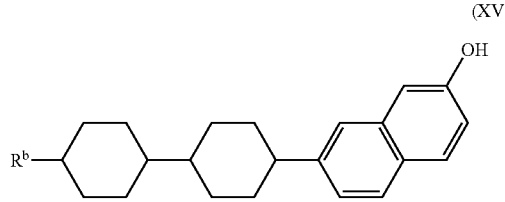

(XVIIIa)

wherein $R^b$ is as defined above.

The compound represented by the general formula (XIXa) can be nitrated with a mixture of nitric acid and sulfuric acid, and then subjected to reduction to obtain a compound represented by the following general formula (XXa):

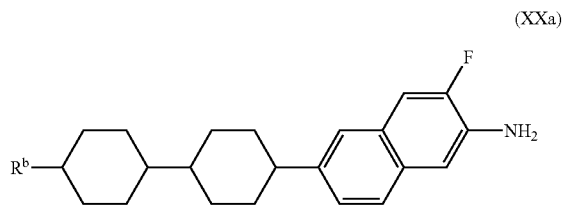

(XXa)

wherein $R^b$ is as defined above.

(xv) The compound (XXa) obtained in the foregoing process (xiv) can be reacted with a nitrite to produce a compound represented by the following general formula (XXIa):

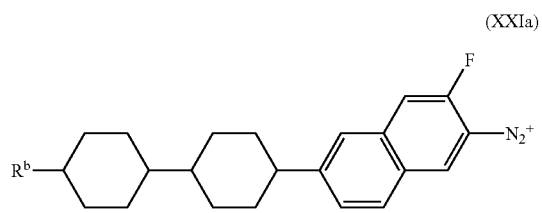

(XXIa)

wherein $R^b$ is as defined above, and then reacted with a fluorine source such as hydrofluoric acid to obtain a compound represented by the general formula (Iaac).

(xvi) The compound (XXIa) obtained in the foregoing process (xv) can be reacted with a chlorine source such as copper chloride (I) to obtain a compound represented by the general formula (Iabc) wherein R is an alkyl group.

(xvii) The compound (XXIa) obtained in the foregoing process (xv) can be reacted with water to obtain a compound represented by the following general formula (XXIIa):

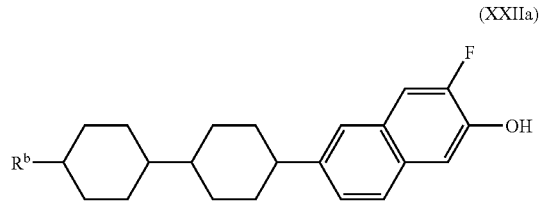

(XXIIa)

wherein $R^b$ is as defined above.

(xviii) The compounds represented by the general formulae (XIIIa), (XVa) and (XXa) can be processed in accordance with the foregoing processes (ii) to (v), (vii) and (viii) to obtain compounds represented by the general formulae (Iabb), (Iabd), (Iacb), (Iacc), (Iacd), (Iadb), (Iadc), (Iadd), (Iaeb), (Iaec), (Iaed), (Iafb), (Iafc) and (Iafd) wherein R is an alkyl group.

(xix) The procedure of the processes (i) to (viii) can be followed except that the compound (IVa) is replaced by the compound (XXIIIa):

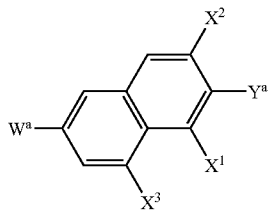

(XXIIIa)

wherein $W^a$, $Y^a$, $X^1$, $X^2$ and $X^3$ are as defined above, to obtain compounds represented by the general formulae (Iaaa) to (Iafe) wherein R is an alkyl group.

(2) Compound prepared from a group represented by the following general formula (IIIb):

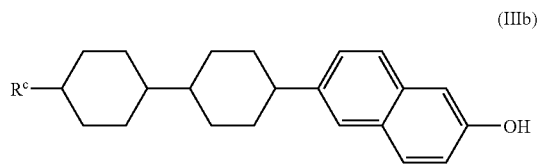

(IIIb)

wherein $R^c$ represents an alkenyl group as a key intermediate (i) The naphthalene derivative represented by the general formula (IVa) is reacted with magnesium to produce a Grignard reagent or lithioated with an alkyl lithium such as butyl lithium to produce an organic metal reagent. The Grignard reagent or organic metal reagent thus prepared is then reacted with a compound represented by the following general formula (Vb):

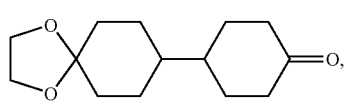

(Vb)

dehydrated in the presence of an acid catalyst, optionally re-acetalated, subjected to catalytic reduction, and then deacetalated to obtain a naphthylcyclohexyl cyclohexanene derivative represented by the following general formula (XXIVb):

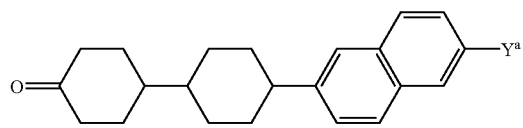

(XXIVb)

wherein $Y^a$ is as defined above. The naphthylcyclohexyl cyclohexanene derivative (XXIVb) is reacted with a Wittig reagent represented by the following general formula (XXVb):

(XXVb)

and then hydrolyzed with an acid to obtain a cyclohexane carbaldehyde derivative represented by the following general formula (XXVIb):

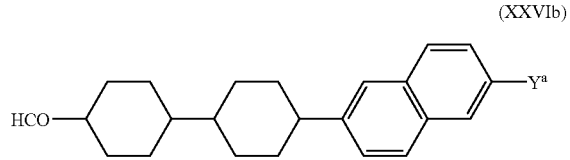

(XXVIb)

The cyclohexane carbaldehyde derivative represented by the general formula (XXVIb) can be reacted with a Wittig reagent represented by the following general formula (XXVIIb):

$CH_2=PPh_3$     (XXVIIb), and then freed of phenolic hydroxyl group of $Z^a$ to produce a compound represented by the general formula (IIIb) wherein $R^b$ is a vinyl group. The cyclohexane carbaldehyde derivative (XXVIb) can be further reacted with the Wittig reagent (XXVb) twice, reacted with the Wittig reagent (XXVIIb), and then freed of phenolic hydroxyl group of $Z^a$ to produce a compound represented by the general formula (IIIb) wherein $R^b$ is a 3-butenyl group.

(ii) The compound (IIIb) obtained in the process (2)-(i) can be processed in accordance with the processes (1)-(i) to (1)-(viii) to produce compounds represented by the general formulae (Iaaa) to (Iafe) wherein R is an alkenyl group.

[II] Process for the Preparation of Compounds Represented by the General Formulae (Iaga) to (Iane)

(1) Compound prepared from a group represented by the following general formula (IIIc):

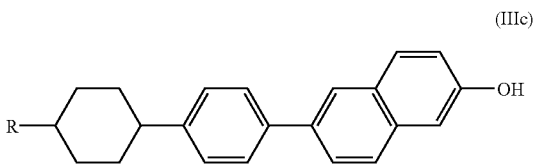

(IIIc)

wherein R is as defined above as a key intermediate (i) The naphthalene derivative represented by the following general formula (IVa) is reacted with magnesium to produce a Grignard reagent or lithioated with an alkyl lithium such as butyl lithium to produce an organic metal reagent which is reacted with trimethyl boron and then demethylated to obtain a boric acid derivative. The Grignard reagent or boric acid derivative thus produced can be reacted with a benzene derivative represented by the following general formula (Vc):

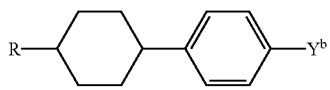
(Vc)

wherein R is as defined above; and $Y^b$ represents a releasing group such as trifluoromethanesulfonyloxy of halogen atom such as chlorine, bromine and iodine, preferably trifluoromethanesulfonyloxy of bromine, in the presence of a transition metal catalyst, and then subjected to demethoxylation of $Z^a$ to produce the desired compound.

Alternatively, the benzene derivative represented by the general formula (Vc) can be reacted with magnesium to produce a Grignard reagent or lithionatad with an alkyl lithium such as butyl lithium to obtain an organic metal reagent, reacted with trimethyl boron, demethylated to obtain a boric acid derivative, and then reacted with a benzene derivative represented by the following general formula (IVb):

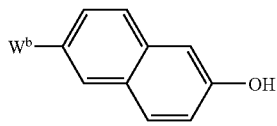
(IVb)

wherein $W^b$ is as defined above in the presence of a transition metal catalyst to produce the desired compound.

(ii) The procedure of the process [II]-(1)-(i) can be followed except that the compound (IIIc) is replaced by the compound (XVIIa) and the compound (IVb) is replaced by a compound represented by the following general formula (IVb'):

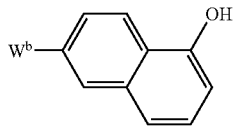
(IVb')

wherein $Z^b$ is as defined above, to obtain a compound represented by the following general formula (XXVIIIb):

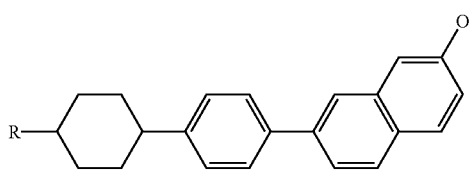
(XXVIIIb)

wherein R is as defined above.

(iii) The procedure of the above processes [I]-(1)-(ii) to [I]-(1)-(xix) can be followed except that the compound (IIIa) is replaced by the compound (IIIb) and the compound (XVIIIa) is replaced by the compound (XVIIIb) to obtain compounds represented by the general formulae (Iaga) to (Iane).

[III] Process for the Preparation of Compounds Represented by the General Formulae (IaGa) to (IaMe), (IaZa) to (IaZe), (Ibaa) to (Ibde) and (Ibva) to (Ibye)

The procedure of the above process [I] can be followed except that the compound (Va) in replaced by compounds represented by the following general formulae (Vd) to (Vg):

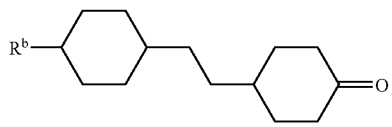
(Vd)

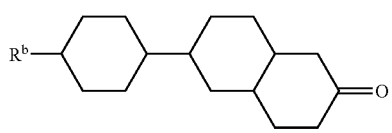
(Ve)

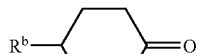
(Vf)

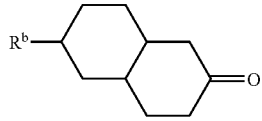
(Vg)

wherein $R^b$ is as defined above, and the compound (Vb) is replaced by compounds represented by the following general formulae (Vd') to (Vg'):

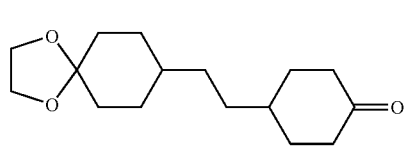
(Vd')

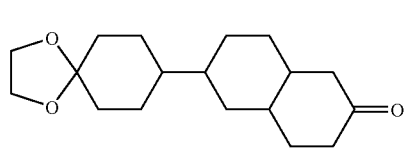
(Ve')

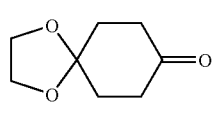
(Vf')

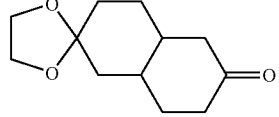
(Vg')

to obtain compounds represented by the general formulae (IaGa) to (IaMe), (IaZa) to (IaZe), (Ibaa) to (Ibde) and (Ibva) to (Ibye).

[IV] Process for the Preparation of Compounds Represented by the General Formulae (IaAa) to (IaFe), (IaNa) to (IaSe), (IaTa) to (IaXe) and (Ibsa) to (Ibue)

The procedure of the above process [I] can be followed except that the compound (Va) is replaced by compounds represented by the following general formulae (Vh) to (Vk):

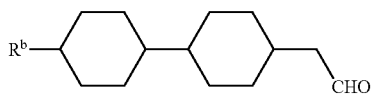

(Vh)

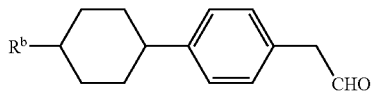

(Vi)

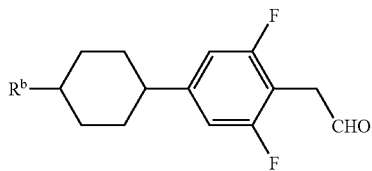

(Vj)

(Vk)

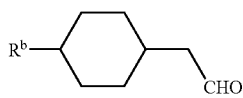

wherein $R^b$ is as defined above, and the compound (Vb) is replaced by the foregoing General Formulae (Vd') to (Vg') to obtain compounds represented by the General Formulae (IaAa) to (IaFe), (IaNa) to (IaSe), (IaTa) to (IaXe) and (Ibsa) to (Ibue).

[V] Process for the Preparation of Compounds Represented by the General Formulae (Iana) to (Iase), (Iata) to (Iaye), (Ibea) to (Ibhe), (Ibfa) to (Ibme) and (Ibna) to (Ibqe)

The procedure of the above process [II] can be followed except that the compound (Vc) is replaced by compounds represented by the following general formulae (Vm) to (Vr):

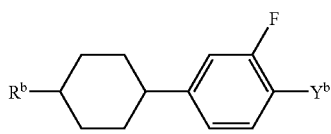

(Vm)

(Vn)

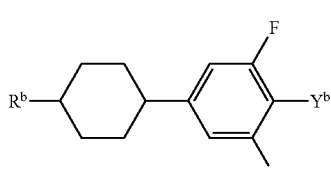

(Vp)

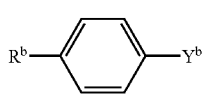

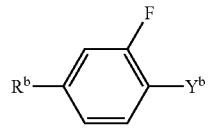

(Vq)

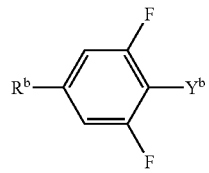

(Vr)

wherein R and $Y^b$ are as defined above, to obtain compounds represented by the General Formulae (Iana) to (Iases), (Iata) to (Iaye), (Ibea) to (Ibhe), (Ibfa) to (Ibme) and (Ibna) to (Ibqe).

[VI] Process for the Preparation of Compounds Represented by the General Formulae (Icaa) to (Icch)

(i) The procedure of the above process [I]-(i) can be followed except that the compound (Va) is replaced by the compound represented by the general formula (Vf) to obtain a compound represented by the following general formula (XXIVa):

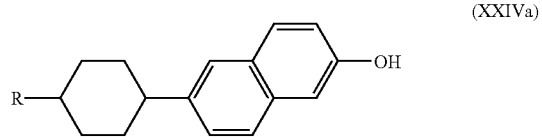

(XXIVa)

The procedure of the process [I]-(1)-(ix) can be followed except that the compound (IIIa) is replaced by the compound (XXIVa) to obtain compounds represented by the following general formulae (XXva) and (XXVIa):

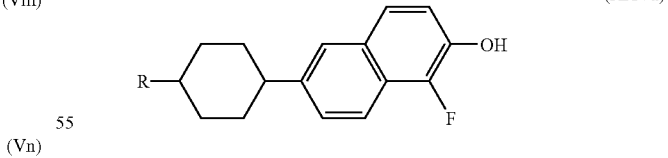

(XXVa)

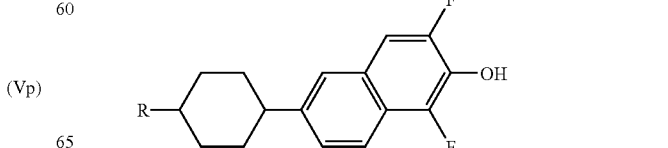

(XXVIa)

The compounds (XXIVa), (XXVa) and (XXVIa) can be reacted with trifluoromethanesulfonic acid anhydride or trifluoromethane sulfonic acid chloride in the presence of a base such as pyridine to obtain a sulfonate which is then allowed to undergo cross coupling reaction with a compound represented by the following general formula (XXVIIa):

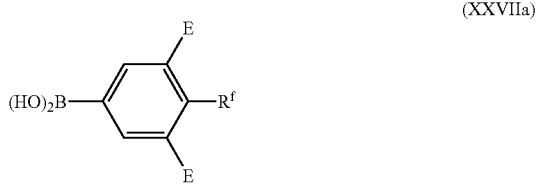

(XXVIIa)

wherein $R^f$ represents a hydrogen atom, fluoro group, trifluoromethoxy group, difluoromethoxy group or methoxy group; and E represents a hydrogen atom or fluorine atom, in the presence of a transition metal catalyst to produce compounds represented by the general formulae (Icaa) to (Icaf), (Icba) to (Icbf), (Icca) to (Iccf), (XXVIIIa) and (XXIXa):

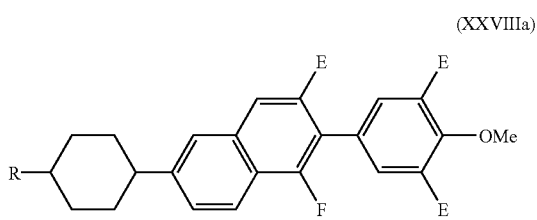

(XXVIIIa)

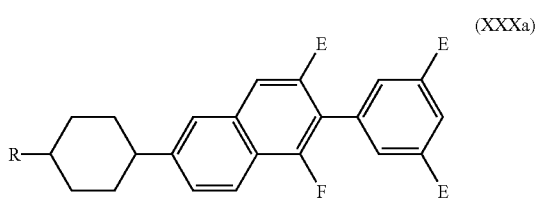

(XXXa)

wherein E is as defined above.

The compound (XXVIIa) thus obtained can be deprotected with hydrobromic acid, and then reacted with trifluoromethanesulfonic acid anhydride or trifluoromethane sulfonic acid chloride in the presence of a base such as pyridine to obtain a sulfonate which is then reacted with copper cyanide (I) or reacted with sodium cyanide or potassium cyanide in the presence of a transition metal catalyst to obtain compounds represented by the general formulae (Icag), (Icah), (Icbg), (Icbh), (Iccg) and (Icch).

[VII] Process for the Preparation of Compounds Represented by the General Formulae (Icda) to (Iceh)

The procedure of the above process [VI] can be followed except that the compound (Vf) is replaced by the compound (Vk) to produce compounds represented by the general formulae (Icda) to (Iceh).

[VIII] Process for the Preparation of Compounds Represented by the General Formulae (Icfa) to (Icgh)

(i) The procedure of the above process [II]-(1)-(i) can be followed except that the compound (Vc) is replaced by the compound (Vp) to obtain a compound represented by the following general formula (XXXa):

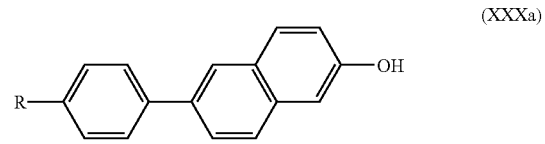

(XXXa)

(ii) The procedure of the above process [VI] can be followed except that the compound (XXIVa) is replaced by the compound (XXXa) to obtain compounds represented by the general formulae (Icfa) to (Icgh).

[IX] Process for the Preparation of Compounds Represented by the general formulae (Icha) to (Ichm), (Icia) to (Icim), (Idba) to (Idbm) and (Idca) to (Idcm)

The procedure of the above process [VIII] can be followed except that the compound (Vp) is replaced by compounds represented by the General Formulae (Vq), (Vr) and (Vs):

R—$Y^b$ (Vs)

to produce compounds represented by the general formulae (Icha) to (Ichm), (Icia) to (Icim), (Idba) to (Idbm) and (Idca) to (Idcm).

[X] Process for the Preparation of Compounds Represented by the General Formulae (Idba) to (Iefm)

The procedure of the above process [IX] can be followed except that the compound (XXVIIa) is replaced by a compound represented by the following general formula (XXVIIb):

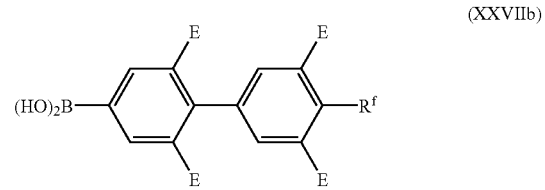

(XXVIIb)

to produce compounds represented by the general formulae (Icfa) to (Icgh).

Specific representative examples of the compound (I) of the present invention thus produced will be set forth in Tables 1 to 3 below together with their phase transition temperature.

TABLE 1
Compound represented by the general formula (Ib):
| No. | R—A—L$^a$— | 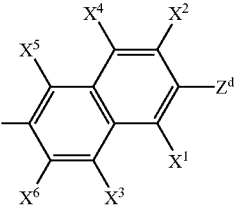 | Phase Transition Temperature (° C.) |
|---|---|---|---|
| Ib-1 |  | 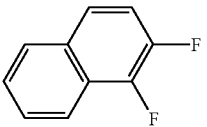 | Cr 48 (N 39) I |
| Ib-2 | 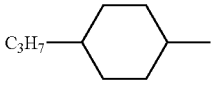 |  | Cr 42 I |
| Ib-3 | 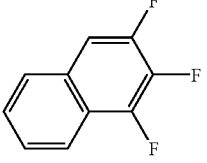 | 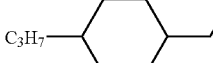 | C 69 N 142 I |
| Ib-4 |  | 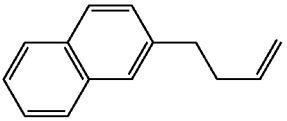 | C 118 N 176 I |

TABLE 2
Compound represented by the general formula (Ic):
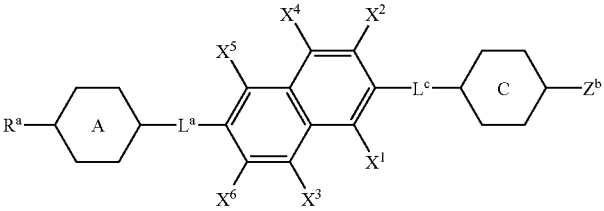
(Ic)
| No. | $R^a$—⬡(A)—$L^a$— | (naphthalene with $X^1$–$X^6$) | —$L^c$—⬡(C)—$Z^b$ | Phase Transition Temperature (° C.) |
|---|---|---|---|---|
| Ic-1 | 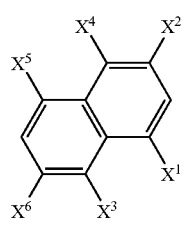 | 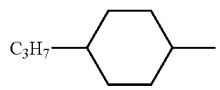 | 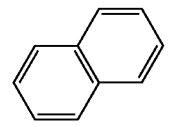 | Cr 99 N 200.5 I |
| Ic-2 | 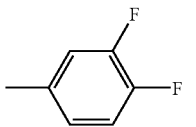 | 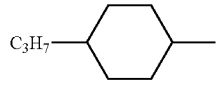 | 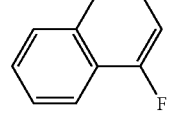 | Cr 85 N 198.5 I |
| Ic-3 | 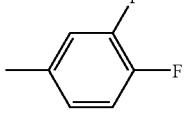 | 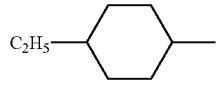 | 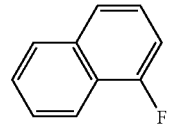 | C 79 I |
| Ic-4 | 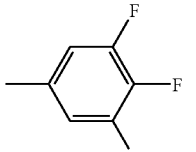 | 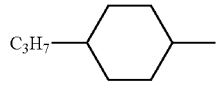 | 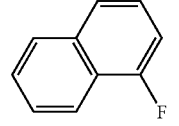 | Cr 92.5 N 158 I |
| Ic-5 | 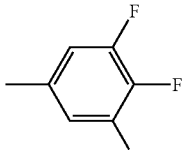 | 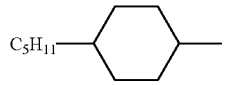 | 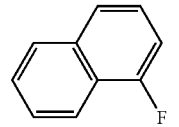 | Cr 72.5 N 155.5 I |
| Ic-6 | 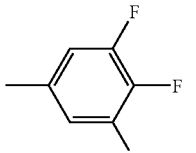 | 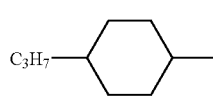 | 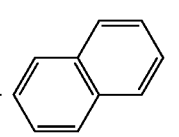 | Cr 110 N 166 I |

TABLE 2-continued
Compound represented by the general formula (Ic):
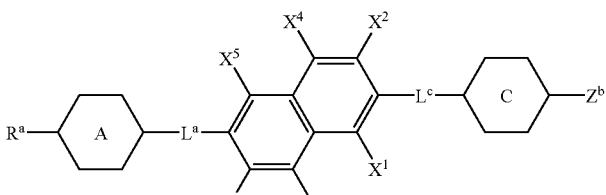
| No. | Rª—A—Lª— | 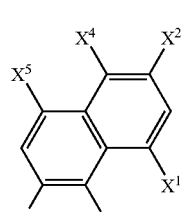 | —Lᶜ—C—Zᵇ | Phase Transition Temperature (° C.) |
|---|---|---|---|---|
| Ic-7 | 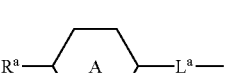 | 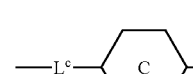 | 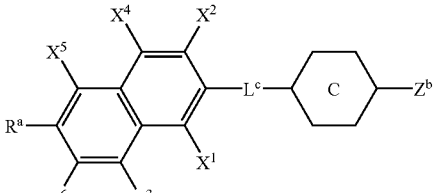 | Cr 134.5 N 134 I |
TABLE 3
Compound represented by the general formula (Id):
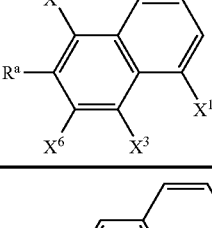
| No. | Rª—(naphthalene)— | —Lᶜ—C—Zᵇ | Phase Transition Temperature (° C.) |
|---|---|---|---|
| Id-1 | 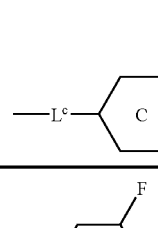 | 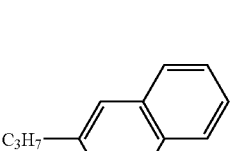 | Cr 62 I |
| Id-2 | 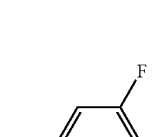 | | Cr 50 I |

TABLE 3-continued
Compound represented by the general formula (Id):
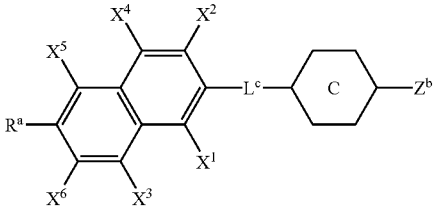
(Id)
| No. | 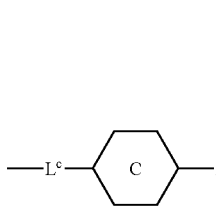 | 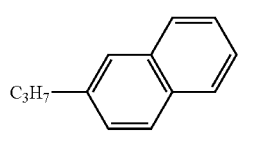 | Phase Transition Temperature (° C.) |
|---|---|---|---|
| Id-3 | 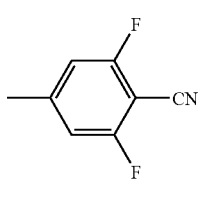 | 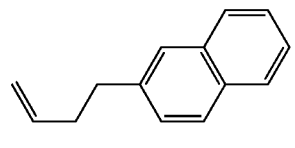 | C 112 (N 78.5) I |
| Id-4 | 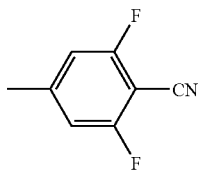 | 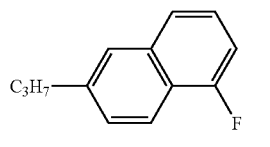 | Cr 128 I |
| Id-5 | 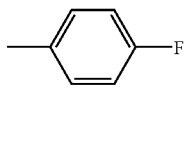 | 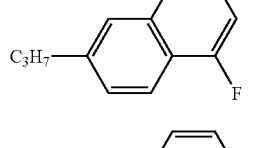 | Cr 109 I |
| Id-6 | 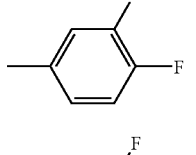 | 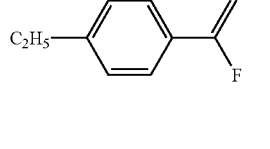 | Cr 74 (N 63) I |
| Id-7 | 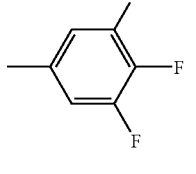 | | Cr −16 N 13 I |
| Id-8 | | | Cr 69.5 I |

TABLE 3-continued
Compound represented by the general formula (Id):
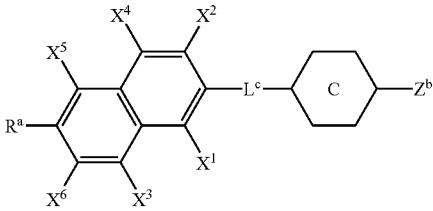
(Id)
| No. | 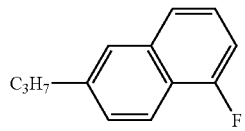 | —L$^c$—C—Z$^b$ | Phase Transition Temperature (° C.) |
|---|---|---|---|
| Id-9 | 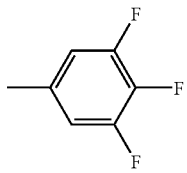 | 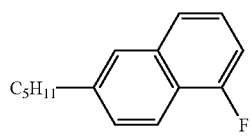 | Cr 38 I |
| Id-10 | 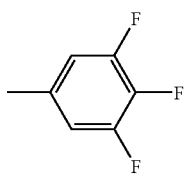 | 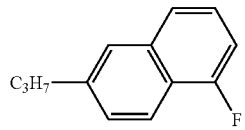 | Cr 27.5 I |
| Id-11 | 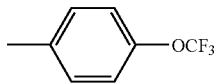 | 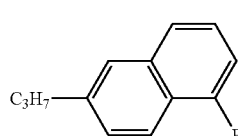 | Cr 70 S$_B$ 113 S$_A$ 119 I |
| Id-12 | 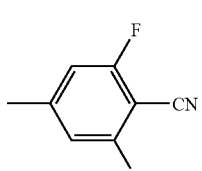 | | Cr 113 I |
(Cr represents crystalline phase, N represents nematic phase, and I represents isotropic liquid phase.)

The effects exerted by the incorporation of the compound (I) in the liquid crystal composition will be described hereinafter.

The compound represented by the general formula (Ib-1) set forth in Table 1:

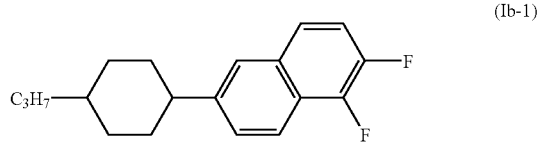

(Ib-1)

is added to a low viscosity host liquid crystal (H) having a wide operating temperature range, particularly a host liquid crystal (H) suitable for active matrix driving represented by the following general formula:

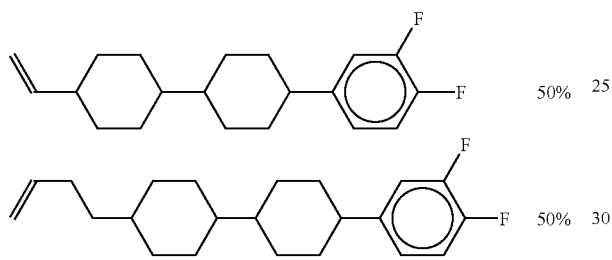

in an amount of 20% to prepare a nematic liquid crystal composition (M-1). The upper nematic phase temperature limit ($T_{N-1}$) was 98.2° C. The nematic liquid crystal composition (M-1) was allowed to stand at a temperature of 150° C. for 20 hours, and then measured for $T_{N-1}$. The results were 97.8° C., demonstrating that the nematic liquid crystal composition (M-1) showed little or no change of $T_{N-1}$ from before heating. The nematic liquid crystal composition (M-1) was irradiated with ultraviolet rays for 20 hours. However, the nematic liquid crystal composition (M-1) showed no change of $T_{N-1}$. The composition was then measured for voltage holding ratio. As a result, the composition exhibited a sufficiently high voltage holding ratio similarly to the host liquid crystal (H) during preparation, after heating and after irradiation with ultraviolet rays.

Subsequently, the nematic liquid crystal composition (M-1) was filled in a TN cell having a thickness of 4.5 μm to prepare a liquid crystal device. The liquid crystal device was then measured for electro-optical properties. The results are as follows:

| Upper nematic phase | |
|---|---|
| Temperature limit ($T_{N-1}$) | 98.6° C. |
| Dielectric anisotropy ($\Delta\epsilon$) | 4.60 |
| Threshold voltage (Vth) | 1.76 V |
| Response ($\tau$) | 21.5 m sec. |

On the other hand, the physical properties and electro-optical properties of the host liquid crystal (H) alone are as follows:

| Upper nematic phase | |
|---|---|
| temperature limit ($T_{N-1}$) | 116.7° C. |
| Dielectric anisotropy ($\Delta\epsilon$) | 4.80 |
| Threshold voltage (Vth) | 1.88 V |
| Response ($\tau$) | 21.5 m sec. |

The term "response" as used herein is meant to indicate the response time shown during the application of voltage at which the rise time ($\tau r$) and the drop time ($\tau d$) are equal to each other. The results show that the compound (Ib-1) exhibits a smaller dielectric anisotropy than the host liquid crystal (H) and a threshold voltage drop of about 10% from the host liquid crystal (H).

The compound represented by the general formula (Ib-2) set forth in Table 1:

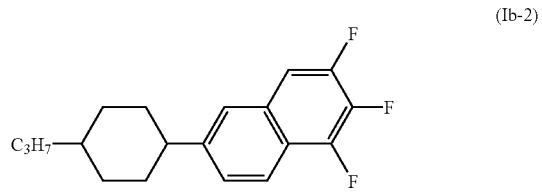

(Ib-2)

was then added to the host liquid crystal (H) in the same amount as mentioned above (20%) to prepare a liquid crystal composition (M-2).

$T_{N-1}$ of the nematic liquid crystal composition (M-2) and the electro-optical properties of the liquid crystal device prepared in the same manner as above from the composition (M-2) are as follows:

| Upper nematic phase | |
|---|---|
| temperature limit ($T_{N-1}$) | 92.7° C. |
| Dielectric anisotropy ($\Delta\epsilon$) | 5.7 |
| Threshold voltage (Vth) | 1.53 V |
| Response ($\tau$) | 28.0 m sec. |

It can thus be seen that the compound (Ib-2) exhibits a smaller dielectric anisotropy than the host liquid crystal (H) and a threshold voltage drop of about 20% from the host liquid crystal (H).

The nematic liquid crystal composition (M-2) was then subjected to thermal stability test and ultraviolet ray irradiation test in the same manner as the composition (M-1). As a result, the composition (M-2) showed no change of $T_{N-1}$ after these tests. The nematic liquid crystal composition (M-2) was then measured for voltage holding ratio. As a result, the composition (M-2) exhibited a sufficiently high voltage holding ratio during preparation, after heating and after irradiation with ultraviolet rays.

As mentioned above, the compound represented by the general formula (I) is very useful in the preparation of a liquid crystal composition having (a) a wide nematic phase operating temperature range, (b) a threshold voltage low enough to drive at a low voltage, (c) a quick response and (d) a voltage holding ratio high enough for active matrix driving.

The compound represented by the general formula (Ic-7) set forth in Table 2:

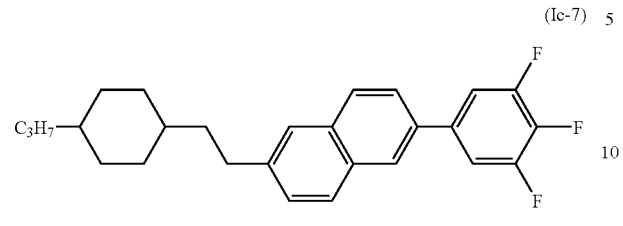

(Ic-7)

was added to a host liquid crystal composition (H) having a wide operating temperature range and a low viscosity which can be used also in active matrix driving in an amount of 20% by weight to prepare a liquid crystal composition (M-3). The physical properties of the host liquid crystal composition (H) and the electro-optical properties of the liquid crystal device prepared therefrom are as follows:

| | |
|---|---|
| $T_{N-I}$: | 116.7° C. |
| $T_{C-N}$: | +11° C. |
| Threshold voltage | 2.14 V |
| Dielectric anisotropy (Δε): | 4.8 |
| Birefringence index (Δn): | 0.090 |

For the measurement of threshold voltage (Vth), the nematic liquid crystal composition is packed into a TN cell having a thickness of 6 μm. The measurement is effected at a temperature of 20° C.

The physical properties of the nematic liquid crystal composition (M-3) and the electro-optical properties of the liquid crystal device prepared therefrom are as follows:

| | |
|---|---|
| $T_{N-I}$: | 120.0° C. |
| $T_{C-N}$: | –2° C. |
| Threshold voltage | 2.06 V |
| Dielectric anisotropy (Δε): | 5.5 |
| Birefringence index (Δn): | 0.110 |

It can thus be seen that the addition of the compound (Ic-7) makes it possible to raise the upper nematic phase temperature limit ($T_{N-I}$) by not lower than 3°. The nematic liquid crystal composition (M-3) was cooled to a temperature of –60° C. to undergo crystallization. The nematic liquid crystal composition (M-3) thus crystallized was then measured for melting point ($T_{C-N}$). The results were –2° C., demonstrating that the composition (M-3) exhibits a melting point drop of as much as 13° from the host liquid crystal composition (H). Accordingly, the stable temperature range of nematic phase can be expanded by as much as about 16°. It can also be seen that the incorporation of the compound (Ic-7) makes it possible to increase the dielectric anisotropy of liquid crystal composition and lower the threshold voltage of liquid crystal composition. The increase in the birefringence index could be suppressed to 0.02 from that of the host liquid crystal (H).

The liquid crystal device was then measured for voltage holding ratio at room temperature and 80° C. The results were extremely good at any of the two temperature ranges, demonstrating that it can be sufficiently used in active matrix driving.

A compound represented by the following general formula (R-1) having a structure similar to the compound (Ic-7) but having 1,4-phenylene group instead of 2,6-naphthylene group:

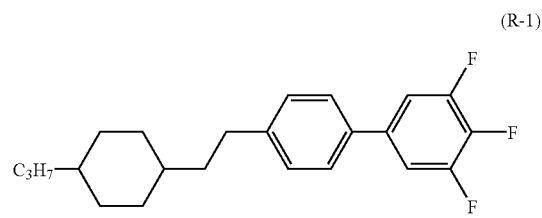

(R-1)

was added to the host liquid crystal composition (H) in the same amount as mentioned above (20%) to prepare a liquid crystal composition (HR-1). The upper nematic phase temperature limit ($T_{N-I}$) of the liquid crystal composition (HR-1) was 101° C., which is far lower than that of the composition (M-3) as expected. The liquid crystal composition (HR-1) exhibited a melting point ($T_{C-N}$) of 5° C., which is higher than that of the composition (M-3). Accordingly, the liquid crystal composition (HR-1) exhibited a nematic phase temperature range of as much as 25° or more smaller than the composition (M-3).

It can thus be seen that the composition (M-3) exerts a better effect than the conventional compounds to obtain a liquid crystal composition having a wide operating temperature range, a low threshold voltage and a proper birefringence index.

The compound represented by the general formula (Id-1) set forth in Table 3:

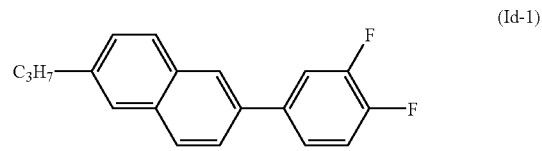

(Id-1)

was added to a host liquid crystal composition (H) having a wide operating temperature range and a low viscosity in an amount of 20% by weight to prepare a liquid crystal composition (M-4).

The physical properties of the compound (Id-1) and the electro-optical properties of the liquid crystal device prepared therefrom are as follows:

| | |
|---|---|
| $T_{N-I}$: | 91.0° C. |
| Threshold voltage (Vth) | 1.94 V |
| Dielectric anisotropy (Δε): | 4.85 |
| Response (τr = τd): | 28.4 m sec. |
| Birefringence index (Δn): | 0.112 |

It can thus be seen that the incorporation of the compound (Id-1) in an amount of 20% causes a slight drop of the upper nematic phase temperature limit ($T_{N-I}$) but makes it possible to lower the threshold voltage of the liquid crystal composition and drastically raise the birefringence index of the liquid crystal composition (by about 0.02 from that of the host liquid crystal composition (H)) without drastically deteriorating the response. Subsequently, the liquid crystal composition was allowed to stand at room temperature for 1 month. However, no crystallization or phase separation were observed. It can thus be seen that the compound (Id-1) has an excellent miscibility with the conventional liquid crystals. The liquid crystal composition (M-4) was cooled to a temperature of −15° C. to undergo crystallization, and then measured for melting point ($T_{C-N}$). The results were 14° C.

On the other hand, a compound represented by the general formula (R-2) having a structure similar to that of the compound (Id-1) but having a biphenyl skeleton:

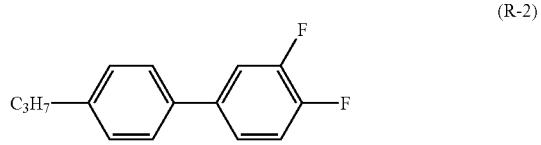

(R-2)

was added to the host liquid crystal composition (H) in the same amount as mentioned above (20% by weight) to prepare a liquid crystal composition (HR-2). The liquid crystal composition (HR-2) thus prepared was then measured for physical properties and electro-optical properties in the same manner as mentioned above. The results are as follows:

| | |
|---|---|
| $T_{N-1}$: | 86.0° C. |
| Threshold voltage (Vth): | 1.86 V |
| Dielectric anisotropy (Δε): | 4.92 |
| Response (τr = τd): | 27.0 m sec. |
| Birefringence index (Δn): | 0.096 |

The comparison of the liquid crystal composition (HR-2) with the liquid crystal composition (H-1) shows that the liquid crystal composition (HR-2) exhibits a slightly higher response and a slightly lower threshold voltage (Vth). However, the upper nematic phase temperature limit ($T_{N-1}$) of the liquid crystal composition (HR-2) showed a further drop. The liquid crystal composition (HR-2) also showed only a slight increase in birefringence index.

Subsequently, the compound represented by the general formula (Id-2) set forth in Table 1:

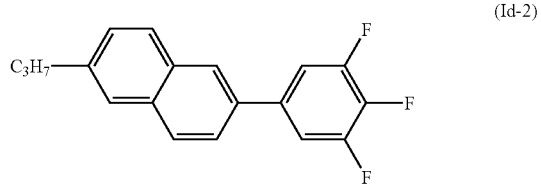

(Id-2)

was added to the liquid crystal composition (H) in the same amount as mentioned above (20%) to prepare a liquid crystal composition (M-5). The physical properties of the liquid crystal composition (M-5) and the electro-optical properties of the liquid crystal device prepared therefrom are as follows:

| | |
|---|---|
| $T_{N-1}$: | 85.1° C. |
| Threshold voltage (Vth): | 1.74 V |

-continued

| | |
|---|---|
| Dielectric anisotropy (Δε): | 5.7 |
| Response (τr = τd): | 31.1 m sec. |
| Birefringence index (Δn): | 0.107 |

The comparison of the liquid crystal composition (M-5) with the liquid crystal composition (M-4) shows that the liquid crystal composition (M-5) exhibits a slightly lower $T_{N-1}$ and a slightly reduced birefringence index but has a quick response similarly to the liquid crystal composition (M-4) and a further drop of threshold voltage.

The compound represented by the general formula (Id-7) set forth in Table 3:

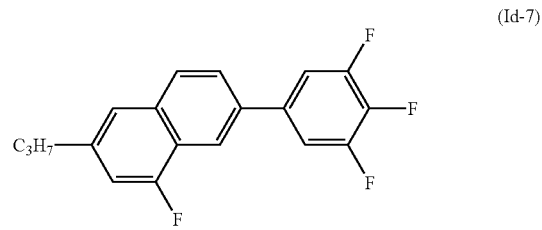

(Id-7)

exhibits a melting point of −16° C. and a nematic phase up to 13° C. On the contrary, the compound (Id-1) having a skeleton structure similar to that of the compound (Id-7) but having naphthalene ring not substituted by fluorine is a crystalline material having a melting point of 62.5° C. which shows no liquid-crystallinity. The liquid crystal composition obtained by adding the liquid crystal composition (Id-1) to a widely used host liquid crystal showed $T_{N-1}$ of −12° C. Thus, the compound (Id-7) exhibits a better liquid-crystallinity.

It can thus be seen that the compound represented by the general formula (Id-7) causes no deterioration of liquid-crystallinity despite of the drop of melting point due to the incorporation of fluorine in naphthalene ring.

The foregoing compound (Id-7) was added to the host liquid crystal composition (H) in an amount of 20% by weight to prepare a liquid crystal composition (M-6).

| | |
|---|---|
| $T_{N-1}$: | 86.0° C. |
| $T_{C-N}$: | 12° C. |
| Threshold voltage (Vth): | 1.65 V |
| Dielectric anisotropy (Δε): | 6.5 |
| Birefringence index (Δn): | 0.107 |
| Response (τr = τd): | 28.8 m sec. |

The incorporation of the compound (Id-7) in an amount of 20% causes a slight drop of the upper nematic phase temperature limit ($T_{N-1}$) but can provide a high speed response similarly to the host liquid crystal composition (H) and makes it possible to drastically lower the threshold voltage of the liquid crystal composition (by 0.3 V). Further, the birefringence of the liquid crystal composition can be drastically increased from the host liquid crystal composition (H).

The liquid crystal device was then measured for voltage holding ratio at room temperature and 80° C. The results were good at any of the two temperature ranges, demonstrating that the liquid crystal device can be sufficiently used in active matrix driving.

It can thus be seen that the compound represented by the general formula (Id) of the present invention exerts a better effect than the conventional compounds to obtain a low viscosity, an excellent response, a large birefringence index, a wide nematic phase operating temperature range, and a low threshold voltage.

Accordingly, the compound (I), when used in admixture with other nematic liquid crystal compounds, can be preferably used as a liquid crystal material for field effect type display call such as TN type and STN type display cells, particularly liquid crystal material which can operate at a wide temperature range and can be driven at a low voltage. Further, the compound represented by the general formula (I) has no strongly polar group in its molecule and thus can easily provide a large specific resistivity and a high voltage holding ratio. Thus, the compound represented by the general formula (I) can also be used as a constituent of liquid crystal material for active matrix driving. The present invention provides a liquid crystal composition comprising as a constituent at least one of the compounds represented by the general formula (I) and a liquid crystal device comprising the liquid crystal composition.

Specific representative examples of the nematic liquid crystal compound which can be used in admixture with the compound represented by the general formula (I) include phenyl benzoate derivative, phenyl cyclohexanecarboxylate derivative, biphenyl-4-yl cyclohexanecarboxylate derivative, phenyl cyclohexanecarbonyloxybenzoate derivative, phenyl cyclohexanecarboxylate derivative, phenyl cyclohexylbenzoate derivative, cyclohexyl cyclohexylbenzoate derivative, biphenyl derivative, cyclohexylbenzene derivative, terphenyl derivative, bicyclohexane derivative, 4-cyclohexylbiphenyl derivative, 4-phenylbicyclohexane derivative, tercyclohexane derivative, 1,2-dicyclohexylethane derivative, 1,2-diphenylethane derivative, 1,2-diphenylethine derivative, (2-cyclohexylethyl)benzene derivative, 4-phenethylbicyclohexane derivative, 4-(2-cyclohexylethyl)biphenyl derivative, 1-(4-phenyl)cyclohexyl-2-cyclohexylethane derivative, 1-(4-cyclohexylphenyl)-2-phenylethine derivative, phenylpyrimidine derivative, (4-biphenyl-4-yl) pyrimidine derivative, phenylpyridine derivative, and (4-biphenyl-4-yl)pyridine derivative. Particularly preferred for active matrix drive among these derivatives are biphenyl derivative, cyclohexylbenzene derivative, terphenyl derivative, bicyclohexane derivative, 4-cyclohexylbiphenyl derivative, 4-phenylbicyclohexane derivative, tercyclohexane derivative, 1,2-dicyclohexylethane derivative, 1,2-diphenylethane derivative, 1,2-diphenylethine derivative, (2-cyclohexylethyl)benzene derivative, 4-phenethylbicyclohexane derivative, 4-(2-cyclohexylethyl)biphenyl derivative, 1-(4-phenyl)cyclohexyl-2-cyclohexylethane derivative, and 1-(4-cyclohexylphenyl)-2-phenylethine derivative.

EXAMPLES

The present invention will be further described in the following examples, but the present invention should not be construed as being limited thereto.

The structure of compounds were identified by nuclear magnetic resonance spectrum (NMR), mass spectrum (MS) and infrared absorption spectrum (IR). The term "%" as used hereinafter is meant to indicate % by weight.

Example 1

Synthesis of 2-(3,4-difluorophenyl)-6-(trans-4-propylcyclohexyl)naphthalene (1-a) Synthesis of 2-methoxy-6-(4-propylcyclohexa-1-ene-1-yl)naphthalene 5.7 g of magnesium was suspended in 12 ml of tetrahydrofuran. To the suspension was then added dropwise a solution of 50 g of 6-bromo-2-methoxynaphthalone in 200 ml of tetrahydrofuran at a rate such that tetrahydrofuran was gently refluxed. The reaction mixture was then further stirred for 1 hour. To the reaction solution was then added dropwise a solution of 30 g of 4-propylcyclohexanene in 120 ml of tetrahydrofuran at room temperature. The reaction mixture was then further stirred for 1 hour. To the reaction solution was then added 200 ml of a 10% hydrochloric acid. The reaction mixture was extracted with 300 ml of toluene, washed with water, saturated aqueous solution of sodium bicarbonate and saturated brine, and then dried over anhydrous sodium sulfate. The solvent was then distilled off. To the residue were then added 280 ml of toluene and 4.0 g of p-toluenesulfonic acid monohydrate. The reaction mixture was then heated under reflux for 3 hours. The reaction solution was allowed to cool to room temperature, washed with water, saturated aqueous solution of sodium bicarbonate and saturated brine, and then dried over anhydrous sodium sulfate. The solvent was then distilled off. The residue was then recrystallized from ethanol to obtain 44.8 g of 2-methoxy-6-(4-propylcyclohexa-1-ene-1-yl)naphthalene.

(1-b) Synthesis of 2-methoxy-6-(trans-4-propyloyclohexyl)naphthalene 44.8 g of 2-methoxy-6-(4-propylcyclohexa-1-ene-1-yl)naphthalene was dissolved in 800 ml of ethyl acetate. To the solution was then added 10 g of 5% palladium carbon. The reaction mixture was then stirred at a hydrogen pressure of 4 kg/cm$^2$ for 6 hours. The catalyst was then removed by filtration. The solvent was then distilled off. The residue was then dissolved in 180 ml of N,N-dimethylformamide. To the solution was then added 18 g of potassium t-butoxide. The reaction mixture was then heated to a temperature of 120° C. with stirring for 1 hour. The reaction solution was then allowed to cool to room temperature. To the reaction solution was then added 70 ml of a 10% hydrochloric acid to causes crystallization. The crystal thus precipitated was filtered off, washed with water, and then dried under reduced pressure. The crystal was then recrystallized from ethanol to obtain 28.0 g of 2-methoxy-6-(trans-4-propylcyclohexyl)naphthalene.

(1-c) Synthesis of 6-(trans-4-propylcyclohexyl)-2-naphthol

To 28.0 g of 2-methoxy-6-(trans-4-propylcyclohexyl) naphthalene were added 280 ml of acetic acid and 280 ml of 48% hydxobromic acid. The reaction mixture was then heated under reflux for 12 hours. The reaction solution was then allowed to cool to room temperature. To the reaction solution was then added 500 ml of water to cause crystallization. The crystal thus precipitated was then filtered off. The crystal was washed with water, and then dried under reduced pressure to obtain 26.8 g of 6-(trans-4-propylcyclohexyl)-2-naphthol.

(1-d) Synthesis of 6-(trans-4-propylcyclohexyl)naphthalene-2-yl trifluoromethanesulfonate To 25.0 g of 6-(trans-4-propylcyclohexyl)-2-naphthol were added 100 ml of dichloromethane and 30 g of trifluoromethanesulfonic anhydride. The reaction mixture was then cooled to a temperature of 5° C. To the reaction mixture was then added a solution of 11.0 g of pyridine in 40 ml of dichloromethane at a rate such that the resulting temperature didn't exceed 20° C. After the termination of dropwise addition, the reaction mixture was returned to room temperature with stirring. To the reaction mixture was then added 150 ml of water. The resulting organic phase was washed with water and saturated brine, and then dried over anhydrous sodium sulfate. The solvent was then distilled off. The residue was then purified through silica gel column chromatography (solvent: dichloromethane) to obtain 36.7 g of 6-(trans-4-propylcyclohexyl)naphthalene-2-yl trifluoromethane sulfonate.

(1-e) Synthesis of 2-(3,4-difluorophenyl)-6-(trans-4-propylcyclohexyl)naphthalene 1.0 g of magnesium was suspended in 2 ml of tetrahydrofuran. To the suspension was then added dropwise a solution of 7.0 g of 3,4-difluoro-1-bromobenzene in 35 ml of tetrahydrofuran at a rate such that tetrahydrofuran was gently refluxed. The reaction mixture was then further stirred at room temperature for 1 hour. Excessive magnesium was removed by filtration. The reaction solution was then added dropwise to a solution of 10.0 g of 6-(trans-4-propylcyclohexyl)naphthalene-2-yl trifluoromethane sulfonate and 0.3 g of tetrakis(triphenylphosphine)palladium in 50 ml of tetrahydrofuran at room temperature. The reaction mixture was then stirred at room temperature for 1 hour. To the reaction mixture was then added 100 ml of water. The reaction mixture was extracted with 200 ml of toluene, washed with water and saturated brine, and then dried over anhydrous sodium sulfate. The solvent was then distilled off. The residue was purified through silica gel column chromatography (hexane), and then recrystallized from ethanol to obtain 7.1 g of a purified material. (Cr 90 N 200.5 I)

The following compounds were similarly obtained.

2-(3,4-Difluorophenyl)-6-(trans-4-ethylcyclohexyl)naphthalene 2-(3,4-Difluorophenyl)-6-(trans-4-butylcyclohexyl)naphthalene 2-(3,4-Difluorophenyl)-6-(trans-4-pentylcyclohexyl)naphthalene 2-(3,4,5-Trifluorophenyl)-6-(trans-4-ethylcyclohexyl)naphthalene 2-(3,4,5-Trifluorophenyl)-6-(trans-4-propylcyclohexyl)naphthalene 2-(3,4,5-Trifluorophenyl)-6-(trans-4-butylcyclohexyl)naphthalene 2-(3,4,5-Trifluorophenyl)-6-(trans-4-pentylcyclohexyl)naphthalene Example 2

Synthesis of 2-(3,4,5-trifluorophenyl)-6-[2-(trans-4-propyloyclohexyl)ethyl]naphthalene (2-a) Synthesis of 6-(3,4,5-trifluorophenyl)naphthalene-2-yl trifluoromethanesulfonate To 25.0 g of 6-(3,4,5-trifluorophenyl)-2-hydroxynaphthalene were added 200 ml of dichloromethane and 34.0 g of trifluoromethanesulfonic anhydride. The reaction mixture was then cooled to a temperature of 5° C. To the reaction mixture was then added a solution of 12.0 g of pyridine in 48 ml of dichloromethane at a rate such that the resulting temperature didn't exceed 20° C. After the termination of dropwise addition, the reaction mixture was returned to room temperature with stirring. To the reaction mixture was then added 200 ml of water. The resulting organic phase was washed with water and saturated brine, and then dried over anhydrous sodium sulfate. The solvent was then distilled off. The residue was then purified through silica gel column chromatography (dichloromethane) to obtain 37.3 g of 6-(3,4,5-trifluorophenyl)naphthalene-2-yl trifluoromethanesulfonate.

(2-b) Synthesis of 2-(trans-4-propylcyclohexyl)ethynyl-6-(3,4,5-trifluorophenyl)naphthalene 25.0 g of 6-(3,4,5-trifluorophenyl)naphthalene-2-yl trifluoromethanesulfonate and 1-ethynyl-4-propylcyclohexane were dissolved in a mixture of 125 ml of N,N-dimethylformamide and 25 ml of triethylamine. To the solution were then added 0.7 g of tetrakis(triphenylphosphine)palladium and 0.2 g of copper iodide (I). The reaction mixture was then stirred at a temperature of 50° C. for 3 hours. The reaction solution was then allowed to cool to room temperature. To the reaction solution was then added 150 ml of water. The reaction solution was extracted with 200 ml of toluene, washed with water and saturated brine, and then dried over anhydrous sodium sulfate. The solvent was then distilled off. The residue was then recrystallized from ethanol to obtain 17.6 g of 2-(trans-4-propylcyclohexyl)ethynyl-6-(3,4,5-trifluorophenyl)naphthalene.

(2-c) Synthesis of 2-(3,4,5-trifluorophenyl)-6-[2-(trans-4-propylcyclohexyl)ethyl]naphthalene 17.6 g of 2-(trans-4-propylcyclohexyl)ethynyl-6-(3,4,5-trifluorophenyl)naphthalene was dissolved in 400 ml of tetrahydrofuran. To the solution was then added 5 g of 5% palladium carbon. The reaction mixture was then stirred at a hydrogen pressure of 5 kg/cm$^2$ for 6 hours. The catalyst was then removed by filtration. The solvent was then distilled off. The residue was purified through silica gel column chromatography (hexane), and then recrystallized from ethanol to obtain 11.5 g of a purified product. (Cr 62 N 134 I)

The following compounds were prepared in the same manner as mentioned above.

2-(3,4,5-Trifluorophenyl)-6-[2-(trans-4-ethylcyclohexyl)ethyl]naphthalene 2-(3,4,5-Trifluorophenyl)-6-[2-(trans-4-butylcyclohexyl)ethyl]naphthalene 2-(3,4,5-Trifluorophenyl)-6-[2-(trans-4-pentylcyclohexyl)ethyl]naphthalene 2-(3,4-Difluorophenyl)-6-[2-(trans-4-ethylcyclohexyl)ethyl]naphthalene 2-(3,4-Difluorophenyl)-6-[2-(trans-4-propylcyclohexyl)
ethyl]naphthalene Cr 110 N 166 I
2-(3,4-Difluorophenyl)-6-[2-(trans-4-butylcyclohexyl)
ethyl]naphthalene
2-(3,4-Difluorophenyl)-6-[2-(trans-4-pentylcyclohexyl)
ethyl]naphthalene Example 3

Synthesis of 2-(3,4-difluorophenyl)-6-(trans-4-vinylcyclohexyl)naphthalene

The Grignard reaction of Example (1-a) was followed except that 1,4-cyclohexadione monoethylene acetal was used instead of 4-propylcyclohexanene. The reaction product was then dehydrated with potassium hydrogensulfate. To the toluene solution was then added ethylene glycol. The reaction mixture was then heated under reflux while the azeotropically distilled water was being driven out of the system. The reaction solution was allowed to cool to room temperature, washed sequentially with water, saturated aqueous solution of sodium bicarbonate and saturated brine, and then dehydrated and dried over anhydrous sodium sulfate. The solvent was then distilled off to obtain 4-(6-methoxynaphthalene-2-yl)-3-cyclohexenone ethylene acetal. The product was dissolved in toluene, and then subjected to catalytic reduction in the same manner as (1-b). To the reaction solution was then added formic acid. The reaction mixture was heated with stirring, and then cooled. To the reaction solution was then added water. The resulting toluene phase was then washed. The solvent was then distilled off. The resulting crude crystal was then recrystallized from ethanol to obtain 4-(6-methoxy naphthalene-2-yl)cyclohexanene in crystal form. The crystal thus obtained was dissolved in a mixture of toluene and THF, and then cooled. To the reaction solution was then added a Wittig reagent prepared from methoxymethyltriphenylphosphonium bromide and potassium t-butoxide. The reaction mixture was then returned to room temperature. To the reaction mixture were then added water and hexane. Insoluble matters were then removed from the resulting hexane phase by filtration. The residue was then washed with a mixture of water and methanol. The solvent was then distilled off. The residue was then dissolved in THF. To the solution was then added diluted hydrochloric acid. The reaction solution was heated under reflux for 1 hour, and then cooled. To the reaction solution was then added water. The reaction solution was then extracted with ethyl acetate. The solvent was then distilled off. The residue was then dissolved in ethanol. To the solution was then added a 20% aqueous solution of sodium hydroxide. The reaction mixture was then stirred at room temperature. To the reaction solution was then added water. The reaction solution was extracted with toluene, washed, and then dried. The solvent was then distilled off to obtain trans-4-(6-methoxynaphthalene-2-yl)cyclohexanecarbaldehyde in crystal form. The crystal thus obtained was dissolved in THF. To the reaction solution was then added a Wittig reagent prepared from methyltriphanylphosphonium iodide and potassium t-butoxide. The reaction mixture was then returned to room temperature. To the reaction mixture were then added water and hexane. Insoluble matters were then removed from the resulting hexane phase by filtration. The residue was washed with a mixture of water and methanol, and then dried. The solvent was then distilled off. The residue was then purified through silica gel column chromatography (toluene) to obtain 2-(trans-4-vinylcyclohexyl)-6-methoxynaphthalene in crystal form. The crystal was then processed in the same manner as (1-c), (1-d) and (1-e) to obtain the titled 2-(3,4-difluorophenyl)-6-(trans-4-vinylcyclohexyl)naphthalene.

The following compounds were prepared in the same manner as mentioned above.

2-(3,4-Difluorophenyl)-6-[trans-4-(3-butenyl)cyclohexyl] naphthalene
2-(3,4,5-Trifluorophenyl)-6-(trans-4-vinylcyclohexyl)naphthalene
2-(3,4,5-Trifluorophenyl)-6-[trans-4-(3-butenyl)cyclohexyl]naphthalene Example 4

Synthesis of 1-fluoro-2-(3,4-difluorophenyl)-6-propylnaphthalene (4-a) Synthesis of 2-methoxy-6-propylnaphthalene To a solution of 200 g of 2-bromo-6-methoxynaphthalene and 2.5 g of dichloro[1,2-bis(diphenylphosphino)ethane] nickel (II) in 200 ml of tetrahydrofuran (THF) was added dropwise a Grignard reagent prepared from 125 g of propyl bromide and 27 g of magnesium under nitrogen atomsphere. The reaction mixture was further stirred for 1 hour, and then poured into water. To the reaction mixture was then added diluted hydrochloric acid. The resulting organic phase was then separated. The resulting aqueous phase was extracted with toluene. The organic phase and the material thus extracted were together washed sequentially with water, saturated aqueous solution of sodium bicarbonate, water and saturated brine, and then dehydrated and dried over anhydrous sodium sulfate. The solvent was then distilled off to obtain 172 g of 2-methoxy-6-propylnaphthalene.

(4-b) Synthesis of 6-propyl-2-naphthol

The total amount (172 g) of 2-methoxy-6-propylnaphthalene obtained in the process (4-a) was added to a mixture of 680 ml of acetic acid and 680 ml of a 48% hydrobromic acid. The reaction mixture was heated under reflux for 8 hours. The reaction solution was then allowed to cool to room temperature. To the reaction solution was then added 1,300 ml of water. The resulting crystal was filtered off, and then washed with water. The resulting crystal was dissolved in 1,000 ml of ethyl acetate, and then washed sequentially with water, saturated aqueous solution of sodium bicarbonate, water and saturated brine. The product was then dehydrated and dried over anhydrous sodium sulfate. The solvent was then distilled off to obtain 152 g of 6-propyl-2-naphthol in the form of crude crystal form.

(4-c) Synthesis of 1-fluoro-6-propyl-2-naphthol

To a solution of 20 g of 6-propyl-2-naphthol and 1.8 g of sodium trifluoromethanesulfonate in 80 ml of dichloromethane was added 23.7 g of N,N'-difluoro-2,21'-dipyridinium bistetrafluoroborate. The reaction mixture was then stirred for 8 hours. The reaction solution was then poured in water. To the reaction mixture was then added diluted hydrochloric acid. The resulting organic phase was then separated. The resulting aqueous phase was extracted with toluene. The organic phase and the material thus extracted were together washed sequentially with water and saturated brine, and then dehydrated and dried over anhydrous sodium sulfate. The solvent was then distilled off to obtain an oily matter which was then purified through silica gel column chromatography (hexane/ethyl acetate=9/1) to obtain 17.1 g of 1-fluoro-6-propyl-2-naphthol.

(4-d) Synthesis of 1-fluoro-6-propylnaphthalene-2-yl trifluoromethanesulfonate The total amount (17.1 g) of 1-fluoro-6-propyl-2-naphthol obtained in the process (4-c) and 25.1 g of trifluoromethanesulfonic anhydride were dissolved in 80 ml of dichloromethane. To the solution was then added dropwise 15.9 ml of pyridine. The reaction mixture was then further stirred for 1 hour. To the reaction solution was then added diluted hydrochloric acid. The resulting organic phase was separated. The resulting aqueous phase was then extracted with toluene. The organic phase and the material thus extracted were washed sequentially with water and saturated brine, and then dehydrated and dried over anhydrous sodium sulfate. The solvent was distilled off to obtain a crystal which was then purified though silica gel column chromatography to obtain 24.2 g of 1-fluoro-6-propylnaphthalene-2-yl trifluoromethanesulfonate.

(4-e) Synthesis of 1-fluoro-2-(3,4-difluorophenyl)-6-propyl naphthalene 20 g of 1-fluoro-6-propylnaphthalene-2-yl trifluoromethanesulfonate obtained in the process (4-d) and dibromobis(triphenylphosphine)nickel (II) were dissolved in 80 ml of THF. To the solution was added dropwise a Grignard reagent prepared from 25.8 g of 3,4-difluorobromobenzene and 3.2 g of magnesium under a nitrogen atomsphere. The reaction mixture was further stirred for 1 hour. To the reaction solution was then added diluted hydrochloric acid. The resulting organic phase was then separated. The resulting aqueous phase was then extracted with toluene. The organic phase and the material thus extracted were together washed sequentially with water, saturated aqueous solution of sodium bicarbonate and saturated brine, and then dehydrated and dried over anhydrous sodium sulfate. The solvent was then distilled off to obtain a crystal. The crystal thus obtained was purified through silica gal column chromatography (hexane), and then subjected to distillation to obtain 6.5 g of 1-fluoro-2-(3,4-difluorophenyl)-6-propylnaphthalene. Cr-16 N 13 I The following compounds were prepared in the same manner as mentioned above.
1-Fluoro-2-(3,4-difluorophenyl)-6-ethylnaphthalene
1-Fluoro-2-(3,4-difluorophenyl)-6-butylnaphthalene
1-Fluoro-2-(3,4-difluorophenyl)-6-pentylnaphthalene
1-Fluoro-2-(3,4-difluorophenyl)-6-hexylnaphthalene
1-Fluoro-2-(3,4-difluorophenyl)-6-heptylnaphthalene
1-Fluoro-2-(3,4-difluorophenyl)-6-(3-butenyl)naphthalene
1-Fluoro-2-(3,4,5-trifluorophenyl)-6-ethylnaphthalene
1-Fluoro-2-(3,4,5-trifluorophenyl)-6-propylnaphthalene
1-Fluoro-2-(3,4,5-trifluorophenyl)-6-butylnaphthalene
1-Fluoro-2-(3,4,5-trifluorophenyl)-6-pentylnaphthalene
1-Fluoro-2-(3,4,5-trifluorophenyl)-6-hexylnaphthalene
1-Fluoro-2-(3,4,5-trifluorophenyl)-6-heptylnaphthalene
1-Fluoro-2-(3,4,5-trifluorophenyl-6-naphthalene
1-Fluoro-2-(4-fluorophenyl)-6-ethylnaphthalene
1-Fluoro-2-(4-fluorophenyl)-6-propylnaphthalene
1-Fluoro-2-(4-fluorophenyl)-6-butylnaphthalene
1-Fluoro-2-(4-fluorophenyl)-6-pentylnaphthalene
1-Fluoro-2-(4-fluorophenyl)-6-hexylnaphthalene
1-Fluoro-2-(4-fluorophenyl)-6-heptylnaphthalene
1-Fluoro-2-(4-fluorophenyl)-6-(3-butenyl)naphthalene
1-Fluoro-2-(3-fluorophenyl)-6-ethylnaphthalene
1-Fluoro-2-(3-fluorophenyl)-6-propylnaphthalene
1-Fluoro-2-(3-fluorophenyl)-6-butylnaphthalene
1-Fluoro-2-(3-fluorophenyl)-6-pentylnaphthalene
1-Fluoro-2-(3-fluorophenyl)-6-hexylnaphthalene
1-Fluoro-2-(3-fluorophenyl)-6-heptylnaphthalene
1-Fluoro-2-(3-fluorophenyl)-6-(3-butenyl)naphthalene
1-Fluoro-2-(3,5-difluorophenyl)-6-ethylnaphthalene
1-Fluoro-2-(3,5-difluorophenyl)-6-propylnaphthalene
1-Fluoro-2-(3,5-difluorophenyl)-6-butylnaphthalene
1-Fluoro-2-(3,5-difluorophenyl)-6-pentylnaphthalene
1-Fluoro-2-(3,5-difluorophenyl)-6-hexylnaphthalene
1-Fluoro-2-(3,5-difluorophenyl)-6-heptylnaphthalene
1-Fluoro-2-(3,5-difluorophenyl)-6-(3-butenyl)naphthalene
1-Fluoro-2- phenyl-6-ethylnaphthalene
1-Fluoro-2-phenyl-6-propylnaphthalene
1-Fluoro-2-phenyl-6-butylnaphthalene
1-Fluoro-2-phenyl-6-pentylnaphthalene
1-Fluoro-2-phenyl-6-hexylnaphthalene
1-Fluoro-2-phenyl-6-heptylnaphthalene
1-Fluoro-2-phenyl-6-(3-butenyl)naphthalene
1-Fluoro-2-(4-chlorophenyl)-6-ethylnaphthalene
1-Fluoro-2-(4-chlorophenyl)-6-propylnaphthalene
1-Fluoro-2-(4-chlorophenyl)-6-butylnaphthalene
1-Fluoro-2-(4-chlorophenyl)-6-pentylnaphthalene
1-Fluoro-2-(4-chlorophenyl)-6-hexylnaphthalene
1-Fluoro-2-(4-chlorophenyl)-6-heptylnaphthalene
1-Fluoro-2-(4-chlorophenyl)-6-(3-butenyl)naphthalene
1-Fluoro-2-(3-fluoro-4-chlorophenyl)-6-ethylnaphthalene
1-Fluoro-2-(3-fluoro-4-chlorophenyl)-6-propylnaphthalene
1-Fluoro-2-(3-fluoro-4-chlorophenyl)-6-butylnaphthalene
1-Fluoro-2-(3-fluoro-4-chlorophenyl)-6-pentylnaphthalene
1-Fluoro-2-(3-fluoro-4-chlorophenyl)-6-hexylnaphthalene
1-Fluoro-2-(3-fluoro-4-chlorophenyl)-6-heptylnaphthalene
1-Fluoro-2-(3-fluoro-4-chlorophenyl)-6-(3-butenyl)naphthalene
1-Fluoro-2-(3,5-difluoro-4-chlorophenyl)-6-ethylnaphthalene
1-Fluoro-2-(3,5-difluoro-4-chlorophenyl)-6-propylnaphthalene
1-Fluoro-2-(3,5-difluoro-4-chlorophenyl)-6-butylnaphthalene
1-Fluoro-2-(3,5-difluoro-4-chlorophenyl)-6-pentylnaphthalene
1-Fluoro-2-(3,5-difluoro-4-chlorophenyl)-6-hexylnaphthalene
1-Fluoro-2-(3,5-difluoro-4-chlorophenyl)-6-heptylnaphthalene
1-Fluoro-2-(3,5-difluoro-4-chlorophenyl)-6-(3-butenyl) naphthalene
1-Fluoro-2-(4-trifluoromethoxyphenyl)-6-ethylnaphthalene
1-Fluoro-2-(4-trifluoromethoxyphenyl)-6-propylnaphthalene
1-Fluoro-2-(4-trifluoromethoxyphenyl)-6-butylnaphthalene
1-Fluoro-2-(4-trifluoromethoxyphenyl)-6-pentylnaphthalene
1-Fluoro-2-(4-trifluoromethoxyphenyl)-6-hexylnaphthalene
1-Fluoro-2-(4-trifluoromethoxyphenyl)-6-heptylnaphthalene
1-Fluoro-2-(4-trifluoromethoxyphenyl)-6-(3-butenyl)naphthalene
1-Fluoro-2-(3-fluoro-4-trifluoromethoxyphenyl)-6-ethylnaphthalene
1-Fluoro-2-(3-fluoro-4-trifluoromethoxyphenyl)-6-propylnaphthalene 1-Fluoro-2-(3-fluoro-4-trifluoromethoxyphenyl)-6-butylnaphthalene
1-Fluoro-2-(3-fluoro-4-trifluoromethoxyphenyl)-6-pentylnaphthalene
1-Fluoro-2-(3-fluoro-4-trifluoromethoxyphenyl)-6-hexylnaphthalene
1-Fluoro-2-(3-fluoro-4-trifluoromethoxyphenyl)-6-heptylnaphthalene
1-Fluoro-2-(3-fluoro-4-trifluoromethoxyphenyl)-6-(3-butenyl)naphthalene
1-Fluoro-2-(3,5-difluoro-4-trifluoromethoxyphenyl)-6-ethylnaphthalene
1-Fluoro-2-(3,5-difluoro-4-trifluoromethoxyphenyl)-6-propylnaphthalene
1-Fluoro-2-(3,5-difluoro-4-trifluoromethoxyphenyl)-6-butylnaphthalene
1-Fluoro-2-(3,5-difluoro-4-trifluoromethoxyphenyl)-6-pentylnaphthalene
1-Fluoro-2-(3,5-difluoro-4-trifluoromethoxyphenyl)-6-hexylnaphthalene
1-Fluoro-2-(3,5-difluoro-4-trifluoromethoxyphenyl)-6-heptylnaphthalene
1-Fluoro-2-(3,5-difluoro-4-trifluoromethoxyphenyl)-6-(3-butenyl)naphthalene
1-Fluoro-2-(4-difluoromethoxyphenyl)-6-ethylnaphthalene
1-Fluoro-2-(4-difluoromethoxyphenyl)-6-propylnaphthalene
1-Fluoro-2-(4-difluoromethoxyphenyl)-6-butylnaphthalene
1-Fluoro-2-(4-difluoromethoxyphenyl)-6-pentylnaphthalene
1-Fluoro-2-(4-difluoromethoxyphenyl)-6-hexylnaphthalene
1-Fluoro-2-(4-difluoromethoxyphenyl)-6-heptylnaphthalene
1-Fluoro-2-(4-difluoromethoxyphenyl)-6-(3-butenyl)naphthalene
1-Fluoro-2-(3-fluoro-4-difluoromethoxyphenyl)-6-ethylnaphthalene
1-Fluoro-2-(3-fluoro-4-difluoromethoxyphenyl)-6-propylnaphthalene
1-Fluoro-2-(3-fluoro-4-difluoromethoxyphenyl)-6-butylnaphthalene
1-Fluoro-2-(3-fluoro-4-difluoromethoxyphenyl)-6-pentylnaphthalene
1-Fluoro-2-(3-fluoro-4-difluoromethoxyphenyl)-6-hexylnaphthalene
1-Fluoro-2-(3-fluoro-4-difluoromethoxyphenyl)-6-heptylnaphthalene
1-Fluoro-2-(3-fluoro-4-difluoromethoxyphenyl)-6-(3-butenyl)naphthalene
1-Fluoro-2-(3,5-difluoro-4-difluoromethoxyphenyl)-6-ethylnaphthalene
1-Fluoro-2-(3,5-difluoro-4-difluoromethoxyphenyl)-6-propylnaphthalene
1-Fluoro-2-(3,5-difluoro-4-difluoromethoxyphenyl)-6-butylnaphthalene
1-Fluoro-2-(3,5-difluoro-4-difluoromethoxyphenyl)-6-pentylnaphthalene
1-Fluoro-2-(3,5-difluoro-4-difluoromethoxyphenyl)-6-hexylnaphthalene
1-Fluoro-2-(3,5-difluoro-4-difluoromethoxyphenyl)-6-heptylnaphthalene
1-Fluoro-2-(3,5-difluoro-4-difluoromethoxyphenyl)-6-(3-butenyl)naphthalene
1-Fluoro-2-(4-trifluoromethylphenyl)-6-ethylnaphthalene
1-Fluoro-2-(4-trifluoromethylphenyl)-6-propylnaphthalene
1-Fluoro-2-(4-trifluoromethylphenyl)-6-butylnaphthalene
1-Fluoro-2-(4-trifluoromethylphenyl)-6-pentylnaphthalene
1-Fluoro-2-(4-trifluoromethylphenyl)-6-hexylnaphthalene
1-Fluoro-2-(4-trifluoromethylphenyl)-6-heptylnaphthalene
1-Fluoro-2-(4-trifluoromethylphenyl)-6-(3-butenyl)naphthalene
1-Fluoro-2-(3-fluoro-4-trifluoromethylphenyl)-6-ethylnaphthalene
1-Fluoro-2-(3-fluoro-4-trifluoromethylphenyl)-6-propylnaphthalene
1-Fluoro-2-(3-fluoro-4-trifluoromethylphenyl)-6-butylnaphthalene
1-Fluoro-2-(3-fluoro-4-trifluoromethylphenyl)-6-pentylnaphthalene
1-Fluoro-2-(3-fluoro-4-trifluoromethylphenyl)-6-hexylnaphthalene
1-Fluoro-2-(3-fluoro-4-trifluoromethylphenyl)-6-heptylnaphthalene
1-Fluoro-2-(3-fluoro-4-trifluoromethylphenylphenyl)-6-(3-butenyl)naphthalene
1-Fluoro-2-(3,5-difluoro-4-trifluoromethylphenyl)-6-ethylnaphthalene
1-Fluoro-2-(3,5-difluoro-4-trifluoromethylphenyl)-6-propylnaphthalene
1-Fluoro-2-(3,5-difluoro-4-trifluoromethylphenyl)-6-butylnaphthalene
1-Fluoro-2-(3,5-difluoro-4-trifluoromethylphenyl)-6-pentylnaphthalene
1-Fluoro-2-(3,5-difluoro-4-trifluoromethylphenyl)-6-hexylnaphthalene
1-Fluoro-2-(3,5-difluoro-4-trifluoromethylphenyl)-6-heptylnaphthalene
1-Fluoro-2-(3,5-difluoro-4-trifluoromethylphenylphenyl)-6-(3-butenyl)naphthalene
1-Fluoro-2-(4-methoxyphenyl)-6-ethylnaphthalene
1-Fluoro-2-(4-methoxyphenyl)-6-propylnaphthalene
1-Fluoro-2-(4-methoxyphenyl)-6-butylnaphthalene
1-Fluoro-2-(4-methoxyphenyl)-6-pentylnaphthalene
1-Fluoro-2-(4-methoxyphenyl)-6-hexylnaphthalene
1-Fluoro-2-(4-methoxyphenyl)-6-heptylnaphthalene
1-Fluoro-2-(4-methoxyphenyl)-6-(3-butenyl)naphthalene
1-Fluoro-2-(3-fluoro-4-methoxyphenyl)-6-ethylnaphthalene
1-Fluoro-2-(3-fluoro-4-methoxyphenyl)-6-propylnaphthalene
1-Fluoro-2-(3-fluoro-4-methoxyphenyl)-6-butylnaphthalene
1-Fluoro-2-(3-fluoro-4-methoxyphenyl)-6-pentylnaphthalene
1-Fluoro-2-(3-fluoro-4-methoxyphenyl)-6-hexylnaphthalene
1-Fluoro-2-(3-fluoro-4-methoxyphenyl)-6-heptylnaphthalene
1-Fluoro-2-(3-fluoro-4-methoxyphenyl)-6-(3-butenyl)naphthalene
1-Fluoro-2-(3,5-difluoro-4-methoxyphenyl)-6-ethylnaphthalene
1-Fluoro-2-(3,5-difluoro-4-methoxyphenyl)-6-propylnaphthalene
1-Fluoro-2-(3,5-difluoro-4-methoxyphenyl)-6-butylnaphthalene
1-Fluoro-2-(3,5-difluoro-4-methoxyphenyl)-6-pentylnaphthalene
1-Fluoro-2-(3,5-difluoro-4-methoxyphenyl)-6-hexylnaphthalene
1-Fluoro-2-(3,5-difluoro-4-methoxyphenyl)-6-heptylnaphthalene
1-Fluoro-2-(3,5-difluoro-4-methoxyphenyl)-6-(3-butenyl)naphthalene
1-Fluoro-2-(4-allyloxyphenyl)-6-ethylnaphthalene
1-Fluoro-2-(4-allyloxyphenyl)-6-propylnaphthalene 1-Fluoro-2-(4-allyloxyphenyl)-6-butylnaphthalene
1-Fluoro-2-(4-allyloxyphenyl)-6-pentylnaphthalene
1-Fluoro-2-(4-allyloxyphenyl)-6-hexylnaphthalene
1-Fluoro-2-(4-allyloxyphenyl)-6-heptylnaphthalene
1-Fluoro-2-(4-allyloxyphenyl)-6-(3-butenyl)naphthalene
1-Fluoro-2-(4-methylphenyl)-6-ethylnaphthalene
1-Fluoro-2-(4-methylphenyl)-6-propylnaphthalene
1-Fluoro-2-(4-methylphenyl)-6-butylnaphthalene
1-Fluoro-2-(4-methylphenyl)-6-pentylnaphthalene
1-Fluoro-2-(4-methylphenyl)-6-hexylnaphthalene
1-Fluoro-2-(4-methylphenyl)-6-heptylnaphthalene
1-Fluoro-2-(4-methylphenyl)-6-(3-butenyl)naphthalene
1-Fluoro-2-[4-(3-butenyl)phenyl]-6-ethylnaphthalene
1-Fluoro-2-[4-(3-butenyl)phenyl]-6-propylnaphthalene
1-Fluoro-2-[4-(3-butenyl)phenyl]-6-butylnaphthalene
1-Fluoro-2-[4-(3-butenyl)phenyl]-6-pentylnaphthalene
1-Fluoro-2-[4-(3-butenyl)phenyl]-6-hexylnaphthalene
1-Fluoro-2-[4-(3-butenyl)phenyl]-6-heptylnaphthalene
1-Fluoro-2-[4-(3-butenyl)phenyl]-6-(3-butenyl)naphthalene
1-Fluoro-2-[4-(3,4-difluorophenyl)phenyl]-6-ethylnaphthalene
1-Fluoro-2-[4-(3,4-difluorophenyl)phenyl]-6-propylnaphthalene
1-Fluoro-2-[4-(3,4-difluorophenyl)phenyl]-6-butylnaphthalene
1-Fluoro-2-[4-(3,4-difluorophenyl)phenyl]-6-pentylnaphthalene
1-Fluoro-2-[4-(3,4-difluorophenyl)phenyl]-6-hexylnaphthalene
1-Fluoro-2-[4-(3,4-difluorophenyl)phenyl]-6-heptylnaphthalene
1-Fluoro-2-[4-(3,4-difluorophenyl)phenyl]-6-(3-butenyl)naphthalene
1-Fluoro-2-[4-(3,4,5-trifluorophenyl)phenyl]-6-ethylnaphthalene
1-Fluoro-2-[4-(3,4,5-trifluorophenyl)phenyl]-6-propylnaphthalene
1-Fluoro-2-[4-(3,4,5-trifluorophenyl)phenyl]-6-butylnaphthalene
1-Fluoro-2-[4-(3,4,5-trifluorophenyl)phenyl]-6-pentylnaphthalene
1-Fluoro-2-[4-(3,4,5-trifluorophenyl)phenyl]-6-hexylnaphthalene
1-Fluoro-2-[4-(3,4,5-trifluorophenyl)phenyl]-6-heptylnaphthalene
1-Fluoro-2-[4-(3,4,5-trifluorophenyl)phenyl]-6-(3-butenyl)naphthalene
1-Fluoro-2-[4-(4-fluorophenyl)phenyl]-6-ethylnaphthalene
1-Fluoro-2-[4-(4-fluorophenyl)phenyl]-6-propylnaphthalene
1-Fluoro-2-[4-(4-fluorophenyl)phenyl]-6-butylnaphthalene
1-Fluoro-2-[4-(4-fluorophenyl)phenyl]-6-pentylnaphthalene
1-Fluoro-2-[4-(4-fluorophenyl)phenyl]-6-hexylnaphthalene
1-Fluoro-2-[4-(4-fluorophenyl)phenyl]-6-heptylnaphthalene
1-Fluoro-2-[4-(4-fluorophenyl)phenyl]-6-(3-butenyl)naphthalene
1-Fluoro-2-[4-(4–3-fluorophenyl)phenyl]-6-ethylnaphthalene
1-Fluoro-2-[4-(4–3-fluorophenyl)phenyl]-6-propylnaphthalene
1-Fluoro-2-[4-(4–3-fluorophenyl)phenyl]-6-butylnaphthalene
1-Fluoro-2-[4-(4–3-fluorophenyl)phenyl]-6-pentylnaphthalene
1-Fluoro-2-[4-(4–3-fluorophenyl)phenyl]-6-hexylnaphthalene
1-Fluoro-2-[4-(4–3-fluorophenyl)phenyl]-6-heptylnaphthalene
1-Fluoro-2-[4-(4–3-fluorophenyl)phenyl]-6-(3-butenyl)naphthalene
1-Fluoro-2-[4-(3,5-difluorophenyl)phenyl]-6-ethylnaphthalene
1-Fluoro-2-[4-(3,5-difluorophenyl)phenyl]-6-propylnaphthalene
1-Fluoro-2-[4-(3,5-difluorophenyl)phenyl]-6-butylnaphthalene
1-Fluoro-2-[4-(3,5-difluorophenyl)phenyl]-6-pentylnaphthalene
1-Fluoro-2-[4-(3,5-difluorophenyl)phenyl]-6-hexylnaphthalene
1-Fluoro-2-[4-(3,5-difluorophenyl)phenyl]-6-heptylnaphthalene
1-Fluoro-2-[4-(3,5-difluorophenyl)phenyl]-6-(3-butenyl)naphthalene
1-Fluoro-2-[4-(3,5-difluorophenyl)phenyl]-6-ethylnaphthalene
1-Fluoro-2-[4-(3,5-difluorophenyl)phenyl]-6-propylnaphthalene
1-Fluoro-2-[4-(3,5-difluorophenyl)phenyl]-6-butylnaphthalene
1-Fluoro-2-[4-(3,5-difluorophenyl)phenyl]-6-pentylnaphthalene
1-Fluoro-2-[4-(3,5-difluorophenyl)phenyl]-6-hexylnaphthalene
1-Fluoro-2-[4-(3,5-difluorophenyl)phenyl]-6-heptylnaphthalene
1-Fluoro-2-[4-(3,5-difluorophenyl)phenyl]-6-(3-butenyl)naphthalene
1-Fluoro-2-[4-(4-chlorophenyl)phenyl]-6-ethylnaphthalene
1-Fluoro-2-[4-(4-chlorophenyl)phenyl]-6-propylnaphthalene
1-Fluoro-2-[4-(4-chlorophenyl)phenyl]-6-butylnaphthalene
1-Fluoro-2-[4-(4-chlorophenyl)phenyl]-6-pentylnaphthalene
1-Fluoro-2-[4-(4-chlorophenyl)phenyl]-6-hexylnaphthalene
1-Fluoro-2-[4-(4-chlorophenyl)phenyl]-6-heptylnaphthalene
1-Fluoro-2-[4-(4-chlorophenyl)phenyl]-6-(3-butenyl)naphthalene
1-Fluoro-2-[4-(3-fluoro-4-chlorophenyl)phenyl]-6-ethylnaphthalene
1-Fluoro-2-[4-(3-fluoro-4-chlorophenyl)phenyl]-6-propylnaphthalene
1-Fluoro-2-[4-(3-fluoro-4-chlorophenyl)phenyl]-6-butylnaphthalene
1-Fluoro-2-[4-(3-fluoro-4-chlorophenyl)phenyl]-6-pentylnaphthalene
1-Fluoro-2-[4-(3-fluoro-4-chlorophenyl)phenyl]-6-hexylnaphthalene
1-Fluoro-2-[4-(3-fluoro-4-chlorophenyl)phenyl]-6-heptylnaphthalene
1-Fluoro-2-[4-(3-fluoro-4-chlorophenyl)phenyl]-6-(3-butenyl)naphthalene
1-Fluoro-2-[4-(3,5-difluoro-4-chlorophenyl)phenyl]-6-ethylnaphthalene
1-Fluoro-2-[4-(3,5-difluoro-4-chlorophenyl)phenyl]-6-propylnaphthalene
1-Fluoro-2-[4-(3,5-difluoro-4-chlorophenyl)phenyl]-6-butylnaphthalene
1-Fluoro-2-[4-(3,5-difluoro-4-chlorophenyl)phenyl]-6-pentylnaphthalene
1-Fluoro-2-[4-(3,5-difluoro-4-chlorophenyl)phenyl]-6-hexylnaphthalene 1-Fluoro-2-[4-(3,5-difluoro-4-chlorophenyl)phenyl]-6-heptylnaphthalene
1-Fluoro-2-[4-(3,5-difluoro-4-chlorophenyl)phenyl]-6-(3-butenyl)naphthalene
1-Fluoro-2-[4-(4-trifluoromethoxyphenyl)phenyl]-6-ethylnaphthalene
1-Fluoro-2-[4-(4-trifluoromethoxyphenyl)phenyl]-6-propylnaphthalene
1-Fluoro-2-[4-(4-trifluoromethoxyphenyl)phenyl]-6-butylnaphthalene
1-Fluoro-2-[4-(4-trifluoromethoxyphenyl)phenyl]-6-pentylnaphthalene
1-Fluoro-2-[4-(4-trifluoromethoxyphenyl)phenyl]-6-hexylnaphthalene
1-Fluoro-2-[4-(4-trifluoromethoxyphenyl)phenyl]-6-heptylnaphthalene
1-Fluoro-2-[4-(4-trifluoromethoxyphenyl)phenyl]-6-(3-butenyl)naphthalene
1-Fluoro-2-[4-(3-fluoro-4-trifluoromethoxyphenyl)phenyl]-6-ethylnaphthalene
1-Fluoro-2-[4-(3-fluoro-4-trifluoromethoxyphenyl)phenyl]-6-propylnaphthalene
1-Fluoro-2-[4-(3-fluoro-4-trifluoromethoxyphenyl)phenyl]-6-butylnaphthalene
1-Fluoro-2-[4-(3-fluoro-4-trifluoromethoxyphenyl)phenyl]-6-pentylnaphthalene
1-Fluoro-2-[4-(3-fluoro-4-trifluoromethoxyphenyl)phenyl]-6-hexylnaphthalene
1-Fluoro-2-[4-(3-fluoro-4-trifluoromethoxyphenyl)phenyl]-6-heptylnaphthalene
1-Fluoro-2-[4-(3-fluoro-4-trifluoromethoxyphenyl)phenyl]-6-(3-butenyl)naphthalene
1-Fluoro-2-[4-(3,5-difluoro-4-trifluoromethoxyphenyl)phenyl]-6-ethylnaphthalene
1-Fluoro-2-[4-(3,5-difluoro-4-trifluoromethoxyphenyl)phenyl]-6-propylnaphthalene
1-Fluoro-2-[4-(3,5-difluoro-4-trifluoromethoxyphenyl)phenyl]-6-butylnaphthalene
1-Fluoro-2-[4-(3,5-difluoro-4-trifluoromethoxyphenyl)phenyl]-6-pentylnaphthalene
1-Fluoro-2-[4-(3,5-difluoro-4-trifluoromethoxyphenyl)phenyl]-6-hexylnaphthalene
1-Fluoro-2-[4-(3,5-difluoro-4-trifluoromethoxyphenyl)phenyl]-6-heptylnaphthalene
1-Fluoro-2-[4-(3,5-difluoro-4-trifluoromethoxyphenyl)phenyl]-6-(3-butenyl)naphthalene
1-Fluoro-2-[4-(4-difluoromethoxyphenyl)phenyl]-6-ethylnaphthalene
1-Fluoro-2-[4-(4-difluoromethoxyphenyl)phenyl]-6-propylnaphthalene
1-Fluoro-2-[4-(4-difluoromethoxyphenyl)phenyl]-6-butylnaphthalene
1-Fluoro-2-[4-(4-difluoromethoxyphenyl)phenyl]-6-pentylnaphthalene
1-Fluoro-2-[4-(4-difluoromethoxyphenyl)phenyl]-6-hexylnaphthalene
1-Fluoro-2-[4-(4-difluoromethoxyphenyl)phenyl]-6-heptylnaphthalene
1-Fluoro-2-[4-(4-difluoromethoxyphenyl)phenyl]-6-(3-butenyl)naphthalene
1-Fluoro-2-[4-(3-fluoro-4-difluoromethoxyphenyl)phenyl]-6-ethylnaphthalene
1-Fluoro-2-[4-(3-fluoro-4-difluoromethoxyphenyl)phenyl]-6-propylnaphthalene
1-Fluoro-2-[4-(3-fluoro-4-difluoromethoxyphenyl)phenyl]-6-butylnaphthalene
1-Fluoro-2-[4-(3-fluoro-4-difluoromethoxyphenyl)phenyl]-6-pentylnaphthalene
1-Fluoro-2-[4-(3-fluoro-4-difluoromethoxyphenyl)phenyl]-6-hexylnaphthalene
1-Fluoro-2-[4-(3-fluoro-4-difluoromethoxyphenyl)phenyl]-6-heptylnaphthalene
1-Fluoro-2-[4-(3-fluoro-4-difluoromethoxyphenyl)phenyl]-6-(3-butenyl)naphthalene
1-Fluoro-2-[4-(3,5-difluoro-4-difluoromethoxyphenyl)phenyl]-6-ethylnaphthalene
1-Fluoro-2-[4-(3,5-difluoro-4-difluoromethoxyphenyl)phenyl]-6-propylnaphthalene
1-Fluoro-2-[4-(3,5-difluoro-4-difluoromethoxyphenyl)phenyl]-6-butylnaphthalene
1-Fluoro-2-[4-(3,5-difluoro-4-difluoromethoxyphenyl)phenyl]-6-pentylnaphthalene
1-Fluoro-2-[4-(3,5-difluoro-4-difluoromethoxyphenyl)phenyl]-6-hexylnaphthalene
1-Fluoro-2-[4-(3,5-difluoro-4-difluoromethoxyphenyl)phenyl]-6-heptylnaphthalene
1-Fluoro-2-[4-(3,5-difluoro-4-difluoromethoxyphenyl)phenyl]-6-(3-butenyl)naphthalene
1-Fluoro-2-[4-(4-trifluoromethylphenyl)phenyl]-6-ethylnaphthalene
1-Fluoro-2-[4-(4-trifluoromethylphenyl)phenyl]-6-propylnaphthalene
1-Fluoro-2-[4-(4-trifluoromethylphenyl)phenyl]-6-butylnaphthalene
1-Fluoro-2-[4-(4-trifluoromethylphenyl)phenyl]-6-pentylnaphthalene
1-Fluoro-2-[4-(4-trifluoromethylphenyl)phenyl]-6-hexylnaphthalene
1-Fluoro-2-[4-(4-trifluoromethylphenyl)phenyl]-6-heptylnaphthalene
1-Fluoro-2-[4-(4-trifluoromethylphenyl)phenyl]-6-(3-butenyl)naphthalene
1-Fluoro-2-[4-(3-fluoro-4-trifluoromethylphenyl)phenyl]-6-ethylnaphthalene
1-Fluoro-2-[4-(3-fluoro-4-trifluoromethylphenyl)phenyl]-6-propylnaphthalene
1-Fluoro-2-[4-(3-fluoro-4-trifluoromethylphenyl)phenyl]-6-butylnaphthalene
1-Fluoro-2-[4-(3-fluoro-4-trifluoromethylphenyl)phenyl]-6-pentylnaphthalene
1-Fluoro-2-[4-(3-fluoro-4-trifluoromethylphenyl)phenyl]-6-hexylnaphthalene
1-Fluoro-2-[4-(3-fluoro-4-trifluoromethylphenyl)phenyl]-6-heptylnaphthalene
1-Fluoro-2-[4-(3-fluoro-4-trifluoromethylphenylphenyl)phenyl]-6-(3-butenyl)naphthalene
1-Fluoro-2-[4-(3,5-difluoro-4-trifluoromethylphenyl)phenyl]-6-ethylnaphthalene
1-Fluoro-2-[4-(3,5-difluoro-4-trifluoromethylphenyl)phenyl]-6-propylnaphthalene
1-Fluoro-2-[4-(3,5-difluoro-4-trifluoromethylphenyl)phenyl]-6-butylnaphthalene
1-Fluoro-2-[4-(3,5-difluoro-4-trifluoromethylphenyl)phenyl]-6-pentylnaphthalene
1-Fluoro-2-[4-(3,5-difluoro-4-trifluoromethylphenyl)phenyl]-6-hexylnaphthalene
1-Fluoro-2-[4-(3,5-difluoro-4-trifluoromethylphenyl)phenyl]-6-heptylnaphthalene
1-Fluoro-2-[4-(3,5-difluoro-4-trifluoromethylphenylphenyl)phenyl]-6-(3-butenyl)naphthalene
1-Fluoro-2-[4-(4-methoxyphenyl)phenyl]-6-ethylnaphthalene 1-Fluoro-2-[4-(4-methoxyphenyl)phenyl]-6-propylnaphthalene
1-Fluoro-2-[4-(4-methoxyphenyl)phenyl]-6-butylnaphthalene
1-Fluoro-2-[4-(4-methoxyphenyl)phenyl]-6-pentylnaphthalene
1-Fluoro-2-[4-(4-methoxyphenyl)phenyl]-6-hexylnaphthalene
1-Fluoro-2-[4-(4-methoxyphenyl)phenyl]-6-heptylnaphthalene
1-Fluoro-2-[4-(4-methoxyphenyl)phenyl]-6-(3-butenyl)naphthalene
1-Fluoro-2-[4-(3-fluoro-4-methoxyphenyl)phenyl]-6-ethylnaphthalene
1-Fluoro-2-[4-(3-fluoro-4-methoxyphenyl)phenyl]-6-propylnaphthalene
1-Fluoro-2-[4-(3-fluoro-4-methoxyphenyl)phenyl]-6-butylnaphthalene
1-Fluoro-2-[4-(3-fluoro-4-methoxyphenyl)phenyl]-6-pentylnaphthalene
1-Fluoro-2-[4-(3-fluoro-4-methoxyphenyl)phenyl]-6-hexylnaphthalene
1-Fluoro-2-[4-(3-fluoro-4-methoxyphenyl)phenyl]-6-heptylnaphthalene
1-Fluoro-2-[4-(3-fluoro-4-methoxyphenyl)phenyl]-6-(3-butenyl)naphthalene
1-Fluoro-2-[4-(3,5-difluoro-4-methoxyphenyl)phenyl]-6-ethyl naphthalene
1-Fluoro-2-[4-(3,5-difluoro-4-methoxyphenyl)phenyl]-6-propylnaphthalene
1-Fluoro-2-[4-(3,5-difluoro-4-methoxyphenyl)phenyl]-6-butylnaphthalene
1-Fluoro-2-[4-(3,5-difluoro-4-methoxyphenyl)phenyl]-6-pentylnaphthalene
1-Fluoro-2-[4-(3,5-difluoro-4-methoxyphenyl)phenyl]-6-hexylnaphthalene
1-Fluoro-2-[4-(3,5-difluoro-4-methoxyphenyl)phenyl]-6-heptylnaphthalene
1-Fluoro-2-[4-(3,5-difluoro-4-methoxyphenyl)phenyl]-6-(3-butenyl)naphthalene
1-Fluoro-2-[4-(4-allyloxyphenyl)phenyl]-6-ethylnaphthalene
1-Fluoro-2-[4-(4-allyloxyphenyl)phenyl]-6-propylnaphthalene
1-Fluoro-2-[4-(4-allyloxyphenyl)phenyl]-6-butylnaphthalene
1-Fluoro-2-[4-(4-allyloxyphenyl)phenyl]-6-pentylnaphthalene
1-Fluoro-2-[4-(4-allyloxyphenyl)phenyl]-6-hexylnaphthalene
1-Fluoro-2-[4-(4-allyloxyphenyl)phenyl]-6-heptylnaphthalene
1-Fluoro-2-[4-(4-allyloxyphenyl)phenyl]-6-(3-butenyl)naphthalene
1-Fluoro-2-[4-(4-methylphenyl)phenyl]-6-ethylnaphthalene
1-Fluoro-2-[4-(4-methylphenyl)phenyl]-6-propylnaphthalene
1-Fluoro-2-[4-(4-methylphenyl)phenyl]-6-butylnaphthalene
1-Fluoro-2-[4-(4-methylphenyl)phenyl]-6-pentylnaphthalene
1-Fluoro-2-[4-(4-methylphenyl)phenyl]-6-hexylnaphthalene
1-Fluoro-2-[4-(4-methylphenyl)phenyl]-6-heptylnaphthalene
1-Fluoro-2-[4-(4-methylphenyl)-6-(3-butenyl)naphthalene
1-Fluoro-2-[4-[4-(3-butenyl)phenyl]phenyl]-6-ethylnaphthalene
1-Fluoro-2-[4-[4-(3-butenyl)phenyl]phenyl]-6-propylnaphthalene
1-Fluoro-2-[4-[4-(3-butenyl)phenyl]phenyl]-6-butylnaphthalene
1-Fluoro-2-[4-[4-(3-butenyl)phenyl]phenyl]-6-pentylnaphthalene
1-Fluoro-2-[4-[4-(3-butenyl)phenyl]phenyl]-6-hexylnaphthalene
1-Fluoro-2-[4-[4-(3-butenyl)phenyl]phenyl]-6-heptylnaphthalene
1-Fluoro-2-[4-[4-(3-butenyl)phenyl]phenyl]-6-(3-butenyl)naphthalene
1-Fluoro-2-[3-fluoro-4-(3,4-difluorophenyl)phenyl]-6-ethylnaphthalene
1-Fluoro-2-[3-fluoro-4-(3,4-difluorophenyl)phenyl]-6-propylnaphthalene
1-Fluoro-2-[3-fluoro-4-(3,4-difluorophenyl)phenyl]-6-butylnaphthalene
1-Fluoro-2-[3-fluoro-4-(3,4-difluorophenyl)phenyl]-6-pentylnaphthalene
1-Fluoro-2-[3-fluoro-4-(3,4-difluorophenyl)phenyl]-6-hexylnaphthalene
1-Fluoro-2-[3-fluoro-4-(3,4-difluorophenyl)phenyl]-6-heptylnaphthalene
1-Fluoro-2-[3-fluoro-4-(3,4-difluorophenyl)phenyl]-6-(3-butenyl)naphthalene
1-Fluoro-2-[3-fluoro-4-(3,4,5-trifluorophenyl)phenyl]-6-ethylnaphthalene
1-Fluoro-2-[3-fluoro-4-(3,4,5-trifluorophenyl)phenyl]-6-propylnaphthalene
1-Fluoro-2-[3-fluoro-4-(3,4,5-trifluorophenyl)phenyl]-6-butylnaphthalene
1-Fluoro-2-[3-fluoro-4-(3,4,5-trifluorophenyl)phenyl]-6-pentylnaphthalene
1-Fluoro-2-[3-fluoro-4-(3,4,5-trifluorophenyl)phenyl]-6-hexylnaphthalene
1-Fluoro-2-[3-fluoro-4-(3,4,5-trifluorophenyl)phenyl]-6-heptylnaphthalene
1-Fluoro-2-[3-fluoro-4-(3,4,5-trifluorophenyl)phenyl]-6-(3-butenyl)naphthalene
1-Fluoro-2-[3-fluoro-4-(4-fluorophenyl)phenyl]-6-ethylnaphthalene
1-Fluoro-2-[3-fluoro-4-(4-fluorophenyl)phenyl]-6-propylnaphthalene
1-Fluoro-2-[3-fluoro-4-(4-fluorophenyl)phenyl]-6-butylnaphthalene
1-Fluoro-2-[3-fluoro-4-(4-fluorophenyl)phenyl]-6-pentylnaphthalene
1-Fluoro-2-[3-fluoro-4-(4-fluorophenyl)phenyl]-6-hexylnaphthalene
1-Fluoro-2-[3-fluoro-4-(4-fluorophenyl)phenyl]-6-heptylnaphthalene
1-Fluoro-2-[3-fluoro-4-(4-fluorophenyl)phenyl]-6-(3-butenyl)naphthalene
1-Fluoro-2-[3-fluoro-4-(3-fluorophenyl)phenyl-6-ethylnaphthalene
1-Fluoro-2-[3-fluoro-4-(3-fluorophenyl)phenyl]-6-propylnaphthalene
1-Fluoro-2-[3-fluoro-4-(3-fluorophenyl)phenyl]-6-butylnaphthalene
1-Fluoro-2-[3-fluoro-4-(3-fluorophenyl)phenyl]-6-pentylnaphthalene
1-Fluoro-2-[3-fluoro-4-(3-fluorophenyl)phenyl]-6-hexylnaphthalene
1-Fluoro-2-[3-fluoro-4-(3-fluorophenyl)phenyl]-6-heptylnaphthalene 1-Fluoro-2-[3-fluoro-4-(3-fluorophenyl)phenyl]-6-(3-butenyl)naphthalene
1-Fluoro-2-[3-fluoro-4-(3,5-difluorophenyl)phenyl]-6-ethylnaphthalene
1-Fluoro-2-[3-fluoro-4-(3,5-difluorophenyl)phenyl]-6-propylnaphthalene
1-Fluoro-2-[3-fluoro-4-(3,5-difluorophenyl)phenyl]-6-butylnaphthalene
1-Fluoro-2-[3-fluoro-4-(3,5-difluorophenyl)phenyl]-6-pentylnaphthalene
1-Fluoro-2-[3-fluoro-4-(3,5-difluorophenyl)phenyl]-6-hexylnaphthalene
1-Fluoro-2-[3-fluoro-4-(3,5-difluorophenyl)phenyl]-6-heptylnaphthalene
1-Fluoro-2-[3-fluoro-4-(3,5-difluorophenyl)phenyl]-6-(3-butenyl)naphthalene
1-Fluoro-2-[3-fluoro-4-(4-chlorophenyl)phenyl]-6-ethylnaphthalene
1-Fluoro-2-[3-fluoro-4-(4-chlorophenyl)phenyl]-6-propylnaphthalene
1-Fluoro-2-[3-fluoro-4-(4-chlorophenyl)phenyl]-6-butylnaphthalene
1-Fluoro-2-[3-fluoro-4-(4-chlorophenyl)phenyl]-6-pentylnaphthalene
1-Fluoro-2-[3-fluoro-4-(4-chlorophenyl)phenyl]-6-hexylnaphthalene
1-Fluoro-2-[3-fluoro-4-(4-chlorophenyl)phenyl]-6-heptylnaphthalene
1-Fluoro-2-[3-fluoro-4-(4-chlorophenyl)phenyl]-6-(3-butenyl)naphthalene
1-Fluoro-2-[3-fluoro-4-(4-chlorophenyl)phenyl]-6-ethylnaphthalene
1-Fluoro-2-[3-fluoro-4-(4-chlorophenyl)phenyl]-6-propylnaphthalene
1-Fluoro-2-[3-fluoro-4-(4-chlorophenyl)phenyl]-6-butylnaphthalene
1-Fluoro-2-[3-fluoro-4-(4-chlorophenyl)phenyl]-6-pentylnaphthalene
1-Fluoro-2-[3-fluoro-4-(4-chlorophenyl)phenyl]-6-hexylnaphthalene
1-Fluoro-2-[3-fluoro-4-(4-chlorophenyl)phenyl]-6-heptylnaphthalene
1-Fluoro-2-[3-fluoro-4-(4-chlorophenyl)phenyl]-6-(3-butenyl)naphthalene
1-Fluoro-2-[3-fluoro-4-(3-fluoro-4-chlorophenyl)phenyl]-6-ethylnaphthalene
1-Fluoro-2-[3-fluoro-4-(3-fluoro-4-chlorophenyl)phenyl]-6-propylnaphthalene
1-Fluoro-2-[3-fluoro-4-(3-fluoro-4-chlorophenyl)phenyl]-6-butylnaphthalene
1-Fluoro-2-[3-fluoro-4-(3-fluoro-4-chlorophenyl)phenyl]-6-pentylnaphthalene
1-Fluoro-2-[3-fluoro-4-(3-fluoro-4-chlorophenyl)phenyl]-6-hexylnaphthalene
1-Fluoro-2-[3-fluoro-4-(3-fluoro-4-chlorophenyl)phenyl]-6-heptylnaphthalene
1-Fluoro-2-[3-fluoro-4-(3-fluoro-4-chlorophenyl)phenyl]-6-(3-butenyl)naphthalene
1-Fluoro-2-[3-fluoro-4-(3,5-difluoro-4-chlorophenyl)phenyl]-6-ethylnaphthalene
1-Fluoro-2-[3-fluoro-4-(3,5-difluoro-4-chlorophenyl)phenyl]-6-propylnaphthalene
1-Fluoro-2-[3-fluoro-4-(3,5-difluoro-4-chlorophenyl)phenyl]-6-butylnaphthalene
1-Fluoro-2-[3-fluoro-4-(3,5-difluoro-4-chlorophenyl)phenyl]-6-pentylnaphthalene
1-Fluoro-2-[3-fluoro-4-(3,5-difluoro-4-chlorophenyl)phenyl]-6-hexylnaphthalene
1-Fluoro-2-[3-fluoro-4-(3,5-difluoro-4-chlorophenyl)phenyl]-6-heptylnaphthalene
1-Fluoro-2-[3-fluoro-4-(3,5-difluoro-4-chlorophenyl)phenyl]-6-(3-butenyl)naphthalene
1-Fluoro-2-[3-fluoro-4-(4-trifluoromethoxyphenyl)phenyl]-6-ethylnaphthalene
1-Fluoro-2-[3-fluoro-4-(4-trifluoromethoxyphenyl)phenyl]-6-propylnaphthalene
1-Fluoro-2-[3-fluoro-4-(4-trifluoromethoxyphenyl)phenyl]-6-butylnaphthalene
1-Fluoro-2-[3-fluoro-4-(4-trifluoromethoxyphenyl)phenyl]-6-pentylnaphthalene
1-Fluoro-2-[3-fluoro-4-(4-trifluoromethoxyphenyl)phenyl]-6-hexylnaphthalene
1-Fluoro-2-[3-fluoro-4-(4-trifluoromethoxyphenyl)phenyl]-6-heptylnaphthalene
1-Fluoro-2-[3-fluoro-4-(4-trifluoromethoxyphenyl)phenyl]-6-(3-butenyl)naphthalene
1-Fluoro-2-[3-fluoro-4-(3-fluoro-4-trifluoromethoxyphenyl)phenyl]-6-ethylnaphthalene
1-Fluoro-2-[3-fluoro-4-(3-fluoro-4-trifluoromethoxyphenyl)phenyl]-6-propylnaphthalene
1-Fluoro-2-[3-fluoro-4-(3-fluoro-4-trifluoromethoxyphenyl)phenyl]-6-butylnaphthalene
1-Fluoro-2-[3-fluoro-4-(3-fluoro-4-trifluoromethoxyphenyl)phenyl]-6-pentylnaphthalene
1-Fluoro-2-[3-fluoro-4-(3-fluoro-4-trifluoromethoxyphenyl)phenyl]-6-hexylnaphthalene
1-Fluoro-2-[3-fluoro-4-(3-fluoro-4-trifluoromethoxyphenyl)phenyl]-6-heptylnaphthalene
1-Fluoro-2-[3-fluoro-4-(3-fluoro-4-trifluoromethoxyphenyl)phenyl]-6-(3-butenyl)naphthalene
1-Fluoro-2-[3-fluoro-4-(3,5-difluoro-4-trifluoromethoxyphenyl)phenyl]-6-ethylnaphthalene
1-Fluoro-2-[3-fluoro-4-(3,5-difluoro-4-trifluoromethoxyphenyl)phenyl]-6-propylnaphthalene
1-Fluoro-2-[3-fluoro-4-(3,5-difluoro-4-trifluoromethoxyphenyl)phenyl]-6-butylnaphthalene
1-Fluoro-2-[3-fluoro-4-(3,5-difluoro-4-trifluoromethoxyphenyl)phenyl]-6-pentylnaphthalene
1-Fluoro-2-[3-fluoro-4-(3,5-difluoro-4-trifluoromethoxyphenyl)phenyl]-6-hexylnaphthalene
1-Fluoro-2-[3-fluoro-4-(3,5-difluoro-4-trifluoromethoxyphenyl)phenyl]-6-heptylnaphthalene
1-Fluoro-2-[3-fluoro-4-(3,5-difluoro-4-trifluoromethoxyphenyl)phenyl]-6-(3-butenyl)naphthalene
1-Fluoro-2-[3-fluoro-4-(4-difluoromethoxyphenyl)phenyl]-6-ethylnaphthalene
1-Fluoro-2-[3-fluoro-4-(4-difluoromethoxyphenyl)phenyl]-6-propylnaphthalene
1-Fluoro-2-[3-fluoro-4-(4-difluoromethoxyphenyl)phenyl]-6-butylnaphthalene
1-Fluoro-2-[3-fluoro-4-(4-difluoromethoxyphenyl)phenyl]-6-pentylnaphthalene
1-Fluoro-2-[3-fluoro-4-(4-difluoromethoxyphenyl)phenyl]-6-hexylnaphthalene
1-Fluoro-2-[3-fluoro-4-(4-difluoromethoxyphenyl)phenyl]-6-heptylnaphthalene
1-Fluoro-2-[3-fluoro-4-(4-difluoromethoxyphenyl)phenyl]-6-(3-butenyl)naphthalene
1-Fluoro-2-[3-fluoro-4-(3-fluoro-4-difluoromethoxyphenyl)phenyl]-6-ethylnaphthalene
1-Fluoro-2-[3-fluoro-4-(3-fluoro-4-difluoromethoxyphenyl)phenyl]-6-propylnaphthalene 1-Fluoro-2-[3-fluoro-4-(3-fluoro-4-difluoromethoxyphenyl)phenyl]-6-butylnaphthalene
1-Fluoro-2-[3-fluoro-4-(3-fluoro-4-difluoromethoxyphenyl)phenyl]-6-pentylnaphthalene
1-Fluoro-2-[3-fluoro-4-(3-fluoro-4-difluoromethoxyphenyl)phenyl]-6-hexylnaphthalene
1-Fluoro-2-[3-fluoro-4-(3-fluoro-4-difluoromethoxyphenyl)phenyl]-6-heptylnaphthalene
1-Fluoro-2-[3-fluoro-4-(3-fluoro-4-difluoromethoxyphenyl)phenyl]-6-(3-butenyl)naphthalene
1-Fluoro-2-[3-fluoro-4-(3,5-difluoro-4-difluoromethoxyphenyl)phenyl]-6-ethylnaphthalene
1-Fluoro-2-[3-fluoro-4-(3,5-difluoro-4-difluoromethoxyphenyl)phenyl]-6-propylnaphthalene
1-Fluoro-2-[3-fluoro-4-(3,5-difluoro-4-difluoromethoxyphenyl)phenyl]-6-butylnaphthalene
1-Fluoro-2-[3-fluoro-4-(3,5-difluoro-4-difluoromethoxyphenyl)phenyl]-6-pentylnaphthalene
1-Fluoro-2-[3-fluoro-4-(3,5-difluoro-4-difluoromethoxyphenyl)phenyl]-6-hexylnaphthalene
1-Fluoro-2-[3-fluoro-4-(3,5-difluoro-4-difluoromethoxyphenyl)phenyl]-6-heptylnaphthalene
1-Fluoro-2-[3-fluoro-4-(3,5-difluoro-4-difluoromethoxyphenyl)phenyl]-6-(3-butenyl)naphthalene
1-Fluoro-2-[3-fluoro-4-(4-trifluoromethylphenyl)phenyl]-6-ethylnaphthalene
1-Fluoro-2-[3-fluoro-4-(4-trifluoromethylphenyl)phenyl]-6-propylnaphthalene
1-Fluoro-2-[3-fluoro-4-(4-trifluoromethylphenyl)phenyl]-6-butylnaphthalene
1-Fluoro-2-[3-fluoro-4-(4-trifluoromethylphenyl)phenyl]-6-pentylnaphthalene
1-Fluoro-2-[3-fluoro-4-(4-trifluoromethylphenyl)phenyl]-6-hexylnaphthalene
1-Fluoro-2-[3-fluoro-4-(4-trifluoromethylphenyl)phenyl]-6-heptylnaphthalene
1-Fluoro-2-[3-fluoro-4-(4-trifluoromethylphenyl)phenyl]-6-(3-butenyl)naphthalene
1-Fluoro-2-[3-fluoro-4-(3-fluoro-4-trifluoromethylphenyl)phenyl]-6-ethylnaphthalene
1-Fluoro-2-[3-fluoro-4-(3-fluoro-4-trifluoromethylphenyl)phenyl]-6-propylnaphthalene
1-Fluoro-2-[3-fluoro-4-(3-fluoro-4-trifluoromethylphenyl)phenyl]-6-butylnaphthalene
1-Fluoro-2-[3-fluoro-4-(3-fluoro-4-trifluoromethylphenyl)phenyl]-6-pentylnaphthalene
1-Fluoro-2-[3-fluoro-4-(3-fluoro-4-trifluoromethylphenyl)phenyl]-6-hexylnaphthalene
1-Fluoro-2-[3-fluoro-4-(3-fluoro-4-trifluoromethylphenyl)phenyl]-6-heptylnaphthalene
1-Fluoro-2-[3-fluoro-4-(3-fluoro-4-trifluoromethylphenylphenyl)phenyl]-6-(3-butenyl)naphthalene
1-Fluoro-2-[3-fluoro-4-(3,5-difluoro-4-trifluoromethylphenyl)phenyl]-6-ethylnaphthalene
1-Fluoro-2-[3-fluoro-4-(3,5-difluoro-4-trifluoromethylphenyl)phenyl]-6-propylnaphthalene
1-Fluoro-2-[3-fluoro-4-(3,5-difluoro-4-trifluoromethylphenyl)phenyl]-6-butylnaphthalene
1-Fluoro-2-[3-fluoro-4-(3,5-difluoro-4-trifluoromethylphenyl)phenyl]-6-pentylnaphthalene
1-Fluoro-2-[3-fluoro-4-(3,5-difluoro-4-trifluoromethylphenyl)phenyl]-6-hexylnaphthalene
1-Fluoro-2-[3-fluoro-4-(3,5-difluoro-4-trifluoromethylphenyl)phenyl]-6-heptylnaphthalene
1-Fluoro-2-[3-fluoro-4-(3,5-difluoro-4-trifluoromethylphenylphenyl)phenyl]-6-(3-butenyl)naphthalene
1-Fluoro-2-[3-fluoro-4-(4-methoxyphenyl)phenyl]-6-ethylnaphthalene
1-Fluoro-2-[3-fluoro-4-(4-methoxyphenyl)phenyl]-6-propylnaphthalene
1-Fluoro-2-[3-fluoro-4-(4-methoxyphenyl)phenyl]-6-butylnaphthalene
1-Fluoro-2-[3-fluoro-4-(4-methoxyphenyl)phenyl]-6-pentylnaphthalene
1-Fluoro-2-[3-fluoro-4-(4-methoxyphenyl)phenyl]-6-hexylnaphthalene
1-Fluoro-2-[3-fluoro-4-(4-methoxyphenyl)phenyl]-6-heptylnaphthalene
1-Fluoro-2-[3-fluoro-4-(4-methoxyphenyl)phenyl]-6-(3-butenyl)naphthalene
1-Fluoro-2-[3-fluoro-4-(3-fluoro-4-methoxyphenyl)phenyl]-6-ethylnaphthalene
1-Fluoro-2-[3-fluoro-4-(3-fluoro-4-methoxyphenyl)phenyl]-6-propylnaphthalene
1-Fluoro-2-[3-fluoro-4-(3-fluoro-4-methoxyphenyl)phenyl]-6-butylnaphthalene
1-Fluoro-2-[3-fluoro-4-(3-fluoro-4-methoxyphenyl)phenyl]-6-pentylnaphthalene
1-Fluoro-2-[3-fluoro-4-(3-fluoro-4-methoxyphenyl)phenyl]-6-hexylnaphthalene
1-Fluoro-2-[3-fluoro-4-(3-fluoro-4-methoxyphenyl)phenyl]-6-heptylnaphthalene
1-Fluoro-2-[3-fluoro-4-(3-fluoro-4-methoxyphenyl)phenyl]-6-(3-butenyl)naphthalene
1-Fluoro-2-[3-fluoro-4-(3,5difluoro-4-methoxyphenyl)phenyl]-6-ethylnaphthalene
1-Fluoro-2-[3-fluoro-4-(3,5-difluoro-4-methoxyphenyl)phenyl]-6-propylnaphthalene
1-Fluoro-2-[3-fluoro-4-(3,5-difluoro-4-methoxyphenyl)phenyl]-6-butylnaphthalene
1-Fluoro-2-[3-fluoro-4-(3,5-difluoro-4-methoxyphenyl)phenyl]-6-pentylnaphthalene
1-Fluoro-2-[3-fluoro-4-(3,5-difluoro-4-methoxyphenyl)phenyl]-6-hexylnaphthalene
1-Fluoro-2-[3-fluoro-4-(3,5-difluoro-4-methoxyphenyl)phenyl]-6-heptylnaphthalene
1-Fluoro-2-[3-fluoro-4-(3,5-difluoro-4-methoxyphenyl)phenyl]-6-(3-butenyl)naphthalene
1-Fluoro-2-[3-fluoro-4-(4-allyloxyphenyl)phenyl]-6-ethylnaphthalene
1-Fluoro-2-[3-fluoro-4-(4-allyloxyphenyl)phenyl]-6-propylnaphthalene
1-Fluoro-2-[3-fluoro-4-(4-allyloxyphenyl)phenyl]-6-butylnaphthalene
1-Fluoro-2-[3-fluoro-4-(4-allyloxyphenyl)phenyl]-6-pentylnaphthalene
1-Fluoro-2-[3-fluoro-4-(4-allyloxyphenyl)phenyl]-6-hexylnaphthalene
1-Fluoro-2-[3-fluoro-4-(4-allyloxyphenyl)phenyl]-6-heptylnaphthalene
1-Fluoro-2-[3-fluoro-4-(4-allyloxyphenyl)phenyl]-6-(3-butenyl)naphthalene
1-Fluoro-2-[3-fluoro-4-(4-methylphenyl)phenyl]-6-ethylnaphthalene
1-Fluoro-2-[3-fluoro-4-(4-methylphenyl)phenyl]-6-propylnaphthalene
1-Fluoro-2-[3-fluoro-4-(4-methylphenyl)phenyl]-6-butylnaphthalene
1-Fluoro-2-[3-fluoro-4-(4-methylphenyl)phenyl]-6-pentylnaphthalene
1-Fluoro-2-[3-fluoro-4-(4-methylphenyl)phenyl]-6-hexylnaphthalene 1-Fluoro-2-[3-fluoro-4-(4-methylphenyl)phenyl]-6-heptylnaphthalene
1-Fluoro-2-[3-fluoro-4-(4-methylphenyl)phenyl]-6-(3-butenyl)naphthalene
1-Fluoro-2-[3-fluoro-4-[4-(3-butenyl)phenyl]phenyl]-6-ethylnaphthalene
1-Fluoro-2-[3-fluoro-4-[4-(3-butenyl)phenyl]phenyl]-6-propylnaphthalene
1-Fluoro-2-[3-fluoro-4-[4-(3-butenyl)phenyl]phenyl]-6-butylnaphthalene
1-Fluoro-2-[3-fluoro-4-[4-(3-butenyl)phenyl]phenyl]-6-pentylnaphthalene
1-Fluoro-2-[3-fluoro-4-[4-(3-butenyl)phenyl]phenyl]-6-hexylnaphthalene
1-Fluoro-2-[3-fluoro-4-[4-(3-butenyl)phenyl]phenyl]-6-heptylnaphthalene
1-Fluoro-2-[3-fluoro-4-[4-(3-butenyl)phenyl]phenyl]-6-(3-butenyl)naphthalene
1-Fluoro-2-[3,5-difluoro-4-(3,4-difluorophenyl)phenyl]-6-ethylnaphthalene
1-Fluoro-2-[3,5-difluoro-4-(3,4-difluorophenyl)phenyl]-6-propylnaphthalene
1-Fluoro-2-[3,5-difluoro-4-(3,4-difluorophenyl)phenyl]-6-butylnaphthalene
1-Fluoro-2-[3,5-difluoro-4-(3,4-difluorophenyl)phenyl]-6-pentylnaphthalene
1-Fluoro-2-[3,5-difluoro-4-(3,4-difluorophenyl)phenyl]-6-hexylnaphthalene
1-Fluoro-2-[3,5-difluoro-4-(3,4-difluorophenyl)phenyl]-6-heptylnaphthalene
1-Fluoro-2-[3,5-difluoro-4-(3,4-difluorophenyl)phenyl]-6-(3-butenyl)naphthalene
1-Fluoro-2-[3,5-difluoro-4-(3,4,5-trifluorophenyl)phenyl]-6-ethylnaphthalene
1-Fluoro-2-[3,5-difluoro-4-(3,4,5-trifluorophenyl)phenyl]-6-propylnaphthalene
1-Fluoro-2-[3,5-difluoro-4-(3,4,5-trifluorophenyl)phenyl]-6-butylnaphthalene
1-Fluoro-2-[3,5-difluoro-4-(3,4,5-trifluorophenyl)phenyl]-6-pentylnaphthalene
1-Fluoro-2-[3,5-difluoro-4-(3,4,5-trifluorophenyl)phenyl]-6-hexylnaphthalene
1-Fluoro-2-[3,5-difluoro-4-(3,4,5-trifluorophenyl)phenyl]-6-heptylnaphthalene
1-Fluoro-2-[3,5-difluoro-4-(3,4,5-trifluorophenyl)phenyl]-6-(3-butenyl)naphthalene
1-Fluoro-2-[3,5-difluoro-4-(4-fluorophenyl)phenyl]-6-ethylnaphthalene
1-Fluoro-2-[3,5-difluoro-4-(4-fluorophenyl)phenyl]-6-propylnaphthalene
1-Fluoro-2-[3,5-difluoro-4-(4-fluorophenyl)phenyl]-6-butylnaphthalene
1-Fluoro-2-[3,5-difluoro-4-(4-fluorophenyl)phenyl]-6-pentylnaphthalene
1-Fluoro-2-[3,5-difluoro-4-(4-fluorophenyl)phenyl]-6-hexylnaphthalene
1-Fluoro-2-[3,5-difluoro-4-(4-fluorophenyl)phenyl]-6-heptylnaphthalene
1-Fluoro-2-[3,5-difluoro-4-(4-fluorophenyl)phenyl]-6-(3-butenyl)naphthalene
1-Fluoro-2-[3,5-difluoro-4-(3-fluorophenyl)phenyl]-6-ethylnaphthalene
1-Fluoro-2-[3,5-difluoro-4-(3-fluorophenyl)phenyl]-6-propylnaphthalene
1-Fluoro-2-[3,5-difluoro-4-(3-fluorophenyl)phenyl]-6-butylnaphthalene
1-Fluoro-2-[3,5-difluoro-4-(3-fluorophenyl)phenyl]-6-pentylnaphthalene
1-Fluoro-2-[3,5-difluoro-4-(3-fluorophenyl)phenyl]-6-hexylnaphthalene
1-Fluoro-2-[3,5-difluoro-4-(3-fluorophenyl)phenyl]-6-heptylnaphthalene
1-Fluoro-2-[3,5-difluoro-4-(3-fluorophenyl)phenyl]-6-(3-butenyl)naphthalene
1-Fluoro-2-[3,5-difluoro-4-(3,5-difluorophenyl)phenyl]-6-ethylnaphthalene
1-Fluoro-2-[3,5-difluoro-4-(3,5-difluorophenyl)phenyl]-6-propylnaphthalene
1-Fluoro-2-[3,5-difluoro-4-(3,5-difluorophenyl)phenyl]-6-butylnaphthalene
1-Fluoro-2-[3,5-difluoro-4-(3,5-difluorophenyl)phenyl]-6-pentylnaphthalene
1-Fluoro-2-[3,5-difluoro-4-(3,5-difluorophenyl)phenyl]-6-hexylnaphthalene
1-Fluoro-2-[3,5-difluoro-4-(3,5-difluorophenyl)phenyl]-6-heptylnaphthalene
1-Fluoro-2-[3,5-difluoro-4-(3,5-difluorophenyl)phenyl]-6-(3-butenyl)naphthalene
1-Fluoro-2-[3,5-difluoro-4-(3,5-difluorophenyl)phenyl]-6-ethylnaphthalene
1-Fluoro-2-[3,5-difluoro-4-(3,5-difluorophenyl)phenyl]-6-propylnaphthalene
1-Fluoro-2-[3,5-difluoro-4-(3,5-difluorophenyl)phenyl]-6-butylnaphthalene
1-Fluoro-2-[3,5-difluoro-4-(3,5-difluorophenyl)phenyl]-6-pentylnaphthalene
1-Fluoro-2-[3,5-difluoro-4-(3,5-difluorophenyl)phenyl]-6-hexylnaphthalene
1-Fluoro-2-[3,5-difluoro-4-(3,5-difluorophenyl)phenyl]-6-heptylnaphthalene
1-Fluoro-2-[3,5-difluoro-4-(3,5-difluorophenyl)phenyl]-6-(3-butenyl)naphthalene
1-Fluoro-2-[3,5-difluoro-4-(4-chlorophenyl)phenyl]-6-ethylnaphthalene
1-Fluoro-2-[3,5-difluoro-4-(4-chlorophenyl)phenyl]-6-propylnaphthalene
1-Fluoro-2-[3,5-difluoro-4-(4-chlorophenyl)phenyl]-6-butylnaphthalene
1-Fluoro-2-[3,5-difluoro-4-(4-chlorophenyl)phenyl]-6-pentylnaphthalene
1-Fluoro-2-[3,5-difluoro-4-(4-chlorophenyl)phenyl]-6-hexylnaphthalene
1-Fluoro-2-[3,5-difluoro-4-(4-chlorophenyl)phenyl]-6-heptylnaphthalene
1-Fluoro-2-[3,5-difluoro-4-(4-chlorophenyl)phenyl]-6-(3-butenyl)naphthalene
1-Fluoro-2-[3,5-difluoro-4-(3-fluoro-4-chlorophenyl)phenyl]-6-ethylnaphthalene
1-Fluoro-2-[3,5-difluoro-4-(3-fluoro-4-chlorophenyl)phenyl]-6-propylnaphthalene
1-Fluoro-2-[3,5-difluoro-4-(3-fluoro-4-chlorophenyl)phenyl]-6-butylnaphthalene
1-Fluoro-2-[3,5-difluoro-4-(3-fluoro-4-chlorophenyl)phenyl]-6-pentylnaphthalene
1-Fluoro-2-[3,5-difluoro-4-(3-fluoro-4-chlorophenyl)phenyl]-6-hexylnaphthalene
1-Fluoro-2-[3,5-difluoro-4-(3-fluoro-4-chlorophenyl)phenyl]-6-heptylnaphthalene
1-Fluoro-2-[3,5-difluoro-4-(3-fluoro-4-chlorophenyl)phenyl]-6-(3-butenyl)naphthalene
1-Fluoro-2-[3,5-difluoro-4-(3,5-difluoro-4-chlorophenyl)phenyl]-6-ethylnaphthalene 1-Fluoro-2-[3,5-difluoro-4-(3,5-difluoro-4-chlorophenyl)phenyl]-6-propylnaphthalene
1-Fluoro-2-[3,5-difluoro-4-(3,5-difluoro-4-chlorophenyl)phenyl]-6-butylnaphthalene
1-Fluoro-2-[3,5-difluoro-4-(3,5-difluoro-4-chlorophenyl)phenyl]-6-pentylnaphthalene
1-Fluoro-2-[3,5-difluoro-4-(3,5-difluoro-4-chlorophenyl)phenyl]-6-hexylnaphthalene
1-Fluoro-2-[3,5-difluoro-4-(3,5-difluoro-4-chlorophenyl)phenyl]-6-heptylnaphthalene
1-Fluoro-2-[3,5-difluoro-4-(3,5-difluoro-4-chlorophenyl)phenyl]-6-(3-butenyl)naphthalene
1-Fluoro-2-[3,5-difluoro-4-(4-trifluoromethoxyphenyl)phenyl]-6-ethylnaphthalene
1-Fluoro-2-[3,5-difluoro-4-(4-trifluoromethoxyphenyl)phenyl]-6-propylnaphthalene
1-Fluoro-2-[3,5-difluoro-4-(4-trifluoromethoxyphenyl)phenyl]-6-butylnaphthalene
1-Fluoro-2-[3,5-difluoro-4-(4-trifluoromethoxyphenyl)phenyl]-6-pentylnaphthalene
1-Fluoro-2-[3,5-difluoro-4-(4-trifluoromethoxyphenyl)phenyl]-6-hexylnaphthalene
1-Fluoro-2-[3,5-difluoro-4-(4-trifluoromethoxyphenyl)phenyl]-6-heptylnaphthalene
1-Fluoro-2-[3,5-difluoro-4-(4-trifluoromethoxyphenyl)phenyl]-6-(3-butenyl)naphthalene
1-Fluoro-2-[3,5-difluoro-4-(3-fluoro-4-trifluoromethoxyphenyl)phenyl]-6-ethylnaphthalene
1-Fluoro-2-[3,5-difluoro-4-(3-fluoro-4-trifluoromethoxyphenyl)phenyl]-6-propylnaphthalene
1-Fluoro-2-[3,5-difluoro-4-(3-fluoro-4-trifluoromethoxyphenyl)phenyl]-6-butylnaphthalene
1-Fluoro-2-[3,5-difluoro-4-(3-fluoro-4-trifluoromethoxyphenyl)phenyl]-6-pentylnaphthalene
1-Fluoro-2-[3,5-difluoro-4-(3-fluoro-4-trifluoromethoxyphenyl)phenyl]-6-hexylnaphthalene
1-Fluoro-2-[3,5-difluoro-4-(3-fluoro-4-trifluoromethoxyphenyl)phenyl]-6-heptylnaphthalene
1-Fluoro-2-[3,5-difluoro-4-(3-fluoro-4-trifluoromethoxyphenyl)phenyl]-6-(3-butenyl)naphthalene
1-Fluoro-2-[3,5-difluoro-4-(3,5-difluoro-4-trifluoromethoxyphenyl)phenyl]-6-ethylnaphthalene
0-Fluoro-2-[3,5-difluoro-4-(3,5-difluoro-4-trifluoromethoxyphenyl)phenyl]-6-propylnaphthalene
1-Fluoro-2-[3,5-difluoro-4-(3,5-difluoro-4-trifluoromethoxyphenyl)phenyl]-6-butylnaphthalene
1-Fluoro-2-[3,5-difluoro-4-(3,5-difluoro-4-trifluoromethoxyphenyl)phenyl]-6-pentylnaphthalene
1-Fluoro-2-[3,5-difluoro-4-(3,5-difluoro-4-trifluoromethoxyphenyl)phenyl]-6-hexylnaphthalene
1-Fluoro-2-[3,5-difluoro-4-(3,5-difluoro-4-trifluoromethoxyphenyl)phenyl]-6-heptylnaphthalene
1-Fluoro-2-[3,5-difluoro-4-(3,5-difluoro-4-trifluoromethoxyphenyl)phenyl]-6-(3-butenyl)naphthalene
1-Fluoro-2-[3,5-difluoro-4-(4-difluoromethoxyphenyl)phenyl]-6-ethylnaphthalene
1-Fluoro-2-[3,5-difluoro-4-(4-difluoromethoxyphenyl)phenyl]-6-propylnaphthalene
1-Fluoro-2-[3,5-difluoro-4-(4-difluoromethoxyphenyl)phenyl]-6-butylnaphthalene
1-Fluoro-2-[3,5-difluoro-4-(4-difluoromethoxyphenyl)phenyl]-6-pentylnaphthalene
1-Fluoro-2-[3,5-difluoro-4-(4-difluoromethoxyphenyl)phenyl]-6-hexylnaphthalene
1-Fluoro-2-[3,5-difluoro-4-(4-difluoromethoxyphenyl)phenyl]-6-heptylnaphthalene
1-Fluoro-2-[3,5-difluoro-4-(4-difluoromethoxyphenyl)phenyl]-6-(3-butenyl)naphthalene
1-Fluoro-2-[3,5-difluoro-4-(3-fluoro-4-difluoromethoxyphenyl)phenyl]-6-ethylnaphthalene
1-Fluoro-2-[3,5-difluoro-4-(3-fluoro-4-difluoromethoxyphenyl)phenyl]-6-propylnaphthalene
1-Fluoro-2-[3,5-difluoro-4-(3-fluoro-4-difluoromethoxyphenyl)phenyl]-6-butylnaphthalene
1-Fluoro-2-[3,5-difluoro-4-(3-fluoro-4-difluoromethoxyphenyl)phenyl]-6-pentylnaphthalene
1-Fluoro-2-[3,5-difluoro-4-(3-fluoro-4-difluoromethoxyphenyl)phenyl]-6-hexylnaphthalene
1-Fluoro-2-[3,5-difluoro-4-(3-fluoro-4-difluoromethoxyphenyl)phenyl]-6-heptylnaphthalene
1-Fluoro-2-[3,5-difluoro-4-(3-fluoro-4-difluoromethoxyphenyl)phenyl]-6-(3-butenyl)naphthalene
1-Fluoro-2-[3,5-difluoro-4-(3,5-difluoro-4-difluoromethoxyphenyl)phenyl]-6-ethylnaphthalene
1-Fluoro-2-[3,5-difluoro-4-(3,5-difluoro-4-difluoromethoxyphenyl)phenyl]-6-propylnaphthalene
1-Fluoro-2-[3,5-difluoro-4-(3,5-difluoro-4-difluoromethoxyphenyl)phenyl]-6-butylnaphthalene
1-Fluoro-2-[3,5-difluoro-4-(3,5-difluoro-4-difluoromethoxyphenyl)phenyl]-6-pentylnaphthalene
1-Fluoro-2-[3,5-difluoro-4-(3,5-difluoro-4-difluoromethoxyphenyl)phenyl]-6-hexylnaphthalene
1-Fluoro-2-[3,5-difluoro-4-(3,5-difluoro-4-difluoromethoxyphenyl)phenyl]-6-heptylnaphthalene
1-Fluoro-2-[3,5-difluoro-4-(3,5-difluoro-4-difluoromethoxyphenyl)phenyl]-6-(3-butenyl)naphthalene
1-Fluoro-2-[3,5-difluoro-4-(4-trifluoromethylphenyl)phenyl]-6-ethylnaphthalene
1-Fluoro-2-[3,5-difluoro-4-(4-trifluoromethylphenyl)phenyl]-6-propylnaphthalene
1-Fluoro-2-[3,5-difluoro-4-(4-trifluoromethylphenyl)phenyl]-6-butylnaphthalene
1-Fluoro-2-[3,5-difluoro-4-(4-trifluoromethylphenyl)phenyl]-6-pentylnaphthalene
1-Fluoro-2-[3,5-difluoro-4-(4-trifluoromethylphenyl)phenyl]-6-hexylnaphthalene
1-Fluoro-2-[3,5-difluoro-4-(4-trifluoromethylphenyl)phenyl]-6-heptylnaphthalene
1-Fluoro-2-[3,5-difluoro-4-(4-trifluoromethylphenyl)phenyl]-6-(3-butenyl)naphthalene
1-Fluoro-2-[3,5-difluoro-4-(3-fluoro-4-trifluoromethylphenyl)phenyl]-6-ethylnaphthalene
1-Fluoro-2-[3,5-difluoro-4-(3-fluoro-4-trifluoromethylphenyl)phenyl]-6-propylnaphthalene
1-Fluoro-2-[3,5-difluoro-4-(3-fluoro-4-trifluoromethylphenyl)phenyl]-6-butylnaphthalene
1-Fluoro-2-[3,5-difluoro-4-(3-fluoro-4-trifluoromethylphenyl)phenyl]-6-pentylnaphthalene
1-Fluoro-2-[3,5-difluoro-4-(3-fluoro-4-trifluoromethylphenyl)phenyl]-6-hexylnaphthalene
1-Fluoro-2-[3,5-difluoro-4-(3-fluoro-4-trifluoromethylphenyl)phenyl]-6-heptylnaphthalene
1-Fluoro-2-[3,5-difluoro-4-(3-fluoro-4-trifluoromethylphenylphenyl)phenyl]-6-(3-butenyl)naphthalene
1-Fluoro-2-[3,5-difluoro-4-(3,5-difluoro-4-trifluoromethylphenyl)phenyl]-6-ethylnaphthalene
1-Fluoro-2-[3,5-difluoro-4-(3,5-difluoro-4-trifluoromethylphenyl)phenyl]-6-propylnaphthalene
1-Fluoro-2-[3,5-difluoro-4-(3,5-difluoro-4-trifluoromethylphenyl)phenyl]-6-butylnaphthalene
1-Fluoro-2-[3,5-difluoro-4-(3,5-difluoro-4-trifluoromethylphenyl)phenyl]-6-pentylnaphthalene 1-Fluoro-2-[3,5-difluoro-4-(3,5-difluoro-4-trifluoromethylphenyl)phenyl]-6-hexylnaphthalene
1-Fluoro-2-[3,5-difluoro-4-(3,5-difluoro-4-trifluoromethylphenyl)phenyl]-6-heptylnaphthalene
1-Fluoro-2-[3,5-difluoro-4-(3,5-difluoro-4-trifluoromethylphenylphenyl)phenyl]-6-(3-butenyl)naphthalene
1-Fluoro-2-[3,5-difluoro-4-(4-methoxyphenyl)phenyl]-6-ethylnaphthalene
1-Fluoro-2-[3,5-difluoro-4-(4-methoxyphenyl)phenyl]-6-propylnaphthalene
1-Fluoro-2-[3,5-difluoro-4-(4-methoxyphenyl)phenyl]-6-butylnaphthalene
1-Fluoro-2-[3,5-difluoro-4-(4-methoxyphenyl)phenyl]-6-pentylnaphthalene
1-Fluoro-2-[3,5-difluoro-4-(4-methoxyphenyl)phenyl]-6-hexylnaphthalene
1-Fluoro-2-[3,5-difluoro-4-(4-methoxyphenyl)phenyl]-6-heptylnaphthalene
1-Fluoro-2-[3,5-difluoro-4-(4-methoxyphenyl)phenyl]-6-(3-butenyl)naphthalene
1-Fluoro-2-[3,5-difluoro-4-(3-fluoro-4-methoxyphenyl)phenyl]-6-ethylnaphthalene
1-Fluoro-2-[3,5-difluoro-4-(3-fluoro-4-methoxyphenyl)phenyl]-6-propylnaphthalene
1-Fluoro-2-[3,5-difluoro-4-(3-fluoro-4-methoxyphenyl)phenyl]-6-butylnaphthalene
1-Fluoro-2-[3,5-difluoro-4-(3-fluoro-4-methoxyphenyl)phenyl]-6-pentylnaphthalene
1-Fluoro-2-[3,5-difluoro-4-(3-fluoro-4-methoxyphenyl)phenyl]-6-hexylnaphthalene
1-Fluoro-2-[3,5-difluoro-4-(3-fluoro-4-methoxyphenyl)phenyl]-6-heptylnaphthalene
1-Fluoro-2-[3,5-difluoro-4-(3-fluoro-4-methoxyphenyl)phenyl]-6-(3-butenyl)naphthalene
1-Fluoro-2-[3,5-difluoro-4-(3,5-difluoro-4-methoxyphenyl)phenyl]-6-ethylnaphthalene
1-Fluoro-2-[3,5-difluoro-4-(3,5-difluoro-4-methoxyphenyl)phenyl]-6-propylnaphthalene
1-Fluoro-2-[3,5-difluoro-4-(3,5-difluoro-4-methoxyphenyl)phenyl]-6-butylnaphthalene
1-Fluoro-2-[3,5-difluoro-4-(3,5-difluoro-4-methoxyphenyl)phenyl]-6-pentylnaphthalene
1-Fluoro-2-[3,5-difluoro-4-(3,5-difluoro-4-methoxyphenyl)phenyl]-6-hexylnaphthalene
1-Fluoro-2-[3,5-difluoro-4-(3,5-difluoro-4-methoxyphenyl)phenyl]-6-heptylnaphthalene
1-Fluoro-2-[3,5-difluoro-4-(3,5-difluoro-4-methoxyphenyl)phenyl]-6-(3-butenyl)naphthalene
1-Fluoro-2-[3,5-difluoro-4-(4-allyloxyphenyl)phenyl]-6-ethylnaphthalene
1-Fluoro-2-[3,5-difluoro-4-(4-allyloxyphenyl)phenyl]-6-propylnaphthalene
1-Fluoro-2-[3,5-difluoro-4-(4-allyloxyphenyl)phenyl]-6-butylnaphthalene
1-Fluoro-2-[3,5-difluoro-4-(4-allyloxyphenyl)phenyl]-6-pentylnaphthalene
1-Fluoro-2-[3,5-difluoro-4-(4-allyloxyphenyl)phenyl]-6-hexylnaphthalene
1-Fluoro-2-[3,5-difluoro-4-(4-allyloxyphenyl)phenyl]-6-heptylnaphthalene
1-Fluoro-2-[3,5-difluoro-4-(4-allyloxyphenyl)phenyl]-6-(3-butenyl)naphthalene
1-Fluoro-2-[3,5-difluoro-4-(4-methylphenyl)phenyl]-6-ethylnaphthalene
1-Fluoro-2-[3,5-difluoro-4-(4-methylphenyl)phenyl]-6-propylnaphthalene
1-Fluoro-2-[3,5-difluoro-4-(4-methylphenyl)phenyl]-6-butylnaphthalene
1-Fluoro-2-[3,5-difluoro-4-(4-methylphenyl)phenyl]-6-pentylnaphthalene
1-Fluoro-2-[3,5-difluoro-4-(4-methylphenyl)phenyl]-6-hexylnaphthalene
1-Fluoro-2-[3,5-difluoro-4-(4-methylphenyl)phenyl]-6-heptylnaphthalene
1-Fluoro-2-[3,5-difluoro-4-(4-methylphenyl)phenyl]-6-(3-butenyl)naphthalene
1-Fluoro-2-[3,5-difluoro-4-[4-(3-butenyl)phenyl]phenyl]-6-ethylnaphthalene
1-Fluoro-2-[3,5-difluoro-4-[4-(3-butenyl)phenyl]phenyl]-6-propylnaphthalene
1-Fluoro-2-[3,5-difluoro-4-[4-(3-butenyl)phenyl]phenyl]-6-butylnaphthalene
1-Fluoro-2-[3,5-difluoro-4-[4-(3-butenyl)phenyl]phenyl]-6-pentylnaphthalene
1-Fluoro-2-[3,5-difluoro-4-[4-(3-butenyl)phenyl]phenyl]-6-hexylnaphthalene
1-Fluoro-2-[3,5-difluoro-4-[4-(3-butenyl)phenyl]phenyl]-6-heptylnaphthalene
1-Fluoro-2-[3,5-difluoro-4-[4-(3-butenyl)phenyl]phenyl]-6-(3-butenyl)naphthalene Example 5

Synthesis of 1-fluoro-2-(3,4-difluorophenyl)-6-(trans-4-propylcyclohexyl)naphthalene (5-a) Synthesis of 2-methoxy-6-(4-propylcyclohexa-1-ene-1-yl)naphthalene 22.6 g of magnesium was suspended in 30 ml of THF. To the suspension was then added dropwise a solution of 20 g of 2-bromo-6-methoxynaphthalene in 100 ml of THF at a rate such that THF was gently refluxed in about 2 hours. The reaction mixture was then further stirred for 1 hour. To the reaction solution was then added dropwise a solution of 130.1 g of 4-propylcyclohexanene in 520 ml of THF in 1 hour. The reaction mixture was further stirred for 2 hours. To the reaction solution was then added 200 ml of a 10% hydrochloric acid. To the reaction mixture was then added 200 ml of hexane. The resulting organic phase was then separated. The resulting aqueous phase was then extracted with 100 ml of hexane. To the material thus extracted was then added the organic phase. The mixture was washed with water, saturated aqueous solution of sodium bicarbonate and saturated brine, and then dried over anhydrous sodium sulfate. The solvent was distilled off. To the residue were then added 280 ml of toluene and 4.0 g of p-toluenesulfonic acid monohydrate. The reaction mixture was then heated under reflux for 3 hours. The reaction solution was allowed to cool to room temperature, washed with water, saturated aqueous solution of sodium bicarbonate and saturated brine, and then dried over anhydrous sodium sulfate. The solvent was then distilled off to obtain 260 g of an oily cyclohexanol derivative. The total amount of the cyclohexanol derivative thus obtained was then dissolved in 800 ml of toluene. To the solution was then added 16.1 g of p-toluenesulfonic monohydrate. The reaction mixture was then heated to a temperature of 110° C. with stirring while the distilled water was being removed away. After the termination of distillation of water, the reaction solution was then returned to room temperature. To the reaction solution was then added 300 ml of water. The resulting organic phase was then separated.

The organic phase thus separated was washed with saturated aqueous solution of sodium bicarbonate, water and saturated brine, and then dried over anhydrous sodium sulfate. The solvent was then distilled off to obtain 246 g of 2-methoxy-6-(4-propylcyclohexa-1-ene-1-yl)naphthalene in the for of an oily crude product.

(5-b) Synthesis of 2-methoxy-6-(trans-4-propylcyclohexyl)naphthalene

The total amount of 2-methoxy-6-(4-propylcyclohexa-1-ene-1-yl)naphthalene obtained in the process (5-a) was dissolved in 1.2 l of ethyl acetate. To the solution was then added 47 g of 5% palladium/carbon (hydrous). The reaction mixture was then stirred in an autoclave at a hydrogen pressure of 4 kg/cm$^2$. The reaction mixture was than stirred at room temperature for 5 hours. The catalyst was then removed by filtration through Celite. The solvent was then distilled off to obtain 260 g of a trans/cis mixture of 2-methoxy-6-(4-propylcyclohexyl)naphthalene. The total amount of the product was then dissolved in 1.3 l of N,N-dimethylformamide (DMF). To the solution was then added 125 g of potassium t-butoxide. The reaction mixture was then heated under reflux for 5 hours. The reaction solution was then allowed to cool to room temperature. To the reaction solution was then added 200 ml of water. The reaction solution was then extracted twice with 200 ml of toluene. The material thus extracted and the organic phase were together washed with diluted hydrochloric acid, saturated aqueous solution of sodium bicarbonate, water and saturated brine, and then dried over anhydrous sodium sulfate. The solvent was distilled off. The residue was purified through silica gel column chromatography (toluene), and then recrystallized twice from ethanol to obtain 115 g of 2-methoxy-6-(trans-4-propylcyclohexyl)naphthalene in the form of white crystal.

(5-c) Synthesis of 6-(trans-4-propylcyclohexyl)-2-naphthol

To the total amount of 2-methoxy-6-(trans-4-propylcyclohexyl)naphthalene obtained in the process (5-b) were added 700 ml of acetic acid and 700 ml of a 48% hydrobromic acid. The reaction mixture was then heated under reflux for 20 hours. The reaction solution was then allowed to cool to room temperature. To the reaction solute on was then added 200 ml of water. The reaction solution was then extracted twice with 400 ml of toluene. The material thus extracted and the organic phase were together washed with water and then with saturated brine, and then dehydrated and dried over anhydrous sodium sulfate. The solvent was then distilled off to obtain 109 g of 6-(trans-4-propylcyclohexyl)-2-naphthol in the form of white crystal.

(5-d) Synthesis of 1-fluoro-6-(trans-4-propylcyclohexyl)-2-naphthol

The total amount of 6-(trans-4-propylcyclohexyl)-2-naphthol obtained in the process (5-c) was dissolved in 500 ml of dichloromethane. To the solution was then added 7 g of sodium trifluoromethanesulfonate. The reaction mixture was then vigorously stirred. To the reaction solution was then added gradually 86.7 g of N,N'-difluoro-2,2'-dipyridinium bistetrafluoroborate. The reaction mixture was then further stirred at room temperature for 5 hours. To the reaction solution were added water and then a 10% aqueous solution of sodium hydroxide so that excess fluorinating agent was decomposed. The reaction solution was then returned to acidity with diluted hydrochloric acid. The resulting organic phase was then separated. The resulting aqueous phase was then extracted with 100 ml of anhydrous sodium sulfate. The material thus extracted and the organic phase were together washed with water and then with saturated brine, and then dehydrated and dried over sodium sulfate. The solvent was distilled off to obtain 131.5 g of a crude crystal which was then purified through silica gel column chromatography (toluene) to obtain 83 g of 1-fluoro-6-(trans-4-proopylcyclohexyl)-2-naphthol in the torn of white crystal

(5-e) Synthesis of 6-(trans-4-propylcyclohexyl)naphthalene-2-yl trifluoromethanesulfonate The total amount of 1-fluoro-6-(trans-4-propylcyclohexyl)-2-naphthol obtained in the process (5-d) was dissolved in 450 ml of dichloromethane. To the solution was added 55.3 ml of trifluoromethanesulfonic anhydride to make a suspension which was then cooled to a temperature of 5° C. To the suspension was then added dropwise 54 ml of pyridine with vigorous stirring. The reaction mixture was then further stirred for 1 hour. To the reaction mixture was then added 100 ml of water to terminate the reaction. The resulting organic phase was then separated. The resulting aqueous phase was then extracted with 100 ml of dichloromethane. The material thus extracted and the organic phase were together washed sequentially with diluted hydrochloric acid, saturated aqueous solution of sodium bicarbonate, water and saturated brine, and then dehydrated and dried over anhydrous sodium sulfate. The solvent was distilled off to obtain 105 g of a crude crystal which was then purified through silica gel column chromatography (hexane) to obtain 96 g of 6-(trans-4-propylcyclohexyl)naphthalene-2-yl trifluoromethanesulfonate in the form of white crystal.

(5-f) Synthesis of 1-fluoro-2-(3,4-difluorophenyl)-6-(trans-4-propylcyclohexyl)naphthalene 1 g of magnesium was suspended in 1 ml of THF. To the suspension was then added dropwise a solution of 7.9 g of 3,4-difluoro-1-bromobenzene in 32 ml of THF at a rate such that THF was gently refluxed. The reaction mixture was then stirred at room temperature for 1 hour. Excess magnesium was then removed by filtration. The residue was then added dropwise to a solution of 10 g of 6-(trans-4-propylcyclohexyl)naphthalene-2-yl trifluoromethanesulfonate obtained in the process (2-e) and 0.5 g of dibromobis(triphenylphosphine)nickel (II) in 40 ml of THF at a temperature of 40° C. The reaction mixture was then stirred for 1 hour. To the reaction mixture was then added 50 ml of water. The reaction mixture was extracted with 50 ml of toluene, washed with water and saturated brine, and then dried over anhydrous sodium sulfate. The solvent was then distilled off. The residue was purified through silica gel column chromatography (hexane), and then recrystallized from ethanol to obtain 2.6 g of purified 1-fluoro-2-(3,4-difluorophenyl)-6-(trans-4-propylcyclohexyl)naphthalene. (Cr 85 N 198.5 I)

The following compounds were prepared in the same manner as mentioned above.

1-Fluoro-2-(3,4-difluorophenyl)-6-(trans-4-ethylcyclohexyl)naphthalene

1-Fluoro-2-(3,4-difluorophenyl)-6-(trans-4-butylcyclohexyl)naphthalene

1-Fluoro-2-(3,4-difluorophenyl)-6-(trans-4-pentylcyclohexyl)naphthalene
1-Fluoro-2-(3,4,5-trifluorophenyl)-6-(trans-4-ethylcyclohexyl)naphthalene
1-Fluoro-2-(3,4,5-trifluorophenyl)-6-(trans-4-propylcyclohexyl)naphthalene
1-Fluoro-2-(3,4,5-trifluorophenyl)-6-(trans-4-butylcyclohexyl)naphthalene
1-Fluoro-2-(3,4,5-trifluorophenyl)-6-(trans-4-pentylcyclohexyl)naphthalene
1-Fluoro-2-(4-fluorophenyl)-6-(trans-4-ethylcyclohexyl)naphthalene
1-Fluoro-2-(4-fluorophenyl)-6-(trans-4-propylcyclohexyl)naphthalene
1-Fluoro-2-(4-fluorophenyl)-6-(trans-4-butylcyclohexyl)naphthalene
1-Fluoro-2-(4-fluorophenyl)-6-(trans-4-pentylcyclohexyl)naphthalene
1-Fluoro-2-(4-fluorophenyl)-6-(trans-4-hexylcyclohexyl)naphthalene
1-Fluoro-2-(4-fluorophenyl)-6-(trans-4-heptylcyclohexyl)naphthalene
1-Fluoro-2-(3-fluorophenyl)-6-(trans-4-ethylcyclohexyl)naphthalene
1-Fluoro-2-(3-fluorophenyl)-6-(trans-4-propylcyclohexyl)naphthalene
1-Fluoro-2-(3-fluorophenyl)-6-(trans-4-butylcyclohexyl)naphthalene
1-Fluoro-2-(3-fluorophenyl)-6-(trans-4-pentylcyclohexyl)naphthalene
1-Fluoro-2-(3-fluorophenyl)-6-(trans-4-hexylcyclohexyl)naphthalene
1-Fluoro-2-(3-fluorophenyl)-6-(trans-4-heptylcyclohexyl)naphthalene
1-Fluoro-2-(3,5-difluorophenyl)-6-(trans-4-ethylcyclohexyl)naphthalene
1-Fluoro-2-(3,5-difluorophenyl)-6-(trans-4-propylcyclohexyl)naphthalene
1-Fluoro-2-(3,5-difluorophenyl)-6-(trans-4-butylcyclohexyl)naphthalene
1-Fluoro-2-(3,5-difluorophenyl)-6-(trans-4-pentylcyclohexyl)naphthalene
1-Fluoro-2-(3,5-difluorophenyl)-6-(trans-4-hexylcyclohexyl)naphthalene
1-Fluoro-2-(3,5-difluorophenyl)-6-(trans-4-heptylcyclohexyl)naphthalene
1-Fluoro-2-phenyl-6-(trans-4-ethylcyclohexyl)naphthalene
1-Fluoro-2-phenyl-6-(trans-4-propylcyclohexyl)naphthalene
1-Fluoro-2-phenyl-6-(trans-4-butylcyclohexyl)naphthalene
1-Fluoro-2-phenyl-6-(trans-4-pentylcyclohexyl)naphthalene
1-Fluoro-2-phenyl-6-(trans-4-hexylcyclohexyl)naphthalene
1-Fluoro-2-phenyl-6-(trans-4-heptylcyclohexyl)naphthalene
1-Fluoro-2-(4-chlorophenyl)-6-(trans-4-ethylcyclohexyl)naphthalene
1-Fluoro-2-(4-chlorophenyl)-6-(trans-4-propylcyclohexyl)naphthalene
1-Fluoro-2-(4-chlorophenyl)-6-(trans-4-butylcyclohexyl)naphthalene
1-Fluoro-2-(4-chlorophenyl)-6-(trans-4-pentylcyclohexyl)naphthalene
1-Fluoro-2-(4-chlorophenyl)-6-(trans-4-hexylcyclohexyl)naphthalene
1-Fluoro-2-(4-chlorophenyl)-6-(trans-4-heptylcyclohexyl)naphthalene
1-Fluoro-2-(3-fluoro-4-chlorophenyl)-6-(trans-4-ethylcyclohexyl)naphthalene
1-Fluoro-2-(3-fluoro-4-chlorophenyl)-6-(trans-4-propylcyclohexyl)naphthalene
1-Fluoro-2-(3-fluoro-4-chlorophenyl)-6-(trans-4-butylcyclohexyl)naphthalene
1-Fluoro-2-(3-fluoro-4-chlorophenyl)-6-(trans-4-pentylcyclohexyl)naphthalene
1-Fluoro-2-(3-fluoro-4-chlorophenyl)-6-(trans-4-hexylcyclohexyl)naphthalene
1-Fluoro-2-(3-fluoro-4-chlorophenyl)-6-(trans-4-heptylcyclohexyl)naphthalene
1-Fluoro-2-(3,5-difluoro-4-chlorophenyl)-6-(trans-4-ethylcyclohexyl)naphthalene
1-Fluoro-2-(3,5-difluoro-4-chlorophenyl)-6-(trans-4-propylcyclohexyl)naphthalene
1-Fluoro-2-(3,5-difluoro-4-chlorophenyl)-6-(trans-4-butylcyclohexyl)naphthalene
1-Fluoro-2-(3,5-difluoro-4-chlorophenyl)-6-(trans-4-pentylcyclohexyl)naphthalene
1-Fluoro-2-(3,5-difluoro-4-chlorophenyl)-6-(trans-4-hexylcyclohexyl)naphthalene
1-Fluoro-2-(3,5-difluoro-4-chlorophenyl)-6-(trans-4-heptylcyclohexyl)naphthalene
1-Fluoro-2-(4-trifluoromethoxyphenyl)-6-(trans-4-ethylcyclohexyl)naphthalene
1-Fluoro-2-(4-trifluoromethoxyphenyl)-6-(trans-4-propylcyclohexyl)naphthalene
1-Fluoro-2-(4-trifluoromethoxyphenyl)-6-(trans-4-butylcyclohexyl)naphthalene
1-Fluoro-2-(4-trifluoromethoxyphenyl)-6-(trans-4-pentylcyclohexyl)naphthalene
1-Fluoro-2-(4-trifluoromethoxyphenyl)-6-(trans-4-hexylcyclohexyl)naphthalene
1-Fluoro-2-(4-trifluoromethoxyphenyl)-6-(trans-4-heptylcyclohexyl)naphthalene
1-Fluoro-2-(3-fluoro-4-trifluoromethoxyphenyl)-6-(trans-4-ethylcyclohexyl)naphthalene
1-Fluoro-2-(3-fluoro-4-trifluoromethoxyphenyl)-6-(trans-4-propylcyclohexyl)naphthalene
1-Fluoro-2-(3-fluoro-4-trifluoromethoxyphenyl)-6-(trans-4-butylcyclohexyl)naphthalene
1-Fluoro-2-(3-fluoro-4-trifluoromethoxyphenyl)-6-(trans-4-pentylcyclohexyl)naphthalene
1-Fluoro-2-(3-fluoro-4-trifluoromethoxyphenyl)-6-(trans-4-hexylcyclohexyl)naphthalene
1-Fluoro-2-(3-fluoro-4-trifluoromethoxyphenyl)-6-(trans-4-heptylcyclohexyl)naphthalene
1-Fluoro-2-(3,5-difluoro-4-trifluoromethoxyphenyl)-6-(trans-4-ethylcyclohexyl)naphthalene
1-Fluoro-2-(3,5-difluoro-4-trifluoromethoxyphenyl)-6-(trans-4-propylcyclohexyl)naphthalene
1-Fluoro-2-(3,5-difluoro-4-trifluoromethoxyphenyl)-6-(trans-4-butylcyclohexyl)naphthalene
1-Fluoro-2-(3,5-difluoro-4-trifluoromethoxyphenyl)-6-(trans-4-pentylcyclohexyl)naphthalene
1-Fluoro-2-(3,5-difluoro-4-trifluoromethoxyphenyl)-6-(trans-4-hexylcyclohexyl)naphthalene
1-Fluoro-2-(3,5-difluoro-4-trifluoromethoxyphenyl)-6-(trans-4-heptylcyclohexyl)naphthalene
1-Fluoro-2-(4-difluoromethoxyphenyl)-6-(trans-4-ethylcyclohexyl)naphthalene
1-Fluoro-2-(4-difluoromethoxyphenyl)-6-(trans-4-propylcyclohexyl)naphthalene
1-Fluoro-2-(4-difluoromethoxyphenyl)-6-(trans-4-butylcyclohexyl)naphthalene 1-Fluoro-2-(4-difluoromethoxyphenyl)-6-(trans-4-pentylcyclohexyl)naphthalene
1-Fluoro-2-(4-difluoromethoxyphenyl)-6-(trans-4-hexylcyclohexyl)naphthalene
1-Fluoro-2-(4-difluoromethoxyphenyl)-6-(trans-4-heptylcyclohexyl)naphthalene
1-Fluoro-2-(3-fluoro-4-difluoromethoxyphenyl)-6-(trans-4-ethylcyclohexyl)naphthalene
1-Fluoro-2-(3-fluoro-4-difluoromethoxyphenyl)-6-(trans-4-propylcyclohexyl)naphthalene
1-Fluoro-2-(3-fluoro-4-difluoromethoxyphenyl)-6-(trans-4-butylcyclohexyl)naphthalene
1-Fluoro-2-(3-fluoro-4-difluoromethoxyphenyl)-6-(trans-4-pentylcyclohexyl)naphthalene
1-Fluoro-2-(3-fluoro-4-difluoromethoxyphenyl)-6-(trans-4-hexylcyclohexyl)naphthalene
1-Fluoro-2-(3-fluoro-4-difluoromethoxyphenyl)-6-(trans-4-heptylcyclohexyl)naphthalene
1-Fluoro-2-(3,5-difluoro-4-difluoromethoxyphenyl)-6-(trans-4-ethylcyclohexyl)naphthalene
1-Fluoro-2-(3,5-difluoro-4-difluoromethoxyphenyl)-6-(trans-4-propylcyclohexyl)naphthalene
1-Fluoro-2-(3,5-difluoro-4-difluoromethoxyphenyl)-6-(trans-4-butylcyclohexyl)naphthalene
1-Fluoro-2-(3,5-difluoro-4-difluoromethoxyphenyl)-6-(trans-4-pentylcyclohexyl)naphthalene
1-Fluoro-2-(3,5-difluoro-4-difluoromethoxyphenyl)-6-(trans-4-hexylcyclohexyl)naphthalene
1-Fluoro-2-(3,5-difluoro-4-difluoromethoxyphenyl)-6-(trans-4-heptylcyclohexyl)naphthalene
1-Fluoro-2-(4-trifluoromethylphenyl)-6-(trans-4-ethylcyclohexyl)naphthalene
1-Fluoro-2-(4-trifluoromethylphenyl)-6-(trans-4-propylcyclohexyl)naphthalene
1-Fluoro-2-(4-trifluoromethylphenyl)-6-(trans-4-butylcyclohexyl)naphthalene
1-Fluoro-2-(4-trifluoromethylphenyl)-6-(trans-4-pentylcyclohexyl)naphthalene
1-Fluoro-2-(4-trifluoromethylphenyl)-6-(trans-4-hexylcyclohexyl)naphthalene
1-Fluoro-2-(4-trifluoromethylphenyl)-6-(trans-4-heptylcyclohexyl)naphthalene
1-Fluoro-2-(3-fluoro-4-trifluoromethylphenyl)-6-(trans-4-ethylcyclohexyl)naphthalene
1-Fluoro-2-(3-fluoro-4-trifluoromethylphenyl)-6-(trans-4-propylcyclohexyl)naphthalene
1-Fluoro-2-(3-fluoro-4-trifluoromethylphenyl)-6-(trans-4-butylcyclohexyl)naphthalene
1-Fluoro-2-(3-fluoro-4-trifluoromethylphenyl)-6-(trans-4-pentylcyclohexyl)naphthalene
1-Fluoro-2-(3-fluoro-4-trifluoromethylphenyl)-6-(trans-4-hexylcyclohexyl)naphthalene
1-Fluoro-2-(3-fluoro-4-trifluoromethylphenyl)-6-(trans-4-heptylcyclohexyl)naphthalene
1-Fluoro-2-(3,5-difluoro-4-trifluoromethylphenyl)-6-(trans-4-ethylcyclohexyl)naphthalene
1-Fluoro-2-(3,5-difluoro-4-trifluoromethylphenyl)-6-(trans-4-propylcyclohexyl)naphthalene
1-Fluoro-2-(3,5-difluoro-4-trifluoromethylphenyl)-6-(trans-4-butylcyclohexyl)naphthalene
1-Fluoro-2-(3,5-difluoro-4-trifluoromethylphenyl)-6-(trans-4-pentylcyclohexyl)naphthalene
1-Fluoro-2-(3,5-difluoro-4-trifluoromethylphenyl)-6-(trans-4-hexylcyclohexyl)naphthalene
1-Fluoro-2-(3,5-difluoro-4-trifluoromethylphenyl)-6-(trans-4-heptylcyclohexyl)naphthalene
1-Fluoro-2-(4-methoxyphenyl)-6-(trans-4-ethylcyclohexyl)naphthalene
1-Fluoro-2-(4-methoxyphenyl)-6-(trans-4-propylcyclohexyl)naphthalene
1-Fluoro-2-(4-methoxyphenyl)-6-(trans-4-butylcyclohexyl)naphthalene
1-Fluoro-2-(4-methoxyphenyl)-6-(trans-4-pentylcyclohexyl)naphthalene
1-Fluoro-2-(4-methoxyphenyl)-6-(trans-4-hexylcyclohexyl)naphthalene
1-Fluoro-2-(4-methoxyphenyl)-6-(trans-4-heptylcyclohexyl)naphthalene
1-Fluoro-2-(3-fluoro-4-methoxyphenyl)-6-(trans-4-ethylcyclohexyl)naphthalene
1-Fluoro-2-(3-fluoro-4-methoxyphenyl)-6-(trans-4-propylcyclohexyl)naphthalene
1-Fluoro-2-(3-fluoro-4-methoxyphenyl)-6-(trans-4-butylcyclohexyl)naphthalene
1-Fluoro-2-(3-fluoro-4-methoxyphenyl)-6-(trans-4-pentylcyclohexyl)naphthalene
1-Fluoro-2-(3-fluoro-4-methoxyphenyl)-6-(trans-4-hexylcyclohexyl)naphthalene
1-Fluoro-2-(3-fluoro-4-methoxyphenyl)-6-(trans-4-heptylcyclohexyl)naphthalene
1-Fluoro-2-(3,5-difluoro-4-methoxyphenyl)-6-(trans-4-ethylcyclohexyl)naphthalene
1-Fluoro-2-(3,5-difluoro-4-methoxyphenyl)-6-(trans-4-propylcyclohexyl)naphthalene
1-Fluoro-2-(3,5-difluoro-4-methoxyphenyl)-6-(trans-4-butylcyclohexyl)naphthalene
1-Fluoro-2-(3,5-difluoro-4-methoxyphenyl)-6-(trans-4-pentylcyclohexyl)naphthalene
1-Fluoro-2-(3,5-difluoro-4-methoxyphenyl)-6-(trans-4-hexylcyclohexyl)naphthalene
1-Fluoro-2-(3,5-difluoro-4-methoxyphenyl)-6-(trans-4-heptylcyclohexyl)naphthalene
1-Fluoro-2-(4-allyloxyphenyl)-6-(trans-4-ethylcyclohexyl)naphthalene
1-Fluoro-2-(4-allyloxyphenyl)-6-(trans-4-propylcyclohexyl)naphthalene
1-Fluoro-2-(4-allyloxyphenyl)-6-(trans-4-butylcyclohexyl)naphthalene
1-Fluoro-2-(4-allyloxyphenyl)-6-(trans-4-pentylcyclohexyl)naphthalene
1-Fluoro-2-(4-allyloxyphenyl)-6-(trans-4-hexylcyclohexyl)naphthalene
1-Fluoro-2-(4-allyloxyphenyl)-6-(trans-4-heptylcyclohexyl)naphthalene
1-Fluoro-2-(4-methylphenyl)-6-(trans-4-ethylcyclohexyl)naphthalene
1-Fluoro-2-(4-methylphenyl)-6-(trans-4-propylcyclohexyl)naphthalene
1-Fluoro-2-(4-methylphenyl)-6-(trans-4-butylcyclohexyl)naphthalene
1-Fluoro-2-(4-methylphenyl)-6-(trans-4-pentylcyclohexyl)naphthalene
1-Fluoro-2-(4-methylphenyl)-6-(trans-4-hexylcyclohexyl)naphthalene
1-Fluoro-2-(4-methylphenyl)-6-(trans-4-heptylcyclohexyl)naphthalene
1-Fluoro-2-[4-(3-butenyl)phenyl]-6-(trans-4-ethylcyclohexyl)naphthalene
1-Fluoro-2-[4-(3-butenyl)phenyl]-6-(trans-4-propylcyclohexyl)naphthalene
1-Fluoro-2-[4-(3-butenyl)phenyl]-6-(trans-4-butylcyclohexyl)naphthalene 1-Fluoro-2-(4-(3-butenyl)phenyl]-6-(trans-4-pentylcyclohexyl)naphthalene
1-Fluoro-2-[4-(3-butenyl)phenyl]-6-(trans-4-hexylcyclohexyl)naphthalene
1-Fluoro-2-[4-(3-butenyl)phenyl]-6-(trans-4-heptylcyclohexyl)naphthalene Example 6

Synthesis of 1-fluoro-2-(3,4-difluorophenyl)-6-[2-(trans-4-propylcyclohexyl)ethyl]naphthalene The procedure of Example 5 was followed except that trans-4-propylcyclohexane ethanol was used instead of 4-propylcyclohexanene and isomerization in the process (5-b) was not effected to obtain 1-fluoro-2-(3,4-difluorophenyl)-6-[2-(trans-4-propylcyclohexylethyl]naphthalene in the form of white crystal.

The following compounds were prepared in the same manner as mentioned above.

1-Fluoro-2-(3,4-difluorophenyl)-6-[2-(trans-4-ethylcyclohexyl)ethyl]naphthalene
1-Fluoro-2-(3,4-difluorophenyl)-6-[2-(trans-4-butylcyclohexyl)ethyl]naphthalene
1-Fluoro-2-(3,4-difluorophenyl)-6-[2-(trans-4-pentylcyclohexyl)ethyl]naphthalene
1-Fluoro-2-(3,4,5-trifluorophenyl)-6-[2-(trans-4-ethylcyclohexyl)ethyl]naphthalene
1-Fluoro-2-(3,4,5-trifluorophenyl)-6-[2-(trans-4-propylcyclohexyl)ethyl]naphthalene
1-Fluoro-2-(3,4,5-trifluorophenyl)-6-[2-(trans-4-butylcyclohexyl)ethyl]naphthalene
1-Fluoro-2-(3,4,5-trifluorophenyl)-6-[2-(trans-4-pentylcyclohexyl)ethyl]naphthalene
1-Fluoro-2-(4-fluorophenyl)-6-[2-(trans-4-ethylcyclohexyl)ethyl]naphthalene
1-Fluoro-2-(4-fluorophenyl)-6-[2-(trans-4-propylcyclohexyl)ethyl]naphthalene
1-Fluoro-2-(4-fluorophenyl)-6-[2-(trans-4-butylcyclohexyl)ethyl]naphthalene
1-Fluoro-2-(4-fluorophenyl)-6-[2-(trans-4-pentylcyclohexyl)ethyl]naphthalene
1-Fluoro-2-(4-fluorophenyl)-6-[2-(trans-4-hexylcyclohexyl)ethyl]naphthalene
1-Fluoro-2-(4-fluorophenyl)-6-[2-(trans-4-heptylcyclohexyl)ethyl]naphthalene
1-Fluoro-2-(3-fluorophenyl)-6-[2-(trans-4-ethylcyclohexyl)ethyl]naphthalene
1-Fluoro-2-(3-fluorophenyl)-6-[2-(trans-4-propylcyclohexyl)ethyl]naphthalene
1-Fluoro-2-(3-fluorophenyl)-6-[2-(trans-4-butylcyclohexyl)ethyl]naphthalene
1-Fluoro-2-(3-fluorophenyl)-6-[2-(trans-4-pentylcyclohexyl)ethyl]naphthalene
1-Fluoro-2-(3-fluorophenyl)-6-[2-(trans-4-hexylcyclohexyl)ethyl]naphthalene
1-Fluoro-2-(3-fluorophenyl)-6-[2-(trans-4-heptylcyclohexyl)ethyl]naphthalene
1-Fluoro-2-(3,5-difluorophenyl)-6-[2-(trans-4-ethylcyclohexyl)ethyl]naphthalene
1-Fluoro-2-(3,5-difluorophenyl)-6-[2-(trans-4-propylcyclohexyl)ethyl]naphthalene
1-Fluoro-2-(3,5-difluorophenyl)-6-[2-(trans-4-butylcyclohexyl)ethyl]naphthalene
1-Fluoro-2-(3,5-difluorophenyl)-6-[2-(trans-4-pentylcyclohexyl)ethyl]naphthalene
1-Fluoro-2-(3,5-difluorophenyl)-6-[2-(trans-4-hexylcyclohexyl)ethyl]naphthalene
1-Fluoro-2-(3,5-difluorophenyl)-6-[2-(trans-4-heptylcyclohexyl)ethyl]naphthalene
1-Fluoro-2-phenyl-6-[2-(trans-4-ethylcyclohexyl)ethyl]naphthalene
1-Fluoro-2-phenyl-6-[2-(trans-4-propylcyclohexyl)ethyl]naphthalene
1-Fluoro-2-phenyl-6-[2-(trans-4-butylcyclohexyl)ethyl]naphthalene
1-Fluoro-2-phenyl-6-[2-(trans-4-pentylcyclohexyl)ethyl]naphthalene
1-Fluoro-2-phenyl-6-[2-(trans-4-hexylcyclohexyl)ethyl]naphthalene
1-Fluoro-2-phenyl-6-[2-(trans-4-heptylcyclohexyl)ethyl]naphthalene
1-Fluoro-2-(4-chlorophenyl)-6-[2-(trans-4-ethylcyclohexyl)ethyl]naphthalene
1-Fluoro-2-(4-chlorophenyl)-6-[2-(trans-4-propylcyclohexyl)ethyl]naphthalene
1-Fluoro-2-(4-chlorophenyl)-6-[2-(trans-4-butylcyclohexyl)ethyl]naphthalene
1-Fluoro-2-(4-chlorophenyl)-6-[2-(trans-4-pentylcyclohexyl)ethyl]naphthalene
1-Fluoro-2-(4-chlorophenyl)-6-[2-(trans-4-hexylcyclohexyl)ethyl]naphthalene
1-Fluoro-2-(4-chlorophenyl)-6-[2-(trans-4-heptylcyclohexyl)ethyl]naphthalene
1-Fluoro-2-(3-fluoro-4-chlorophenyl)-6-[2-(trans-4-ethylcyclohexyl)ethyl]naphthalene
1-Fluoro-2-(3-fluoro-4-chlorophenyl)-6-[2-(trans-4-propylcyclohexyl)ethyl]naphthalene
1-Fluoro-2-(3-fluoro-4-chlorophenyl)-6-[2-(trans-4-butylcyclohexyl)ethyl]naphthalene
1-Fluoro-2-(3-fluoro-4-chlorophenyl)-6-[2-(trans-4-pentylcyclohexyl)ethyl]naphthalene
1-Fluoro-2-(3-fluoro-4-chlorophenyl)-6-[2-(trans-4-hexylcyclohexyl)ethyl]naphthalene
1-Fluoro-2-(3-fluoro-4-chlorophenyl)-6-[2-(trans-4-heptylcyclohexyl)ethyl]naphthalene
1-Fluoro-2-(3,5-difluoro-4-chlorophenyl)-6-[2-(trans-4-ethylcyclohexyl)ethyl]naphthalene
1-Fluoro-2-(3,5-difluoro-4-chlorophenyl)-6-[2-(trans-4-propylcyclohexyl)ethyl]naphthalene
1-Fluoro-2-(3,5-difluoro-4-chlorophenyl)-6-[2-(trans-4-butylcyclohexyl)ethyl]naphthalene
1-Fluoro-2-(3,5-difluoro-4-chlorophenyl)-6-[2-(trans-4-pentylcyclohexyl)ethyl]naphthalene
1-Fluoro-2-(3,5-difluoro-4-chlorophenyl)-6-[2-(trans-4-hexylcyclohexyl)ethyl]naphthalene
1-Fluoro-2-(3,5-difluoro-4-chlorophenyl)-6-[2-(trans-4-heptylcyclohexyl)ethyl]naphthalene
1-Fluoro-2-(4-trifluoromethoxyphenyl)-6-[2-(trans-4-ethylcyclohexyl)ethyl]naphthalene
1-Fluoro-2-(4-trifluoromethoxyphenyl)-6-[2-(trans-4-propylcyclohexyl)ethyl]naphthalene
1-Fluoro-2-(4-trifluoromethoxyphenyl)-6-[2-(trans-4-butylcyclohexyl)ethyl]naphthalene
1-Fluoro-2-(4-trifluoromethoxyphenyl)-6-[2-(trans-4-pentylcyclohexyl)ethyl]naphthalene
1-Fluoro-2-(4-trifluoromethoxyphenyl)-6-[2-(trans-4-hexylcyclohexyl)ethyl]naphthalene
1-Fluoro-2-(4-trifluoromethoxyphenyl)-6-[2-(trans-4-heptylcyclohexyl)ethyl]naphthalene
1-Fluoro-2-(3-fluoro-4-trifluoromethoxyphenyl)-6-[2-(trans-4-ethylcyclohexyl)ethyl]naphthalene 1-Fluoro-2-(3-fluoro-4-trifluoromethoxyphenyl)-6-[2-(trans-4-propylcyclohexyl)ethyl]naphthalene
1-Fluoro-2-(3-fluoro-4-trifluoromethoxyphenyl)-6-[2-(trans-4-butylcyclohexyl)ethyl]naphthalene
1-Fluoro-2-(3-fluoro-4-trifluoromethoxyphenyl)-6-[2-(trans-4-pentylcyclohexyl)ethyl]naphthalene
1-Fluoro-2-(3-fluoro-4-trifluoromethoxyphenyl)-6-[2-(trans-4-hexylcyclohexyl)ethyl]naphthalene
1-Fluoro-2-(3-fluoro-4-trifluoromethoxyphenyl)-6-[2-(trans-4-heptylcyclohexyl)ethyl]naphthalene
1-Fluoro-2-(3,5-difluoro-4-trifluoromethoxyphenyl)-6-[2-(trans-4-ethylcyclohexyl)ethyl]naphthalene
1-Fluoro-2-(3,5-difluoro-4-trifluoromethoxyphenyl)-6-[2-(trans-4-propylcyclohexyl)ethyl]naphthalene
1-Fluoro-2-(3,5-difluoro-4-trifluoromethoxyphenyl)-6-[2-(trans-4-butylcyclohexyl)ethyl]naphthalene
1-Fluoro-2-(3,5-difluoro-4-trifluoromethoxyphenyl)-6-[2-(trans-4-pentylcyclohexyl)ethyl]naphthalene
1-Fluoro-2-(3,5-difluoro-4-trifluoromethoxyphenyl)-6-[2-(trans-4-hexylcyclohexyl)ethyl]naphthalene
1-Fluoro-2-(3,5-difluoro-4-trifluoromethoxyphenyl)-6-[2-(trans-4-heptylcyclohexyl)ethyl]naphthalene
1-Fluoro-2-(4-difluoromethoxyphenyl)-6-[2-(trans-4-ethylcyclohexyl)ethyl]naphthalene
1-Fluoro-2-(4-difluoromethoxyphenyl)-6-[2-(trans-4-propylcyclohexyl)ethyl]naphthalene
1-Fluoro-2-(4-difluoromethoxyphenyl)-6-[2-(trans-4-butylcyclohexyl)ethyl]naphthalene
1-Fluoro-2-(4-difluoromethoxyphenyl)-6-[2-(trans-4-pentylcyclohexyl)ethyl]naphthalene
1-Fluoro-2-(4-difluoromethoxyphenyl)-6-[2-(trans-4-hexylcyclohexyl)ethyl]naphthalene
1-Fluoro-2-(4-difluoromethoxyphenyl)-6-[2-(trans-4-heptylcyclohexyl)ethyl]naphthalene
1-Fluoro-2-(3-fluoro-4-difluoromethoxyphenyl)-6-[2-(trans-4-ethylcyclohexyl)ethyl]naphthalene
1-Fluoro-2-(3-fluoro-4-difluoromethoxyphenyl)-6-[2-(trans-4-propylcyclohexyl)ethyl]naphthalene
1-Fluoro-2-(3-fluoro-4-difluoromethoxyphenyl)-6-[2-(trans-4-butylcyclohexyl)ethyl]naphthalene
1-Fluoro-2-(3-fluoro-4-difluoromethoxyphenyl)-6-[2-(trans-4-pentylcyclohexyl)ethyl]naphthalene
1-Fluoro-2-(3-fluoro-4-difluoromethoxyphenyl)-6-[2-(trans-4-hexylcyclohexyl)ethyl]naphthalene
1-Fluoro-2-(3-fluoro-4-difluoromethoxyphenyl)-6-[2-(trans-4-heptylcyclohexyl)ethyl]naphthalene
1-Fluoro-2-(3,5-difluoro-4-difluoromethoxyphenyl)-6-[2-(trans-4-ethylcyclohexyl)ethyl]naphthalene
1-Fluoro-2-(3,5-difluoro-4-difluoromethoxyphenyl)-6-[2-(trans-4-propylcyclohexyl)ethyl]naphthalene
1-Fluoro-2-(3,5-difluoro-4-difluoromethoxyphenyl)-6-[2-(trans-4-butylcyclohexyl)ethyl]naphthalene
1-Fluoro-2-(3,5-difluoro-4-difluoromethoxyphenyl)-6-[2-(trans-4-pentylcyclohexyl)ethyl]naphthalene
1-Fluoro-2-(3,5-difluoro-4-difluoromethoxyphenyl)-6-[2-(trans-4-hexylcyclohexyl)ethyl]naphthalene
1-Fluoro-2-(3,5-difluoro-4-difluoromethoxyphenyl)-6-[2-(trans-4-heptylcyclohexyl)ethyl]naphthalene
1-Fluoro-2-(4-trifluoromethylphenyl)-6-[2-(trans-4-ethylcyclohexyl)ethyl]naphthalene
1-Fluoro-2-(4-trifluoromethylphenyl)-6-[2-(trans-4-propylcyclohexyl)ethyl]naphthalene
1-Fluoro-2-(4-trifluoromethylphenyl)-6-[2-(trans-4-butylcyclohexyl)ethyl]naphthalene
1-Fluoro-2-(4-trifluoromethylphenyl)-6-[2-(trans-4-pentylcyclohexyl)ethyl]naphthalene
1-Fluoro-2-(4-trifluoromethylphenyl)-6-[2-(trans-4-hexylcyclohexyl)ethyl]naphthalene
1-Fluoro-2-(4-trifluoromethylphenyl)-6-[2-(trans-4-heptylcyclohexyl)ethyl]naphthalene
1-Fluoro-2-(3-fluoro-4-trifluoromethylphenyl)-6-[2-(trans-4-ethylcyclohexyl)ethyl]naphthalene
1-Fluoro-2-(3-fluoro-4-trifluoromethylphenyl)-6-[2-(trans-4-propylcyclohexyl)ethyl]naphthalene
1-Fluoro-2-(3-fluoro-4-trifluoromethylphenyl)-6-[2-(trans-4-butylcyclohexyl)ethyl]naphthalene
1-Fluoro-2-(3-fluoro-4-trifluoromethylphenyl)-6-[2-(trans-4-pentylcyclohexyl)ethyl]naphthalene
1-Fluoro-2-(3-fluoro-4-trifluoromethylphenyl)-6-[2-(trans-4-hexylcyclohexyl)ethyl]naphthalene
1-Fluoro-2-(3-fluoro-4-trifluoromethylphenyl)-6-[2-(trans-4-heptylcyclohexyl)ethyl]naphthalene
1-Fluoro-2-(3,5-difluoro-4-trifluoromethylphenyl)-6-[2-(trans-4-ethylcyclohexyl)ethyl]naphthalene
1-Fluoro-2-(3,5-difluoro-4-trifluoromethylphenyl)-6-[2-(trans-4-propylcyclohexyl)ethyl]naphthalene
1-Fluoro-2-(3,5-difluoro-4-trifluoromethylphenyl)-6-[2-(trans-4-butylcyclohexyl)ethyl]naphthalene
1-Fluoro-2-(3,5-difluoro-4-trifluoromethylphenyl)-6-[2-(trans-4-pentylcyclohexyl)ethyl]naphthalene
1-Fluoro-2-(3,5-difluoro-4-trifluoromethylphenyl)-6-[2-(trans-4-hexylcyclohexyl)ethyl]naphthalene
1-Fluoro-2-(3,5-difluoro-4-trifluoromethylphenyl)-6-[2-(trans-4-heptylcyclohexyl)ethyl]naphthalene
1-Fluoro-2-(4-methoxyphenyl)-6-[2-(trans-4-ethylcyclohexyl)ethyl]naphthalene
1-Fluoro-2-(4-methoxyphenyl)-6-[2-(trans-4-propylcyclohexyl)ethyl]naphthalene
1-Fluoro-2-(4-methoxyphenyl)-6-[2-(trans-4-butylcyclohexyl)ethyl]naphthalene
1-Fluoro-2-(4-methoxyphenyl)-6-[2-(trans-4-pentylcyclohexyl)ethyl]naphthalene
1-Fluoro-2-(4-methoxyphenyl)-6-[2-(trans-4-hexylcyclohexyl)ethyl]naphthalene
1-Fluoro-2-(4-methoxyphenyl)-6-[2-(trans-4-heptylcyclohexyl)ethyl]naphthalene
1-Fluoro-2-(3-fluoro-4-methoxyphenyl)-6-[2-(trans-4-ethylcyclohexyl)ethyl]naphthalene
1-Fluoro-2-(3-fluoro-4-methoxyphenyl)-6-[2-(trans-4-propylcyclohexyl)ethyl]naphthalene
1-Fluoro-2-(3-fluoro-4-methoxyphenyl)-6-[2-(trans-4-butylcyclohexyl)ethyl]naphthalene
1-Fluoro-2-(3-fluoro-4-methoxyphenyl)-6-[2-(trans-4-pentylcyclohexyl)ethyl]naphthalene
1-Fluoro-2-(3-fluoro-4-methoxyphenyl)-6-[2-(trans-4-hexylcyclohexyl)ethyl]naphthalene
1-Fluoro-2-(3-fluoro-4-methoxyphenyl)-6-[2-(trans-4-heptylcyclohexyl)ethyl]naphthalene
1-Fluoro-2-(3,5-difluoro-4-methoxyphenyl)-6-[2-(trans-4-ethylcyclohexyl)ethyl]naphthalene
1-Fluoro-2-(3,5-difluoro-4-methoxyphenyl)-6-[2-(trans-4-propylcyclohexyl)ethyl]naphthalene
1-Fluoro-2-(3,5-difluoro-4-methoxyphenyl)-6-[2-(trans-4-butylcyclohexyl)ethyl]naphthalene
1-Fluoro-2-(3,5-difluoro-4-methoxyphenyl)-6-[2-(trans-4-pentylcyclohexyl)ethyl]naphthalene
1-Fluoro-2-(3,5-difluoro-4-methoxyphenyl)-6-[2-(trans-4-hexylcyclohexyl)ethyl]naphthalene
1-Fluoro-2-(3,5-difluoro-4-methoxyphenyl)-6-[2-(trans-4-heptylcyclohexyl)ethyl]naphthalene
1-Fluoro-2-(4-allyloxyphenyl)-6-[2-(trans-4-ethylcyclohexyl)ethyl]naphthalene 1-Fluoro-2-(4-allyloxyphenyl)-6-[2-(trans-4-propylcyclohexyl)ethyl]naphthalene
1-Fluoro-2-(4-allyloxyphenyl)-6-[2-(trans-4-butylcyclohexyl)ethyl]naphthalene
1-Fluoro-2-(4-allyloxyphenyl)-6-[2-(trans-4-pentylcyclohexyl)ethyl]naphthalene
1-Fluoro-2-(4-allyloxyphenyl)-6-[2-(trans-4-hexylcyclohexyl)ethyl]naphthalene
1-Fluoro-2-(4-allyloxyphenyl)-6-[2-(trans-4-heptylcyclohexyl)ethyl]naphthalene
1-Fluoro-2-(4-methylphenyl)-6-[2-(trans-4-ethylcyclohexyl)ethyl]naphthalene
1-Fluoro-2-(4-methylphenyl)-6-[2-(trans-4-propylcyclohexyl)ethyl]naphthalene
1-Fluoro-2-(4-methylphenyl)-6-[2-(trans-4-butylcyclohexyl)ethyl]naphthalene
1-Fluoro-2-(4-methylphenyl)-6-[2-(trans-4-pentylcyclohexyl)ethyl]naphthalene
1-Fluoro-2-(4-methylphenyl)-6-[2-(trans-4-hexylcyclohexyl)ethyl]naphthalene
1-Fluoro-2-(4-methylphenyl)-6-[2-(trans-4-heptylcyclohexyl)ethyl]naphthalene
1-Fluoro-2-[4-(3-butenyl)phenyl]-6-[2-(trans-4-ethylcyclohexyl)ethyl]naphthalene
1-Fluoro-2-[4-(3-butenyl)phenyl]-6-[2-(trans-4-propylcyclohexyl)ethyl]naphthalene
1-Fluoro-2-[4-(3-butenyl)phenyl]-6-[2-(trans-4-butylcyclohexyl)ethyl]naphthalene
1-Fluoro-2-[4-(3-butenyl)phenyl]-6-[2-(trans-4-pentylcyclohexyl)ethyl]naphthalene
1-Fluoro-2-[4-(3-butenyl)phenyl]-6-[2-(trans-4-hexylcyclohexyl)ethyl]naphthalene
1-Fluoro-2-[4-(3-butenyl)phenyl]-6-[2-(trans-4-heptylcyclohexyl)ethyl]naphthalene
1-Fluoro-2-(3,4-difluorophenyl)-6-[2-(4-ethylphenyl)ethyl]naphthalene
1-Fluoro-2-(3,4-difluorophenyl)-6-[2-(4-butylphenyl)ethyl]naphthalene
1-Fluoro-2-(3,4-difluorophenyl)-6-[2-(4-pentylphenyl)ethyl]naphthalene
1-Fluoro-2-(3,4,5-trifluorophenyl)-6-[2-(4-ethylphenyl)ethyl]naphthalene
1-Fluoro-2-(3,4,5-trifluorophenyl)-6-[2-(4-propylphenyl)ethyl]naphthalene
1-Fluoro-2-(3,4,5-trifluorophenyl)-6-[2-(4-butylphenyl)ethyl]naphthalene
1-Fluoro-2-(3,4,5-trifluorophenyl)-6-[2-(4-pentylphenyl)ethyl]naphthalene
1-Fluoro-2-(4-fluorophenyl)-6-[2-(4-ethylphenyl)ethyl]naphthalene
1-Fluoro-2-(4-fluorophenyl)-6-[2-(4-propylphenyl)ethyl]naphthalene
1-Fluoro-2-(4-fluorophenyl)-6-[2-(4-butylphenyl)ethyl]naphthalene
1-Fluoro-2-(4-fluorophenyl)-6-[2-(4-pentylphenyl)ethyl]naphthalene
1-Fluoro-2-(4-fluorophenyl)-6-[2-(4-hexylphenyl)ethyl]naphthalene
1-Fluoro-2-(4-fluorophenyl)-6-[2-(4-heptylphenyl)ethyl]naphthalene
1-Fluoro-2-(3-fluorophenyl)-6-[2-(4-ethylphenyl)ethyl]naphthalene
1-Fluoro-2-(3-fluorophenyl)-6-[2-(4-propylphenyl)ethyl]naphthalene
1-Fluoro-2-(3-fluorophenyl)-6-[2-(4-butylphenyl)ethyl]naphthalene
1-Fluoro-2-(3-fluorophenyl)-6-[2-(4-pentylphenyl)ethyl]naphthalene
1-Fluoro-2-(3-fluorophenyl)-6-[2-(4-hexylphenyl)ethyl]naphthalene
1-Fluoro-2-(3-fluorophenyl)-6-[2-(4-heptylphenyl)ethyl]naphthalene
1-Fluoro-2-(3,5-difluorophenyl)-6-[2-(4-ethylphenyl)ethyl]naphthalene
1-Fluoro-2-(3,5-difluorophenyl)-6-[2-(4-propylphenyl)ethyl]naphthalene
1-Fluoro-2-(3,5-difluorophenyl)-6-[2-(4-butylphenyl)ethyl]naphthalene
1-Fluoro-2-(3,5-difluorophenyl)-6-[2-(4-pentylphenyl)ethyl]naphthalene
1-Fluoro-2-(3,5-difluorophenyl)-6-[2-(4-hexylphenyl)ethyl]naphthalene
1-Fluoro-2-(3,5-difluorophenyl)-6-[2-(4-heptylphenyl)ethyl]naphthalene
1-Fluoro-2-phenyl-6-[2-(4-ethylphenyl)ethyl]naphthalene
1-Fluoro-2-phenyl-6-[2-(4-propylphenyl)ethyl]naphthalene
1-Fluoro-2-phenyl-6-[2-(4-butylphenyl)ethyl]naphthalene
1-Fluoro-2-phenyl-6-[2-(4-pentylphenyl)ethyl]naphthalene
1-Fluoro-2-phenyl-6-[2-(4-hexylphenyl)ethyl]naphthalene
1-Fluoro-2-phenyl-6-[2-(4-heptylphenyl)ethyl]naphthalene
1-Fluoro-2-(4-chlorophenyl)-6-[2-(4-ethylphenyl)ethyl]naphthalene
1-Fluoro-2-(4-chlorophenyl)-6-[2-(4-propylphenyl)ethyl]naphthalene
1-Fluoro-2-(4-chlorophenyl)-6-[2-(4-butylphenyl)ethyl]naphthalene
1-Fluoro-2-(4-chlorophenyl)-6-[2-(4-pentylphenyl)ethyl]naphthalene
1-Fluoro-2-(4-chlorophenyl)-6-[2-(4-hexylphenyl)ethyl]naphthalene
1-Fluoro-2-(4-chlorophenyl)-6-[2-(4-heptylphenyl)ethyl]naphthalene
1-Fluoro-2-(3-fluoro-4-chlorophenyl)-6-[2-(4-ethylphenyl)ethyl]naphthalene
1-Fluoro-2-(3-fluoro-4-chlorophenyl)-6-[2-(4-propylphenyl)ethyl]naphthalene
1-Fluoro-2-(3-fluoro-4-chlorophenyl)-6-[2-(4-butylphenyl)ethyl]naphthalene
1-Fluoro-2-(3-fluoro-4-chlorophenyl)-6-[2-(4-pentylphenyl)ethyl]naphthalene
1-Fluoro-2-(3-fluoro-4-chlorophenyl)-6-[2-(4-hexylphenyl)ethyl]naphthalene
1-Fluoro-2-(3-fluoro-4-chlorophenyl)-6-[2-(4-heptylphenyl)ethyl]naphthalene
1-Fluoro-2-(3,5-difluoro-4-chlorophenyl)-6-[2-(4-ethylphenyl)ethyl]naphthalene
1-Fluoro-2-(3,5-difluoro-4-chlorophenyl)-6-[2-(4-propylphenyl)ethyl]naphthalene
1-Fluoro-2-(3,5-difluoro-4-chlorophenyl)-6-[2-(4-butylphenyl)ethyl]naphthalene
1-Fluoro-2-(3,5-difluoro-4-chlorophenyl)-6-[2-(4-pentylphenyl)ethyl]naphthalene
1-Fluoro-2-(3,5-difluoro-4-chlorophenyl)-6-[2-(4-hexylphenyl)ethyl]naphthalene
1-Fluoro-2-(3,5-difluoro-4-chlorophenyl)-6-[2-(4-heptylphenyl)ethyl]naphthalene
1-Fluoro-2-(4-trifluoromethoxyphenyl)-6-[2-(4-ethylphenyl)ethyl]naphthalene
1-Fluoro-2-(4-trifluoromethoxyphenyl)-6-[2-(4-propylphenyl)ethyl]naphthalene
1-Fluoro-2-(4-trifluoromethoxyphenyl)-6-[2-(4-butylphenyl)ethyl]naphthalene 1-Fluoro-2-(4-trifluoromethoxyphenyl)-6-[2-(4-pentylphenyl)ethyl]naphthalene
1-Fluoro-2-(4-trifluoromethoxyphenyl)-6-[2-(4-hexylphenyl)ethyl]naphthalene
1-Fluoro-2-(4-trifluoromethoxyphenyl)-6-[2-(4-heptylphenyl)ethyl]naphthalene
1-Fluoro-2-(3-fluoro-4-trifluoromethoxyphenyl)-6-[2-(4-ethylphenyl)ethyl]naphthalene
1-Fluoro-2-(3-fluoro-4-trifluoromethoxyphenyl)-6-[2-(4-propylphenyl)ethyl]naphthalene
1-Fluoro-2-(3-fluoro-4-trifluoromethoxyphenyl)-6-[2-(4-butylphenyl)ethyl]naphthalene
1-Fluoro-2-(3-fluoro-4-trifluoromethoxyphenyl)-6-[2-(4-pentylphenyl)ethyl]naphthalene
1-Fluoro-2-(3-fluoro-4-trifluoromethoxyphenyl)-6-[2-(4-hexylphenyl)ethyl]naphthalene
1-Fluoro-2-(3-fluoro-4-trifluoromethoxyphenyl)-6-[2-(4-heptylphenyl)ethyl]naphthalene
1-Fluoro-2-(3,5-difluoro-4-trifluoromethoxyphenyl)-6-[2-(4-ethylphenyl)ethyl]naphthalene
1-Fluoro-2-(3,5-difluoro-4-trifluoromethoxyphenyl)-6-[2-(4-propylphenyl)ethyl]naphthalene
1-Fluoro-2-(3,5-difluoro-4-trifluoromethoxyphenyl)-6-[2-(4-butylphenyl)ethyl]naphthalene
1-Fluoro-2-(3,5-difluoro-4-trifluoromethoxyphenyl)-6-[2-(4-pentylphenyl)ethyl]naphthalene
1-Fluoro-2-(3,5-difluoro-4-trifluoromethoxyphenyl)-6-[2-(4-hexylphenyl)ethyl]naphthalene
1-Fluoro-2-(3,5-difluoro-4-trifluoromethoxyphenyl)-6-[2-(4-heptylphenyl)ethyl]naphthalene
1-Fluoro-2-(4-difluoromethoxyphenyl)-6-[2-(4-ethylphenyl)ethyl]naphthalene
1-Fluoro-2-(4-difluoromethoxyphenyl)-6-[2-(4-propylphenyl)ethyl]naphthalene
1-Fluoro-2-(4-difluoromethoxyphenyl)-6-[2-(4-butylphenyl)ethyl]naphthalene
1-Fluoro-2-(4-difluoromethoxyphenyl)-6-[2-(4-pentylphenyl)ethyl]naphthalene
1-Fluoro-2-(4-difluoromethoxyphenyl)-6-[2-(4-hexylphenyl)ethyl]naphthalene
1-Fluoro-2-(4-difluoromethoxyphenyl)-6-[2-(4-heptylphenyl)ethyl]naphthalene
1-Fluoro-2-(3-fluoro-4-difluoromethoxyphenyl)-6-[2-(4-ethylphenyl)ethyl]naphthalene
1-Fluoro-2-(3-fluoro-4-difluoromethoxyphenyl)-6-[2-(4-propylphenyl)ethyl]naphthalene
1-Fluoro-2-(3-fluoro-4-difluoromethoxyphenyl)-6-[2-(4-butylphenyl)ethyl]naphthalene
1-Fluoro-2-(3-fluoro-4-difluoromethoxyphenyl)-6-[2-(4-pentylphenyl)ethyl]naphthalene
1-Fluoro-2-(3-fluoro-4-difluoromethoxyphenyl)-6-[2-(4-hexylphenyl)ethyl]naphthalene
1-Fluoro-2-(3-fluoro-4-difluoromethoxyphenyl)-6-[2-(4-heptylphenyl)ethyl]naphthalene
1-Fluoro-2-(3,5-difluoro-4-difluoromethoxyphenyl)-6-[2-(4-ethylphenyl)ethyl]naphthalene
1-Fluoro-2-(3,5-difluoro-4-difluoromethoxyphenyl)-6-[2-(4-propylphenyl)ethyl]naphthalene
1-Fluoro-2-(3,5-difluoro-4-difluoromethoxyphenyl)-6-[2-(4-butylphenyl)ethyl]naphthalene
1-Fluoro-2-(3,5-difluoro-4-difluoromethoxyphenyl)-6-[2-(4-pentylphenyl)ethyl]naphthalene
1-Fluoro-2-(3,5-difluoro-4-difluoromethoxyphenyl)-6-[2-(4-hexylphenyl)ethyl]naphthalene
1-Fluoro-2-(3,5-difluoro-4-difluoromethoxyphenyl)-6-[2-(4-heptylphenyl)ethyl]naphthalene
1-Fluoro-2-(4-trifluoromethylphenyl)-6-[2-(4-ethylphenyl)ethyl]naphthalene
1-Fluoro-2-(4-trifluoromethylphenyl)-6-[2-(4-propylphenyl)ethyl]naphthalene
1-Fluoro-2-(4-trifluoromethylphenyl)-6-[2-(4-butylphenyl)ethyl]naphthalene
1-Fluoro-2-(4-trifluoromethylphenyl)-6-[2-(4-pentylphenyl)ethyl]naphthalene
1-Fluoro-2-(4-trifluoromethylphenyl)-6-[2-(4-hexylphenyl)ethyl]naphthalene
1-Fluoro-2-(4-trifluoromethylphenyl)-6-[2-(4-heptylphenyl)ethyl]naphthalene
1-Fluoro-2-(3-fluoro-4-trifluoromethylphenyl)-6-[2-(4-ethylphenyl)ethyl]naphthalene
1-Fluoro-2-(3-fluoro-4-trifluoromethylphenyl)-6-[2-(4-propylphenyl)ethyl]naphthalene
1-Fluoro-2-(3-fluoro-4-trifluoromethylphenyl)-6-[2-(4-butylphenyl)ethyl]naphthalene
1-Fluoro-2-(3-fluoro-4-trifluoromethylphenyl)-6-[2-(4-pentylphenyl)ethyl]naphthalene
1-Fluoro-2-(3-fluoro-4-trifluoromethylphenyl)-6-[2-(4-hexylphenyl)ethyl]naphthalene
1-Fluoro-2-(3-fluoro-4-trifluoromethylphenyl)-6-[2-(4-heptylphenyl)ethyl]naphthalene
1-Fluoro-2-(3,5-difluoro-4-trifluoromethylphenyl)-6-[2-(4-ethylphenyl)ethyl]naphthalene
1-Fluoro-2-(3,5-difluoro-4-trifluoromethylphenyl)-6-[2-(4-propylphenyl)ethyl]naphthalene
1-Fluoro-2-(3,5-difluoro-4-trifluoromethylphenyl)-6-[2-(4-butylphenyl)ethyl]naphthalene
1-Fluoro-2-(3,5-difluoro-4-trifluoromethylphenyl)-6-[2-(4-pentylphenyl)ethyl]naphthalene
1-Fluoro-2-(3,5-difluoro-4-trifluoromethylphenyl)-6-[2-(4-hexylphenyl)ethyl]naphthalene
1-Fluoro-2-(3,5-difluoro-4-trifluoromethylphenyl)-6-[2-(4-heptylphenyl)ethyl]naphthalene
1-Fluoro-2-(4-methoxyphenyl)-6-[2-(4-ethylphenyl)ethyl]naphthalene
1-Fluoro-2-(4-methoxyphenyl)-6-[2-(4-propylphenyl)ethyl]naphthalene
1-Fluoro-2-(4-methoxyphenyl)-6-[2-(4-butylphenyl)ethyl]naphthalene
1-Fluoro-2-(4-methoxyphenyl)-6-[2-(4-pentylphenyl)ethyl]naphthalene
1-Fluoro-2-(4-methoxyphenyl)-6-[2-(4-hexylphenyl)ethyl]naphthalene
1-Fluoro-2-(4-methoxyphenyl)-6-[2-(4-heptylphenyl)ethyl]naphthalene
1-Fluoro-2-(3-fluoro-4-methoxyphenyl)-6-[2-(4-ethylphenyl)ethyl]naphthalene
1-Fluoro-2-(3-fluoro-4-methoxyphenyl)-6-[2-(4-propylphenyl)ethyl]naphthalene
1-Fluoro-2-(3-fluoro-4-methoxyphenyl)-6-[2-(4-butylphenyl)ethyl]naphthalene
1-Fluoro-2-(3-fluoro-4-methoxyphenyl)-6-[2-(4-pentylphenyl)ethyl]naphthalene
1-Fluoro-2-(3-fluoro-4-methoxyphenyl)-6-[2-(4-hexylphenyl)ethyl]naphthalene
1-Fluoro-2-(3-fluoro-4-methoxyphenyl)-6-[2-(4-heptylphenyl)ethyl]naphthalene
1-Fluoro-2-(3,5-difluoro-4-methoxyphenyl)-6-[2-(4-ethylphenyl)ethyl]naphthalene
1-Fluoro-2-(3,5-difluoro-4-methoxyphenyl)-6-[2-(4-propylphenyl)ethyl]naphthalene
1-Fluoro-2-(3,5-difluoro-4-methoxyphenyl)-6-[2-(4-butylphenyl)ethyl]naphthalene 0-Fluoro-2-(3,5-difluoro-4-methoxyphenyl)-6-[2-(4-pentylphenyl)ethyl]naphthalene
1-Fluoro-2-(3,5-difluoro-4-methoxyphenyl)-6-[2-(4-hexylphenyl)ethyl]naphthalene
1-Fluoro-2-(3,5-difluoro-4-methoxyphenyl)-6-[2-(4-heptylphenyl)ethyl]naphthalene
1-Fluoro-2-(4-allyloxyphenyl)-6-[2-(4-ethylphenyl)ethyl]naphthalene
1-Fluoro-2-(4-allyloxyphenyl)-6-[2-(4-propylphenyl)ethyl]naphthalene
1-Fluoro-2-(4-allyloxyphenyl)-6-[2-(4-butylphenyl)ethyl]naphthalene
1-Fluoro-2-(4-allyloxyphenyl)-6-[2-(4-pentylphenyl)ethyl]naphthalene
1-Fluoro-2-(4-allyloxyphenyl)-6-[2-(4-hexylphenyl)ethyl]naphthalene
1-Fluoro-2-(4-allyloxyphenyl)-6-[2-(4-heptylphenyl)ethyl]naphthalene
1-Fluoro-2-(4-methylphenyl)-6-[2-(4-ethylphenyl)ethyl]naphthalene
1-Fluoro-2-(4-methylphenyl)-6-[2-(4-propylphenyl)ethyl]naphthalene
1-Fluoro-2-(4-methylphenyl)-6-[2-(4-butylphenyl)ethyl]naphthalene
1-Fluoro-2-(4-methylphenyl)-6-[2-(4-pentylphenyl)ethyl]naphthalene
1-Fluoro-2-(4-methylphenyl)-6-[2-(4-hexylphenyl)ethyl]naphthalene
1-Fluoro-2-(4-methylphenyl)-6-[2-(4-heptylphenyl)ethyl]naphthalene
1-Fluoro-2-[4-(3-butenyl)phenyl]-6-[2-(4-ethylphenyl)ethyl]naphthalene
1-Fluoro-2-[4-(3-butenyl)phenyl]-6-[2-(4-propylphenyl)ethyl]naphthalene
1-Fluoro-2-[4-(3-butenyl)phenyl]-6-[2-(4-butylphenyl)ethyl]naphthalene
1-Fluoro-2-[4-(3-butenyl)phenyl]-6-[2-(4-pentylphenyl)ethyl]naphthalene
1-Fluoro-2-[4-(3-butenyl)phenyl]-6-[2-(4-hexylphenyl)ethyl]naphthalene
1-Fluoro-2-[4-(3-butenyl)phenyl]-6-[2-(4-heptylphenyl)ethyl]naphthalene Example 7

Synthesis of 1-fluoro-2-(3,4,5-trifluorophenyl)-6-(4-propylphenyl)naphthalene

Synthesis of 6-(4-propylphenyl)-2-naphthol 50 g of 6-bromo-2-naphthol and 48 g of 4-propylphenylboric acid (synthesized by reacting a Grignard reagent prepared from 4-propylbromobenzene with trimethyl borate, and then subjecting the reaction product to hydrolysis with hydrochloric acid) were dissolved in a mixture of 200 ml of toluene and 100 ml of ethanol. To the solution was then added 200 ml of a 2 N aqueous solution of potassium carbonate. To the reaction mixture was then added 2.6 g of tetrakis(triphenylphophine)palladium (0). The reaction mixture was then heated under reflux for 6 hours. The reaction solution was then allowed to cool to room temperature. The resulting organic phase was then separated. The resulting aqueous phase was then extracted with toluene. The material thus extracted and the organic phase were together washed sequentially with diluted hydrochloric acid, water and saturated brine, and then dehydrated and dried over anhydrous sodium sulfate. The solvent was then distilled off to obtain 47 g of 6-(4-propylphenyl)-2-naphthol in crystal form.

The crystal thus obtained was then processed in the same manner as (5-d) and (5-e) to obtain 1-fluoro-2-(3,4,5-trifluorophenyl)-6-(4-propylphenyl)naphthalene in the form of white crystal.

The following compounds were prepared in the same manner as mentioned above.
1-Fluoro-2-(3,4-difluorophenyl)-6-(4-ethylphenyl)naphthalene
1-Fluoro-2-(3,4-difluorophenyl)-6-(4-propylphenyl)naphthalene
1-Fluoro-2-(3,4-difluorophenyl)-6-(4-butylphenyl)naphthalene
1-Fluoro-2-(3,4-difluorophenyl)-6-(4-pentylphenyl)naphthalene
1-Fluoro-2-(3,4,5-trifluorophenyl)-6-(4-ethylphenyl)naphthalene
1-Fluoro-2-(3,4,5-trifluorophenyl)-6-(4-propylphenyl)naphthalene
1-Fluoro-2-(3,4,5-trifluorophenyl)-6-(4-butylphenyl)naphthalene
1-Fluoro-2-(3,4,5-trifluorophenyl)-6-(4-pentylphenyl)naphthalene
1-Fluoro-2-(4-fluorophenyl)-6-(4-ethylphenyl)naphthalene
1-Fluoro-2-(4-fluorophenyl)-6-(4-propylphenyl)naphthalene
1-Fluoro-2-(4-fluorophenyl)-6-(4-butylphenyl)naphthalene
1-Fluoro-2-(4-fluorophenyl)-6-(4-pentylphenyl)naphthalene
1-Fluoro-2-(4-fluorophenyl)-6-(4-hexylphenyl)naphthalene
1-Fluoro-2-(4-fluorophenyl)-6-(4-heptylphenyl)naphthalene
1-Fluoro-2-(4-fluorophenyl)-6-[4-(3-butenyl)phenyl]naphthalene
1-Fluoro-2-(3-fluorophenyl)-6-(4-ethylphenyl)naphthalene
1-Fluoro-2-(3-fluorophenyl)-6-(4-propylphenyl)naphthalene
1-Fluoro-2-(3-fluorophenyl)-6-(4-butylphenyl)naphthalene
1-Fluoro-2-(3-fluorophenyl)-6-(4-pentylphenyl)naphthalene
1-Fluoro-2-(3-fluorophenyl)-6-(4-hexylphenyl)naphthalene
1-Fluoro-2-(3-fluorophenyl)-6-(4-heptylphenyl)naphthalene
1-Fluoro-2-(3-fluorophenyl)-6-[4-(3-butenyl)phenyl]naphthalene
1-Fluoro-2-(3,5-difluorophenyl)-6-(4-ethylphenyl)naphthalene
1-Fluoro-2-(3,5-difluorophenyl)-6-(4-propylphenyl)naphthalene
1-Fluoro-2-(3,5-difluorophenyl)-6-(4-butylphenyl)naphthalene
1-Fluoro-2-(3,5-difluorophenyl)-6-(4-pentylphenyl)naphthalene
1-Fluoro-2-(3,5-difluorophenyl)-6-(4-hexylphenyl)naphthalene
1-Fluoro-2-(3,5-difluorophenyl)-6-(4-heptylphenyl)naphthalene
1-Fluoro-2-(3,5-difluorophenyl)-6-[4-(3-butenyl)phenyl]naphthalene
1-Fluoro-2-phenyl-6-(4-ethylphenyl)naphthalene
1-Fluoro-2-phenyl-6-(4-propylphenyl)naphthalene
1-Fluoro-2-phenyl-6-(4-butylphenyl)naphthalene
1-Fluoro-2-phenyl-6-(4-pentylphenyl)naphthalene
1-Fluoro-2-phenyl-6-(4-hexylphenyl)naphthalene
1-Fluoro-2-phenyl-6-(4-heptylphenyl)naphthalene
1-Fluoro-2-phenyl-6-[4-(3-butenyl)phenyl]naphthalene
1-Fluoro-2-(4-chlorophenyl)-6-(4-ethylphenyl)naphthalene
1-Fluoro-2-(4-chlorophenyl)-6-(4-propylphenyl)naphthalene
1-Fluoro-2-(4-chlorophenyl)-6-(4-butylphenyl)naphthalene 1-Fluoro-2-(4-chlorophenyl)-6-(4-pentylphenyl)naphthalene
1-Fluoro-2-(4-chlorophenyl)-6-(4-hexylphenyl)naphthalene
1-Fluoro-2-(4-chlorophenyl)-6-(4-heptylphenyl)naphthalene
1-Fluoro-2-(4-chlorophenyl)-6-[4-(3-butenyl)phenyl]naphthalene
1-Fluoro-2-(3-fluoro-4-chlorophenyl)-6-(4-ethylphenyl)naphthalene
1-Fluoro-2-(3-fluoro-4-chlorophenyl)-6-(4-propylphenyl)naphthalene
1-Fluoro-2-(3-fluoro-4-chlorophenyl)-6-(4-butylphenyl)naphthalene
1-Fluoro-2-(3-fluoro-4-chlorophenyl)-6-(4-pentylphenyl)naphthalene
1-Fluoro-2-(3-fluoro-4-chlorophenyl)-6-(4-hexylphenyl)naphthalene
1-Fluoro-2-(3-fluoro-4-chlorophenyl)-6-(4-heptylphenyl)naphthalene
1-Fluoro-2-(3-fluoro-4-chlorophenyl)-6-[4-(3-butenyl)phenyl]naphthalene
1-Fluoro-2-(3,5-difluoro-4-chlorophenyl)-6-(4-ethylphenyl)naphthalene
1-Fluoro-2-(3,5-difluoro-4-chlorophenyl)-6-(4-propylphenyl)naphthalene
1-Fluoro-2-(3,5-difluoro-4-chlorophenyl)-6-(4-butylphenyl)naphthalene
1-Fluoro-2-(3,5-difluoro-4-chlorophenyl)-6-(4-pentylphenyl)naphthalene
1-Fluoro-2-(3,5-difluoro-4-chlorophenyl)-6-(4-hexylphenyl)naphthalene
1-Fluoro-2-(3,5-difluoro-4-chlorophenyl)-6-(4-heptylphenyl)naphthalene
1-Fluoro-2-(3,5-difluoro-4-chlorophenyl)-6-[4-(3-butenyl)phenyl]naphthalene
1-Fluoro-2-(4-trifluoromethoxyphenyl)-6-(4-ethylphenyl)naphthalene
1-Fluoro-2-(4-trifluoromethoxyphenyl)-6-(4-propylphenyl)naphthalene
1-Fluoro-2-(4-trifluoromethoxyphenyl)-6-(4-butylphenyl)naphthalene
1-Fluoro-2-(4-trifluoromethoxyphenyl)-6-(4-pentylphenyl)naphthalene
1-Fluoro-2-(4-trifluoromethoxyphenyl)-6-(4-hexylphenyl)naphthalene
1-Fluoro-2-(4-trifluoromethoxyphenyl)-6-(4-heptylphenyl)naphthalene
1-Fluoro-2-(4-trifluoromethoxyphenyl)-6-[4-(3-butenyl)phenyl]naphthalene
1-Fluoro-2-(3-fluoro-4-trifluoromethoxyphenyl)-6-(4-ethylphenyl)naphthalene
1-Fluoro-2-(3-fluoro-4-trifluoromethoxyphenyl)-6-(4-propylphenyl)naphthalene
1-Fluoro-2-(3-fluoro-4-trifluoromethoxyphenyl)-6-(4-butylphenyl)naphthalene
1-Fluoro-2-(3-fluoro-4-trifluoromethoxyphenyl)-6-(4-pentylphenyl)naphthalene
1-Fluoro-2-(3-fluoro-4-trifluoromethoxyphenyl)-6-(4-hexylphenyl)naphthalene
1-Fluoro-2-(3-fluoro-4-trifluoromethoxyphenyl)-6-(4-heptylphenyl)naphthalene
1-Fluoro-2-(3-fluoro-4-trifluoromethoxyphenyl)-6-[4-(3-butenyl)phenyl]naphthalene
1-Fluoro-2-(3,5-difluoro-4-trifluoromethoxyphenyl)-6-(4-ethylphenyl)naphthalene
1-Fluoro-2-(3,5-difluoro-4-trifluoromethoxyphenyl)-6-(4-propylphenyl)naphthalene
1-Fluoro-2-(3,5-difluoro-4-trifluoromethoxyphenyl)-6-(4-butylphenyl)naphthalene
1-Fluoro-2-(3,5-difluoro-4-trifluoromethoxyphenyl)-6-(4-pentylphenyl)naphthalene
1-Fluoro-2-(3,5-difluoro-4-trifluoromethoxyphenyl)-6-(4-hexylphenyl)naphthalene
1-Fluoro-2-(3,5-difluoro-4-trifluoromethoxyphenyl)-6-(4-heptylphenyl)naphthalene
1-Fluoro-2-(3,5-difluoro-4-trifluoromethoxyphenyl)-6-[4-(3-butenyl)phenyl]naphthalene
1-Fluoro-2-(4-difluoromethoxyphenyl)-6-(4-ethylphenyl)naphthalene
1-Fluoro-2-(4-difluoromethoxyphenyl)-6-(4-propylphenyl)naphthalene
1-Fluoro-2-(4-difluoromethoxyphenyl)-6-(4-butylphenyl)naphthalene
1-Fluoro-2-(4-difluoromethoxyphenyl)-6-(4-pentylphenyl)naphthalene
1-Fluoro-2-(4-difluoromethoxyphenyl)-6-(4-hexylphenyl)naphthalene
1-Fluoro-2-(4-difluoromethoxyphenyl)-6-(4-heptylphenyl)naphthalene
1-Fluoro-2-(4-difluoromethoxyphenyl)-6-[4-(3-butenyl)phenyl]naphthalene
1-Fluoro-2-(3-fluoro-4-difluoromethoxyphenyl)-6-(4-ethylphenyl)naphthalene
1-Fluoro-2-(3-fluoro-4-difluoromethoxyphenyl)-6-(4-propylphenyl)naphthalene
1-Fluoro-2-(3-fluoro-4-difluoromethoxyphenyl)-6-(4-butylphenyl)naphthalene
1-Fluoro-2-(3-fluoro-4-difluoromethoxyphenyl)-6-(4-pentylphenyl)naphthalene
1-Fluoro-2-(3-fluoro-4-difluoromethoxyphenyl)-6-(4-hexylphenyl)naphthalene
1-Fluoro-2-(3-fluoro-4-difluoromethoxyphenyl)-6-(4-heptylphenyl)naphthalene
1-Fluoro-2-(3-fluoro-4-difluoromethoxyphenyl)-6-[4-(3-butenyl)phenyl]naphthalene
1-Fluoro-2-(3,5-difluoro-4-difluoromethoxyphenyl)-6-(4-ethylphenyl)naphthalene
1-Fluoro-2-(3,5-difluoro-4-difluoromethoxyphenyl)-6-(4-propylphenyl)naphthalene
1-Fluoro-2-(3,5-difluoro-4-difluoromethoxyphenyl)-6-(4-butylphenyl)naphthalene
1-Fluoro-2-(3,5-difluoro-4-difluoromethoxyphenyl)-6-(4-pentylphenyl)naphthalene
1-Fluoro-2-(3,5-difluoro-4-difluoromethoxyphenyl)-6-(4-hexylphenyl)naphthalene
1-Fluoro-2-(3,5-difluoro-4-difluoromethoxyphenyl)-6-(4-heptylphenyl)naphthalene
1-Fluoro-2-(3,5-difluoro-4-difluoromethoxyphenyl)-6-[4-(3-butenyl)phenyl]naphthalene
1-Fluoro-2-(4-trifluoromethylphenyl)-6-(4-ethylphenyl)naphthalene
1-Fluoro-2-(4-trifluoromethylphenyl)-6-(4-propylphenyl)naphthalene
1-Fluoro-2-(4-trifluoromethylphenyl)-6-(4-butylphenyl)naphthalene
1-Fluoro-2-(4-trifluoromethylphenyl)-6-(4-pentylphenyl)naphthalene
1-Fluoro-2-(4-trifluoromethylphenyl)-6-(4-hexylphenyl)naphthalene
1-Fluoro-2-(4-trifluoromethylphenyl)-6-(4-heptylphenyl)naphthalene
1-Fluoro-2-(4-trifluoromethylphenyl)-6-[4-(3-butenyl)phenyl]naphthalene 1-Fluoro-2-(3-fluoro-4-trifluoromethylphenyl)-6-(4-ethylphenyl)naphthalene
1-Fluoro-2-(3-fluoro-4-trifluoromethylphenyl)-6-(4-propylphenyl)naphthalene
1-Fluoro-2-(3-fluoro-4-trifluoromethylphenyl)-6-(4-butylphenyl)naphthalene
1-Fluoro-2-(3-fluoro-4-trifluoromethylphenyl)-6-(4-pentylphenyl)naphthalene
1-Fluoro-2-(3-fluoro-4-trifluoromethylphenyl)-6-(4-hexylphenyl)naphthalene
1-Fluoro-2-(3-fluoro-4-trifluoromethylphenyl)-6-(4-heptylphenyl)naphthalene
1-Fluoro-2-(3-fluoro-4-trifluoromethylphenylphenyl)-6-[4-(3-butenyl)phenyl]naphthalene
1-Fluoro-2-(3,5-difluoro-4-trifluoromethylphenyl)-6-(4-ethylphenyl)naphthalene
1-Fluoro-2-(3,5-difluoro-4-trifluoromethylphenyl)-6-(4-propylphenyl)naphthalene
1-Fluoro-2-(3,5-difluoro-4-trifluoromethylphenyl)-6-(4-butylphenyl)naphthalene
1-Fluoro-2-(3,5-difluoro-4-trifluoromethylphenyl)-6-(4-pentylphenyl)naphthalene
1-Fluoro-2-(3,5-difluoro-4-trifluoromethylphenyl)-6-(4-hexylphenyl)naphthalene
1-Fluoro-2-(3,5-difluoro-4-trifluoromethylphenyl)-6-(4-heptylphenyl)naphthalene
1-Fluoro-2-(3,5-difluoro-4-trifluoromethylphenylphenyl)-6-[4-(3-butenyl)phenyl]naphthalene
1-Fluoro-2-(4-methoxyphenyl)-6-(4-ethylphenyl)naphthalene
1-Fluoro-2-(4-methoxyphenyl)-6-(4-propylphenyl)naphthalene
1-Fluoro-2-(4-methoxyphenyl)-6-(4-butylphenyl)naphthalene
1-Fluoro-2-(4-methoxyphenyl)-6-(4-pentylphenyl)naphthalene
1-Fluoro-2-(4-methoxyphenyl)-6-(4-hexylphenyl)naphthalene
1-Fluoro-2-(4-methoxyphenyl)-6-(4-heptylphenyl)naphthalene
1-Fluoro-2-(4-methoxyphenyl)-6-[4-(3-butenyl)phenyl]naphthalene
1-Fluoro-2-(3-fluoro-4-methoxyphenyl)-6-(4-ethylphenyl)naphthalene
1-Fluoro-2-(3-fluoro-4-methoxyphenyl)-6-(4-propylphenyl)naphthalene
1-Fluoro-2-(3-fluoro-4-methoxyphenyl)-6-(4-butylphenyl)naphthalene
1-Fluoro-2-(3-fluoro-4-methoxyphenyl)-6-(4-pentylphenyl)naphthalene
1-Fluoro-2-(3-fluoro-4-methoxyphenyl)-6-(4-hexylphenyl)naphthalene
1-Fluoro-2-(3-fluoro-4-methoxyphenyl)-6-(4-heptylphenyl)naphthalene
1-Fluoro-2-(3-fluoro-4-methoxyphenyl)-6-[4-(3-butenyl)phenyl]naphthalene
1-Fluoro-2-(3,5-difluoro-4-methoxyphenyl)-6-(4-ethylphenyl)naphthalene
1-Fluoro-2-(3,5-difluoro-4-methoxyphenyl)-6-(4-propylphenyl)naphthalene
1-Fluoro-2-(3,5-difluoro-4-methoxyphenyl)-6-(4-butylphenyl)naphthalene
1-Fluoro-2-(3,5-difluoro-4-methoxyphenyl)-6-(4-pentylphenyl)naphthalene
1-Fluoro-2-(3,5-difluoro-4-methoxyphenyl)-6-(4-hexylphenyl)naphthalene
1-Fluoro-2-(3,5-difluoro-4-methoxyphenyl)-6-(4-heptylphenyl)naphthalene
1-Fluoro-2-(3,5-difluoro-4-methoxyphenyl)-6-[4-(3-butenyl)phenyl]naphthalene
1-Fluoro-2-(4-allyloxyphenyl)-6-(4-ethylphenyl)naphthalene
1-Fluoro-2-(4-allyloxyphenyl)-6-(4-propylphenyl)naphthalene
1-Fluoro-2-(4-allyloxyphenyl)-6-(4-butylphenyl)naphthalene
1-Fluoro-2-(4-allyloxyphenyl)-6-(4-pentylphenyl)naphthalene
1-Fluoro-2-(4-allyloxyphenyl)-6-(4-hexylphenyl)naphthalene
1-Fluoro-2-(4-allyloxyphenyl)-6-(4-heptylphenyl)naphthalene
1-Fluoro-2-(4-allyloxyphenyl)-6-[4-(3-butenyl)phenyl]naphthalene
1-Fluoro-2-(4-methylphenyl)-6-(4-ethylphenyl)naphthalene
1-Fluoro-2-(4-methylphenyl)-6-(4-propylphenyl)naphthalene
1-Fluoro-2-(4-methylphenyl)-6-(4-butylphenyl)naphthalene
1-Fluoro-2-(4-methylphenyl)-6-(4-pentylphenyl)naphthalene
1-Fluoro-2-(4-methylphenyl)-6-(4-hexylphenyl)naphthalene
1-Fluoro-2-(4-methylphenyl)-6-(4-heptylphenyl)naphthalene
1-Fluoro-2-(4-methylphenyl)-6-[4-(3-butenyl)phenyl]naphthalene
1-Fluoro-2-[4-(3-butenyl)phenyl]-6-(4-ethylphenyl)naphthalene
1-Fluoro-2-[4-(3-butenyl)phenyl]-6-(4-propylphenyl)naphthalene
1-Fluoro-2-[4-(3-butenyl)phenyl]-6-(4-butylphenyl)naphthalene
1-Fluoro-2-[4-(3-butenyl)phenyl]-6-(4-pentylphenyl)naphthalene
1-Fluoro-2-[4-(3-butenyl)phenyl]-6-(4-hexylphenyl)naphthalene
1-Fluoro-2-[4-(3-butenyl)phenyl]-6-(4-heptylphenyl)naphthalene
1-Fluoro-2-[4-(3-butenyl)phenyl]-6-[4-(3-butenyl)phenyl]naphthalene Example 8

Synthesis of 1-fluoro-2-(3,4-difluorophenyl)-6-(trans-4-vinylcyclohexyl)naphthalene The Grignard reaction of Example 5 was followed except that 1,4-cyclohexadione monoethylene acetal was used instead of 4-propylcyclohexanene. The reaction product was then dehydrated with potassium hydrogensulfate instead of p-toluenesulfonic acid. To the toluene solution was then added ethylene glycol. The reaction mixture was then heated under reflux while the azeotropically distilled water was being driven out of the system. The reaction solution was allowed to cool to room temperature, washed sequentially with water, saturated aqueous solution of sodium bicarbonate and saturated brine, and then dehydrated and dried over anhydrous sodium sulfate. The solvent was then distilled off to obtain 4-(6-methoxynaphthalene-2-yl)-3-cyclohexenone ethylene acetal. The product was dissolved in toluene, and then subjected to catalytic reduction in the same manner as (2-b). To the reaction solution was than added formic acid. The reaction mixture was heated with stirring, and then cooled. To the reaction solution was then added water. The resulting toluene phase was then washed. The solvent was then distilled off. The resulting crude crystal was then recrystallized from ethanol to obtain 4-(6-methoxy naphthalene-2-yl)cyclohexanene in crystal form. The crystal thus obtained was dissolved in a mixture of toluene and THF, and then cooled. To the reaction solution was then added a Wittig reagent prepared from methoxymethyltriphenylphosphonium bromide and potassium t-butoxide. The reaction mixture was then returned to room temperature. To the reaction mixture were then added water and hexane. Insoluble matters were then removed from the resulting hexane phase by filtration. The residue was then washed with a mixture of water and methanol. The solvent was then distilled off. The residue was then dissolved in THF. To the solution was then added diluted hydrochloric acid. The reaction solution was heated under reflux for 1 hour, and then cooled. To the reaction solution was then added water. The reaction solution was then extracted with ethyl acetate. The solvent was then distilled off. The residue was then dissolved in ethanol. To the solution was then added a 20% aqueous solution of sodium hydroxide. The reaction mixture was then stirred at room temperature. To the reaction solution was then added water. The reaction solution was extracted with toluene, washed, and then dried. The solvent was then distilled off to obtain trans-4-(6-methoxynaphthalene-2-yl)cyclohexane carbaldehyde in crystal form. The crystal thus obtained was dissolved in THF. To the reaction solution was then added a Wittig reagent prepared from methyltriphenylphosphonium iodide and potassium t-butoxide. The reaction mixture was then returned to room temperature. To the reaction mixture were then added water and hexane. Insoluble matters were then removed from the resulting hexane phase by filtration. The residue was washed with a mixture of water and methanol, and then dried. The solvent was then distilled off. The residue was then purified through silica gel column chromatography (toluene) to obtain 2-(trans-4-vinylcyclohexyl)-6-methoxynaphthalene in crystal form. The crystal was then processed in the same manner as (5-c), (5-d) and (5-e) to obtain the titled 2-(3,4-difluorophenyl)-6-(trans-4-vinylcyclohexyl)naphthalene.

The following compounds were prepared in the same manner as mentioned above.

1-Fluoro-2-(3,4,5-trifluorophenyl)-6-(trans-4-ethylcyclohexyl)naphthalene

1-Fluoro-2-(4-fluorophenyl)-6-(trans-4-vinylcyclohexyl)naphthalene

1-Fluoro-2-(3-fluorophenyl)-6-(trans-4-vinylcyclohexyl)naphthalene

1-Fluoro-2-(3,5-difluorophenyl)-6-(trans-4-vinylcyclohexyl)naphthalene

1-Fluoro-2-phenyl-6-(trans-4-vinylcyclohexyl)naphthalene

1-Fluoro-2-(4-chlorophenyl)-6-(trans-4-vinylcyclohexyl)naphthalene

1-Fluoro-2-(3-fluoro-4-chlorophenyl)-6-(trans-4-vinylcyclohexyl)naphthalene

1-Fluoro-2-(3,5-difluoro-4-chlorophenyl)-6-(trans-4-vinylcyclohexyl)naphthalene

1-Fluoro-2-(4-trifluoromethoxyphenyl)-6-(trans-4-vinylcyclohexyl)naphthalene

1-Fluoro-2-(3-fluoro-4-trifluoromethoxyphenyl)-6-(trans-4-vinylcyclohexyl)naphthalene 1-Fluoro-2-(3,5-difluoro-4-trifluoromethoxyphenyl)-6-(trans-4-vinylcyclohexyl)naphthalene 1-Fluoro-2-(4-difluoromethoxyphenyl)-6-(trans-4-vinylcyclohexyl)naphthalene 1-Fluoro-2-(3-fluoro-4-difluoromethoxyphenyl)-6-(trans-4-vinylcyclohexyl)naphthalene 1-Fluoro-2-(3,5-difluoro-4-difluoromethoxyphenyl)-6-(trans-4-vinylcyclohexyl)naphthalene 1-Fluoro-2-(4-trifluoromethylphenyl)-6-(trans-4-vinylcyclohexyl)naphthalene 1-Fluoro-2-(3-fluoro-4-trifluoromethylphenyl)-6-(trans-4-vinylcyclohexyl)naphthalene 1-Fluoro-2-(3,5-difluoro-4-trifluoromethylphenyl)-6-(trans-4-vinylcyclohexyl)naphthalene 1-Fluoro-2-(4-methoxyphenyl)-6-(trans-4-vinylcyclohexyl)naphthalene 1-Fluoro-2-(3-fluoro-4-methoxyphenyl)-6-(trans-4-vinylcyclohexyl)naphthalene 1-Fluoro-2-(3,5-difluoro-4-methoxyphenyl)-6-(trans-4-vinylcyclohexyl)naphthalene 1-Fluoro-2-(4-allyloxyphenyl)-6-(trans-4-vinylcyclohexyl)naphthalene 1-Fluoro-2-(4-methylphenyl)-6-(trans-4-vinylcyclohexyl)naphthalene 1-Fluoro-2-[4-(3-butenyl)phenyl]-6-(trans-4-vinylcyclohexyl)naphthalene Example 9

Synthesis of 1-fluoro-2-(4-cyanophenyl)-6-(trans-4-propylcyclohexyl)naphthalene

1-Fluoro-2-[4-(4,4-dimethyl-1,3-oxazolidine-2-yl)phenyl]-6-(trans-4-propylcyclohexyl)naphthalene (obtained in the same manner as (5-f) except that 2-(4-bromophenyl)-4,4-dimethyl-1,3-oxazolidine was used instead of 3,4-difluoro-1-bromobenzene) was dissolved in 50 ml of pyridine. To the solution was then added dropwise 5.6 g of phosphorus oxychloride at a temperature of 25° C. The reaction mixture was then stirred at a temperature of 110° C. for 5 hours. Excess phosphorus oxychloride was then distilled off under reduced pressure. To the residue was then added diluted hydrochloric acid. The resulting aqueous phase was then extracted with toluene. The material thus extracted and the organic phase were together washed with water, saturated aqueous solution of sodium bicarbonate and saturated brine, and then dehydrated and dried over anhydrous sodium sulfate. The solvent was then distilled off. The residue was purified through silica gel column chromatography (hexane), and then recrystallized from ethanol to obtain 4.4 g of the titled compound.

The following compounds were prepared in the same manner as mentioned above.

1-Fluoro-2-(4-cyanophenyl)-6-(trans-4-ethylcyclohexyl)naphthalene

1-Fluoro-2-(4-cyanophenyl)-6-(trans-4-butylcyclohexyl)naphthalene

1-Fluoro-2-(4-cyanophenyl)-6-(trans-4-pentylcyclohexyl)naphthalene

1-Fluoro-2-(4-cyanophenyl)-6-(trans-4-hexylcyclohexyl)naphthalene

1-Fluoro-2-(4-cyanophenyl)-6-(trans-4-heptylcyclohexyl)naphthalene

Example 10

Synthesis of 1-fluoro-2-(3-fluoro-4-cyanophenyl)-6-(trans-4-propylcyclohexyl)naphthalene (10-a) 1-Fluoro-2-(3-fluoro-4-trifluoromethanesulfonyloxyphenyl)-6-(trans-4-propylcyclohexyl)naphthalene 20 g of 1-fluoro-2(3-fluoro-4-hydroxyphenyl)-6-(trans-4-propylcyclohexyl)naphthalene (obtained in the same manner as in (5-f) except that 1-bromo-3-fluoro-4-methoxybenzene was used instead of 3,4-difluoro-1-bromobenzene to obtain 1-fluoro-2-(3-fluoro-4-methoxyphenyl)-6-(trans-4-propylcyclohexyl)naphthalene which was then demethylated with hydrobromic acid) was dissolved in 80 ml of dichloromethane. To the solution was then added dropwise 15.8 g of trifluoromethanesulfonic anhydride under cooling with ice. To the reaction mixture was then added dropwise 10 ml of pyridine in such a manner that the temperature thereof didn't exceed 5° C. After the termination of dropwise addition, the reaction mixture was stirred at the same temperature for 1 hour. To the reaction mixture was then added 20 ml of water to terminate the reaction. The resulting organic phase was washed twice with 20 ml of water, and then dehydrated and dried over anhydrous sodium sulfate. Subsequently, the solvent was distilled off. The residue was then purified through silica gel column chromatography (hexane) to obtain 24.3 g of 1-fluoro-2-(3-fluoro-4-trifluoromethanesulfonyloxyphenyl)-6-(trans-4-propylcyclohexyl)naphthalene.

(10-b) Synthesis of 1-fluoro-2-(3-fluoro-4-cyanophenyl)-6-(trans-4-propylcyclohexyl)naphthalene The total amount of 1-fluoro-2-(3-fluoro-4-trifluoromethanesulfonyloxyphenyl)-6-(trans-4-propylcyclohexyl)naphthalene obtained in the process (10-a) was dissolved in 100 ml of acetonitrile. To the solution were then added 1.2 g of dibromobis(triphenylphosphine)nickel (II), 1 g of triphenyl phosphine, 0.25 g of zinc powder and 6.2 g of potassium cyanide. The reaction mixture was then heated to a temperature of 80° C. with stirring for 16 hours. To the reaction solution was then added 20 ml of water to terminate the reaction. The resulting organic phase was washed twice with 20 ml of water, and then dehydrated and dried over anhydrous sodium sulfate. The product was purified through silica gel column chromatography (hexane/dichloromethane=6/4), and then recrystallized from ethanol to obtain 14.6 g of 5-fluoro-6-cyano-2-(trans-4-propylcyclohexyl)naphthalene.

The following compounds were prepared in the same manner as mentioned above.

5-fluoro-6-cyano-2-(trans-4-ethylcyclohexyl)naphthalene
5-fluoro-6-cyano-2-(trans-4-butylcyclohexyl)naphthalene
5-fluoro-6-cyano-2-(trans-4-pentylcyclohexyl)naphthalene
5-fluoro-6-cyano-2-(trans-4-hexylcyclohexyl)naphthalene
5-fluoro-6-cyano-2-(trans-4-heptylcyclohexyl)naphthalene

Example 11

Synthesis of 1-fluoro-2-(3,5-difluoro-4-cyanophenyl)-6-(trans-4-propylcyclohexyl)naphthalene 10 g of 2-(4-carbamoyl-3,5-difluorophenyl)-6-(trans-4-propylcyclohexyl)naphthalene (synthesized by lithioating 1-fluoro-2-(3,5-difluorophenyl)-6-(trans-4-propylcyclohexyl)naphthalene obtained in Example 5 with butyl lithium, blowing carbon dioxide through the material to produce benzoic acid, reacting the product with thionyl chloride to produce acid chloride, and then blowing ammonia gas through the material) was dissolved in 40 ml of DMF. To the solution was then added 2.5 ml of phosphorus oxychloride. The reaction mixture was then allowed to undergo reaction at a temperature of 25° C. for 2 hours. The reaction solution was then poured into ice water. To the reaction solution was then added diluted hydrochloric acid. The resulting aqueous phase was then extracted with toluene. The material thus extracted and the organic phase were together washed with water, saturated aqueous solution of sodium bicarbonate and saturated brine, and then dehydrated and dried over anhydrous sodium sulfate. The residue was purified through silica gel column chromatography (hexane/dichloromethane=6/4), and then recrystallized from ethanol to obtain 7.4 g of 1-fluoro-2-(3,5-difluoro-4-cyanophenyl)-6-(trans-4-propylcyclohexyl)naphthalene.

The following compounds were prepared in the same manner as mentioned above.

1-Fluoro-2-(3,5-difluoro-4-cyanophenyl)-6-(trans-4-ethylcyclohexyl)naphthalene
1-Fluoro-2-(3,5-difluoro-4-cyanophenyl)-6-(trans-4-butylcyclohexyl)naphthalene
1-Fluoro-2-(3,5-difluoro-4-cyanophenyl)-6-(trans-4-pentylcyclohexyl)naphthalene
1-Fluoro-2-(3,5-difluoro-4-cyanophenyl)-6-(trans-4-hexylcyclohexyl)naphthalene
1-Fluoro-2-(3,5-difluoro-4-cyanophenyl)-6-(trans-4-heptylcyclohexyl)naphthalene

Example 12

Synthesis of 2-(3,4-difluorophenyl)-6-propylnaphthalene (12-a) Synthesis of 6-(3,4-difluorophenyl)-2-naphthol To 25.0 g of 6-bromo-2-naphthol and 22.0 g of 3,4-difluorophenylboric acid were added 100 ml of toluene, 50 ml of ethanol, 50 ml of a 2 N aqueous solution of potassium carbonate and 1.3 g of tetrakis(triphenylphosphine)palladium (0). The reaction mixture was heated under reflux for 3 hours. The reaction solution was then allowed to cool to room temperature. The resulting organic phase was separated, washed with water and saturated brine, and then dried over anhydrous sodium sulfate. The solvent was then distilled off. The residue was purified through silica gel column chromatography (dichloromethane) to obtain 25.3 g of 6-(3,4-difluorophenyl)-2-naphthol.

(12-b) Synthesis of 6-(3,4-difluorophenyl)-2-naphthyl trifluoromethanesulfonate 7.6 g of 6-(3,4-difluorophenyl)-2-naphthol was dissolved in 30 ml of pyridine. The solution was then cooled to a temperature of not higher than 10° C. with ice. To the reaction solution was then added dropwise 10.0 g of trifluoromethanesulfonic anhydride at a rate such that the temperature thereof was kept at 10° C. with stirring. The reaction solution was then returned to room temperature. The reaction solution was then stirred for 1 hour. To the reaction solution was then added 50 ml of water. The reaction solution was extracted with 100 ml of dichloromethane, washed with water and saturated brine, and then dried over anhydrous sodium sulfate. The solvent was then distilled off to obtain 11.4 g of 6-(3,4-difluorophenyl)-2-naphthyl trifluoromethanesulfonate.

(12-c) Synthesis of 2-(3,4-difluorophenyl)-6-(1-propynyl)naphthalene 11.4 g of 6-(3,4-difluorophenyl)-2-naphthyl trifluoromethanesulfonate and 60 ml of DMF were dissolved in 20 ml of triethylamine. To the solution were then added 0.4 g of tetrakis(triphenylphosphine)palladium (0) and 0.1 g of copper iodide (I). Methyl acetylene was then introduced into the reaction mixture at ordinary temperature and pressure. The reaction mixture was then stirred for 2 hours. The reaction solution was neutralized with a 10% hydrochloric acid, extracted with 100 ml of toluene, and then washed with water and saturated brine. The solvent was then distilled off. The residue was then purified through silica gel column chromatography (hexane) to obtain 7.4 g of 2-(3,4-difluorophenyl)-6-(1-propinyl)naphthalene.

(12-d) Synthesis of 2-(3,4-difluorophenyl)-6-propylnaphthalene 7.4 g of 2-(3,4-difluorophenyl)-6-(1-propynyl)naphthalene was dissolved in 80 ml of ethyl acetate. To the solution was then added 1.5 g of 5% palladium carbon. Hydrogen was then introduced into the reaction mixture at ordinary temperature and pressure. The reaction mixture was then stirred for 6 hours. The catalyst was then removed by filtration. The solvent was then distilled off to obtain 7.2 g of 2-(3,4-difluorophenyl)-6-propylnaphthalene. The product was then recrystallized from methanol to obtain 4.2 g of a purified product. (Cr 62.5 I)

Example 13

Synthesis of 2-(3,4,5-trifluorophenyl)-6-propylnaphthalene

The procedure of Example 12 was followed except that 3,4,5-trifluorophenylboric acid was used instead of 3,4-difluorophenylboric acid to prepare 7 g of 2-(3,4,5-trifluorophenyl)-6-propyl naphthalene from 7 g of 6-bromo-2-naphthol. (Cr 50 I)

The following compounds were prepared in the same manner as Examples 12 and 13.
2-(3,4-Difluorophenyl)-6-ethylnaphthalene
2-(3,4-Difluorophenyl)-6-butylnaphthalene
2-(3,4-Difluorophenyl)-6pentylnaphthalene
2-(3,4-Difluorophenyl)-6-hexylnaphthalene
2-(3,4-Difluorophenyl)-6-heptylnaphthalene
2-(3,4-Difluorophenyl)-6-(3-butenyl)naphthalene
2-(3,4,5-Trifluorophenyl)-6-ethylnaphthalene
2-(3,4,5-Trifluorophenyl)-6-propylnaphthalene
2-(3,4,5-Trifluorophenyl)-6-butylnaphthalene
2-(3,4,5-Trifluorophenyl)-6-pentylnaphthalene
2-(3,4,5-Trifluorophenyl)-6-hexylnaphthalene
2-(3,4,5-Trifluorophenyl)-6-heptylnaphthalene
2-(3,4,5-Trifluorophenyl)-6-(3-butenyl)naphthalene
2-(4-Fluorophenyl)-6-ethylnaphthalene
2-(4-Fluorophenyl)-6-propylnaphthalene
2-(4-Fluorophenyl)-6-butylnaphthalene
2-(4-Fluorophenyl)-6-pentylnaphthalene
2-(4-Fluorophenyl)-6-hexylnaphthalene
2-(4-Fluorophenyl)-6-heptylnaphthalene
2-(4-Fluorophenyl)-6-(3-butenyl)naphthalene
2-(3-Fluorophenyl)-6-ethylnaphthalene
2-(3-Fluorophenyl)-6-propylnaphthalene
2-(3-Fluorophenyl)-6-butylnaphthalene
2-(3-Fluorophenyl)-6-pentylnaphthalene
2-(3-Fluorophenyl)-6-hexylnaphthalene
2-(3-Fluorophenyl)-6-heptylnaphthalene
2-(3-Fluorophenyl)-6-(3-butenyl)naphthalene
2-(3,5-Difluorophenyl)-6-ethylnaphthalene
2-(3,5-Difluorophenyl)-6-propylnaphthalene
2-(3,5-Difluorophenyl)-6-butylnaphthalene
2-(3,5-Difluorophenyl)-6-pentylnaphthalene
2-(3,5-Difluorophenyl)-6-hexylnaphthalene
2-(3,5-Difluorophenyl)-6-heptylnaphthalene
2-(3,5-Difluorophenyl)-6-(3-butenyl)naphthalene
2-Phenyl-6-ethylnaphthalene
2-Phenyl-6-propylnaphthalene
2-Phenyl-6-butylnaphthalene
2-Phenyl-6-pentylnaphthalene
2-Phenyl-6-hexylnaphthalene
2-Phenyl-6-heptylnaphthalene
2-Phenyl-6-(3-butenyl)naphthalene
2-(4-Chlorophenyl)-6-ethylnaphthalene
2-(4-Chlorophenyl)-6-propylnaphthalene
2-(4-Chlorophenyl)-6-butylnaphthalene
2-(4-Chlorophenyl)-6-pentylnaphthalene
2-(4-Chlorophenyl)-6-hexylnaphthalene
2-(4-Chlorophenyl)-6-heptylnaphthalene
2-(4-Chlorophenyl)-6-(3-butenyl)naphthalene
2-(3-Fluoro-4-chlorophenyl)-6-ethylnaphthalene
2-(3-Fluoro-4-chlorophenyl)-6-propylnaphthalene
2-(3-Fluoro-4-chlorophenyl)-6-butylnaphthalene
2-(3-Fluoro-4-chlorophenyl)-6-pentylnaphthalene
2-(3-Fluoro-4-chlorophenyl)-6-hexylnaphthalene
2-(3-Fluoro-4-chlorophenyl)-6-heptylnaphthalene
2-(3-Fluoro-4-chlorophenyl)-6-(3-butenyl)naphthalene
2-(3,5-Difluoro-4-chlorophenyl)-6-ethylnaphthalene
2-(3,5-Difluoro-4-chlorophenyl)-6-propylnaphthalene
2-(3,5-Difluoro-4-chlorophenyl)-6-butylnaphthalene
2-(3,5-Difluoro-4-chlorophenyl)-6-pentylnaphthalene
2-(3,5-Difluoro-4-chlorophenyl)-6-hexylnaphthalene
2-(3,5-Difluoro-4-chlorophenyl)-6-heptylnaphthalene
2-(3,5-Difluoro-4-chlorophenyl)-6-(3-butenyl)naphthalene
2-(4-Trifluoromethoxyphenyl)-6-ethylnaphthalene
2-(4-Trifluoromethoxyphenyl)-6-propylnaphthalene
2-(4-Trifluoromethoxyphenyl)-6-butylnaphthalene
2-(4-Trifluoromethoxyphenyl)-6-pentylnaphthalene
2-(4-Trifluoromethoxyphenyl)-6-hexylnaphthalene
2-(4-Trifluoromethoxyphenyl)-6-heptylnaphthalene
2-(4-Trifluoromethoxyphenyl)-6-(3-butenyl)naphthalene
2-(3-Fluoro-4-trifluoromethoxyphenyl)-6-ethylnaphthalene
2-(3-Fluoro-4-trifluoromethoxyphenyl)-6-propylnaphthalene
2-(3-Fluoro-4-trifluoromethoxyphenyl)-6-butylnaphthalene
2-(3-Fluoro-4-trifluoromethoxyphenyl)-6-pentylnaphthalene
2-(3-Fluoro-4-trifluoromethoxyphenyl)-6-hexylnaphthalene
2-(3-Fluoro-4-trifluoromethoxyphenyl)-6-heptylnaphthalene
2-(3-Fluoro-4-trifluoromethoxyphenyl)-6-(3-butenyl)naphthalene
2-(3,5-Difluoro-4-trifluoromethoxyphenyl)-6-ethylnaphthalene
2-(3,5-Difluoro-4-trifluoromethoxyphenyl)-6-propylnaphthalene
2-(3,5-Difluoro-4-trifluoromethoxyphenyl)-6-butylnaphthalene 2-(3,5-Difluoro-4-trifluoromethoxyphenyl)-6-pentylnaphthalene
2-(3,5-Difluoro-4-trifluoromethoxyphenyl)-6-hexylnaphthalene
2-(3,5-Difluoro-4-trifluoromethoxyphenyl)-6-heptylnaphthalene
2-(3,5-Difluoro-4-trifluoromethoxyphenyl)-6-(3-butenyl)naphthalene
2-(4-Difluoromethoxyphenyl)-6-ethylnaphthalene
2-(4-Difluoromethoxyphenyl)-6-propylnaphthalene
2-(4-Difluoromethoxyphenyl)-6-butylnaphthalene
2-(4-Difluoromethoxyphenyl)-6-pentylnaphthalene
2-(4-Difluoromethoxyphenyl)-6-hexylnaphthalene
2-(4-Difluoromethoxyphenyl)-6-heptylnaphthalene
2-(4-Difluoromethoxyphenyl)-6-(3-butenyl)naphthalene
2-(3-Fluoro-4-difluoromethoxyphenyl)-6-ethylnaphthalene
2-(3-Fluoro-4-difluoromethoxyphenyl)-6-propylnaphthalene
2-(3-Fluoro-4-difluoromethoxyphenyl)-6-butylnaphthalene
2-(3-Fluoro-4-difluoromethoxyphenyl)-6-pentylnaphthalene
2-(3-Fluoro-4-difluoromethoxyphenyl)-6-hexylnaphthalene
2-(3-Fluoro-4-difluoromethoxyphenyl)-6-heptylnaphthalene
2-(3-Fluoro-4-difluoromethoxyphenyl)-6-(3-butenyl)naphthalene
2-(3,5-Difluoro-4-difluoromethoxyphenyl)-6-ethylnaphthalene
2-(3,5-Difluoro-4-difluoromethoxyphenyl)-6-propylnaphthalene
2-(3,5-Difluoro-4-difluoromethoxyphenyl)-6-butylnaphthalene
2-(3,5-Difluoro-4-difluoromethoxyphenyl)-6-pentylnaphthalene
2-(3,5-Difluoro-4-difluoromethoxyphenyl)-6-hexylnaphthalene
2-(3,5-Difluoro-4-difluoromethoxyphenyl)-6-heptylnaphthalene
2-(3,5-Difluoro-4-difluoromethoxyphenyl)-6-(3-butenyl)naphthalene
2-[4-(3,4-Difluorophenyl)phenyl]-6-ethylnaphthalene
2-[4-(3,4-Difluorophenyl)phenyl]-6-propylnaphthalene
2-[4-(3,4-Difluorophenyl)phenyl]-6-butylnaphthalene
2-[4-(3,4-Difluorophenyl)phenyl]-6-pentylnaphthalene
2-[4-(3,4-Difluorophenyl)phenyl]-6-hexylnaphthalene
2-[4-(3,4-Difluorophenyl)phenyl]-6-heptylnaphthalene
2-[4-(3,4-Difluorophenyl)phenyl]-6-(3-butenyl)naphthalene
2-[4-(3,4,5-Trifluorophenyl)phenyl]-6-ethylnaphthalene
2-[4-(3,4,5-Trifluorophenyl)phenyl]-6-propylnaphthalene
2-[4-(3,4,5-Trifluorophenyl)phenyl]-6-butylnaphthalene
2-[4-(3,4,5-Trifluorophenyl)phenyl]-6-pentylnaphthalene
2-[4-(3,4,5-Trifluorophenyl)phenyl]-6-hexylnaphthalene
2-[4-(3,4,5-Trifluorophenyl)phenyl]-6-heptylnaphthalene
2-[4-(3,4,5-Trifluorophenyl)phenyl]-6-(3-butenyl)naphthalene
2-[4-(4-Fluorophenyl)phenyl]-6-ethylnaphthalene
2-[4-(4-Fluorophenyl)phenyl]-6-propylnaphthalene
2-[4-(4-Fluorophenyl)phenyl]-6-butylnaphthalene
2-[4-(4-Fluorophenyl)phenyl]-6-pentylnaphthalene
2-[4-(4-Fluorophenyl)phenyl]-6-hexylnaphthalene
2-[4-(4-Fluorophenyl)phenyl]-6-heptylnaphthalene
2-[4-(4-Fluorophenyl)phenyl]-6-(3-butenyl)naphthalene
2-[4-(3-Fluorophenyl)phenyl]-6-ethylnaphthalene
2-[4-(3-Fluorophenyl)phenyl]-6-propylnaphthalene
2-[4-(3-Fluorophenyl)phenyl]-6-butylnaphthalene
2-[4-(3-Fluorophenyl)phenyl]-6-pentylnaphthalene
2-[4-(3-Fluorophenyl)phenyl]-6-hexylnaphthalene
2-[4-(3-Fluorophenyl)phenyl]-6-heptylnaphthalene
2-[4-(3-Fluorophenyl)phenyl]-6-(3-butenyl)naphthalene
2-[4-(3,5-Difluorophenyl)phenyl]-6-ethylnaphthalene
2-[4-(3,5-Difluorophenyl)phenyl]-6-propylnaphthalene
2-[4-(3,5-Difluorophenyl)phenyl]-6-butylnaphthalene
2-[4-(3,5-Difluorophenyl)phenyl]-6-pentylnaphthalene
2-[4-(3,5-Difluorophenyl)phenyl]-6-hexylnaphthalene
2-[4-(3,5-Difluorophenyl)phenyl]-6-heptylnaphthalene
2-[4-(3,5-Difluorophenyl)phenyl]-6-(3-butenyl)naphthalene
2-[4-(3,5-Difluorophenyl)phenyl]-6-ethylnaphthalene
2-[4-(3,5-Difluorophenyl)phenyl]-6-propylnaphthalene
2-[4-(3,5-Difluorophenyl)phenyl]-6-butylnaphthalene
2-[4-(3,5-Difluorophenyl)phenyl]-6-pentylnaphthalene
2-[4-(3,5-Difluorophenyl)phenyl]-6-hexylnaphthalene
2-[4-(3,5-Difluorophenyl)phenyl]-6-heptylnaphthalene
2-[4-(3,5-Difluorophenyl)phenyl]-6-(3-butenyl)naphthalene
2-[4-(4-Chlorophenyl)phenyl]-6-ethylnaphthalene
2-[4-(4-Chlorophenyl)phenyl]-6-propylnaphthalene
2-[4-(4-Chlorophenyl)phenyl]-6-butylnaphthalene
2-[4-(4-Chlorophenyl)phenyl]-6-pentylnaphthalene
2-[4-(4-Chlorophenyl)phenyl]-6-hexylnaphthalene
2-[4-(4-Chlorophenyl)phenyl]-6-heptylnaphthalene
2-[4-(4-Chlorophenyl)phenyl]-6-(3-butenyl)naphthalene
2-[4-(3-Fluoro-4-chlorophenyl)phenyl]-6-ethylnaphthalene
2-[4-(3-Fluoro-4-chlorophenyl)phenyl]-6-propylnaphthalene
2-[4-(3-Fluoro-4-chlorophenyl)phenyl]-6-butylnaphthalene
2-[4-(3-Fluoro-4-chlorophenyl)phenyl]-6-pentylnaphthalene
2-[4-(3-Fluoro-4-chlorophenyl)phenyl]-6-hexylnaphthalene
2-[4-(3-Fluoro-4-chlorophenyl)phenyl]-6-heptylnaphthalene
2-[4-(3-Fluoro-4-chlorophenyl)phenyl]-6-(3-butenyl)naphthalene
2-[4-(3,5-Difluoro-4-chlorophenyl)phenyl]-6-ethylnaphthalene
2-[4-(3,5-Difluoro-4-chlorophenyl)phenyl]-6-propylnaphthalene
2-[4-(3,5-Difluoro-4-chlorophenyl)phenyl]-6-butylnaphthalene
2-[4-(3,5-Difluoro-4-chlorophenyl)phenyl]-6-pentylnaphthalene
2-[4-(3,5-Difluoro-4-chlorophenyl)phenyl]-6-hexylnaphthalene
2-[4-(3,5-Difluoro-4-chlorophenyl)phenyl]-6-heptylnaphthalene
2-[4-(3,5-Difluoro-4-chlorophenyl)phenyl]-6-(3-butenyl)naphthalene
2-[4-(4-Trifluoromethoxyphenyl)phenyl]-6-ethylnaphthalene
2-[4-(4-Trifluoromethoxyphenyl)phenyl]-6-propylnaphthalene
2-[4-(4-Trifluoromethoxyphenyl)phenyl]-6-butylnaphthalene
2-[4-(4-Trifluoromethoxyphenyl)phenyl]-6-pentylnaphthalene
2-[4-(4-Trifluoromethoxyphenyl)phenyl]-6-hexylnaphthalene
2-[4-(4-Trifluoromethoxyphenyl)phenyl]-6-heptylnaphthalene
2-[4-(4-Trifluoromethoxyphenyl)phenyl]-6-(3-butenyl)naphthalene
2-[4-(3-Fluoro-4-trifluoromethoxyphenyl)phenyl]-6-ethylnaphthalene
2-[4-(3-Fluoro-4-trifluoromethoxyphenyl)phenyl]-6-propylnaphthalene 2-[4-(3-Fluoro-4-trifluoromethoxyphenyl)phenyl]-6-butyl-naphthalene
2-[4-(3-Fluoro-4-trifluoromethoxyphenyl)phenyl]-6-pentyl-naphthalene
2-[4-(3-Fluoro-4-trifluoromethoxyphenyl)phenyl]-6-hexyl-naphthalene
2-[4-(3-Fluoro-4-trifluoromethoxyphenyl)phenyl]-6-heptyl-naphthalene
2-[4-(3-Fluoro-4-trifluoromethoxyphenyl)phenyl]-6-(3-butenyl)naphthalene
2-[4-(3,5-Difluoro-4-trifluoromethoxyphenyl)phenyl]-6-ethylnaphthalene
2-[4-(3,5-Difluoro-4-trifluoromethoxyphenyl)phenyl]-6-propylnaphthalene
2-[4-(3,5-Difluoro-4-trifluoromethoxyphenyl)phenyl]-6-butylnaphthalene
2-[4-(3,5-Difluoro-4-trifluoromethoxyphenyl)phenyl]-6-pentylnaphthalene
2-[4-(3,5-Difluoro-4-trifluoromethoxyphenyl)phenyl]-6-hexylnaphthalene
2-[4-(3,5-Difluoro-4-trifluoromethoxyphenyl)phenyl]-6-heptylnaphthalene
2-[4-(3,5-Difluoro-4-trifluoromethoxyphenyl)phenyl]-6-(3-butenyl)naphthalene
2-[4-(4-Difluoromethoxyphenyl)phenyl]-6-ethylnaphthalene
2-[4-(4-Difluoromethoxyphenyl)phenyl]-6-propylnaphthalene
2-[4-(4-Difluoromethoxyphenyl)phenyl]-6-butylnaphthalene
2-[4-(4-Difluoromethoxyphenyl)phenyl]-6-pentylnaphthalene
2-[4-(4-Difluoromethoxyphenyl)phenyl]-6-hexylnaphthalene
2-[4-(4-Difluoromethoxyphenyl)phenyl]-6-heptylnaphthalene
2-[4-(4-Difluoromethoxyphenyl)phenyl]-6-(3-butenyl)naphthalene
2-[4-(3-Fluoro-4-difluoromethoxyphenyl)phenyl]-6-ethylnaphthalene
2-[4-(3-Fluoro-4-difluoromethoxyphenyl)phenyl]-6-propylnaphthalene
2-[4-(3-Fluoro-4-difluoromethoxyphenyl)phenyl]-6-butylnaphthalene
2-[4-(3-Fluoro-4-difluoromethoxyphenyl)phenyl]-6-pentylnaphthalene
2-[4-(3-Fluoro-4-difluoromethoxyphenyl)phenyl]-6-hexylnaphthalene
2-[4-(3-Fluoro-4-difluoromethoxyphenyl)phenyl]-6-heptylnaphthalene
2-[4-(3-Fluoro-4-difluoromethoxyphenyl)phenyl]-6-(3-butenyl)naphthalene
2-[4-(3,5-Difluoro-4-difluoromethoxyphenyl)phenyl]-6-ethylnaphthalene
2-[4-(3,5-Difluoro-4-difluoromethoxyphenyl)phenyl]-6-propylnaphthalene
2-[4-(3,5-Difluoro-4-difluoromethoxyphenyl)phenyl]-6-butylnaphthalene
2-[4-(3,5-Difluoro-4-difluoromethoxyphenyl)phenyl]-6-pentylnaphthalene
2-[4-(3,5-Difluoro-4-difluoromethoxyphenyl)phenyl]-6-hexylnaphthalene
2-[4-(3,5-Difluoro-4-difluoromethoxyphenyl)phenyl]-6-heptylnaphthalene
2-[4-(3,5-Difluoro-4-difluoromethoxyphenyl)phenyl]-6-(3-butenyl)naphthalene
2-[4-(4-Trifluoromethylphenyl)phenyl]-6-ethylnaphthalene
2-[4-(4-Trifluoromethylphenyl)phenyl]-6-propylnaphthalene
2-[4-(4-Trifluoromethylphenyl)phenyl]-6-butylnaphthalene
2-[4-(4-Trifluoromethylphenyl)phenyl]-6-pentylnaphthalene
2-[4-(4-Trifluoromethylphenyl)phenyl]-6-hexylnaphthalene
2-[4-(4-Trifluoromethylphenyl)phenyl]-6-heptylnaphthalene
2-[4-(4-Trifluoromethylphenyl)phenyl]-6-(3-butenyl)naphthalene
2-[4-(3-Fluoro-4-trifluoromethylphenyl)phenyl]-6-ethylnaphthalene
2-[4-(3-Fluoro-4-trifluoromethylphenyl)phenyl]-6-propylnaphthalene
2-[4-(3-Fluoro-4-trifluoromethylphenyl)phenyl]-6-butylnaphthalene
2-[4-(3-Fluoro-4-trifluoromethylphenyl)phenyl]-6-pentylnaphthalene
2-[4-(3-Fluoro-4-trifluoromethylphenyl)phenyl]-6-hexylnaphthalene
2-[4-(3-Fluoro-4-trifluoromethylphenyl)phenyl]-6-heptylnaphthalene
2-[4-(3-Fluoro-4-trifluoromethylphenylphenyl)phenyl]-6-(3-butenyl)naphthalene
2-[4-(3,5-Difluoro-4-trifluoromethylphenyl)phenyl]-6-ethylnaphthalene
2-[4-(3,5-Difluoro-4-trifluoromethylphenyl)phenyl]-6-propylnaphthalene
2-[4-(3,5-Difluoro-4-trifluoromethylphenyl)phenyl]-6-butylnaphthalene
2-[4-(3,5-Difluoro-4-trifluoromethylphenyl)phenyl]-6-pentylnaphthalene
2-[4-(3,5-Difluoro-4-trifluoromethylphenyl)phenyl]-6-hexylnaphthalene
2-[4-(3,5-Difluoro-4-trifluoromethylphenyl)phenyl]-6-heptylnaphthalene
2-[4-(3,5-Difluoro-4-trifluoromethylphenylphenyl)phenyl]-6-(3-butenyl)naphthalene
2-[4-(4-Methoxyphenyl)phenyl]-6-ethylnaphthalene
2-[4-(4-Methoxyphenyl)phenyl]-6-propylnaphthalene
2-[4-(4-Methoxyphenyl)phenyl]-6-butylnaphthalene
2-[4-(4-Methoxyphenyl)phenyl]-6-pentylnaphthalene
2-[4-(4-Methoxyphenyl)phenyl]-6-hexylnaphthalene
2-[4-(4-Methoxyphenyl)phenyl]-6-heptylnaphthalene
2-[4-(4-Methoxyphenyl)phenyl]-6-(3-butenyl)naphthalene
2-[4-(3-Fluoro-4-methoxyphenyl)phenyl]-6-ethylnaphthalene
2-[4-(3-Fluoro-4-methoxyphenyl)phenyl]-6-propylnaphthalene
2-[4-(3-Fluoro-4-methoxyphenyl)phenyl]-6-butylnaphthalene
2-[4-(3-Fluoro-4-methoxyphenyl)phenyl]-6-pentylnaphthalene
2-[4-(3-Fluoro-4-methoxyphenyl)phenyl]-6-hexylnaphthalene
2-[4-(3-Fluoro-4-methoxyphenyl)phenyl]-6-heptylnaphthalene
2-[4-(3-Fluoro-4-methoxyphenyl)phenyl]-6-(3-butenyl)naphthalene
2-[4-(3,5-Difluoro-4-methoxyphenyl)phenyl]-6-ethylnaphthalene
2-[4-(3,5-Difluoro-4-methoxyphenyl)phenyl]-6-propylnaphthalene
2-[4-(3,5-Difluoro-4-methoxyphenyl)phenyl]-6-butylnaphthalene
2-[4-(3,5-Difluoro-4-methoxyphenyl)phenyl]-6-pentylnaphthalene 2-[4-(3,5-Difluoro-4-methoxyphenyl)phenyl]-6-hexylnaphthalene
2-[4-(3,5-Difluoro-4-methoxyphenyl)phenyl]-6-heptylnaphthalene
2-[4-(3,5-Difluoro-4-methoxyphenyl)phenyl]-6-(3-butenyl)naphthalene
2-[4-(4-Allyloxyphenyl)phenyl]-6-ethylnaphthalene
2-[4-(4-Allyloxyphenyl)phenyl]-6-propylnaphthalene
2-[4-(4-Allyloxyphenyl)phenyl]-6-butylnaphthalene
2-[4-(4-Allyloxyphenyl)phenyl]-6-pentylnaphthalene
2-[4-(4-Allyloxyphenyl)phenyl]-6-hexylnaphthalene
2-[4-(4-Allyloxyphenyl)phenyl]-6-heptylnaphthalene
2-[4-(4-Allyloxyphenyl)phenyl]-6-(3-butenyl)naphthalene
2-[4-(4-Methylphenyl)phenyl]-6-ethylnaphthalene
2-[4-(4-Methylphenyl)phenyl]-6-propylnaphthalene
2-[4-(4-Methylphenyl)phenyl]-6-butylnaphthalene
2-[4-(4-Methylphenyl)phenyl]-6-pentylnaphthalene
2-[4-(4-Methylphenyl)phenyl]-6-hexylnaphthalene
2-[4-(4-Methylphenyl)phenyl]-6-heptylnaphthalene
2-[4-(4-Methylphenyl)phenyl]-6-(3-butenyl)naphthalene
2-[4-[4-(3-Butenyl)phenyl]phenyl]-6-ethylnaphthalene
2-[4-[4-(3-Butenyl)phenyl]phenyl]-6-propylnaphthalene
2-[4-[4-(3-Butenyl)phenyl]phenyl]-6-butylnaphthalene
2-[4-[4-(3-Butenyl)phenyl]phenyl]-6-pentylnaphthalene
2-[4-[4-(3-Butenyl)phenyl]phenyl]-6-hexylnaphthalene
2-[4-[4-(3-Butenyl)phenyl]phenyl]-6-heptylnaphthalene
2-[4-[4-(3-Butenyl)phenyl]phenyl]-6-(3-butenyl)naphthalene
2-[3-Fluoro-4-(3,4-difluorophenyl)phenyl]-6-ethylnaphthalene
2-[3-Fluoro-4-(3,4-difluorophenyl)phenyl]-6-propylnaphthalene
2-[3-Fluoro-4-(3,4-difluorophenyl)phenyl]-6-butylnaphthalene
2-[3-Fluoro-4-(3,4-difluorophenyl)phenyl]-6-pentylnaphthalene
2-[3-Fluoro-4-(3,4-difluorophenyl)phenyl]-6-hexylnaphthalene
2-[3-Fluoro-4-(3,4-difluorophenyl)phenyl]-6-heptylnaphthalene
2-[3-Fluoro-4-(3,4-difluorophenyl)phenyl]-6-(3-butenyl)naphthalene
2-[3-Fluoro-4-(3,4,5-trifluorophenyl)phenyl]-6-ethylnaphthalene
2-[3-Fluoro-4-(3,4,5-trifluorophenyl)phenyl]-6-propylnaphthalene
2-[3-Fluoro-4-(3,4,5-trifluorophenyl)phenyl]-6-butylnaphthalene
2-[3-Fluoro-4-(3,4,5-trifluorophenyl)phenyl]-6-pentylnaphthalene
2-[3-Fluoro-4-(3,4,5-trifluorophenyl)phenyl]-6-hexylnaphthalene
2-[3-Fluoro-4-(3,4,5-trifluorophenyl)phenyl]-6-heptylnaphthalene
2-[3-Fluoro-4-(3,4,5-trifluorophenyl)phenyl]-6-(3-butenyl)naphthalene
2-[3-Fluoro-4-(4-fluorophenyl)phenyl]-6-ethylnaphthalene
2-[3-Fluoro-4-(4-fluorophenyl)phenyl]-6-propylnaphthalene
2-[3-Fluoro-4-(4-fluorophenyl)phenyl]-6-butylnaphthalene
2-[3-Fluoro-4-(4-fluorophenyl)phenyl]-6-pentylnaphthalene
2-[3-Fluoro-4-(4-fluorophenyl)phenyl]-6-hexylnaphthalene
2-[3-Fluoro-4-(4-fluorophenyl)phenyl]-6-heptylnaphthalene
2-[3-Fluoro-4-(4-fluorophenyl)phenyl]-6-(3-butenyl)naphthalene
2-[3-Fluoro-4-(3-fluorophenyl)phenyl]-6-ethylnaphthalene
2-[3-Fluoro-4-(3-fluorophenyl)phenyl]-6-propylnaphthalene
2-[3-Fluoro-4-(3-fluorophenyl)phenyl]-6-butylnaphthalene
2-[3-Fluoro-4-(3-fluorophenyl)phenyl]-6-pentylnaphthalene
2-[3-Fluoro-4-(3-fluorophenyl)phenyl]-6-hexylnaphthalene
2-[3-Fluoro-4-(3-fluorophenyl)phenyl]-6-heptylnaphthalene
2-[3-Fluoro-4-(3-fluorophenyl)phenyl]-6-(3-butenyl)naphthalene
2-[3-Fluoro-4-(3,5-Difluorophenyl)phenyl]-6-ethylnaphthalene
2-[3-Fluoro-4-(3,5-difluorophenyl)phenyl]-6-propylnaphthalene
2-[3-Fluoro-4-(3,5-difluorophenyl)phenyl]-6-butylnaphthalene
2-[3-Fluoro-4-(3,5-difluorophenyl)phenyl]-6-pentylnaphthalene
2-[3-Fluoro-4-(3,5-difluorophenyl)phenyl]-6-hexylnaphthalene
2-[3-Fluoro-4-(3,5-difluorophenyl)phenyl]-6-heptylnaphthalene
2-[3-Fluoro-4-(3,5-difluorophenyl)phenyl]-6-(3-butenyl)naphthalene
2-[3-Fluoro-4-(4-chlorophenyl)phenyl]-6-ethylnaphthalene
2-[3-Fluoro-4-(4-chlorophenyl)phenyl]-6-propylnaphthalene
2-[3-Fluoro-4-(4-chlorophenyl)phenyl]-6-butylnaphthalene
2-[3-Fluoro-4-(4-chlorophenyl)phenyl]-6-pentylnaphthalene
2-[3-Fluoro-4-(4-chlorophenyl)phenyl]-6-hexylnaphthalene
2-[3-Fluoro-4-(4-chlorophenyl)phenyl]-6-heptylnaphthalene
2-[3-Fluoro-4-(4-chlorophenyl)phenyl]-6-(3-butenyl)naphthalene
2-[3-Fluoro-4-(4-chlorophenyl)phenyl]-6-ethylnaphthalene
2-[3-Fluoro-4-(4-chlorophenyl)phenyl]-6-propylnaphthalene
2-[3-Fluoro-4-(4-chlorophenyl)phenyl]-6-butylnaphthalene
2-[3-Fluoro-4-(4-chlorophenyl)phenyl]-6-pentylnaphthalene
2-[3-Fluoro-4-(4-chlorophenyl)phenyl]-6-hexylnaphthalene
2-[3-Fluoro-4-(4-chlorophenyl)phenyl]-6-heptylnaphthalene
2-[3-Fluoro-4-(4-chlorophenyl)phenyl]-6-(3-butenyl)naphthalene
2-[3-Fluoro-4-(3-fluoro-4-chlorophenyl)phenyl]-6-ethylnaphthalene
2-[3-Fluoro-4-(3-fluoro-4-chlorophenyl)phenyl]-6-propylnaphthalene
2-[3-Fluoro-4-(3-fluoro-4-chlorophenyl)phenyl]-6-butylnaphthalene
2-[3-Fluoro-4-(3-fluoro-4-chlorophenyl)phenyl]-6-pentylnaphthalene
2-[3-Fluoro-4-(3-fluoro-4-chlorophenyl)phenyl]-6-hexylnaphthalene
2-[3-Fluoro-4-(3-fluoro-4-chlorophenyl)phenyl]-6-heptylnaphthalene
2-[3-Fluoro-4-(3-fluoro-4-chlorophenyl)phenyl]-6-(3-butenyl)naphthalene
2-[3-Fluoro-4-(3,5-difluoro-4-chlorophenyl)phenyl]-6-ethylnaphthalene
2-[3-Fluoro-4-(3,5-difluoro-4-chlorophenyl)phenyl]-6-propylnaphthalene
2-[3-Fluoro-4-(3,5-difluoro-4-chlorophenyl)phenyl]-6-butylnaphthalene
2-[3-Fluoro-4-(3,5-difluoro-4-chlorophenyl)phenyl]-6-pentylnaphthalene 2-[3-Fluoro-4-(3,5-difluoro-4-chlorophenyl)phenyl]-6-hexylnaphthalene
2-[3-Fluoro-4-(3,5-difluoro-4-chlorophenyl)phenyl]-6-heptylnaphthalene
2-[3-Fluoro-4-(3,5-difluoro-4-chlorophenyl)phenyl]-6-(3-butenyl)naphthalene
2-[3-Fluoro-4-(4-trifluoromethoxyphenyl)phenyl]-6-ethylnaphthalene
2-[3-Fluoro-4-(4-trifluoromethoxyphenyl)phenyl]-6-propylnaphthalene
2-[3-Fluoro-4-(4-trifluoromethoxyphenyl)phenyl]-6-butylnaphthalene
2-[3-Fluoro-4-(4-trifluoromethoxyphenyl)phenyl]-6-pentylnaphthalene
2-[3-Fluoro-4-(4-trifluoromethoxyphenyl)phenyl]-6-hexylnaphthalene
2-[3-Fluoro-4-(4-trifluoromethoxyphenyl)phenyl]-6-heptylnaphthalene
2-[3-Fluoro-4-(4-trifluoromethoxyphenyl)phenyl]-6-(3-butenyl)naphthalene
2-[3-Fluoro-4-(3-fluoro-4-trifluoromethoxyphenyl)phenyl]-6-ethylnaphthalene
2-[3-Fluoro-4-(3-fluoro-4-trifluoromethoxyphenyl)phenyl]-6-propylnaphthalene
2-[3-Fluoro-4-(3-fluoro-4-trifluoromethoxyphenyl)phenyl]-6-butylnaphthalene
2-[3-Fluoro-4-(3-fluoro-4-trifluoromethoxyphenyl)phenyl]-6-pentylnaphthalene
2-[3-Fluoro-4-(3-fluoro-4-trifluoromethoxyphenyl)phenyl]-6-hexylnaphthalene
2-[3-Fluoro-4-(3-fluoro-4-trifluoromethoxyphenyl)phenyl]-6-heptylnaphthalene
2-[3-Fluoro-4-(3-fluoro-4-trifluoromethoxyphenyl)phenyl]-6-(3-butenyl)naphthalene
2-[3-Fluoro-4-(3,5-difluoro-4-trifluoromethoxyphenyl)phenyl]-6-ethylnaphthalene
2-[3-Fluoro-4-(3,5-difluoro-4-trifluoromethoxyphenyl)phenyl]-6-propylnaphthalene
2-[3-Fluoro-4-(3,5-difluoro-4-trifluoromethoxyphenyl)phenyl]-6-butylnaphthalene
2-[3-Fluoro-4-(3,5-difluoro-4-trifluoromethoxyphenyl)phenyl]-6-pentylnaphthalene
2-[3-Fluoro-4-(3,5-difluoro-4-trifluoromethoxyphenyl)phenyl]-6-hexylnaphthalene
2-[3-Fluoro-4-(3,5-difluoro-4-trifluoromethoxyphenyl)phenyl]-6-heptylnaphthalene
2-[3-Fluoro-4-(3,5-difluoro-4-trifluoromethoxyphenyl)phenyl]-6-(3-butenyl)naphthalene
2-[3-Fluoro-4-(4-difluoromethoxyphenyl)phenyl]-6-ethylnaphthalene
2-[3-Fluoro-4-(4-difluoromethoxyphenyl)phenyl]-6-propylnaphthalene
2-[3-Fluoro-4-(4-difluoromethoxyphenyl)phenyl]-6-butylnaphthalene
2-[3-Fluoro-4-(4-difluoromethoxyphenyl)phenyl]-6-pentylnaphthalene
2-[3-Fluoro-4-(4-difluoromethoxyphenyl)phenyl]-6-hexylnaphthalene
2-[3-Fluoro-4-(4-difluoromethoxyphenyl)phenyl]-6-heptylnaphthalene
2-[3-Fluoro-4-(4-difluoromethoxyphenyl)phenyl]-6-(3-butenyl)naphthalene
2-[3-Fluoro-4-(3-fluoro-4-difluoromethoxyphenyl)phenyl]-6-ethylnaphthalene
2-[3-Fluoro-4-(3-fluoro-4-difluoromethoxyphenyl)phenyl]-6-propylnaphthalene
2-[3-Fluoro-4-(3-fluoro-4-difluoromethoxyphenyl)phenyl]-6-butylnaphthalene
2-[3-Fluoro-4-(3-fluoro-4-difluoromethoxyphenyl)phenyl]-6-pentylnaphthalene
2-[3-Fluoro-4-(3-fluoro-4-difluoromethoxyphenyl)phenyl]-6-hexylnaphthalene
2-[3-Fluoro-4-(3-fluoro-4-difluoromethoxyphenyl)phenyl]-6-heptylnaphthalene
2-[3-Fluoro-4-(3-fluoro-4-difluoromethoxyphenyl)phenyl]-6-(3-butenyl)naphthalene
2-[3-Fluoro-4-(3,5-difluoro-4-difluoromethoxyphenyl)phenyl]-6-ethylnaphthalene
2-[3-Fluoro-4-(3,5-difluoro-4-difluoromethoxyphenyl)phenyl]-6-propylnaphthalene
2-[3-Fluoro-4-(3,5-difluoro-4-difluoromethoxyphenyl)phenyl]-6-butylnaphthalene
2-[3-Fluoro-4-(3,5-difluoro-4-difluoromethoxyphenyl)phenyl]-6-pentylnaphthalene
2-[3-Fluoro-4-(3,5-difluoro-4-difluoromethoxyphenyl)phenyl]-6-hexylnaphthalene
2-[3-Fluoro-4-(3,5-difluoro-4-difluoromethoxyphenyl)phenyl]-6-heptylnaphthalene
2-[3-Fluoro-4-(3,5-difluoro-4-difluoromethoxyphenyl)phenyl]-6-(3-butenyl)naphthalene
2-[3-Fluoro-4-(4-trifluoromethylphenyl)phenyl]-6-ethylnaphthalene
2-[3-Fluoro-4-(4-trifluoromethylphenyl)phenyl]-6-propylnaphthalene
2-[3-Fluoro-4-(4-trifluoromethylphenyl)phenyl]-6-butylnaphthalene
2-[3-Fluoro-4-(4-trifluoromethylphenyl)phenyl]-6-pentylnaphthalene
2-[3-Fluoro-4-(4-trifluoromethylphenyl)phenyl]-6-hexylnaphthalene
2-[3-Fluoro-4-(4-trifluoromethylphenyl)phenyl]-6-heptylnaphthalene
2-[3-Fluoro-4-(4-trifluoromethylphenyl)phenyl]-6-(3-butenyl)naphthalene
2-[3-Fluoro-4-(3-fluoro-4-trifluoromethylphenyl)phenyl]-6-ethylnaphthalene
2-[3-Fluoro-4-(3fluoro-4-trifluoromethylphenyl)phenyl]-6-propylnaphthalene
2-[3-Fluoro-4-(3-fluoro-4-trifluoromethylphenyl)phenyl]-6-butylnaphthalene
2-[3-Fluoro-4-(3-fluoro-4-trifluoromethylphenyl)phenyl]-6-pentylnaphthalene
2-[3-Fluoro-4-(3-fluoro-4-trifluoromethylphenyl)phenyl]-6-hexylnaphthalene
2-[3-Fluoro-4-(3-fluoro-4-trifluoromethylphenyl)phenyl]-6-heptylnaphthalene
2-[3-Fluoro-4-(3-fluoro-4-trifluoromethylphenylphenyl)phenyl]-6-(3-butenyl)naphthalene
2-[3-Fluoro-4-(3,5-difluoro-4-trifluoromethylphenyl)phenyl]-6-ethylnaphthalene
2-[3-Fluoro-4-(3,5-difluoro-4-trifluoromethylphenyl)phenyl]-6-propylnaphthalene
2-[3-Fluoro-4-(3,5-difluoro-4-trifluoromethylphenyl)phenyl]-6-butylnaphthalene
2-[3-Fluoro-4-(3,5-difluoro-4-trifluoromethylphenyl)phenyl]-6-pentylnaphthalene
2-[3-Fluoro-4-(3,5-difluoro-4-trifluoromethylphenyl)phenyl]-6-hexylnaphthalene
2-[3-Fluoro-4-(3,5-difluoro-4-trifluoromethylphenyl)phenyl]-6-heptylnaphthalene
2-[3-Fluoro-4-(3,5-difluoro-4-trifluoromethylphenylphenyl)phenyl]-6-(3-butenyl)naphthalene 2-[3-Fluoro-4-(4-methoxyphenyl)phenyl]-6-ethylnaphthalene
2-[3-Fluoro-4-(4-methoxyphenyl)phenyl]-6-propylnaphthalene
2-[3-Fluoro-4-(4-methoxyphenyl)phenyl]-6-butylnaphthalene
2-[3-Fluoro-4-(4-methoxyphenyl)phenyl]-6-pentylnaphthalene
2-[3-Fluoro-4-(4-methoxyphenyl)phenyl]-6-hexylnaphthalene
2-[3-Fluoro-4-(4-methoxyphenyl)phenyl]-6-heptylnaphthalene
2-[3-Fluoro-4-(4-methoxyphenyl)phenyl]-6-(3-butenyl)naphthalene
2-[3-Fluoro-4-(3-fluoro-4-methoxyphenyl)phenyl]-6-ethylnaphthalene
2-[3-Fluoro-4-(3-fluoro-4-methoxyphenyl)phenyl]-6-propylnaphthalene
2-[3-Fluoro-4-(3-fluoro-4-methoxyphenyl)phenyl]-6-butylnaphthalene
2-[3-Fluoro-4-(3-fluoro-4-methoxyphenyl)phenyl]-6-pentylnaphthalene
2-[3-Fluoro-4-(3-fluoro-4-methoxyphenyl)phenyl]-6-hexylnaphthalene
2-[3-Fluoro-4-(3-fluoro-4-methoxyphenyl)phenyl]-6-heptylnaphthalene
2-[3-Fluoro-4-(3-fluoro-4-methoxyphenyl)phenyl]-6-(3-butenyl)naphthalene
2-[3-Fluoro-4-(3,5-difluoro-4-methoxyphenyl)phenyl]-6-ethylnaphthalene
2-[3-Fluoro-4-(3,5-difluoro-4-methoxyphenyl)phenyl]-6-propylnaphthalene
2-[3-Fluoro-4-(3,5-difluoro-4-methoxyphenyl)phenyl]-6-butylnaphthalene
2-[3-Fluoro-4-(3,5-difluoro-4-methoxyphenyl)phenyl]-6-pentylnaphthalene
2-[3-Fluoro-4-(3,5-difluoro-4-methoxyphenyl)phenyl]-6-hexylnaphthalene
2-[3-Fluoro-4-(3,5-difluoro-4-methoxyphenyl)phenyl]-6-heptylnaphthalene
2-[3-Fluoro-4-(3,5-difluoro-4-methoxyphenyl)phenyl]-6-(3-butenyl)naphthalene
2-[3-Fluoro-4-(4-allyloxyphenyl)phenyl]-6-ethylnaphthalene
2-[3-Fluoro-4-(4-allyloxyphenyl)phenyl]-6-propylnaphthalene
2-[3-Fluoro-4-(4-allyloxyphenyl)phenyl]-6-butylnaphthalene
2-[3-Fluoro-4-(4-allyloxyphenyl)phenyl]-6-pentylnaphthalene
2-[3-Fluoro-4-(4-allyloxyphenyl)phenyl]-6-hexylnaphthalene
2-[3-Fluoro-4-(4-allyloxyphenyl)phenyl]-6-heptylnaphthalene
2-[3-Fluoro-4-(4-allyloxyphenyl)phenyl]-6-(3-butenyl)naphthalene
2-[3-Fluoro-4-(4-methylphenyl)phenyl]-6-ethylnaphthalene
2-[3-Fluoro-4-(4-methylphenyl)phenyl]-6-propylnaphthalene
2-[3-Fluoro-4-(4-methylphenyl)phenyl]-6-butylnaphthalene
2-[3-Fluoro-4-(4-methylphenyl)phenyl]-6-pentylnaphthalene
2-[3-Fluoro-4-(4-methylphenyl)phenyl]-6-hexylnaphthalene
2-[3-Fluoro-4-(4-methylphenyl)phenyl]-6-heptylnaphthalene
2-[3-Fluoro-4-(4-methylphenyl)phenyl]-6-(3-butenyl)naphthalene
2-[3-Fluoro-4-[4-(3-butenyl)phenyl]phenyl]-6-ethylnaphthalene
2-[3-Fluoro-4-[4-(3-butenyl)phenyl]phenyl]-6-propylnaphthalene
2-[3-Fluoro-4-[4-(3-butenyl)phenyl]phenyl]-6-butylnaphthalene
2-[3-Fluoro-4-[4-(3-butenyl)phenyl]phenyl]-6-pentylnaphthalene
2-[3-Fluoro-4-[4-(3-butenyl)phenyl]phenyl]-6-hexylnaphthalene
2-[3-Fluoro-4-[4-(3-butenyl)phenyl]phenyl]-6-heptylnaphthalene
2-[3-Fluoro-4-[4-(3-butenyl)phenyl]phenyl]-6-(3-butenyl)naphthalene
2-[3,5-Difluoro-4-(3,4-difluorophenyl)phenyl]-6-ethylnaphthalene
2-[3,5-Difluoro-4-(3,4-difluorophenyl)phenyl]-6-propylnaphthalene
2-[3,5-Difluoro-4-(3,4-difluorophenyl)phenyl]-6-butylnaphthalene
2-[3,5-Difluoro-4-(3,4-difluorophenyl)phenyl]-6-pentylnaphthalene
2-[3,5-Difluoro-4-(3,4-difluorophenyl)phenyl]-6-hexylnaphthalene
2-[3,5-Difluoro-4-(3,4-difluorophenyl)phenyl]-6-heptylnaphthalene
2-[3,5-Difluoro-4-(3,4-difluorophenyl)phenyl]-6-(3-butenyl)naphthalene
2-[3,5-Difluoro-4-(3,4,5-trifluorophenyl)phenyl]-6-ethylnaphthalene
2-[3,5-Difluoro-4-(3,4,5-trifluorophenyl)phenyl]-6-propylnaphthalene
2-[3,5-Difluoro-4-(3,4,5-trifluorophenyl)phenyl]-6-butylnaphthalene
2-[3,5-Difluoro-4-(3,4,5-trifluorophenyl)phenyl]-6-pentylnaphthalene
2-[3,5-Difluoro-4-(3,4,5-trifluorophenyl)phenyl]-6-hexylnaphthalene
2-[3,5-Difluoro-4-(3,4,5-trifluorophenyl)phenyl]-6-heptylnaphthalene
2-[3,5-Difluoro-4-(3,4,5-trifluorophenyl)phenyl]-6-(3-butenyl)naphthalene
2-[3,5-Difluoro-4-(4-fluorophenyl)phenyl]-6-ethylnaphthalene
2-[3,5-Difluoro-4-(4-fluorophenyl)phenyl]-6-propylnaphthalene
2-[3,5-Difluoro-4-(4-fluorophenyl)phenyl]-6-butylnaphthalene
2-[3,5-Difluoro-4-(4-fluorophenyl)phenyl]-6-pentylnaphthalene
2-[3,5-Difluoro-4-(4-fluorophenyl)phenyl]-6-hexylnaphthalene
2-[3,5-Difluoro-4-(4-fluorophenyl)phenyl]-6-heptylnaphthalene
2-[3,5-Difluoro-4-(4-fluorophenyl)phenyl]-6-(3-butenyl)naphthalene
2-[3,5-Difluoro-4-(3-fluorophenyl)phenyl]-6-ethylnaphthalene
2-[3,5-Difluoro-4-(3-fluorophenyl)phenyl]-6-propylnaphthalene
2-[3,5-Difluoro-4-(3-fluorophenyl)phenyl]-6-butylnaphthalene
2-[3,5-Difluoro-4-(3-fluorophenyl)phenyl]-6-pentylnaphthalene 2-[3,5-Difluoro-4-(3-fluorophenyl)phenyl]-6-hexylnaphthalene
2-[3,5-Difluoro-4-(3-fluorophenyl)phenyl]-6-heptylnaphthalene
2-[3,5-Difluoro-4-(3-fluorophenyl)phenyl]-6-(3-butenyl)naphthalene
2-[3,5-Difluoro-4-(3,5-difluorophenyl)phenyl]-6-ethylnaphthalene
2-[3,5-Difluoro-4-(3,5-difluorophenyl)phenyl]-6-propylnaphthalene
2-[3,5-Difluoro-4-(3,5-difluorophenyl)phenyl]-6-butylnaphthalene
2-[3,5-Difluoro-4-(3,5-difluorophenyl)phenyl]-6-pentylnaphthalene
2-[3,5-Difluoro-4-(3,5-difluorophenyl)phenyl]-6-hexylnaphthalene
2-[3,5-Difluoro-4-(3,5-difluorophenyl)phenyl]-6-heptylnaphthalene
2-[3,5-Difluoro-4-(3,5-difluorophenyl)phenyl]-6-(3-butenyl)naphthalene
2-[3,5-Difluoro-4-(3,5-difluorophenyl)phenyl]-6-ethylnaphthalene
2-[3,5-Difluoro-4-(3,5-difluorophenyl)phenyl]-6-propylnaphthalene
2-[3,5-Difluoro-4-(3,5-difluorophenyl)phenyl]-6-butylnaphthalene
2-[3,5-Difluoro-4-(3,5-difluorophenyl)phenyl]-6-pentylnaphthalene
2-[3,5-Difluoro-4-(3,5-difluorophenyl)phenyl]-6-hexylnaphthalene
2-[3,5-Difluoro-4-(3,5-difluorophenyl)phenyl]-6-heptylnaphthalene
2-[3,5-Difluoro-4-(3,5-difluorophenyl)phenyl]-6-(3-butenyl)naphthalene
2-[3,5-Difluoro-4-(4-chlorophenyl)phenyl]-6-ethylnaphthalene
2-[3,5-Difluoro-4-(4-chlorophenyl)phenyl]-6-propylnaphthalene
2-[3,5-Difluoro-4-(4-chlorophenyl)phenyl]-6-butylnaphthalene
2-[3,5-Difluoro-4-(4-chlorophenyl)phenyl]-6-pentylnaphthalene
2-[3,5-Difluoro-4-(4-chlorophenyl)phenyl]-6-hexylnaphthalene
2-[3,5-Difluoro-4-(4-chlorophenyl)phenyl]-6-heptylnaphthalene
2-[3,5-Difluoro-4-(4-chlorophenyl)phenyl]-6-(3-butenyl)naphthalene
2-[3,5-Difluoro-4-(3-fluoro-4-chlorophenyl)phenyl]-6-ethylnaphthalene
2-[3,5-Difluoro-4-(3-fluoro-4-chlorophenyl)phenyl]-6-propylnaphthalene
2-[3,5-Difluoro-4-(3-fluoro-4-chlorophenyl)phenyl]-6-butylnaphthalene
2-[3,5-Difluoro-4-(3-fluoro-4-chlorophenyl)phenyl]-6-pentylnaphthalene
2-[3,5-Difluoro-4-(3-fluoro-4-chlorophenyl)phenyl]-6-hexylnaphthalene
2-[3,5-Difluoro-4-(3-fluoro-4-chlorophenyl)phenyl]-6-heptylnaphthalene
2-[3,5-Difluoro-4-(3-fluoro-4-chlorophenyl)phenyl]-6-(3-butenyl)naphthalene
2-[3,5-Difluoro-4-(3,5difluoro-4-chlorophenyl)phenyl]-6-ethylnaphthalene
2-[3,5-Difluoro-4-(3,5-difluoro-4-chlorophenyl)phenyl]-6-propylnaphthalene
2-[3,5-Difluoro-4-(3,5-difluoro-4-chlorophenyl)phenyl]-6-butylnaphthalene
2-[3,5-Difluoro-4-(3,5-difluoro-4-chlorophenyl)phenyl]-6-pentylnaphthalene
2-[3,5-Difluoro-4-(3,5-difluoro-4-chlorophenyl)phenyl]-6-hexylnaphthalene
2-[3,5-Difluoro-4-(3,5-difluoro-4-chlorophenyl)phenyl]-6-heptylnaphthalene
2-[3,5-Difluoro-4-(3,5-difluoro-4-chlorophenyl)phenyl]-6-(3-butenyl)naphthalene
2-[3,5-Difluoro-4-(4-trifluoromethoxyphenyl)phenyl]-6-ethylnaphthalene
2-[3,5-Difluoro-4-(4-trifluoromethoxyphenyl)phenyl]-6-propylnaphthalene
2-[3,5-Difluoro-4-(4-trifluoromethoxyphenyl)phenyl]-6-butylnaphthalene
2-[3,5-Difluoro-4-(4-trifluoromethoxyphenyl)phenyl]-6-pentylnaphthalene
2-[3,5-Difluoro-4-(4-trifluoromethoxyphenyl)phenyl]-6-hexylnaphthalene
2-[3,5-Difluoro-4-(4-trifluoromethoxyphenyl)phenyl]-6-heptylnaphthalene
2-[3,5-Difluoro-4-(4-trifluoromethoxyphenyl)phenyl]-6-(3-butenyl)naphthalene
2-[3,5-Difluoro-4-(3-fluoro-4-trifluoromethoxyphenyl)phenyl]-6-ethylnaphthalene
2-[3,5-Difluoro-4-(3-fluoro-4-trifluoromethoxyphenyl)phenyl]-6-propylnaphthalene
2-[3,5-Difluoro-4-(3-fluoro-4-trifluoromethoxyphenyl)phenyl]-6-butylnaphthalene
2-[3,5-Difluoro-4-(3-fluoro-4-trifluoromethoxyphenyl)phenyl]-6-pentylnaphthalene
2-[3,5-Difluoro-4-(3-fluoro-4-trifluoromethoxyphenyl)phenyl]-6-hexylnaphthalene
2-[3,5-Difluoro-4-(3-fluoro-4-trifluoromethoxyphenyl)phenyl]-6-heptylnaphthalene
2-[3,5-Difluoro-4-(3-fluoro-4-trifluoromethoxyphenyl)phenyl]-6-(3-butenyl)naphthalene
2-[3,5-Difluoro-4-(3,5-difluoro-4-trifluoromethoxyphenyl)phenyl]-6-ethylnaphthalene
2-[3,5-Difluoro-4-(3,5-difluoro-4-trifluoromethoxyphenyl)phenyl]-6-propylnaphthalene
2-[3,5-Difluoro-4-(3,5-difluoro-4-trifluoromethoxyphenyl)phenyl]-6-butylnaphthalene
2-[3,5-Difluoro-4-(3,5-difluoro-4-trifluoromethoxyphenyl)phenyl]-6-pentylnaphthalene
2-[3,5-Difluoro-4-(3,5-difluoro-4-trifluoromethoxyphenyl)phenyl]-6-hexylnaphthalene
2-[3,5-Difluoro-4-(3,5-difluoro-4-trifluoromethoxyphenyl)phenyl]-6-heptylnaphthalene
2-[3,5-Difluoro-4-(3,5-difluoro-4-trifluoromethoxyphenyl)phenyl]-6-(3-butenyl)naphthalene
2-[3,5-Difluoro-4-(4-difluoromethoxyphenyl)phenyl]-6-ethylnaphthalene
2-[3,5-Difluoro-4-(4-difluoromethoxyphenyl)phenyl]-6-propylnaphthalene
2-[3,5-Difluoro-4-(4-difluoromethoxyphenyl)phenyl]-6-butylnaphthalene
2-[3,5-Difluoro-4-(4-difluoromethoxyphenyl)phenyl]-6-pentylnaphthalene
2-[3,5-Difluoro-4-(4-difluoromethoxyphenyl)phenyl]-6-hexylnaphthalene
2-[3,5-Difluoro-4-(4-difluoromethoxyphenyl)phenyl]-6-heptylnaphthalene
2-[3,5-Difluoro-4-(4-difluoromethoxyphenyl)phenyl]-6-(3-butenyl)naphthalene 2-[3,5-Difluoro-4-(3-fluoro-4-difluoromethoxyphenyl)phenyl]-6-ethylnaphthalene
2-[3,5-Difluoro-4-(3-fluoro-4-difluoromethoxyphenyl)phenyl]-6-propylnaphthalene
2-[3,5-Difluoro-4-(3-fluoro-4-difluoromethoxyphenyl)phenyl]-6-butylnaphthalene
2-[3,5-Difluoro-4-(3-fluoro-4-difluoromethoxyphenyl)phenyl]-6-pentylnaphthalene
2-[3,5-Difluoro-4-(3-fluoro-4-difluoromethoxyphenyl)phenyl]-6-hexylnaphthalene
2-[3,5-Difluoro-4-(3-fluoro-4-difluoromethoxyphenyl)phenyl]-6-heptylnaphthalene
2-[3,5-Difluoro-4-(3-fluoro-4-difluoromethoxyphenyl)phenyl]-6-(3-butenyl)naphthalene
2-[3,5-Difluoro-4-(3,5-difluoro-4-difluoromethoxyphenyl)phenyl]-6-ethylnaphthalene
2-[3,5-Difluoro-4-(3,5-difluoro-4-difluoromethoxyphenyl)phenyl]-6-propylnaphthalene
2-[3,5-Difluoro-4-(3,5-difluoro-4-difluoromethoxyphenyl)phenyl]-6-butylnaphthalene
2-[3,5-Difluoro-4-(3,5-difluoro-4-difluoromethoxyphenyl)phenyl]-6-pentylnaphthalene
2-[3,5-Difluoro-4-(3,5-difluoro-4-difluoromethoxyphenyl)phenyl]-6-hexylnaphthalene
2-[3,5-Difluoro-4-(3,5-difluoro-4-difluoromethoxyphenyl)phenyl]-6-heptylnaphthalene
2-[3,5-Difluoro-4-(3,5-difluoro-4-difluoromethoxyphenyl)phenyl]-6-(3-butenyl)naphthalene
2-[3,5-Difluoro-4-(4-trifluoromethylphenyl)phenyl]-6-ethylnaphthalene
2-[3,5-Difluoro-4-(4-trifluoromethylphenyl)phenyl]-6-propylnaphthalene
2-[3,5-Difluoro-4-(4-trifluoromethylphenyl)phenyl]-6-butylnaphthalene
2-[3,5-Difluoro-4-(4-trifluoromethylphenyl)phenyl]-6-pentylnaphthalene
2-[3,5-Difluoro-4-(4-trifluoromethylphenyl)phenyl]-6-hexylnaphthalene
2-[3,5-Difluoro-4-(4-trifluoromethylphenyl)phenyl]-6-heptylnaphthalene
2-[3,5-Difluoro-4-(4-trifluoromethylphenyl)phenyl]-6-(3-butenyl)naphthalene
2-[3,5-Difluoro-4-(3-fluoro-4-trifluoromethylphenyl)phenyl]-6-ethylnaphthalene
2-[3,5-Difluoro-4-(3-fluoro-4-trifluoromethylphenyl)phenyl]-6-propylnaphthalene
2-[3,5-Difluoro-4-(3-fluoro-4-trifluoromethylphenyl)phenyl]-6-butylnaphthalene
2-[3,5-Difluoro-4-(3-fluoro-4-trifluoromethylphenyl)phenyl]-6-pentylnaphthalene
2-[3,5-Difluoro-4-(3-fluoro-4-trifluoromethylphenyl)phenyl]-6-hexylnaphthalene
2-[3,5-Difluoro-4-(3-fluoro-4-trifluoromethylphenyl)phenyl]-6-heptylnaphthalene
2-[3,5-Difluoro-4-(3-fluoro-4-trifluoromethylphenylphenyl)phenyl]-6-(3-butenyl)naphthalene
2-[3,5-Difluoro-4-(3,5-difluoro-4-trifluoromethylphenyl)phenyl]-6-ethylnaphthalene
2-[3,5-Difluoro-4-(3,5-difluoro-4-trifluoromethylphenyl)phenyl]-6-propylnaphthalene
2-[3,5-Difluoro-4-(3,5-difluoro-4-trifluoromethylphenyl)phenyl]-6-butylnaphthalene
2-[3,5-Difluoro-4-(3,5-difluoro-4-trifluoromethylphenyl)phenyl]-6-pentylnaphthalene
2-[3,5-Difluoro-4-(3,5-difluoro-4-trifluoromethylphenyl)phenyl]-6-hexylnaphthalene
2-[3,5-Difluoro-4-(3,5-difluoro-4-trifluoromethylphenyl)phenyl]-6-heptylnaphthalene
2-[3,5-Difluoro-4-(3,5-difluoro-4-trifluoromethylphenyl)phenyl]-6-(3-butenyl)naphthalene
2-[3,5-Difluoro-4-(4-methoxyphenyl)phenyl]-6-ethylnaphthalene
2-[3,5-Difluoro-4-(4-methoxyphenyl)phenyl]-6-propylnaphthalene
2-[3,5-Difluoro-4-(4-methoxyphenyl)phenyl]-6-butylnaphthalene
2-[3,5-Difluoro-4-(4-methoxyphenyl)phenyl]-6-pentylnaphthalene
2-[3,5-Difluoro-4-(4-methoxyphenyl)phenyl]-6-hexylnaphthalene
2-[3,5-Difluoro-4-(4-methoxyphenyl)phenyl]-6-heptylnaphthalene
2-[3,5-Difluoro-4-(4-methoxyphenyl)phenyl]-6-(3-butenyl)naphthalene
2-[3,5-Difluoro-4-(3-fluoro-4-methoxyphenyl)phenyl]-6-ethylnaphthalene
2-[3,5-Difluoro-4-(3-fluoro-4-methoxyphenyl)phenyl]-6-propylnaphthalene
2-[3,5-Difluoro-4-(3-fluoro-4-methoxyphenyl)phenyl]-6-butylnaphthalene
2-[3,5-Difluoro-4-(3-fluoro-4-methoxyphenyl)phenyl]-6-pentylnaphthalene
2-[3,5-Difluoro-4-(3-fluoro-4-methoxyphenyl)phenyl]-6-hexylnaphthalene
2-[3,5-Difluoro-4-(3-fluoro-4-methoxyphenyl)phenyl]-6-heptylnaphthalene
2-[3,5-Difluoro-4-(3-fluoro-4-methoxyphenyl)phenyl]-6-(3-butenyl)naphthalene
2-[3,5-Difluoro-4-(3,5-difluoro-4-methoxyphenyl)phenyl]-6-ethylnaphthalene
2-[3,5-Difluoro-4-(3,5-difluoro-4-methoxyphenyl)phenyl]-6-propylnaphthalene
2-[3,5-Difluoro-4-(3,5-difluoro-4-methoxyphenyl)phenyl]-6-butylnaphthalene
2-[3,5-Difluoro-4-(3,5-difluoro-4-methoxyphenyl)phenyl]-6-pentylnaphthalene
2-[3,5-Difluoro-4-(3,5-difluoro-4-methoxyphenyl)phenyl]-6-hexylnaphthalene
2-[3,5-Difluoro-4-(3,5-difluoro-4-methoxyphenyl)phenyl]-6-heptylnaphthalene
2-[3,5-Difluoro-4-(3,5-difluoro-4-methoxyphenyl)phenyl]-6-(3-butenyl)naphthalene
2-[3,5-Difluoro-4-(4-allyloxyphenyl)phenyl]-6-ethylnaphthalene
2-[3,5-Difluoro-4-(4-allyloxyphenyl)phenyl]-6-propylnaphthalene
2-[3,5-Difluoro-4-(4-allyloxyphenyl)phenyl]-6-butylnaphthalene
2-[3,5-Difluoro-4-(4-allyloxyphenyl)phenyl]-6-pentylnaphthalene
2-[3,5-Difluoro-4-(4-allyloxyphenyl)phenyl]-6-hexylnaphthalene
2-[3,5-Difluoro-4-(4-allyloxyphenyl)phenyl]-6-heptylnaphthalene
2-[3,5-Difluoro-4-(4-allyloxyphenyl)phenyl]-6-(3-butenyl)naphthalene
2-[3,5-Difluoro-4-(4-methylphenyl)phenyl]-6-ethylnaphthalene
2-[3,5-Difluoro-4-(4-methylphenyl)phenyl]-6-propylnaphthalene
2-[3,5-Difluoro-4-(4-methylphenyl)phenyl]-6-butylnaphthalene 2-[3,5-Difluoro-4-(4-methylphenyl)phenyl]-6-pentylnaphthalene
2-[3,5-Difluoro-4-(4-methylphenyl)phenyl]-6-hexylnaphthalene
2-[3,5-Difluoro-4-(4-methylphenyl)phenyl]-6-heptylnaphthalene
2-[3,5-Difluoro-4-(4-methylphenyl)phenyl]-6-(3-butenyl)naphthalene
2-[3,5-Difluoro-4-[4-(3-butenyl)phenyl]phenyl]-6-ethylnaphthalene
2-[3,5-Difluoro-4-[4-(3-butenyl)phenyl]phenyl]-6-propylnaphthalene
2-[3,5-Difluoro-4-[4-(3-butenyl)phenyl]phenyl]-6-butylnaphthalene
2-[3,5-Difluoro-4-[4-(3-butenyl)phenyl]phenyl]-6-pentylnaphthalene
2-[3,5-Difluoro-4-[4-(3-butenyl)phenyl]phenyl]-6-hexylnaphthalene
2-[3,5-Difluoro-4-[4-(3-butenyl)phenyl]phenyl]-6-heptylnaphthalene
2-[3,5-Difluoro-4-[4-(3-butenyl)phenyl]phenyl]-6-(3-butenyl)naphthalene Example 14

Synthesis of 6-fluoro-2-(trans-4-propylcyclohexyl)naphthalene 3.38 g of 6-fluoro-2-bromonaphthalene (synthesized by converting 6-bromo-2-naphthylamine to a diazonium salt of tetrafluoroboric acid, and then subjecting the diazonium salt to thermal decomposition) was dissolved in 30 ml of tetrahydrofuran (THF), and then cooled to a temperature of −40° C. under a nitrogen atmosphere. To the reaction solution was then added dropwise 10 ml of n-butyl lithium (1.5 M hexane solution) in 5 minutes. The reaction mixture was then further stirred. The reaction solution was then returned to room temperature. To the reaction solution was then added dropwise a solution of 2.20 g of 4-propylcyclohexanene in 10 ml of THF in 5 minutes. The reaction mixture was then stirred for 1 hour. To the reaction solution were then added water and a small amount of diluted hydrochloric acid. The reaction solution was extracted with 50 ml of toluene, washed with water and then with saturated brine, and then dehydrated and dried over anhydrous sodium sulfate. To the residue was then added 300 mg of p-toluenesulfonic acid monohydrate. The reaction mixture was then heated under reflux while the azeotropically distilled water was being driven out of the system for 2 hours. The reaction solution was allowed to cool, washed sequentially with water, saturated aqueous solution of sodium bicarbonate, water and saturated brine, and then dehydrated and dried over anhydrous sodium sulfate. The solvent was distilled off to obtain a crude crystal which was then purified through silica gel column chromatography (hexane) to obtain 2.1 g of 6-fluoro-2-(4-propylcyclohexenyl)naphthalene in the form of white crystal. The total amount of 6-fluoro-2-(4-propylcyclohexenyl)naphthalene was dissolved in 20 ml of ethyl acetate. To the solution was then added 200 mg of 5% palladium carbon. The reaction mixture was then stirred at a hydrogen pressure of 4 atm for 5 hours. The catalyst was then removed by filtration through Celite. The solvent was then distilled off to obtain 2.1 g of 6-fluoro-2-(4-propylcyclohexyl)naphthalene in the form of crude product (cis/trans mixture). The crude product was then dissolved in 20 ml of N,N-dimethylformamide (DMF). To the reaction mixture was then added 400 mg of potassium t-butoxide. The reaction mixture was then stirred at a temperature of from 40° C. to 50° C. for 1 hour. To the reaction mixture were then added hexane and water. The reaction mixture was then treated with diluted hydrochloric acid to become weakly acidic. The resulting hexane phase was then separated. The resulting aqueous phase was then extracted with hexane. The material thus extracted and the hexane phase were together washed with water and saturated brine. The solvent was then distilled off. The residue was purified through silica gel column chromatography (hexane), and then recrystallized twice from ethanol to obtain 0.75 g of 6-fluoro-2-(trans-4-propylcyclohexyl)naphthalene in the form of white crystal.

Example 15

Synthesis of 5,6-difluoro-2-(trans-4-pentylcyclohexyl)naphthalene

The procedure of Example 14 was followed except that 5,6-difluoro-2-bromonaphthalene (synthesized by converting 6-bromo-1-fluoro-2-naphthylamine to a diazonium salt of tetrafluoroboric acid, and then subjecting the diazonium salt to thermal decomposition) was used instead of 6-fluoro-2-bromonaphthalene and 4-pentylcyclohexanene was used instead of 4-propylcyclohexanene to obtain 5,6-difluoro-2-(trans-4-pentylcyclohexyl)naphthalene.

The following compounds were prepared in the same manner as mentioned above.

6-Fluoro-2-(trans-4-pentylcyclohexyl)naphthalene
6-Fluoro-2-(trans-4-heptylcyclohexyl)naphthalene
6-Fluoro-2-(trans-4-methoxymethylcyclohexyl)naphthalene
5,6-Difluoro-2-(trans-4-propylcyclohexyl)naphthalene
5,6-Difluoro-2-(trans-4-heptylcyclohexyl)naphthalene
5,6,7-Trifluoro-2-(trans-4-propylcyclohexyl)naphthalene
5,6,7-Trifluoro-2-(trans-4-pentylcyclohexyl)naphthalene
5,6,7-Trifluoro-2-(trans-4-heptylcyclohexyl)naphthalene
6-Fluoro-2-(trans-4'-ethylbicyclohexane-trans-4-yl)naphthalene
6-Fluoro-2-(trans-4'-propylbicyclohexane-trans-4-yl)naphthalene
6-Fluoro-2-(trans-4'-butylbicyclohexane-trans-4-yl)naphthalene
6-Fluoro-2-(trans-4'-pentylbicyclohexane-trans-4-yl)naphthalene
5,6-Difluoro-2-(trans-4'-ethylbicyclohexane-trans-4-yl)naphthalene
5,6-Difluoro-2-(trans-4'-propylbicyclohexane-trans-4-yl)naphthalene
5,6-Difluoro-2-(trans-4'-butylbicyclohexane-trans-4-yl)naphthalene
5,6-Difluoro-2-(trans-4'-pentylbicyclohexane-trans-4-yl)naphthalene
5,6,7-Trifluoro-2-(trans-4'-ethylbicyclohexane-trans-4-yl)naphthalene
5,6,7-Trifluoro-2-(trans-4'-propylbicyclohexane-trans-4-yl)naphthalene
5,6,7-Trifluoro-2-(trans-4'-butylbicyclohexane-trans-4-yl)naphthalene
5,6,7-Trifluoro-2-(trans-4'-pentylbicyclohexane-trans-4-yl)naphthalene
4,5,6,7-Tetrafluoro-2-(trans-4'-ethylbicyclohexane-trans-4-yl)naphthalene
4,5,6,7-Tetrafluoro-2-(trans-4'-propylbicyclohexane-trans-4-yl)naphthalene
4,5,6,7-Tetrafluoro-2-(trans-4'-butylbicyclohexane-trans-4-yl)naphthalene 4,5,6,7-Tetrafluoro-2-(trans-4'-pentylbicyclohexane-trans-4-yl)naphthalene 6-Fluoro-2-[trans-4-[2-(trans-4-ethylcyclohexyl)ethyl]cyclohexyl]naphthalene 6-Fluoro-2-[trans-4-[2-(trans-4-propylcyclohexyl)ethyl]cyclohexyl]naphthalene 6-Fluoro-2-[trans-4-[2-(trans-4-butylcyclohexyl)ethyl]cyclohexyl]naphthalene 6-Fluoro-2-[trans-4-[2-(trans-4-pentylcyclohexyl)ethyl]cyclohexyl]naphthalene 5,6-Difluoro-2-[trans-4-[2-(trans-4-ethylcyclohexyl)ethyl]cyclohexyl]naphthalene 5,6-Difluoro-2-[trans-4-[2-(trans-4-propylcyclohexyl)ethyl]cyclohexyl]naphthalene 5,6-Difluoro-2-[trans-4-[2-(trans-4-butylcyclohexyl)ethyl]cyclohexyl]naphthalene 5,6-Difluoro-2-[trans-4-[2-(trans-4-pentylcyclohexyl)ethyl]cyclohexyl]naphthalene 5,6,7-Trifluoro-2-[trans-4-[2-(trans-4-ethylcyclohexyl)ethyl]cyclohexyl]naphthalene 5,6,7-Trifluoro-2-[trans-4-[2-(trans-4-propylcyclohexyl)ethyl]cyclohexyl]naphthalene 5,6,7-Trifluoro-2-[trans-4-[2-(trans-4-butylcyclohexyl)ethyl]cyclohexyl]naphthalene 5,6,7-Trifluoro-2-[trans-4-[2-(trans-4-pentylcyclohexyl)ethyl]cyclohexyl]naphthalene Example 16

Synthesis of 5,6-difluoro-2-[2-(trans-4-propylcyclohexyl)ethyl]naphthalene

The procedure of Example 14 was followed except that 5,6-difluoro-2-bromonaphthalene was used instead of 6-fluoro-2-bromonaphthalene, 4-propylcyclohexaneethanal was used instead of 4-propylcyclohexanene and isomerization with potassium t-butoxide was not effected to obtain 5,6-difluoro-2-[2-(trans-4-propylcyclohexyl)ethyl]naphthalene.

The following compounds were prepared in the same manner as mentioned above.

5,6-Difluoro-2-[2-(trans-4-pentylcyclohexyl)ethyl]naphthalene 5,6-Difluoro-2-[2-(trans-4-heptylcyclohexyl)ethyl]naphthalene 6-Fluoro-2-[2-(trans-4-propylcyclohexyl)ethyl]naphthalene 6-Fluoro-2-[2-(trans-4-pentylcyclohexyl)ethyl]naphthalene 6-Fluoro-2-[2-(trans-4-heptylcyclohexyl)ethyl]naphthalene 5,6,7-Trifluoro-2-[2-(trans-4-propylcyclohexyl)ethyl]naphthalene 5,6,7-Trifluoro-2-[2-(trans-4-pentylcyclohexyl)ethyl]naphthalene 5,6,7-Trifluoro-2-[2-(trans-4-heptylcyclohexyl)ethyl]naphthalene 6-Fluoro-2-[2-(trans-4'-ethylbicyclohexane-trans-4-yl)ethyl]naphthalene 6-Fluoro-2-[2-(trans-4'-propylbicyclohexane-trans-4-yl)ethyl]naphthalene 6-Fluoro-2-[2-(trans-4'-butylbicyclohexane-trans-4-yl)ethyl]naphthalene 6-Fluoro-2-[2-(trans-4'-pentylbicyclohexane-trans-4-yl)ethyl]naphthalene 5,6-Difluoro-2-[2-(trans-4'-ethylbicyclohexane-trans-4-yl)ethyl]naphthalene 5,6-Difluoro-2-[2-(trans-4'-propylbicyclohexane-trans-4-yl)ethyl]naphthalene 5,6-Difluoro-2-[2-(trans-4'-butylbicyclohexane-trans-4-yl)ethyl]naphthalene 5,6-Difluoro-2-[2-(trans-4'-pentylbicyclohexane-trans-4-yl)ethyl]naphthalene 5,6,7-Trifluoro-2-[2-(trans-4'-ethylbicyclohexane-trans-4-yl)ethyl]naphthalene 5,6,7-Trifluoro-2-[2-(trans-4'-propylbicyclohexane-trans-4-yl)ethyl]naphthalene(1–5) 5,6,7-Trifluoro-2-[2-(trans-4'-butylbicyclohexane-trans-4-yl)ethyl]naphthalene 5,6,7-Trifluoro-2-[2-(trans-4'-pentylbicyclohexane-trans-4-yl)ethyl]naphthalene 6-Fluoro-2-[2-[4-(trans-4-propylcyclohexyl)phenyl]ethyl]naphthalene 6-Fluoro-2-[2-[4-(trans-4-pentylcyclohexyl)phenyl]ethyl]naphthalene 5,6-Difluoro-2-[2-[4-(trans-4-propylcyclohexyl)phenyl]ethyl]naphthalene 5,6-Difluoro-2-[2-[4-(trans-4-pentylcyclohexyl) phenyl]ethyl]naphthalene 5,6,7-Trifluoro-2-[2-[4-(trans-4-propylcyclohexyl)phenyl]ethyl]naphthalene 5,6,7-Trifluoro-2-[2-[4-(trans-4-pentylcyclohexyl)phenyl]ethyl]naphthalene 6-Fluoro-2-[2-[2–6-difluoro-4-(trans-4-propyloyclohexyl)phenyl]ethyl]naphthalene 6-Fluoro-2-[2-[2–6-difluoro-4-(trans-4-pentylcyclohexyl)phenyl]ethyl]naphthalene 5,6-Difluoro-2-[2-[2–6-difluoro-4-(trans-4-propylcyclohexyl)phenyl]ethyl]naphthalene 5,6-Difluoro-2-[2-[2–6-difluoro-4-(trans-4-pentylcyclohexyl)phenyl]ethyl]naphthalene 5,6,7-Trifluoro-2-[2-[2–6-difluoro-4-(trans-4-propylcyclohexyl)phenyl]ethyl]naphthalene 5,6,7-Trifluoro-2-[2-[2–6-difluoro-4-(trans-4-pentylcyclohexyl)phenyl]ethyl]naphthalene Example 17

Synthesis of 5,6-difluoro-2-(trans-4'-vinylbicyclohexane-trans-4-yl)naphthalene

The procedure of Example 14 was followed except that 5,6-difluoro-2-bromonaphthalene was used instead of 6-fluoro-2-bromonaphthalene and bicyclohexane-4,4'-dionemonoethyleneacetal was used instead of 4-propylcyclohexanene. The foregoing procedure wan followed by deacetalation with formic acid to obtain trans-4'-(5,6-difluoronaphthyl)bicyclohexane-4-one. Separately, a Wittig reagent was prepared from methoxymethyltriphenylphosphonium chloride and potassium t-butoxide in THF under cooling with ice. To the Wittig reagent was then added dropwise a solution of the foregoing trans-4'-(5,6-difluoronaphthyl)bicyclohexane-4-one at a temperature of 0° C. After 1 hour of reaction, the reaction solution was then returned to room temperature. To the reaction solution was then added water. The resulting organic phase was then concentrated. To the organic phase was then added hexane to make a solution. Insoluble triphenylphosphine oxide was then removed by filtration. The residue was then washed with a 1/1 mixture of methanol and water. The resulting hexane phase was then concentrated to obtain a crude product. The crude product was then dissolved in ethanol. To the solution was then added an ethanol solution of potassium hydroxide. The reaction mixture was then stirred at room temperature for 1 hour. To the reaction solution was then added water. The reaction solution was neutralized with diluted hydrochloric acid, and then neutralized with toluene.

The resulting organic phase was washed with water, and then dehydrated and dried over anhydrous sodium sulfate. The solvent was then distilled off to obtain trans-4'-(5,6-difluoronaphthyl)bicyclohexane-trans-4-carbaldehyde in crystal form. The crystal was then reacted with a Wittig reagent prepared from methoxymethyltriphenylphosphonium iodide and potassium t-butoxide to obtain 5,6-difluoro-2-(trans-4'-vinylbicyclohexane-trans-4-yl)naphthalene.

The following compounds were prepared in the same manner as mentioned above.

5,6-Difluoro-2-[trans-4'-(3-butenyl)bicyclohexane-trans-4-yl]naphthalene
6-Fluoro-2-(trans-4'-vinylbicyclohexane-trans-4-yl)naphthalene
6-Fluoro-2-[trans-4'-(3-butenyl)bicyclohexane-trans-4-yl]naphthalene
5,6,7-Trifluoro-2-(trans-4-vinylbicyclohexane-trans-4-yl)naphthalene
5,6,7-Trifluoro-2-[trans-4'-(3-butenyl)bicyclohexane-trans-4-yl]naphthalene
4,5,6,7-Tetrafluoro-2-(trans-4'-vinylbicyclohexane-trans-4-yl)naphthalene
4,5,6,7-Tetrafluoro-2-[trans-4'-(3-butenyl) bicyclohexane-trans-4-yl]naphthalene
6-Fluoro-2-(trans-4-vinylcyclohexyl)naphthalene
6-Fluoro-2-[trans-4(3-butenyl)cyclohexyl]naphthalene
5,6-Difluoro-2-(trans-4-vinylcyclohexyl)naphthalene
5,6-Difluoro-2-[trans-4-(3-butenyl)cyclohexyl]naphthalene
5,6,7-Trifluoro-2-(trans-4-vinylcyclohexyl)naphthalene
5,6,7-Trifluoro-2-[trans-4-(3-butenyl)cyclohexyl]naphthalene Example 18

Synthesis of 5,6-difluoro-2-[4-(trans-4-propylcyclohexyl)phenyl]naphthalene

To a THF solution of an organic lithium reagent prepared from 5,6-difluoro-2-bromonaphthalene were added dropwise 4-iodo-1-(trans-4-propylcyclohexyl)benzene and a THF solution of tetrakis(triphenylphosphine)palladium (0) in the catalytic amount. The reaction mixture was then stirred at room temperature for 3 hours. To the reaction mixture were then added water and toluene to terminate the reaction. To the reaction solution was then added diluted hydrochloric acid until the aqueous phase became weakly acidic. The reaction solution was then extracted with toluene. The material thus extracted and the organic phase were together washed with water and then with saturated brine, and then dried over anhydrous sodium sulfate. The solvent was distilled off under reduced pressure to obtain an oily matter. The oily matter was purified through silica gel column chromatography (hexane), and then recrystallized from ethanol to obtain 5,6-difluoro-2-[4-(trans-4-propylcyclohexyl)phenyl]naphthalene in the form of white crystal.

The following compounds were prepared in the same manner as mentioned above.

5,6-Difluoro-2-[4-(trans-4-ethylcyclohexyl)phenyl]naphthalene
5,6-Difluoro-2-[4-(trans-4-butylcyclohexyl)phenyl)naphthalene
5,6-Difluoro-2-[4-(trans-4-pentylcyclohexyl)phenyl]naphthalene
5,6-Difluoro-2-[4-(trans-4-vinylcyclohexyl)phenyl]naphthalene
6-Fluoro-2-[4-(trans-4-ethylcyclohexyl)phenyl]naphthalene
6-Fluoro-2-[4-(trans-4-propylcyclohexyl)phenyl]naphthalene
6-Fluoro-2-[4-(trans-4-butylcyclohexyl)phenyl]naphthalene
6-Fluoro-2-[4-(trans-4-pentylcyclohexyl)phenyl]naphthalene
6-Fluoro-2-[4-(trans-4-vinylcyclohexyl)phenyl]naphthalene
5,6,7-Trifluoro-2-[4-(trans-4-ethylcyclohexyl)phenyl]naphthalene
5,6,7-Trifluoro-2-[4-(trans-4-propylcyclohexyl)phenyl]naphthalene
5,6,7-Trifluoro-2-[4-(trans-4-butylcyclohexyl)phenyl]naphthalene
5,6,7-Trifluoro-2-[4-(trans-4-pentylcyclohexyl)phenyl]naphthalene
5,6,7-Trifluoro-2-[4-(trans-4-vinylcyclohexyl)phenyl]naphthalene
4,5,6,7-Tetrafluoro-2-[4-(trans-4-ethylcyclohexyl)phenyl]naphthalene
4,5,6,7-Tetrafluoro-2-[4-(trans-4-propylcyclohexyl)phenyl]naphthalene
4,5,6,7-Tetrafluoro-2-[4-(trans-4-butylcyclohexyl)phenyl]naphthalene
4,5,6,7-Tetrafluoro-2-[4-(trans-4-pentylcyclohexyl)phenyl]naphthalene
4,5,6,7-Tetrafluoro-2-[4-(trans-4-vinylcyclohexyl)phenyl]naphthalene
6-Fluoro-2-[2,6-difluoro-4-(trans-4-ethylcyclohexyl)phenyl]naphthalene
6-Fluoro-2-[2,6-difluoro-4-(trans-4-propylcyclohexyl)phenyl]naphthalene
6-Fluoro-2-[2,6-difluoro-4-(trans-4-butylcyclohexyl)phenyl]naphthalene
6-Fluoro-2-[2,6-difluoro-4-(trans-4-pentylcyclohexyl)phenyl]naphthalene
6-Fluoro-2-[2,6-difluoro-4-(trans-4-vinylcyclohexyl)phenyl]naphthalene
5,6-Difluoro-2-[2,6-difluoro-4-(trans-4-ethylcyclohexyl)phenyl]naphthalene
5,6-Difluoro-2-[2,6-difluoro-4-(trans-4-propylcyclohexyl)phenyl]naphthalene
5,6-Difluoro-2-[2,6-difluoro-4-(trans-4-butylcyclohexyl)phenyl]naphthalene
5,6-Difluoro-2-[2,6-difluoro-4-(trans-4-pentylcyclohexyl)phenyl]naphthalene
5,6-Difluoro-2-[2,6-difluoro-4-(trans-4-vinylcyclohexyl)phenyl]naphthalene
5,6,7-Trifluoro-2-[2,6-difluoro-4-(trans-4-ethylcyclohexyl)phenyl]naphthalene
5,6,7-Trifluoro-2-[2,6-difluoro-4-(trans-4-propylcyclohexyl)phenyl]naphthalene
5,6,7-Trifluoro-2-[2,6-difluoro-4-(trans-4-butylcyclohexyl)phenyl]naphthalene
5,6,7-Trifluoro-2-[2,6-difluoro-4-(trans-4-pentylcyclohexyl)phenyl]naphthalene
5,6,7-Trifluoro-2-[2,6-difluoro-4-(trans-4-vinylcyclohexyl)phenyl]naphthalene
4,5,6,7-Tetrafluoro-2-[2,6-difluoro-4-(trans-4-ethylcyclohexyl)phenyl]naphthalene
4,5,6,7-Tetrafluoro-2-[2,6-difluoro-4-(trans-4-propylcyclohexyl)phenyl]naphthalene
4,5,6,7-Tetrafluoro-2-[2,6-difluoro-4-(trans-4-butylcyclohexyl)phenyl]naphthalene
4,5,6,7-Tetrafluoro-2-[2,6-difluoro-4-(trans-4-pentylcyclohexyl)phenyl]naphthalene
4,5,6,7-Tetrafluoro-2-[2,6-difluoro-4-(trans-4-vinylcyclohexyl)phenyl]naphthalene 5,6-Difluoro-2-(2-fluoro-4-(trans-4-ethylcyclohexyl)phenyl]naphthalene 5,6-Difluoro-2-[2-fluoro-4-(trans-4-propylcyclohexyl)phenyl]naphthalene 5,6-Difluoro-2-[2-fluoro-4-(trans-4-butylcyclohexyl)phenyl]naphthalene 5,6-Difluoro-2-[2-fluoro-4-(trans-4-pentylcyclohexyl)phenyl]naphthalene Example 19

Synthesis of 1-fluoro-2-trifluoromethoxy-6-(trans-4-propylcyclohexyl)naphthalene 1.5 g of sodium hydride was suspended in 5 ml of tetrahydrofuran (THF) under cooling by an ice-water bath. To the suspension was then added dropwise 40 ml THF solution of 10.0 g of 1-fluoro-6-(trans-4-propylcyclohexyl)naphthalene-2-ol (obtained by reacting a Grignard reagent prepared from 6-bromo-2-methoxynaphthalene and magnesium with 4-propylcyclohexanone, subjecting the product to dehydration in the presence of an acid to obtain a naphthylcyclohexene derivative, subjecting the naphthylcyclohexene derivative to catalytic reduction, treating the material with a strongly basic potassium t-butoxide in DMF so that the cyclohexane ring was isomerized to trans form, subjecting the material to demethylation with hydrobromic acid, and then fluorinating the material with N-fluoro-5-trifluoromethoxypyridinium-2-sulfonate). After several hours of stirring, to the reaction solution was then added dropwise 30 ml of a THF solution of 7.4 g of S-ethyl chlorodithiocarbonate. After 1 hour of stirring, to the reaction solution was than added 20 ml of water to terminate the reaction. To the reaction solution was then added 50 ml of ethyl acetate. The organic phase was further washed twice with 20 ml of water, and then dehydrated and dried over anhydrous sodium sulfate. Subsequently, the solvent was distilled off under reduced pressure to obtain 12.0 g of S-ethyl-O-1-fluoro-6-(trans-4-propylcyclohexyl)naphthalene-2-yl dithiocarbonate. 12.0 g of S-ethyl-O-1-fluoro-6-(trans-4-propylcyclohexyl)naphthalene-2-yl dithiocarbonate thus obtained was dissolved in 48 ml of dichloromethane, and then added dropwise to 1 liter dichloromethane solution of 300 g of hydrogen fluoride-melamine complex and 1,3-dibromo-5,5-dimethylhydantoin which had been cooled to a temperature of 0° C. After 30 minutes of stirring, to the reaction solution was then added 200 ml of water to terminate the reaction. The resulting organic phase was washed twice with 200 ml of water, and then dehydrated and dried over anhydrous sodium sulfate. The solvent was then distilled off. The residue was then purified through silica gel column chromatography (developing solvent: hexane). The total amount of the purified product was then dissolved in 50 ml of THF. Two the solution was then added dropwise 43 ml of a 1.6 M hexane solution of butyl lithium at a temperature of −78° C. After the termination of dropwise addition, the reaction mixture was then stirred for 10 minutes. To the reaction mixture was then added 10 ml of water. The reaction mixture was then returned to room temperature. To the reaction mixture was then added 20 ml of water. The resulting organic phase was washed twice with 20 ml of water, and then dehydrated and dried over anhydrous sodium sulfate. The product was purified through silica gel column chromatography (hexane/ethyl acetate=9/1), and then recrystalized from ethanol to obtain 7.1 g of 5-fluoro-5-trifluoromethoxy-2-(trans-4-propylcyclohexyl)naphthalene.

Example 20

Synthesis of 1,3-difluoro-2-trifluoromethoxy-6-(trans-4-propylcyclohexyl)naphthalene The procedure of Example 19 was followed except that 1,3-difluoro-6-(trans-4-propylcyclohexyl)naphthalene-2-ol (obtained by reacting a Grignard reagent prepared from 1,3-difluoro-6-bromo-2-methoxynaphthalene with 4-propyl cyclohexanone, subjecting the product to dehydration in the presence of an acid to obtain a naphthylcyclohexene derivative, subjecting the naphthylcyclohexene derivative to catalytic reduction, treating the material with a strongly basic potassium t-butoxide in DMF so that the cyclohexane ring was isomerized to trans form, and then subjecting the material to demethylation with hydrobromic acid) was used instead of 1-fluoro-6-(trans-4-propylcyclohexyl)naphthalene-2-ol to produce S-ethyl-O-1,3-difluoro-6-(trans-4-propylcyclohexyl)naphthalene-2-yl dithiocarbonate. The product was then similarly trifluoromethoxylated to obtain 5,7-difluoro-6-trifluoromethoxy-2-(trans-4-propylcyclohexyl)naphthalene.

The following compounds were prepared in the same manner as in Example 19 or 20.

2-Trifluoromethoxy-6-(trans-4-propylcyclohexyl)naphthalene

2-Trifluoromethoxy-6-(trans-4-butylcyclohexy)naphthalene

2-Trifluoromethoxy-6-(trans-4-pentylcyclohexyl)naphthalene

1-Fluoro-2-trifluoromethoxy-6-(trans-4-butylcyclohexyl)naphthalene

1-Fluoro-2-trifluoromethoxy-6-(trans-4-pentylcyclohexyl)naphthalene 1,3-Difluoro-2-trifluoromethoxy-6-(trans-4-butylcyclohexyl)naphthalene 1,3-Difluoro-2-trifluoromethoxy-6-(trans-4-pentylcyclohexyl)naphthalene trans-4'-Ethyl-trans-4-(2-trifluoromethoxynaphthalene-2-yl)bicyclohexane trans-4'-Propyl-trans-4-(2-trifluoromethoxynaphthalene-2-yl)bicyclohexane trans-4'-Pentyl-trans-4-(2-trifluoromethoxynaphthalene-2-yl)bicyclohexane trans-4'-Ethyl-trans-4-(1-Fluoro-2-trifluoromethoxynaphthalene-2-yl)bicyclohexane trans-4'-Propyl-trans-4-(1-Fluoro-2-trifluoromethoxynaphthalene-2-yl)bicyclohexane trans-4'-Pentyl-trans-4-(1-Fluoro-2-trifluoromethoxynaphthalene-2-yl)bicyclohexane trans-4'-Ethyl-trans-4-(1,3-difluoro-2-trifluoromethoxynaphthalene-2-yl)bicyclohexane trans-4'-Propyl-trans-4-(1,3-difluoro-2-trifluoromethoxynaphthalene-2-yl)bicyclohexane trans-4'-Pentyl-trans-4-(1,3-difluoro-2-trifluoromethoxynaphthalene-2-yl)bicyclohexane trans-4'-Ethyl-trans-4-(1,3,8-trifluoro-2-trifluoromethoxynaphthalene-2-yl)bicyclohexane trans-4'-Propyl-trans-4-(1,3,8-trifluoro-2-trifluoromethoxynaphthalene-2-yl)bicyclohexane trans-4'-Pentyl-trans-4-(1,3,8-trifluoro-2-trifluoromethoxynaphthalene-2-yl)bicyclohexane 2-Trifluoromethoxy-6-[4-[2-(trans-4-propylcyclohexyl)
  ethyl]cyclohexyl]naphthalene
2-Trifluoromethoxy-6-[4-[2-(trans-4-pentylcyclohexyl)
  ethyl]cyclohexyl]naphthalene
1-Fluoro-2-trifluoromethoxy-6-[4-[2-(trans-4-propylcyclo-
  hexyl)ethyl]cyclohexyl]naphthalene
1-Fluoro-2-trifluoromethoxy-6-[4-[2-(trans-4-pentylcyclo-
  hexyl)ethyl]cyclohexyl]naphthalene
1,3-Difluoro-2-trifluoromethoxy-6-[4-[2-(trans-4-propylcy-
  clohexyl)ethyl]cyclohexyl]naphthalene
1,3-Difluoro-2-trifluoromethoxy-6-[4-[2-(trans-4-pentylcy-
  clohexyl)ethyl]cyclohexyl]naphthalene

Example 21

Synthesis of 1-fluoro-2-trifluoromethoxy-6-[2-
(trans-4-propylcyclohexyl)ethyl]naphthalene The procedure of Example 20 was followed except that 1-fluoro-6-bromo-2-methoxynapthalene was used instead of 1,3-difluoro-6-bromo-2-methoxynaphthalene, 4-propylcyclohexane ethanal was used instead of 4-propylcyclohexanene and isomerization with potassium t-butoxide was not effected to obtain 1-fluoro-2-trifluoromethoxy-6-[2-(trans-4-propyl cyclohexyl)ethyl]naphthalene.

The following compounds were prepared in the same manner as mentioned above.
2-Trifluoromethoxy-6-[2-(trans-4-propylcyclohexyl)ethyl]
  naphthalene
2-Trifluoromethoxy-6-[2-(trans-4-pentylcyclohexyl)ethyl]
  naphthalene
1-Fluoro-2-trifluoromethoxy-6-[2-(trans-4-pentylcyclo-
  hexyl)ethyl]naphthalene
1,3-Difluoro-2-trifluoromethoxy-6-[2-(trans-4-propylcyclo-
  hexyl)ethyl]naphthalene
1,3-Difluoro-2-trifluoromethoxy-6-[2-(trans-4-pentylcyclo-
  hexyl)ethyl]naphthalene
Trans-4'-propyl-trans-4-[2-(2-trifluoromethoxynaphthalene-
  6-yl)ethyl]bicyclohexane
Trans-4'-pentyl-trans-4-[2-(2-trifluoromethoxynaphthalene-
  6-yl)ethyl]bicyclohexane
Trans-4'-propyl-trans-4-[2-(1-fluoro-2-trifluoromethox-
  ynaphthalene-6-yl)ethyl]bicyclohexane
Trans-4'-pentyl-trans-4-[2-(1-fluoro-2-trifluoromethox-
  ynaphthalene-6-yl)ethyl]bicyclohexane
Trans-4'-propyl-trans-4-[2-(1,3-difluoro-2-trifluoromethox-
  ynaphthalene-6-yl)ethyl]bicyclohexane
Trans-4'-pentyl-trans-4-[2-(1,3-difluoro-2-trifluoromethox-
  ynaphthalene-6-yl)ethyl]bicyclohexane
2-Trifluoromethoxy-6-[2-[4-(trans-4-propylcyclohexyl)
  phenyl]ethyl]naphthalene
2-Trifluoromethoxy-6-[2-[4-(trans-4-pentylcyclohexyl)phe-
  nyl]ethyl]naphthalene
1-Fluoro-2-trifluoromethoxy-6-[2-[4-(trans-4-propylcyclo-
  hexyl)phenyl]ethyl]naphthalene
1-Fluoro-2-trifluoromethoxy-6-[2-[4-(trans-4-pentylcyclo-
  hexyl)phenyl]ethyl]naphthalene
2-Trifluoromethoxy-6-[2-[3,5-difluoro-4-(trans-4-propylcy-
  clohexyl)phenyl]ethyl]naphthalene
2-Trifluoromethoxy-6-[2-[3,5-difluoro-4-(trans-4-pentylcy-
  clohexyl)phenyl]ethyl]naphthalene
1-Fluoro-2-trifluoromethoxy-6-[2-[3,5-difluoro-4-(trans-4-
  propylcyclohexyl)phenyl]ethyl]naphthalene
1-Fluoro-2-trifluoromethoxy-6-[2-[3,5-difluoro-4-(trans-4-
  pentylcyclohexyl)phenyl]ethyl]naphthalene

Example 22

Synthesis of 1-fluoro-2-trifluoromethoxy-6-(trans-
4'-vinylbicyclohexane-trans-4-yl)naphthalene A Wittig reagent was prepared from methoxymethyl triphenyl phosphonium chloride and potassium t-butoxide in THF under cooling with ice. To the Wittig reagent was then added a THF solution of trans-4'-(1-fluoro-2-trifluoromethoxynaphthalene-6-yl)bicyclohexane-4-one (obtained by reacting a Grignard reagent prepared from 1-fluoro-6-bromo-2-trifluoromethoxynaphthalene with bicyclohexanone-4,4'-dionemonoethyleneacetal, subjecting the product to dehydration in the same manner as mentioned above, subjecting the product to catalytic reduction, and then deacetalating the product with formic acid) at a temperature of 0° C. After 1 hour of reaction, the reaction solution was returned to room temperature. The reaction solution was then added water. The resulting organic phase was then concentrated. To the material thus concentrated was then added hexane to make a solution. Insoluble triphenylphosphine oxide was then removed by filtration. The filtrate was then washed with a 1/1 mixture of methanol and water. The resulting hexane phase was concentrated to obtain a crude product which was then dissolved in ethanol. To the solution was then added an ethanol solution of potassium hydroxide. The reaction mixture was then stirred at room temperature for 1 hour. To the reaction solution was then added water. The reaction solution was neutralized with diluted hydrochloric acid, and then extracted with toluene. The resulting organic phase was washed with water, and then dehydrated and dried over anhydrous sodium sulfate. The solvent was then distilled off to obtain trans-4'-(1-fluoro-2-trifluoromethoxynaphthalene-6-yl)bicyclohexane-trans-4-carbaldehyde in crystal form. The crystal thus obtained was then reacted with a Wittig prepared from methoxymethyl triphenyl phosphonium iodide and potassium t-butoxide to obtain 1-fluoro-2-trifluoromethoxy-6-(trans-4'-vinylbicyclohexane-trans-4-yl)naphthalene.

The following compounds were prepared in the same manner as mentioned above.
2-Trifluoromethoxy-6-(trans-4'-vinylbicyclohexane-trans-
  4-yl)naphthalene
2-Trifluoromethoxy-6-[trans-4'-(3-butenyl)bicyclohexane6-
  trans-4-yl]naphthalene
1-Fluoro-2-trifluoromethoxy-6-[trans-4'-(3-butenyl)bicy-
  clohexane-trans-4-yl]naphthalene
1,3-Difluoro-2-trifluoromethoxy-6-(trans-4'-vinylbicyclo-
  hexane-trans-4-yl)naphthalene
1,3-Difluoro-2-trifluoromethoxy-6-[trans-4'-(3-butenyl)bi-
  cyclohexane-trans-4-yl]naphthalene
1,3,8-Trifluoro-2-trifluoromethoxy-6-(trans-4'-vinylbicy-
  clohexane-trans-4-yl)naphthalene
1,3,8-Trifluoro-2-trifluoromethoxy-6-[trans-4'-(3-butenyl)
  bicyclohexane-trans-4-yl]naphthalene
2-Trifluoromethoxy-6-(trans-4-vinylcyclohexyl)naphtha-
  lene
2-Trifluoromethoxy-6-[trans-4-(3-butenyl)cyclohexyl]
  naphthalene
1-Fluoro-2-trifluoromethoxy-6-(trans-4-vinylcyclohexyl)
  naphthalene
1-Fluoro-2-trifluoromethoxy-6-[trans-4-(3-butenyl)cyclo-
  hexyl]naphthalene
1,3-Difluoro-2-trifluoromethoxy-6-(trans-4-vinylcyclo-
  hexyl)naphthalene
1,3Difluoro-2-trifluoromethoxy-6-[trans-4-(3-butenyl)
  cyclohexyl]naphthalene

Example 23

Synthesis of 1-fluoro-2-trifluoromethoxy-6-(4-propylphenyl)naphthalene 3.4 g of 4-propylphenylboric acid (obtained by reacting a Grignard reagent prepared from 1-bromo-4-propylbenzene with trimethyl borate, and then subjecting the product to hydrolysis with hydrochloric acid) and 25.5 g of 6-bromo-2-naphthol were dissolved in a mixture of 92 ml of toluene, 46 ml of ethanol and 92 ml of water. To the solution were then added 25.5 g of potassium carbonate and 1.3 g of tetrakis(triphenylphosphine)palladium (0). The reaction mixture was then stirred at a temperature of 75° C. for 7 hours. To the reaction solution were then added water and toluene. To the reaction solution was then added diluted hydrochloric acid until the aqueous phase became weakly acidic. The reaction solution was then extracted with toluene. The material thus extracted and the organic phase were together washed with water and then with saturated brine, and then dried over anhydrous sodium sulfate. The solvent was then distilled off under reduced pressure to obtain 41.4 g of 6-(4-propylphenyl)naphthalene-2-ol. 12.7 g of 6-(4-propylphenyl)naphthalene-2-ol was then dissolved in 50 ml of dichloromethane. To the solution was then added 13.1 g of N-fluoro-5-trifluoromethoxypyridinium-2-sulfonate. The reaction mixture was then stirred at room temperature for 18hours. The reaction mixture was post-treated in the same manner as mentioned above to obtain an oily matter which was then purified through silica gel column chromatography (hexane/ethyl acetate=9/1) to obtain 10 g of 1-fluoro-6-(4-propylphenyl)naphthalene-2-ol. The product was converted to S-ethyl dithiocarbonate which was then trifluoromethoxylated in the same manner as in Example 1 to obtain 2.3 g of the titled 1-fluoro-2-trifluoromethoxy-6-(4-propylphenyl)naphthalene.

Example 24

Synthesis of 1,3-difluoro-2-trifluoromethoxy-6-(4-propylphenyl)naphthalene 7.3 g of 4-propylphenylboric acid and 11 g of 1,3-difluoro-2-trifluoromethoxynaphthalene-6-yl trifluoromethanesulfonate (obtained by triflating 1,3-difluoro-2-trifluoromethoxynaphthalene-6-ol with trifluoromethanesulfonic anhydride) were dissolved in 50 ml of DMF. To the solution was then added 0.4 g of tetrakis(triphenylphosphine)palladium (0). The reaction mixture was stirred at a temperature of 85° C. for 8 hours. To the reaction solution were then added water and toluene. The resulting aqueous phase was then extracted with toluene. The material thus extracted and the organic phase were together washed with water and then with saturated brine, and then dried over anhydrous sodium sulfate. The solvent was then distilled off under reduced pressure to obtain an oily matter. The oily matter thus obtained was purified through silica gel column chromatography (hexane/ethyl acetate=9/1), and then recrystallized from ethanol to obtain 6.3 g of 1,3-difluoro-2-trifluoromethoxy-6-(4-propylphenyl)naphthalene in crystal form.

Example 25

Synthesis of 1-fluoro-2-trifluoromethoxy-6-(2-fluoro-4-propylphenyl)naphthalene

The procedure of Example 23 was followed except that 2-fluoro-4-propylphenylboric acid was used instead of 4-propylphenylboric acid to obtain 1-fluoro-2-trifluoromethoxy-6-(2-fluoro-4-propylphenyl)naphthalene.

The following compounds were prepared in the same manner as in Example 23, 24 or 25.

2-Trifluoromethoxy-6-(4-propylphenyl)naphthalene
2-Trifluoromethoxy-6-(4-pentylphenyl)naphthalene
2-Trifluoromethoxy-6-(4-heptylphenyl)naphthalene
1-Fluoro-2-trifluoromethoxy-6-(4-pentylphenyl)naphthalene
1-Fluoro-2-trifluoromethoxy-6-(4-heptylphenyl)naphthalene
1-Fluoro-2-trifluoromethoxy-6-[4-(3-butenyl)phenyl]naphthalene
1,3-Difluoro-2-trifluoromethoxy-6-(4-pentylphenyl)naphthalene
1,3-Difluoro-2-trifluoromethoxy-6-(4-heptylphenyl)naphthalene
1,3-Difluoro-2-trifluoromethoxy-6-[4-(3-butenyl)phenyl]naphthalene
1,3,8-Trifluoro-2-trifluoromethoxy-6-(4-pentylphenyl)naphthalene
1,3,8-Trifluoro-2-trifluoromethoxy-6-(4-heptylphenyl)naphthalene
1,3,8-Trifluoro-2-trifluoromethoxy-6-[4-(3-butenyl)phenyl]naphthalene
2-Trifluoromethoxy-6-(2-fluoro-4-propylphenyl)naphthalene
2-Trifluoromethoxy-6-(2-fluoro-4-pentylphenyl)naphthalene
2-Trifluoromethoxy-6-(2-fluoro-4-heptylphenyl)naphthalene
2-Trifluoromethoxy-6-[2-fluoro-4-(3-butenyl)phenyl]naphthalene
1-Fluoro-2-trifluoromethoxy-6-(2-fluoro-4-pentylphenyl)naphthalene
1-Fluoro-2-trifluoromethoxy-6-(2-fluoro-4-heptylphenyl)naphthalene
1-Fluoro-2-trifluoromethoxy-6-[2-fluoro-4-(3-butenyl)phenyl]naphthalene
2-Trifluoromethoxy-6-(2–6-difluoro-4-propylphenyl)naphthalene
2-Trifluoromethoxy-6-(2-6-difluoro-4-pentylphenyl)naphthalene
2-Trifluoromethoxy-6-(2-6-difluoro-4-heptylphenyl)naphthalene
2-Trifluoromethoxy-6-[2-6-difluoro-4-(3-butenyl)phenyl]naphthalene
1-Fluoro-2-trifluoromethoxy-6-(2-6-difluoro-4-propylphenyl)naphthalene
1-Fluoro-2-trifluoromethoxy-6-(2-6-difluoro-4-pentylphenyl)naphthalene
1-Fluoro-2-trifluoromethoxy-6-(2-6-difluoro-4-heptylphenyl)naphthalene
1-Fluoro-2-trifluoromethoxy-6-[2-6-difluoro-4-(3-butenyl)phenyl]naphthalene
1,3-Difluoro-2-trifluoromethoxy-6-(2-fluoro-4-propylphenyl)naphthalene
1,3-Difluoro-2-trifluoromethoxy-6-(2-fluoro-4-pentylphenyl)naphthalene 1,3-Difluoro-2-trifluoromethoxy-6-(2-fluoro-4-heptylphenyl)naphthalene
1,3-Difluoro-2-trifluoromethoxy-6-[2-fluoro-4-(3-butenyl)phenyl]naphthalene
1,3-Difluoro-2-trifluoromethoxy-6-(2,6-difluoro-4-propylphenyl)naphthalene
1,3-Difluoro-2-trifluoromethoxy-6-(2,6-difluoro-4-pentylphenyl)naphthalene
1,3-Difluoro-2-trifluoromethoxy-6-(2,6-difluoro-4-heptylphenyl)naphthalene
1,3-Difluoro-2-trifluoromethoxy-6-[2,6-difluoro-4-(3-butenyl)phenyl]naphthalene
2-Trifluoromethoxy-6-[4-(trans-4-ethylcyclohexyl)phenyl]naphthalene
2-Trifluoromethoxy-6-[4-(trans-4-propylcyclohexyl)phenyl]naphthalene
2-Trifluoromethoxy-6-[4-(trans-4-butylcyclohexyl)phenyl]naphthalene
2-Trifluoromethoxy-6-[4-(trans-4-pentylcyclohexyl)phenyl]naphthalene
1-Fluoro-2-trifluoromethoxy-6-[4-(trans-4-ethylcyclohexyl)phenyl]naphthalene
1-Fluoro-2-trifluoromethoxy-6-[4-(trans-4-propylcyclohexyl)phenyl]naphthalene
1-Fluoro-2-trifluoromethoxy-6-[4-(trans-4-butylcyclohexyl)phenyl]naphthalene
1-Fluoro-2-trifluoromethoxy-6-[4-(trans-4-pentylcyclohexyl)phenyl]naphthalene
1,3-Difluoro-2-trifluoromethoxy-6-[4-(trans-4-ethylcyclohexyl)phenyl]naphthalene
1,3-Difluoro-2-trifluoromethoxy-6-[4-(trans-4-propylcyclohexyl)phenyl]naphthalene
1,3-Difluoro-2-trifluoromethoxy-6-[4-(trans-4-butylcyclohexyl)phenyl]naphthalene
1,3-Difluoro-2-trifluoromethoxy-6-[4-(trans-4-pentylcyclohexyl)phenyl]naphthalene
1,3,8-Trifluoro-2-trifluoromethoxy-6-[4-(trans-4-ethylcyclohexyl)phenyl]naphthalene
1,3,8-Trifluoro-2-trifluoromethoxy-6-[4-(trans-4-propylcyclohexyl)phenyl]naphthalene
1,3,8-Trifluoro-2-trifluoromethoxy-6-[4-(trans-4-butylcyclohexyl)phenyl]naphthalene
1,3,8-Trifluoro-2-trifluoromethoxy-6-[4-(trans-4-pentylcyclohexyl)phenyl]naphthalene
2-Trifluoromethoxy-6-[2-fluoro-4-(trans-4-ethylcyclohexyl)phenyl]naphthalene
2-Trifluoromethoxy-6-[2-fluoro-4-(trans-4-propylcyclohexyl)phenyl]naphthalene
2-Trifluoromethoxy-6-[2-fluoro-4-(trans-4-butylcyclohexyl)phenyl]naphthalene
2-Trifluoromethoxy-6-[2-fluoro-4-(trans-4-pentylcyclohexyl)phenyl]naphthalene
1-Fluoro-2-trifluoromethoxy-6-[2-fluoro-4-(trans-4-ethylcyclohexyl)phenyl]naphthalene
1-Fluoro-2-trifluoromethoxy-6-[2-fluoro-4-(trans-4-propylcyclohexyl)phenyl]naphthalene
1-Fluoro-2-trifluoromethoxy-6-[2-fluoro-4-(trans-4-butylcyclohexyl)phenyl]naphthalene
1-Fluoro-2-trifluoromethoxy-6-[2-fluoro-4-(trans-4-pentylcyclohexyl)phenyl]naphthalene
1,3-Difluoro-2-trifluoromethoxy-6-[2-fluoro-4-(trans-4-ethylcyclohexyl)phenyl]naphthalene
1,3-Difluoro-2-trifluoromethoxy-6-[2-fluoro-4-(trans-4-propylcyclohexyl)phenyl]naphthalene
1,3-Difluoro-2-trifluoromethoxy-6-[2-fluoro-4-(trans-4-butylcyclohexyl)phenyl]naphthalene
1,3-Difluoro-2-trifluoromethoxy-6-[2-fluoro-4-(trans-4-pentylcyclohexyl)phenyl]naphthalene
2-Trifluoromethoxy-6-[2,6-difluoro-4-(trans-4-ethylcyclohexyl)phenyl]naphthalene
2-Trifluoromethoxy-6-[2,6-difluoro-4-(trans-4-propylcyclohexyl)phenyl]naphthalene
2-Trifluoromethoxy-6-[2,6-difluoro-4-(trans-4-butylcyclohexyl)phenyl]naphthalene
2-Trifluoromethoxy-6-[2,6-difluoro-4-(trans-4-pentylcyclohexyl)phenyl]naphthalene
1-Fluoro-2-trifluoromethoxy-6-[2,6-difluoro-4-(trans-4-ethylcyclohexyl)phenyl]naphthalene
1-Fluoro-2-trifluoromethoxy-6-[2,6-difluoro-4-(trans-4-propylcyclohexyl)phenyl]naphthalene
1-Fluoro-2-trifluoromethoxy-6-[2,6-difluoro-4-(trans-4-butylcyclohexyl)phenyl]naphthalene
1-Fluoro-2-trifluoromethoxy-6-[2,6-difluoro-4-(trans-4-pentylcyclohexyl)phenyl]naphthalene
1,3-Difluoro-2-trifluoromethoxy-6-[2,6-difluoro-4-(trans-4-ethylcyclohexyl)phenyl]naphthalene
1,3-Difluoro-2-trifluoromethoxy-6-[2,6-difluoro-4-(trans-4-propylcyclohexyl)phenyl]naphthalene
1,3-Difluoro-2-trifluoromethoxy-6-[2,6-difluoro-4-(trans-4-butylcyclohexyl)phenyl]naphthalene
1,3-Difluoro-2-trifluoromethoxy-6-[2,6-difluoro-4-(trans-4-pentylcyclohexyl)phenyl]naphthalene
2-Trifluoromethoxy-6-[4-[2-(trans-4-propylcyclohexyl)ethyl]phenyl]naphthalene
2-Trifluoromethoxy-6-[4-[2-(trans-4-pentylcyclohexyl)ethyl]phenyl]naphthalene
1-Fluoro-2-trifluoromethoxy-6-[4-[2-(trans-4-propylcyclohexyl)ethyl]phenyl]naphthalene
1-Fluoro-2-trifluoromethoxy-6-[4-[2-(trans-4-pentylcyclohexyl)ethyl]phenyl]naphthalene
1,3-Difluoro-2-trifluoromethoxy-6-[4-[2-(trans-4-propylcyclohexyl)ethyl]phenyl]naphthalene
1,3-Difluoro-2-trifluoromethoxy-6-[4-[2-(trans-4-pentylcyclohexyl)ethyl]phenyl]naphthalene
2-Trifluoromethoxy-6-[2-fluoro-4-[2-(trans-4-propylcyclohexyl)ethyl]phenyl]naphthalene
2-Trifluoromethoxy-6-[2-fluoro-4-[2-(trans-4-pentylcyclohexyl)ethyl]phenyl]naphthalene
1-Fluoro-2-trifluoromethoxy-6-[2-fluoro-4-[2-(trans-4-propylcyclohexyl)ethyl]phenyl]naphthalene
1-Fluoro-2-trifluoromethoxy-6-[2-fluoro-4-[2-(trans-4-pentylcyclohexyl)ethyl]phenyl]naphthalene
1,3-Difluoro-2-trifluoromethoxy-6-[2-fluoro-4-[2-(trans-4-propylcyclohexyl)ethyl]phenyl]naphthalene
1,3-Difluoro-2-trifluoromethoxy-6-[2-fluoro-4-[2-(trans-4-pentylcyclohexyl)ethyl]phenyl]naphthalene
2-Trifluoromethoxy-6-[2,6-difluoro-4-[2-(trans-4-propylcyclohexyl)ethyl]phenyl]naphthalene
2-Trifluoromethoxy-6-[2,6-difluoro-4-[2-(trans-4-pentylcyclohexyl)ethyl]phenyl]naphthalene
1-Fluoro-2-trifluoromethoxy-6-[2,6-difluoro-4-[2-(trans-4-propylcyclohexyl)ethyl]phenyl]naphthalene
1-Fluoro-2-trifluoromethoxy-6-[2,6-difluoro-4-[2-(trans-4-pentylcyclohexyl)ethyl]phenyl]naphthalene
1,3-Difluoro-2-trifluoromethoxy-6-[2,6-difluoro-4-[2-(trans-4-propylcyclohexyl)ethyl]phenyl]naphthalene
1,3-Difluoro-2-trifluoromethoxy-6-[2,6-difluoro-4-[2-(trans-4-pentylcyclohexyl)ethyl]phenyl]naphthalene
4'-Ethyl-4-(2-trifluoromethoxynaphthalene-6-yl)biphenyl
4'-Propyl-4-(2-trifluoromethoxynaphthalene-6-yl)biphenyl
4'-Butyl-4-(2-trifluoromethoxynaphthalene-6-yl)biphenyl
4'-Pentyl-4-(2-trifluoromethoxynaphthalene-6-yl)biphenyl 4'-(3-Butenyl)-4-(2-trifluoromethoxynaphthalene-6-yl)biphenyl
4'-Ethyl-4-(1-Fluoro-2-trifluoromethoxynaphthalene-6-yl)biphenyl
4'-Propyl-4-(1-Fluoro-2-trifluoromethoxynaphthalene-6-yl)biphenyl
4'-Butyl-4-(1-Fluoro-2-trifluoromethoxynaphthalene-6-yl)biphenyl
4'-Pentyl-4-(1-Fluoro-2-trifluoromethoxynaphthalene-6-yl)biphenyl
4'-(3-Butenyl)-4-(1-Fluoro-2-trifluoromethoxynaphthalene-6-yl)biphenyl
4'-ethyl-4-(1,3-Difluoro-2-trifluoromethoxynaphthalene-6-yl)biphenyl
4'-propyl-4-(1,3-difluoro-2-trifluoromethoxynaphthalene-6-yl)biphenyl
4'-butyl-4-(1,3-difluoro-2-trifluoromethoxynaphthalene-6-yl)biphenyl
4'-pentyl-4-(1,3-difluoro-2-trifluoromethoxynaphthalene-6-yl)biphenyl
4'-(3-butenyl)-4-(1,3-difluoro-2-trifluoromethoxynaphthalene-6-yl)biphenyl
2'-Fluoro-4'-ethyl-4-(2-trifluoromethoxynaphthalene-6-yl)biphenyl
2'-Fluoro-4'-propyl-4-(2-trifluoromethoxynaphthalene-6-yl)biphenyl
2'-Fluoro-4'-butyl-4-(2-trifluoromethoxynaphthalene-6-yl)biphenyl
2'-Fluoro-4'-pentyl-4-(2-trifluoromethoxynaphthalene-6-yl)biphenyl
2'-Fluoro-4'-(3-butenyl)-4-(2-trifluoromethoxynaphthalene-6-yl)biphenyl
2'-Fluoro-4'-ethyl-4-(1-Fluoro-2-trifluoromethoxynaphthalene-6-yl)biphenyl
2'-Fluoro-4'-propyl-4-(1-Fluoro-2-trifluoromethoxynaphthalene-6-yl)biphenyl
2'-Fluoro-4'-butyl-4-(1-Fluoro-2-trifluoromethoxynaphthalene-6-yl)biphenyl
2'-Fluoro-4'-pentyl-4-(1-Fluoro-2-trifluoromethoxynaphthalene-6-yl)biphenyl
2'-Fluoro-4'-(3-butenyl)-4-(1-Fluoro-2-trifluoromethoxynaphthalene-6-yl)biphenyl
2'-Fluoro-4'-ethyl-4-(1,3-difluoro-2-trifluoromethoxynaphthalene-6-yl)biphenyl
2'-Fluoro-4'-propyl-4-(1,3-difluoro-2-trifluoromethoxynaphthalene-6-yl)biphenyl
2'-Fluoro-4'-butyl-4-(1,3-difluoro-2-trifluoromethoxynaphthalene-6-yl)biphenyl
2'-Fluoro-4'-pentyl-4-(1,3-difluoro-2-trifluoromethoxynaphthalene-6-yl)biphenyl
2'-Fluoro-4'-(3-butenyl)-4-(1,3-difluoro-2-trifluoromethoxynaphthalene-6-yl)biphenyl
3,5-Difluoro-4'-ethyl-4-(2-trifluoromethoxynaphthalene-6-yl)biphenyl
3,5-Difluoro-4'-propyl-4-(2-trifluoromethoxynaphthalene-6-yl)biphenyl
3,5-Difluoro-4'-butyl-4-(2-trifluoromethoxynaphthalene-6-yl)biphenyl
3,5-Difluoro-4'-pentyl-4-(2-trifluoromethoxynaphthalene-6-yl)biphenyl
3,5-Difluoro-4t-(3-butenyl)-4-(2-trifluoromethoxynaphthalene-6-yl)biphenyl
3,5-Difluoro-4'-ethyl-4-(1-fluoro-2-trifluoromethoxynaphthalene-6-yl)biphenyl
3,5-Difluoro-4'-propyl-4-(1-fluoro-2-trifluoromethoxynaphthalene-6-yl)biphenyl
3,5-Difluoro-4'-butyl-4-(1-fluoro-2-trifluoromethoxynaphthalene-6-yl)biphenyl
3,5-Difluoro-4'-pentyl-4-(1-fluoro-2-trifluoromethoxynaphthalene-6-yl)biphenyl
3,5-Difluoro-4'-(3-butenyl)-4-(1-fluoro-2-trifluoromethoxynaphthalene-6-yl)biphenyl
3,5-Difluoro-4'-ethyl-4-(1,3-difluoro-2-trifluoromethoxynaphthalene-6-yl)biphenyl
3,5-Difluoro-4'-propyl-4-(1,3-difluoro-2-trifluoromethoxynaphthalene-6-yl)biphenyl
3,5-Difluoro-4'-butyl-4-(1,3-difluoro-2-trifluoromethoxynaphthalene-6-yl)biphenyl
3,5-Difluoro-4'-pentyl-4-(1,3-difluoro-2-trifluoromethoxynaphthalene-6-yl)biphenyl
3,5-Difluoro-4'-(3-butenyl)-4-(1,3-difluoromethoxynaphthalene-6-yl)biphenyl
3-Fluoro-4'-ethyl4-(6-trifluoromethoxynaphthalene-2-yl)biphenyl
3-Fluoro-4'-propyl4-(6-trifluoromethoxynaphthalene-2-yl)biphenyl
3-Fluoro-4'-butyl4-(6-trifluoromethoxynaphthalene-2-yl)biphenyl
3-Fluoro-4'-pentyl4-(6-trifluoromethoxynaphthalene-2-yl)biphenyl
3-Fluoro-4'-(3-butenyl)-4-(6-trifluoromethoxynaphthalene-2-yl)biphenyl
3-Fluoro-4'-ethyl-4-(1-fluoro-2-trifluoromethoxynaphthalene-6-yl)biphenyl
3-Fluoro-4'-propyl-4-(1-fluoro-2-trifluoromethoxynaphthalene-6-yl)biphenyl
3-Fluoro-4'-butyl-4-(1-fluoro-2-trifluoromethoxynaphthalene-6-yl)biphenyl
3-Fluoro-4'-pentyl-4-(1-fluoro-2-trifluoromethoxynaphthalene-6-yl)biphenyl
3-Fluoro-4'-(3-butenyl)-4-(1-fluoro-2-trifluoromethoxynaphthalene-6-yl)biphenyl
3-Fluoro-4'-ethyl-4-(1,3-difluoro-2-trifluoromethoxynaphthalene-6-yl)biphenyl
3-Fluoro-4'-propyl-4-(1,3-difluoro-2-trifluoromethoxynaphthalene-6-yl)biphenyl
3-Fluoro-4'-butyl-4-(1,3-difluoro-2-trifluoromethoxynaphthalene-6-yl)biphenyl
3-Fluoro-4'-pentyl-4-(1,3-difluoro-2-trifluoromethoxynaphthalene-6-yl)biphenyl
3-Fluoro-4'-(3-butenyl)-4-(1,3-difluoro-2-trifluoromethoxynaphthalene-6-yl)biphenyl Example 26

Synthesis of 1-fluoro-2-trifluoromethoxy-6-1(4-propylphenyl)ethynyl]naphthalene 10 g of 4-propyl-1-ethynylbenzene and 19.5 g of 2-bromo-5-fluoro-6-trifluoromethoxynaphthalene were dissolved in 50 ml of N,N-dimethylformamide (DMF). To the solution were then added 50 mg of copper iodide (I) and 100 mg of tetrakis(triphenylphosphine)palladium (0). The reaction mixture was then stirred at room temperature for 5 hours. To the reaction solution was then added toluene. Insoluble matters water removed by filtration. The residue was then washed with water and saturated brine. The solvent was then distilled off. The residue was purified through silica gel column chromatography (hexane/ethyl acetate 9/1), and then recrystallized from ethanol to obtain 8.6 g of 1-fluoro-2-trifluoromethoxy-6-[(4-propylphenyl)ethynyl]naphthalene.

The following compounds were prepared in the same manner as mentioned above.

2-Trifluoromethoxy-6-(4-ethylphenyl)ethynylnaphthalene
2-Trifluoromethoxy-6-(4-propylphenyl)ethynylnaphthalene
2-Trifluoromethoxy-6-(4-butylphenyl) ethynylnaphthalene
2-Trifluoromethoxy-6-(4-pentylphenyl) ethynylnaphthalene
2-Trifluoromethoxy-6-[4-(3-butenyl)phenyl]ethynylnaphthalene
1-Fluoro-2-trifluoromethoxy-6-(4-ethylphenyl)ethynylnaphthalene
1-Fluoro-2-trifluoromethoxy-6-(4-butylphenyl)ethynylnaphthalene
1-Fluoro-2-trifluoromethoxy-6-(4-pentylphenyl)ethynylnaphthalene
1-Fluoro-2-trifluoromethoxy-6-[4-(3-butenyl)phenyl]ethynylnaphthalene
1,3-Difluoro-2-trifluoromethoxy-6-(4-ethylphenyl)ethynylnaphthalene
1,3-Difluoro-2-trifluoromethoxy-6-(4-propylphenyl)ethynylnaphthalene
1,3-Difluoro-2-trifluoromethoxy-6-(4-butylphenyl)ethynylnaphthalene
1,3-Difluoro-2-trifluoromethoxy-6-(4-pentylphenyl)ethynylnaphthalene
1,3-Difluoro-2-trifluoromethoxy-6-[4-(3-butenyl)phenyl]ethynylnaphthalene
2-Trifluoromethoxy-6-(2-fluoro-4-ethylphenyl)ethynylnaphthalene
2-Trifluoromethoxy-6-(2-fluoro-4-propylphenyl)ethynylnaphthalene
2-Trifluoromethoxy-6-(2-fluoro-4-butylphenyl)ethynylnaphthalene
2-Trifluoromethoxy-6-(2-fluoro-4-pentylphenyl)ethynylnaphthalene
2-Trifluoromethoxy-6-[2-fluoro-4-(3-butenyl)phenyl]ethynylnaphthalene
1-Fluoro-2-trifluoromethoxy-6-(2-fluoro-4-ethylphenyl)ethynylnaphthalene
1-Fluoro-2-trifluoromethoxy-6-(2-fluoro-4-propylphenyl)ethynylnaphthalene
1-Fluoro-2-trifluoromethoxy-6-(2-fluoro-4-butylphenyl)ethynylnaphthalene
1-Fluoro-2-trifluoromethoxy-6-(2-fluoro-4-pentylphenyl)ethynylnaphthalene
1-Fluoro-2-trifluoromethoxy-6-[2-fluoro-4-(3-butenyl)phenyl]ethynylnaphthalene
1,3-Difluoro-2-trifluoromethoxy-6-(2-fluoro-4-ethylphenyl)ethynylnaphthalene
1,3-Difluoro-2-trifluoromethoxy-6-(2-fluoro-4-propylphenyl)ethynylnaphthalene
1,3-Difluoro-2-trifluoromethoxy-6-(2-fluoro-4-butylphenyl)ethynylnaphthalene
1,3-Difluoro-2-trifluoromethoxy-6-(2-fluoro-4-pentylphenyl)ethynylnaphthalene
1,3-Difluoro-2-trifluoromethoxy-6-[2-fluoro-4-(3-butenyl)phenyl]ethynylnaphthalene
2-Trifluoromethoxy-6-(2,6-difluoro-4-ethylphenyl)ethynylnaphthalene
2-Trifluoromethoxy-6-(2,6-difluoro-4-propylphenyl)ethynylnaphthalene
2-Trifluoromethoxy-6-(2,6-difluoro-4-butylphenyl)ethynylnaphthalene
2-Trifluoromethoxy-6-(2,6-difluoro-4-pentylphenyl)ethynylnaphthalene
2-Trifluoromethoxy-6-[2,6-difluoro-4-(3-butenyl)phenyl]ethynylnaphthalene
1-Fluoro-2-trifluoromethoxy-6-(2,6-difluoro-4-ethylphenyl)ethynylnaphthalene
1-Fluoro-2-trifluoromethoxy-6-(2,6-difluoro-4-propylphenyl)ethynylnaphthalene
1-Fluoro-2-trifluoromethoxy-6-(2,6-difluoro-4-butylphenyl)ethynylnaphthalene
1-Fluoro-2-trifluoromethoxy-6-(2,6-difluoro-4-pentylphenyl)ethynylnaphthalene
1-Fluoro-2-trifluoromethoxy-6-[2,6-difluoro-4-(3-butenyl)phenyl]ethynylnaphthalene
1,3-Difluoro-2-trifluoromethoxy-6-(2,6-difluoro-4-ethylphenyl)ethynylnaphthalene
1,3-Difluoro-2-trifluoromethoxy-6-(2,6-difluoro-4-propylphenyl)ethynylnaphthalene
1,3-Difluoro-2-trifluoromethoxy-6-(2,6-difluoro-4-butylphenyl)ethynylnaphthalene
1,3-Difluoro-2-trifluoromethoxy-6-(2,6-difluoro-4-pentylphenyl)ethynylnaphthalene
1,3-Difluoro-2-trifluoromethoxy-6-[2,6-difluoro-4-(3-butenyl)phenyl]ethynylnaphthalene
2-Trifluoromethoxy-6-[4-(trans-4-propylcyclohexyl)phenyl]ethynylnaphthalene
2-Trifluoromethoxy-6-[4-(trans-4-butylcyclohexyl)phenyl]ethynylnaphthalene
2-Trifluoromethoxy-6-[4-(trans-4-pentylcyclohexyl)phenyl]ethynylnaphthalene
1-Fluoro-2-trifluoromethoxy-6-[4-(trans-4-propylcyclohexyl)phenyl]ethynylnaphthalene
1-Fluoro-2-trifluoromethoxy-6-[4-(trans-4-butylcyclohexyl)phenyl]ethynylnaphthalene
1-Fluoro-2-trifluoromethoxy-6-[4-(trans-4-pentylcyclohexyl)phenyl]ethynylnaphthalene
1,3-Difluoro-2-trifluoromethoxy-6-[4-(trans-4-propylcyclohexyl)phenyl]ethynylnaphthalene
1,3-Difluoro-2-trifluoromethoxy-6-[4-(trans-4-butylcyclohexyl)phenyl]ethynylnaphthalene
1,3-Difluoro-2-trifluoromethoxy-6-[4-(trans-4-pentylcyclohexyl)phenyl]ethynylnaphthalene
2-Trifluoromethoxy-6-[2,6-difluoro-4-(trans-4-propylcyclohexyl)phenyl]ethynylnaphthalene
2-Trifluoromethoxy-6-[2,6-difluoro-4-(trans-4-butylcyclohexyl)phenyl]ethynylnaphthalene
2-Trifluoromethoxy-6-[2,6-difluoro-4-(trans-4-pentylcyclohexyl)phenyl]ethynylnaphthalene
1-Fluoro-2-trifluoromethoxy-6-[2,6-difluoro-4-(trans-4-propylcyclohexyl)phenyl]ethynylnaphthalene
1-Fluoro-2-trifluoromethoxy-6-[2,6-difluoro-4-(trans-4-butylcyclohexyl)phenyl]ethynylnaphthalene
1-Fluoro-2-trifluoromethoxy-6-[2,6-difluoro-4-(trans-4-pentylcyclohexyl)phenyl]ethynylnaphthalene
1,3-Difluoro-2-trifluoromethoxy-6-[2,6-difluoro-4-(trans-4-propylcyclohexyl)phenyl]ethynylnaphthalene
1,3-Difluoro-2-trifluoromethoxy-6-[2,6-difluoro-4-(trans-4-butylcyclohexyl)phenyl]ethynylnaphthalene
1,3-Difluoro-2-trifluoromethoxy-6-[2,6-difluoro-4-(trans-4-pentylcyclohexyl)phenyl]ethynylnaphthalene Example 27

Synthesis of
2-(4-cyanophenyl)-6-propylnaphthalene

The procedure of Example 9 was followed except that 1-fluoro-2-[4-(4,4-dimethyl-1,3-oxazolidine-2-yl)phenyl]-6-propylnaphthalene was used instead of 1-fluoro-2-[4-(4,4-dimethyl-1,3-oxazolidine-2-yl)phenyl]-6-(trans-4-propyl cyclohexyl)naphthalene to obtain 2-(4-cyanophenyl)-6-propylnaphthalene in the form of white crystal.

Example 28

Synthesis of 2-(3-fluoro-4-cyanophenyl)-6-propylnaphthalene

The procedure of Example 10 was followed except that 1-fluoro-2-(3-fluoro-4-methoxyphenyl)-6-propylnaphthalene was used instead of 1-fluoro-2-(3-fluoro-4-methoxyphenyl)-6-(trans-4-propylcyclohexyl)naphthalene to obtain 2-(3-fluoro-4-cyanophenyl)-6-propylnaphthalene in the form of white crystal.

Example 29

Synthesis of 2-(3,5-difluoro-4-cyanophenyl)-6-propylnaphthalene

The procedure of Example 11 was followed except that 1-fluoro-2-(3,5-difluorophenyl)-6-propylnaphthalene was used instead of 1-fluoro-2-(3,5-difluorophenyl)-6-(trans-4-propylcyclohexyl)naphthalene to obtain 2-(3,5-difluoro-4-cyanophenyl)-6-propylnaphthalene in the form of white crystal.

The following compounds were prepared in the same manner as in Examples 27, 28 and 29.
1-Fluoro-2-(4-cyanophenyl)-6ethylnaphthalene
1-Fluoro-2-(4-cyanophenyl)-6-propylnaphthalene
1-Fluoro-2-(4-cyanophenyl)-6-butylnaphthalene
1-Fluoro-2-(4-cyanophenyl)-6-pentylnaphthalene
1-Fluoro-2-(4-cyanophenyl)-6-hexylnaphthalene
1-Fluoro-2-(4-cyanophenyl)-6-heptylnaphthalene
1-Fluoro-2-(3-fluoro-4-cyanophenyl)-6-ethylnaphthalene
1-Fluoro-2-(3-fluoro-4-cyanophenyl)-6-butylnaphthalene
1-Fluoro-2-(3-fluoro-4-cyanophenyl)-6-pentylnaphthalene
1-Fluoro-2-(3-fluoro-4-cyanophenyl)-6-hexylnaphthalene
1-Fluoro-2-(3-fluoro-4-cyanophenyl)-6-heptylnaphthalene
1-Fluoro-2-(3,5-difluoro-4-cyanophenyl)-6-ethylnaphthalene
1-Fluoro-2-(3,5-difluoro-4-cyanophenyl)-6-butylnaphthalene
1-Fluoro-2-(3,5-difluoro-4-cyanophenyl)-6-pentylnaphthalene
1-Fluoro-2-(3,5-difluoro-4-cyanophenyl)-6-hexylnaphthalene
1-Fluoro-2-(3,5-difluoro-4-cyanophenyl)-6-heptylnaphthalene
2-(4-cyanophenyl)-6-ethylnaphthalene
2-(4-cyanophenyl)-6-propylnaphthalene
2-(4-cyanophenyl)-6-butylnaphthalene
2-(4-cyanophenyl)-6-pentylnaphthalene
2-(4-cyanophenyl)-6-hexylnaphthalene
2-(4-cyanophenyl)-6-heptylnaphthalene
2-[3-Fluoro-4-cyanophenyl)-6-ethylnaphthalene
2-[3-Fluoro-4-cyanophenyl)-6-butylnaphthalene
2-[3-Fluoro-4-cyanophenyl)-6-pentylnaphthalene
2-[3-Fluoro-4-cyanophenyl)-6-hexylnaphthalene
2-[3-Fluoro-4-cyanophenyl)-6-heptylnaphthalene
2-(3,5-Difluoro-4-cyanophenyl)-6-ethylnaphthalene
2-(3,5-Difluoro-4-cyanophenyl)-6-butylnaphthalene
2-(3,5-Difluoro-4-cyanophenyl)-6-pentylnaphthalene
2-(3,5-Difluoro-4-cyanophenyl)-6-hexylnaphthalene
2-(3,5-Difluoro-4-cyanophenyl)-6-heptylnaphthalene
1-Fluoro-2-[4-(4-cyanophenyl)phenyl]-6-ethylnaphthalene
1-Fluoro-2-[4-(4-cyanophenyl)phenyl]-6-propylnaphthalene
1-Fluoro-2-[4-(4-cyanophenyl)phenyl]-6-butylnaphthalene
1-Fluoro-2-[4-(4-cyanophenyl)phenyl]-6-pentylnaphthalene
1-Fluoro-2-[4-(4-cyanophenyl)phenyl]-6-hexylnaphthalene
1-Fluoro-2-[4-(4-cyanophenyl)phenyl]-6-heptylnaphthalene
1-Fluoro-2-[4-(4-cyanophenyl)phenyl]-6-(3-butenyl)naphthalene
1-Fluoro-2-[3-fluoro-4-(4-cyanophenyl)phenyl]-6-ethylnaphthalene
1-Fluoro-2-[3-fluoro-4-(4-cyanophenyl)phenyl]-6-propylnaphthalene
1-Fluoro-2-[3-fluoro-4-(4-cyanophenyl)phenyl]-6-butylnaphthalene
1-Fluoro-2-[3-fluoro-4-(4-cyanophenyl)phenyl]-6-pentylnaphthalene
1-Fluoro-2-[3-fluoro-4-(4-cyanophenyl)phenyl]-6-hexylnaphthalene
1-Fluoro-2-[3-fluoro-4-(4-cyanophenyl)phenyl]-6-heptylnaphthalene
1-Fluoro-2-[3-fluoro-4-(4-cyanophenyl)phenyl]-6-(3-butenyl)naphthalene
1-Fluoro-2-[3,5-difluoro-4-(4-cyanophenyl)phenyl]-6-ethylnaphthalene
1-Fluoro-2-[3,5-difluoro-4-(4-cyanophenyl)phenyl]-6-propylnaphthalene
1-Fluoro-2-[3,5-difluoro-4-(4-cyanophenyl)phenyl]-6-butylnaphthalene
1-Fluoro-2-[3,5-difluoro-4-(4-cyanophenyl)phenyl]-6-pentylnaphthalene
1-Fluoro-2-[3,5-difluoro-4-(4-cyanophenyl)phenyl]-6-hexylnaphthalene
1-Fluoro-2-[3,5-difluoro-4-(4-cyanophenyl)phenyl]-6-heptylnaphthalene
1-Fluoro-2-[3,5-difluoro-4-(4-cyanophenyl)phenyl]-6-(3-butenyl)naphthalene
1-Fluoro-2-[4-(3-fluoro-4-cyanophenyl)phenyl]-6-ethylnaphthalene
1-Fluoro-2-[4-(3-fluoro-4-cyanophenyl)phenyl]-6-propylnaphthalene
1-Fluoro-2-[4-(3-fluoro-4-cyanophenyl)phenyl]-6-butylnaphthalene
1-Fluoro-2-[4-(3-fluoro-4-cyanophenyl)phenyl]-6-pentylnaphthalene
1-Fluoro-2-[4-(3-fluoro-4-cyanophenyl)phenyl]-6-hexylnaphthalene
1-Fluoro-2-[4-(3-fluoro-4-cyanophenyl)phenyl]-6-heptylnaphthalene
1-Fluoro-2-[4-(3-fluoro-4-cyanophenyl)phenyl]-6-(3-butenyl)naphthalene
1-Fluoro-2-[3-fluoro-4-(3-fluoro-4-cyanophenyl)phenyl]-6-ethylnaphthalene
1-Fluoro-2-[3-fluoro-4-(3-fluoro-4-cyanophenyl)phenyl]-6-propylnaphthalene
1-Fluoro-2-[3-fluoro-4-(3-fluoro-4-cyanophenyl)phenyl]-6-butylnaphthalene
1-Fluoro-2-[3-fluoro-4-(3-fluoro-4-cyanophenyl)phenyl]-6-pentylnaphthalene
1-Fluoro-2-[3-fluoro-4-(3-fluoro-4-cyanophenyl)phenyl]-6-hexylnaphthalene
1-Fluoro-2-[3-fluoro-4-(3-fluoro-4-cyanophenyl)phenyl]-6-heptylnaphthalene 1-Fluoro-2-[3-fluoro-4-(3-fluoro-4-cyanophenyl)phenyl]-6-(3-butenyl)naphthalene 1-Fluoro-2-[3,5-difluoro-4-(3-fluoro-4-cyanophenyl)phenyl]-6-ethylnaphthalene 1-Fluoro-2-[3,5-difluoro-4-(3-fluoro-4-cyanophenyl)phenyl]-6-propylnaphthalene 1-Fluoro-2-[3,5-difluoro-4-(3-fluoro-4-cyanophenyl)phenyl]-6-butylnaphthalene 1-Fluoro-2-[3,5-difluoro-4-(3-fluoro-4-cyanophenyl)phenyl]-6-pentylnaphthalene 1-Fluoro-2-[3,5-difluoro-4-(3-fluoro-4-cyanophenyl)phenyl]-6-hexylnaphthalene 1-Fluoro-2-[3,5-difluoro-4-(3-fluoro-4-cyanophenyl)phenyl]-6-heptylnaphthalene 1-Fluoro-2-[3,5-difluoro-4-(3-fluoro-4-cyanophenyl)phenyl]-6-(3-butenyl)naphthalene 1-Fluoro-2-[4-(3,5-difluoro-4-cyanophenyl)phenyl]-6-ethylnaphthalene 1-Fluoro-2-[4-(3,5-difluoro-4-cyanophenyl)phenyl]-6-propylnaphthalene 1-Fluoro-2-[4-(3,5-difluoro-4-cyanophenyl)phenyl]-6-butylnaphthalene 1-Fluoro-2-[4-(3,5-difluoro-4-cyanophenyl)phenyl]-6-pentylnaphthalene 1-Fluoro-2-[4-(3,5-difluoro-4-cyanophenyl)phenyl]-6-hexylnaphthalene 1-Fluoro-2-[4-(3,5-difluoro-4-cyanophenyl)phenyl]-6-heptylnaphthalene 1-Fluoro-2-[4-(3,5-difluoro-4-cyanophenyl)phenyl]-6-(3-butenyl)naphthalene 1-Fluoro-2-[3-fluoro-4-(3,5-difluoro-4-cyanophenyl)phenyl]-6-ethylnaphthalene 1-Fluoro-2-[3-fluoro-4-(3,5-difluoro-4-cyanophenyl)phenyl]-6-propylnaphthalene 1-Fluoro-2-[3-fluoro-4-(3,5-difluoro-4-cyanophenyl)phenyl]-6-butylnaphthalene 1-Fluoro-2-[3-fluoro-4-(3,5-difluoro-4-cyanophenyl)phenyl]-6-pentylnaphthalene 1-Fluoro-2-[3-fluoro-4-(3,5-difluoro-4-cyanophenyl)phenyl]-6-hexylnaphthalene 1-Fluoro-2-[3-fluoro-4-(3,5-difluoro-4-cyanophenyl)phenyl]-6-heptylnaphthalene 1-Fluoro-2-[3-fluoro-4-(3,5-difluoro-4-cyanophenyl)phenyl]-6-(3-butenyl)naphthalene 1-Fluoro-2-[3,5-difluoro-4-(3,5-difluoro-4-cyanophenyl)phenyl]-6-ethylnaphthalene 1-Fluoro-2-[3,5-difluoro-4-(3,5-difluoro-4-cyanophenyl)phenyl]-6-propylnaphthalene 1-Fluoro-2-[3,5-difluoro-4-(3,5-difluoro-4-cyanophenyl)phenyl]-6-butylnaphthalene 1-Fluoro-2-[3,5-difluoro-4-(3,5-difluoro-4-cyanophenyl)phenyl]-6-pentylnaphthalene 1-Fluoro-2-[3,5-difluoro-4-(3,5-difluoro-4-cyanophenyl)phenyl]-6-hexylnaphthalene 1-Fluoro-2-[3,5-difluoro-4-(3,5-difluoro-4-cyanophenyl)phenyl]-6-heptylnaphthalene 1-Fluoro-2-[3,5-difluoro-4-(3,5-difluoro-4-cyanophenyl)phenyl]-6-(3-butenyl)naphthalene

Example 30

Preparation of Liquid Crystal Composition (1)

A general-purpose host liquid crystal (H) having the following structure:

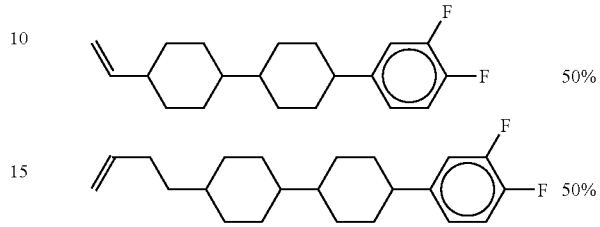

having a wide operating temperature range and a low viscosity which can be also used for active matrix driving was prepared. The host liquid crystal composition (H) exhibited a nematic phase at a temperature of not higher than 116.7° C. and a melting point of +11° C. The physical properties of the liquid crystal composition and the electro-optical properties of the liquid crystal device prepared therefrom are as follows:

| | |
|---|---|
| Threshold voltage (Vth): | 2.14 V |
| Dielectric anisotropy ($\Delta\epsilon$): | 4.8 |
| Response ($\tau r = \tau d$): | 25.3 m sec. |
| Birefringence ($\Delta n$): | 0.090 |

For the measurement of threshold voltage (Vth) and response, the nematic liquid crystal composition is filled in a TN cell having a thickness of 6 μm. The measurement is effected at a temperature of 20° C. The term "response" as used herein is meant to indicate the response time shown during the application of voltage at which the rise time ($\tau r$) and the drop time ($\tau d$) are equal to each other.

80% of the host liquid crystal composition (H) and the compound represented by the formula (Ib-1) of the present invention obtained in Example 15:

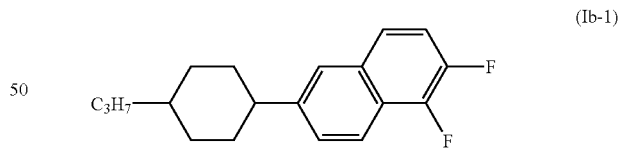

were then added to a host liquid crystal composition (H) having a wide operating temperature range and suitable for low viscosity host liquid crystal composition, particularly for active matrix driving, in an amount of 20% to prepare a nematic liquid crystal composition (M-1). As a result, the upper nematic phase temperature limit ($T_{N-1}$) of the nematic liquid crystal composition (M-1) was 98.2° C. The nematic liquid crystal composition (M-1) was allowed to stand at a temperature of 150° C. for 20 hours, and then measured for $T_{N-1}$. The results were 97.8° C., demonstrating that the nematic liquid crystal composition (M-1) shows little or no change of $T_{N-1}$ from before heating. The nematic liquid crystal composition (M-1) was then irradiated with ultraviolet rays for 20 hours. As a result, the nematic liquid crystal composition (M-1) showed no change of $T_{N-1}$. The nematic liquid crystal composition (M-1) was then measured for voltage holding ratio. As a result, the composition exhibited a sufficiently high voltage holding ratio similarly to the host liquid crystal (H) during preparation, after heating and after irradiation with ultraviolet rays.

Subsequently, the nematic liquid crystal composition (M-1) was filled in a TN cell having a thickness of 4.5 μm to prepare a liquid crystal device. The liquid crystal device was then measured for electro-optical properties. The results are as follows:

| Upper nematic phase | |
| --- | --- |
| temperature limit ($T_{N-1}$) | 98.6° C. |
| Dielectric anisotropy (Δε) | 4.60 |
| Threshold voltage (Vth) | 1.76 V |
| Response (τr = τd) | 24.2 m sec. |

It can thus be seen that the addition of the compound (Ib-1) makes it possible to provide a quick response similarly to the host liquid crystal composition (H), a lower dielectric anisotropy than the host liquid crystal composition (H) and a threshold voltage drop of about 10% from that of the host liquid crystal composition (H). The liquid crystal device thus obtained was then measured for voltage holding ratio at room temperature and 80° C. The results were good at any of the two temperature ranges, demonstrating that the liquid crystal device can be sufficiently used in active matrix driving.

Example 31

Preparation of Liquid Crystal Composition (2)

80% of the host liquid crystal composition (H) and the compound (Ib-2) of the present invention obtained in Example 15:

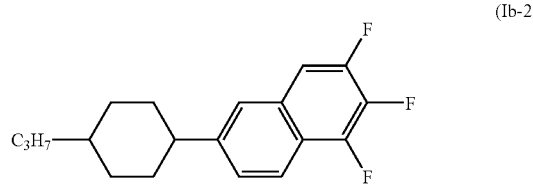

(Ib-2)

were added to a host liquid crystal composition (H) having a wide operating temperature range and suitable for low viscosity host liquid crystal composition, particularly for active matrix driving, in an amount of 20% to prepare a nematic liquid crystal composition (M-2). The electro-optical properties of the nematic liquid crystal composition (M-2) and the liquid crystal device prepared in the same manner as mentioned above therefrom are as follows:

| Upper nematic phase | |
| --- | --- |
| temperature limit ($T_{N-1}$) | 92.7° C. |
| Dielectric anisotropy (Δε) | 5.7 |

-continued

| Upper nematic phase | |
| --- | --- |
| Threshold voltage (Vth) | 1.53 V |
| Response (τr = τd) | 28.0 m sec. |

It can thus be seen that the compound (Ib-1) exhibits a smaller dielectric anisotropy than the host liquid crystal (H) and a threshold voltage drop of about 20% from the host liquid crystal (H).

The nematic liquid crystal composition (M-2) was then subjected to heat stability test and ultraviolet ray irradiation test in the same manner as the nematic liquid crystal composition (M-1). As a result, the composition (M-2) showed no change of $T_{N-1}$ after these tests. The nematic liquid crystal composition (M-2) was then measured for voltage holding ratio. As a result, the composition (M-2) exhibited a sufficiently high voltage holding ratio during preparation, after heating and after irradiation with ultraviolet rays.

As mentioned above, the compound represented by the general formula (I) is very useful in the preparation of a liquid crystal composition having (a) a wide nematic phase operating temperature range, (b) a threshold voltage low enough to drive at a low voltage, (c) a quick response and (d) a voltage holding ratio high enough active matrix driving.

Example 32

Preparation of Liquid Crystal Composition (2)

80% of the host liquid crystal composition (H) and the compound (Ic-7) of the present invention obtained in Example 2:

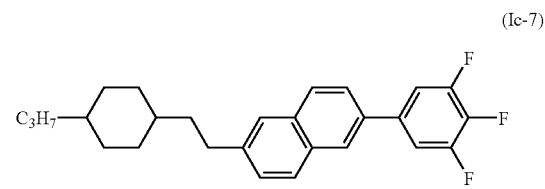

(Ic-7)

were added to a host liquid crystal composition (H) having a wide operating temperature range and suitable for low viscosity host liquid crystal composition, particularly for active matrix driving, in an amount of 20% to prepare a nematic liquid crystal composition (M-3). The electro-optical properties of the nematic liquid crystal composition (M-3) and the liquid crystal device prepared in the same manner as mentioned above therefrom are as follows:

| | |
| --- | --- |
| $T_{N-1}$: | 120.0° C. |
| $T_{C-N}$: | −2° C. |
| Threshold voltage (Vth) | 2.06 V |
| Dielectric anisotropy (Δε): | 5.5 |
| Birefringence index (Δn): | 0.110 |

It can thus be seen that the addition of the compound (Ic-7) makes it possible to raise the upper nematic phase temperature limit ($T_{N-1}$) by not lower than 3°. The nematic liquid crystal composition (M-3) was cooled to a temperature of −60° C. to undergo crystallization. The nematic liquid crystal composition (M-3) thus crystallized was then measured for melting point ($T_{C-N}$) The results were −2° C., demonstrating that the composition (M-3) exhibits a melting point drop of as much as 13° from the host liquid crystal composition (H). Accordingly, the stable temperature range of nematic phase can be expanded by as much as about 16°. It can also be seen that the addition of the compound (Ic-7) makes it possible to increase the dielectric anisotropy of liquid crystal composition and lower the threshold voltage of liquid crystal composition. The increase in the birefringence index could be suppressed to 0.02 from that of the host liquid crystal (H).

The liquid crystal device was then measured for voltage holding ratio at room temperature and 80° C. The results were extremely good at any of the two temperature ranges, demonstrating that it can be sufficiently used in active matrix driving.

Comparative Example 1

A compound represented by the following general formula (R-1) having a structure similar to the compound (Ic-7) but having 1,4-phenylene group instead of 2,6-naphthylene group:

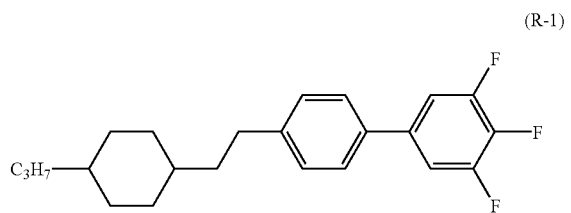
(R-1)

was added to the host liquid crystal composition (H) in the same amount as mentioned above (20%) to prepare a liquid crystal composition (HR-1). The upper nematic phase temperature limit ($T_{N-1}$) of the liquid crystal composition (HR-1) was 101° C., which is far lower than that of the composition (M-3) as expected. The liquid crystal composition (HR-1) exhibited a malting point ($T_{C-N}$) of 5° C., which is higher than that of the composition (M-3). Accordingly, the liquid crystal composition (HR-1) exhibited a nematic phase temperature range of as much as 25° or more smaller than the composition (M-3).

Example 33

Preparation of Liquid Crystal Composition (4)

80% of the host liquid crystal composition (H) and the compound (Id-1) of the present invention obtained in Example 12:

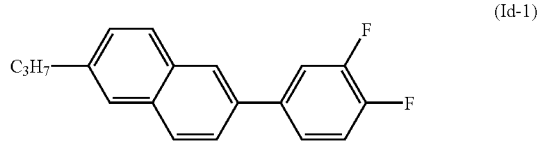
(Id-1)

were added to a host liquid crystal composition (H) having a wide operating temperature range and suitable for low viscosity host liquid crystal composition, particularly for active matrix driving, in an amount of 20% to prepare a nematic liquid crystal composition (M-3). The electro-optical properties of the nematic liquid crystal composition (M-3) and the liquid crystal device prepared in the same manner as mentioned above therefrom are as follows:

| | |
|---|---|
| $T_{N-1}$: | 91.0° C. |
| Threshold voltage (Vth) | 1.94 V |
| Dielectric anisotropy (Δε): | 4.85 |
| Response (τr = τd): | 28.4 m sec. |
| Birefringence index (Δn): | 0.112 |

It can thus be seen that the addition of the compound (Id-1) in an amount of 20% causes a slight drop of the upper nematic phase temperature limit ($T_{N-1}$) but makes it possible to lower the threshold voltage of the liquid crystal composition and drastically raise the birefringence index of the liquid crystal composition (by about 0.02 from that of the host liquid crystal composition (H)) without deteriorating the response. Subsequently, the liquid crystal composition was allowed to stand at room temperature for 1 month. However, no crystallization or phase separation were observed. It can thus be seen that the compound (Id-1) has an excellent miscibility with the conventional liquid crystals. The liquid crystal composition (M-4) was cooled to a temperature of −15° C. to undergo crystallization, and then measured for melting point ($T_{C-N}$). The results were 14° C.

Example 34

Preparation of Liquid Crystal Composition (5)

To 80% of the host liquid crystal composition (H) was added the compound represented by the formula (Id-2) of the present invention obtained in Example 13:

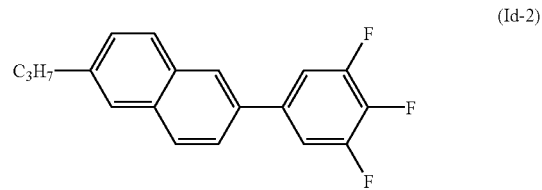
(Id-2)

in the same manner as mentioned above (20%) to prepare a liquid crystal composition (M-5). The physical properties of the liquid crystal composition (M-5) and the electro-optical properties of the liquid crystal device prepared in the same manner as mentioned above therefrom are as follows:

| | |
|---|---|
| $T_{N-1}$: | 85.1° C. |
| Threshold voltage (Vth) | 1.74 V |
| Dielectric anisotropy (Δε): | 5.7 |
| Response (τr = τd): | 31.1 m sec. |
| Birefringence index (Δn): | 0.107 |

The comparison of the liquid crystal composition (M-5) with the liquid crystal composition (M-4) shows that the liquid crystal composition (M-5) exhibits a slightly lower $T_{N-1}$ and a slightly reduced birefringence index but has a quick response similarly to the liquid crystal composition (M-4) and a further drop of threshold voltage.

Example 35

Preparation of Liquid Crystal Composition (6)

To 80% of the host liquid crystal composition (H) was added the compound represented by formula (Id-7) of the present invention obtained in Example 12:

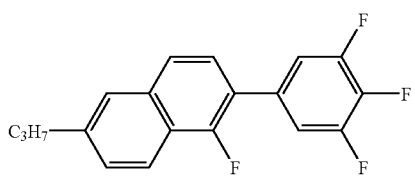
(Id-7)

in the same manner am mentioned above (20%) to prepare a liquid crystal Composition (M-6). The physical properties of the liquid crystal composition (M-6) and the electro-optical properties of the liquid crystal device prepared in the same manner as mentioned above therefrom are as follows:

| | |
|---|---|
| $T_{N-1}$: | 86.0° C. |
| $T_{C-N}$: | 12° C. |
| Threshold voltage (Vth) | 1.65 V |
| Dielectric anisotropy (Δε): | 6.5 |
| Birefringence index (Δn): | 0.107 |
| Response (τr = τd): | 28.8 m sec. |

The addition of the compound (Id-7) in an amount of 20% causes a slight drop of the upper nematic phase temperature limit ($T_{N-1}$) but can provide a quick response similarly to the host liquid crystal composition (H) and makes it possible to drastically lower the threshold voltage of the liquid crystal composition (by 0.3 V). Further, the birefringence index of the liquid crystal composition can be drastically increased from the host liquid crystal composition (H).

Comparative Example 2

The procedure of Examples 33 to 35 were followed except that the compound represented by formula (Ic) was replaced by a compound represented by the following formula (R-2) having a structure similar to that of the compound (Ic) but having 1,4-phenylene group instead of 2,6-naphthylene group:

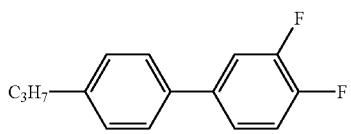
(R-2)

which was added in the same manner as mentioned above (20% by weight) to prepare a liquid crystal composition (HR-2). The liquid crystal composition (HR-2) thus prepared was then measured for physical properties and electro-optical properties in the same manner as mentioned above.

The results are as follows:

| | |
|---|---|
| $T_{N-1}$: | 86.0° C. |
| Threshold voltage (Vth) | 1.86 V |
| Dielectric anisotropy (Δε): | 4.92 |
| Response (τr = τd): | 27.0 m sec. |
| Birefringence index (Δn): | 0.096 |

The comparison of the liquid crystal composition (HR-2) with the liquid crystal composition (H-1) shows that the liquid crystal composition (HR-2) exhibits a slightly more quick response and a slightly lower threshold voltage (Vth). However, the upper nematic phase temperature limit ($T_{N-1}$) of the liquid crystal composition (HR-2) showed a further drop. The liquid crystal composition (HR-2) also showed only a slight increase in birefringence index.

The naphthalene derivative provided by the present invention exhibits an excellent liquid-crystallinity and miscibility with currently widely used liquid crystal compositions or compositions. The addition of the naphthalene derivative makes it possible to drastically lower the threshold voltage of the liquid crystal composition while maintaining its high response. The naphthalene derivative of the present invention is characterized by a large birefringence index. Further, most of the naphthalene derivative of the present invention has no strongly polar group in its molecule and thus can also be used for active matrix driving. Moreover, as shown in the foregoing examples, the naphthalene derivative of the present invention can be easily produced and is colorless and chemically stable. Accordingly, the liquid crystal composition comprising the naphthalene derivative of the present invention is extremely useful as a practical liquid crystal composition, particularly a liquid crystal composition which can operate within a wide temperature range and requires a high speed response and a low voltage driving.

The invention claimed is:

1. A naphthalene derivative represented by the following general formula (I):

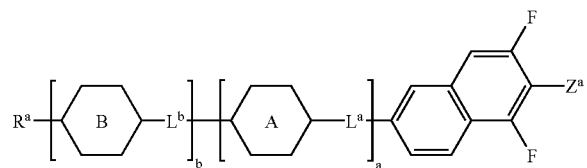
(I)

wherein $R^a$ represents a $C_{1-20}$ alkyl, alkoxy, alkoxyalkyl, alkenyl or alkenyloxy group which may be substituted by a $C_{1-7}$ alkoxyl group or from 1 to 7 fluorine atoms; a and b each represent an integer, where a is 1 and b is 0 or 1; ring A represents an unsubstituted 1,4-phenylene group, 3-fluoro-1,4-phenylene group or 3,5-difluoro-1,4-phenylene group; ring B represents a trans-1,4-cyclohexylene group, 1,4-phenylene group which maybe substituted by one or more fluorine atoms, pyridine-2,5-diyl group, pyrimidine-2,5-diyl group, pyrazine-2,5-diyl group, pyridazine-3,6-diyl group, trans-1,3-dioxane-2,5-diyl group, trans-decahydronaphthalene-2,6-diyl group or tetrahydronaphthalene-2,6-diyl group; $L^a$ represents —CH$_2$CH$_2$—, —CH$_2$CH$_2$CH$_2$CH$_2$—, —CH═CH—, —CH═CHCH$_2$CH$_2$—, —CH$_2$CH$_2$CH═CH—, —CH(CH$_3$)CH$_2$—, —CH$_2$CH(CH$_3$)—, —CF═CF—, —CF$_2$O—, —OCF$_2$—, —COO—, —OCO—, —C≡C— or single bond, and $L^b$ represents —CH$_2$CH$_2$CH$_2$CH$_2$—, —CH=CH—, —CH=CHCH$_2$CH$_2$—, —CH$_2$CH$_2$CH=CH—, —CH(CH$_3$)CH$_2$—, —CH$_2$CH (CH$_3$)—, —CF=CF—, —CF$_2$O—, —OCF$_2$—, —COO—, —OCO—, —C≡C— or single bond with the proviso that when ring A represents an unsubstituted 1,4-phenylene group, $L^b$ represents a single bond and b=1; and $Z^a$ represents a fluorine atom, chlorine atom, trifluoromethoxy group, C$_{1-20}$ alkyl, alkoxyl, alkenyl or alkenyloxy group wherein the C$_{1-20}$ alkyl, alkoxyl, alkenyl or alkenyloxy group may be substituted by a C$_{1-7}$ alkoxy group or from 1 to 7 fluorine atoms provided that when $Z^a$ is a C$_{1-20}$ alkoxy group, $Z^a$ is not substituted by an alkoxy group, or group represented by the following general formula (IIa) or (IIIb):

(IIa)

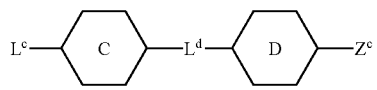

(IIb)

wherein $L^c$ represents —CH$_2$CH$_2$—, —CH$_2$CH$_2$CH$_2$CH$_2$—, —CH=CH—, —CH=CHCH$_2$CH$_2$—, —CH$_2$CH$_2$CHCH—, —CH(CH$_3$)CH$_2$—, —CH$_2$CH(CH$_3$)—, —CF=CF—, —CF$_2$O—, —OCF$_2$—, —OCO—, —C≡C— or single bond; $L^d$ represents —CH$_2$CH$_2$—, —CH$_2$CH$_2$CH$_2$CH$_2$—, —CH=CH—, —CH=CHCH$_2$CH$_2$—, —CH$_2$CH$_2$CH=CH—, —CH (CH$_3$)CH$_2$—, —CH$_2$CH(CH$_3$)—, —CF=CF—, —CF$_2$O—, —OCF$_2$—, —COO—, —OCO—, —C≡C— or single bond; ring C represents a trans-1,4-cyclohexylene group, 1,4-phenylene group which may be substituted by one or more fluorine atoms, pyrazine-2,5-diyl group, pyridazine-3,6-diyl group, trans-1,3-dioxane-2,5-diyl group, trans-dechydronaphthalene-2,6-diyl group or tetrahydronaphthalene-2,6-diyl group; ring D represents a trans-1, 4-cyclohexylene group, 1,4-phenylene group which may be substituted by one or more fluorine atoms, pyridine-2,5-diyl group, pyrimidine-2,5-diyl group, pyrazine-2,5-diyl group, pyridazine-3,6-diyl group, trans-1,3-dioxane-2, 5-diyl group, trans-dechydronaphthalene-2,6-diyl group or tetrahydronaphthalene-2,6-diyl group; $Z^b$ represents a fluorine atom, chlorine atom, bromine atom, iodine atom, hydrogen atom, cyano group, —SCN, OCN, —R', —OR', or —OCOR' wherein R' represents a C$_{1-20}$ alkyl or alkoxy group or C$_{2-20}$ alkenyl or alkenyloxy group and these groups may be substituted by a C$_{1-10}$ alkoxyl, acyl, acyloxy or alkoxycarbonyl group and one or more hydrogen atoms contained in these groups may be substituted by one or more fluorine atoms, and in the case of forming an asymmetric carbon by the substitution or branching, it may form an optically active form or racemic form, with the proviso that when $Z^a$ represents formula (IIa) and ring C represents 1,4-phenylene group, then the phenylene group is substituted by a fluorine atom; and $Z^c$ represents a fluorine atom, chlorine atom, bromine atom, iodine atom, hydrogen atom, cyano group, —SCN, OCN, —R', —OR', —OCOR' or —COOR', wherein R' represents a C$_{1-20}$ alkyl or alkoxy group or C$_{2-20}$ alkenyl or alkenyloxy group and these groups may be substituted by a C$_{1-10}$ alkoxyl, acyl, acyloxy or alkoxycarbonyl group and one or more hydrogen atoms contained in these groups may be substituted by one or more fluorine atoms, and in the case of forming an asymmetric carbon by the substitution or branching, it may form an optically active form or racemic form.

2. A naphthalene derivative represented by one of the following general formulas:

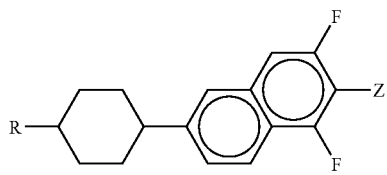

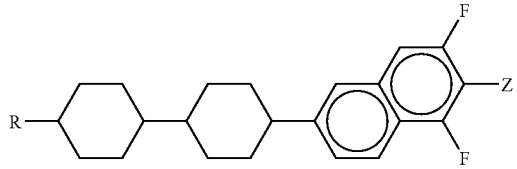

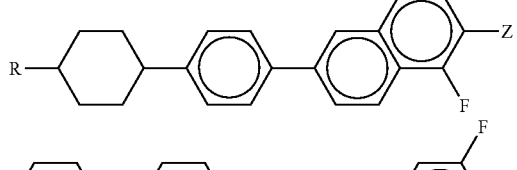

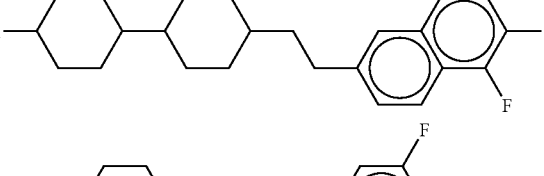

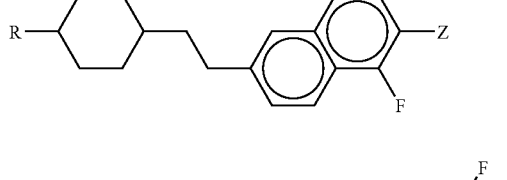

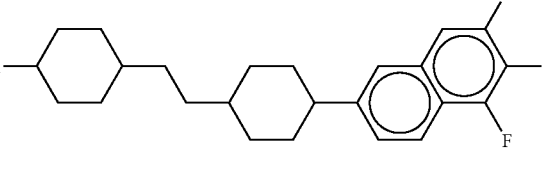

wherein R represents a C$_{1-20}$ alkyl, but not a straight chain hexyl group, alkoxy, alkoxyalkyl, alkenyl or alkenyloxy group which may be substituted by a C1-7 alkoxyl group or from 1 to 7 fluorine atoms; and Z represents a fluorine atom, chlorine atom, trifluoromethoxy group, C$_{1-20}$ alkyl, alkoxyl, alkenyl or alkenyloxy group wherein the C$_{1-20}$ alkyl, alkoxyl, alkenyl or alkenyloxy group may be substituted by a C$_{1-7}$ alkoxy group or from 1 to 7 fluorine atoms provided that when Z is a C$_{1-20}$ alkoxy group, Z is not substituted by an alkoxy group.

3. A naphthalene derivative represented by the following general formula:

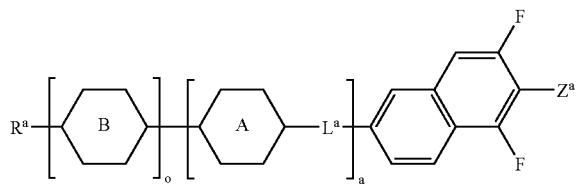

wherein $R^a$ represents a $C_{1-20}$ alkyl, alkoxy, alkoxyalkyl, alkenyl or alkenyloxy group which may be substituted by a $C_{1-7}$ alkoxyl group or from 1 to 7 fluorine atoms; a and b each represent an integer, where a is 1 and b is 0 or 1; ring A represents an unsubstituted 1,4-phenylene group, 3-fluoro-1,4-phenylene group or 3,5-difluoro-1,4-phenylene group, and ring B represents a trans-1,4-cyclohexylene group, 1,4-phenylene group which may be substituted by one or more fluorine atoms, pyridine-2,5-diyl group, pyrimidine-2,5-diyl group, pyrazine-2,5-diyl group, pyridazine-3,6-diyl group, trans-1,3-dioxane-2,5-diyl group, trans-decahydronaphthalene-2,6-diyl group or tetrahydronaphthalene-2,6-diyl group; $L^a$ represents —CH$_2$CH$_2$—, —CH$_2$CH$_2$CH$_2$CH$_2$—, —CH=CH—, —CH=CHCH$_2$CH$_2$—, —CH$_2$CH$_2$CH=CH—, —CH(CH$_3$)CH$_2$—, —CH$_2$CH(CH$_3$)—, —CF=CF—, —CF$_2$O—, —OCF$_2$—, —COO—, -OCO—, —C≡C— or single bond; and $Z^a$ represents a fluorine atom, chlorine atom, trifluoromethoxy group, $C_{1-20}$ alkyl, alkoxyl, alkenyl or alkenyloxy group wherein the $C_{1-20}$ alkyl, alkoxyl, alkenyl or alkenyloxy group may be substituted by a $C_{1-7}$ alkoxy group or from 1 to 7 fluorine atoms provided that when $Z^a$ is a $C_{1-20}$ alkoxy group, $Z^a$ is not substituted by an alkoxy group, or group represented by the following general formula (IIa) or (IIb):

(IIa)

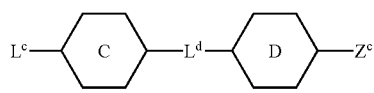

(IIb)

wherein $L^c$ represents —CH$_2$CH$_2$—, —CH$_2$CH$_2$CH$_2$CH$_2$—, —CH=CH—, —CHCHCH$_2$CH$_2$—, —CH$_2$CH$_2$CH=CH—, —CH(CH$_3$)CH$_2$—, —CH$_2$CH(CH$_3$)—, —CF=CF—, —CF$_2$O—, —OCF$_2$—, —OCO—, —C=C— or single bond; $L^d$ represents —CH$_2$CH$_2$—, —CH$_2$CH$_2$CH$_2$CH$_2$—, —CH=CH—, —CH=CHCH$_2$CH$_2$—, —CH$_2$CH$_2$CH=CH—, —CH(CH$_3$)CH$_2$—, —CH$_2$CH(CH$_3$)—, —CF=CF—, —CF$_2$O—, —OCF$_2$—, —COO—, —OCO—, —C≡C— or single bond; ring C represents a trans-1,4-cyclohexylene group, 1,4-phenylene group which may be substituted by one or more fluorine atoms, pyrazine-2,5-diyl group, pyridazine-3,6-diyl group, trans-1,3-dioxane-2,5-diyl group, trans-dechydronaphthalene-2,6-diyl group or tetrahydronaphthalene-2,6-diyl group; ring D represents a trans-1,4-cyclohexylene group, 1,4-phenylene group which may be substituted by one or more fluorine atoms, pyridine-2,5-diyl group, pyrimidine-2,5-diyl group, pyrazine-2,5-diyl group, pyridazine-3,6-diyl group, trans-1,3-dioxane-2,5-diyl group, trans-dechydronaphthalene-2,6-diyl group or tetrahydronaphthalene-2,6-diyl group; $Z^b$ represents a fluorine atom, chlorine atom, bromine atom, iodine atom, hydrogen atom, cyano group, —SCN, OCN, —R', —OR', or —OCOR' wherein R' represents a $C_{1-20}$ alkyl or alkoxy group or $C_{2-20}$ alkenyl or alkenyloxy group and these groups may be substituted by a $C_{1-10}$ alkoxyl, acyl, acyloxy or alkoxycarbonyl group and one or more hydrogen atoms contained in these groups maybe substituted by one or more fluorine atoms, and in the case of forming an asymmetric carbon by the substitution or branching, it may form an optically active form or racemic form, with the proviso that when $Z^a$ represents formula (IIa) and ring C represents 1,4-phenylene group, then the phenylene group is substituted by a fluorine atom; and $Z^c$ represents a fluorine atom, chlorine atom, bromine atom, iodine atom, hydrogen atom, cyano group, —SCN, OCN, —R', —OR', —OCOR' or —COOR', wherein R' represents a $C_{1-20}$ alkyl or alkoxy group or $C_{2-20}$ alkenyl or alkenyloxy group and these groups may be substituted by a $C_{1-10}$ alkoxyl, acyl, acyloxy or alkoxycarbonyl group and one or more hydrogen atoms contained in these groups maybe substituted by one or more fluorine atoms, and in the case of forming an asymmetric carbon by the substitution or branching, it may form an optically active form; and when ring A represents an unsubstituted 1,4-phenylene group, b=1.

4. A naphthalene derivative according to claim 1, which has the structure:

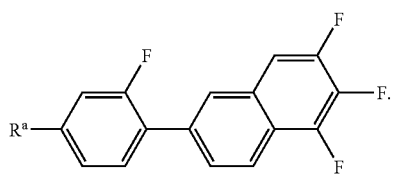

5. A naphthalene derivative according to claim 1, which has the structure:

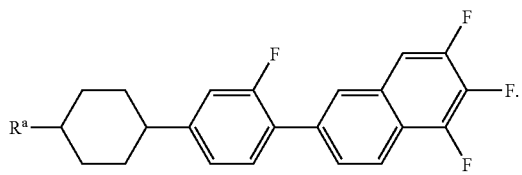

* * * * *